US010316040B2

(12) United States Patent
Zheng et al.

(10) Patent No.: US 10,316,040 B2
(45) Date of Patent: Jun. 11, 2019

(54) EP4 ANTAGONISTS

(71) Applicant: Eisai R&D Management Co., Ltd., Tokyo (JP)

(72) Inventors: Wanjun Zheng, Londonderry, NH (US); Xiaojie Zhu, Andover, MA (US); Hong Du, North Andover, MA (US); Maarten Postema, Dublin, NH (US); Yimin Jiang, Londonderry, NH (US); Jing Li, Andover, MA (US); Robert Yu, Arlington, MA (US); Hyeong-wook Choi, Andover, MA (US); Jaemoon Lee, Andover, MA (US); Frank Fang, Andover, MA (US); Daniel Custar, North Andover, MA (US)

(73) Assignee: Eisai R&D Management Co., LTD., Tokyo (JP)

( * ) Notice: Subject to any disclaimer, the term of this patent is extended or adjusted under 35 U.S.C. 154(b) by 0 days.

(21) Appl. No.: 15/768,668

(22) PCT Filed: Oct. 14, 2016

(86) PCT No.: PCT/US2016/057135
§ 371 (c)(1),
(2) Date: Apr. 16, 2018

(87) PCT Pub. No.: WO2017/066633
PCT Pub. Date: Apr. 20, 2017

(65) Prior Publication Data
US 2018/0305362 A1  Oct. 25, 2018

Related U.S. Application Data

(60) Provisional application No. 62/242,734, filed on Oct. 16, 2015, provisional application No. 62/242,748, filed on Oct. 16, 2015.

(30) Foreign Application Priority Data

Oct. 13, 2016 (BD) ..................................... 252/2016

(51) Int. Cl.
C07D 487/04 (2006.01)
C07D 519/00 (2006.01)
A61P 35/00 (2006.01)

(52) U.S. Cl.
CPC ............ *C07D 487/04* (2013.01); *A61P 35/00* (2018.01); *C07D 519/00* (2013.01)

(58) Field of Classification Search
CPC .................................................. C07D 487/04
See application file for complete search history.

(56) References Cited

U.S. PATENT DOCUMENTS

| 4,728,598 | A | 3/1988 | Bailey et al. |
| 4,788,134 | A | 11/1988 | Ozaki et al. |
| 4,847,256 | A | 7/1989 | Tseng et al. |
| 4,963,553 | A | 10/1990 | Tseng et al. |
| 5,206,130 | A | 4/1993 | Shimada et al. |
| 5,210,200 | A | 5/1993 | Shimada |
| 5,215,982 | A | 6/1993 | Sakane et al. |
| 5,272,051 | A | 12/1993 | Shimada et al. |
| 5,340,706 | A | 8/1994 | Naruse et al. |
| 5,389,641 | A | 2/1995 | Naka et al. |
| 5,405,969 | A | 4/1995 | Wright et al. |
| 5,484,760 | A | 1/1996 | Bussler et al. |
| 5,514,532 | A | 5/1996 | Sato et al. |
| 5,534,534 | A | 7/1996 | Makino et al. |
| 5,583,141 | A | 12/1996 | Naka et al. |
| 5,880,066 | A | 3/1999 | Chupp et al. |
| 6,472,416 | B1 | 10/2002 | Kolasa et al. |
| 8,686,018 | B2 | 4/2014 | Spyvee et al. |
| 9,000,024 | B2 | 4/2015 | Spyvee et al. |
| 2002/0032252 | A1 | 3/2002 | Ishizuka |
| 2003/0024059 | A1 | 2/2003 | Pratt et al. |
| 2004/0127508 | A1 | 7/2004 | Gerlach et al. |
| 2005/0143398 | A1 | 6/2005 | Das et al. |
| 2006/0042024 | A1 | 3/2006 | Glenn et al. |
| 2006/0079520 | A1 | 4/2006 | Singh et al. |
| 2006/0079536 | A1 | 4/2006 | Yasuma et al. |
| 2006/0142355 | A1 | 6/2006 | Singh et al. |
| 2008/0194803 | A1 | 8/2008 | Sinclair et al. |
| 2009/0304821 | A1 | 12/2009 | Notoya et al. |
| 2011/0173726 | A1 | 7/2011 | Gross et al. |
| 2011/0230472 | A1 | 9/2011 | Mitsuoka et al. |
| 2011/0230536 | A1 | 9/2011 | Pei et al. |
| 2011/0262397 | A1 | 10/2011 | Slomczynska et al. |

(Continued)

FOREIGN PATENT DOCUMENTS

CN  102977106 A  3/2013
DE  294943 A5  10/1991

(Continued)

OTHER PUBLICATIONS

Wood, (1983) 118 pp. Avail: Univ. Microfilms Int., Order No. DA8406078 From: Diss. Abstr. Int. B 1984, 45(3), 880 and original full dissertation.
Chen et al., Huagong Shengchan Yu Jishu (2010), 17(3), 37-45 CODEN: HSY JAC: ISSN:1006-6829.
Bondock et al., Journal of Heterocyclic Chemistry (2015), 52(2), 346-351 CODEN: JHTCAD; ISSN: 1943-5193.
Grosse et al., European Journal of Medicinal Chemistry (2014), 84, 718-730 CODEN: EJMCA5; ISSN: 0223-5234.
Selvatici et al., European Journal of Pharmacology (2013), 718(1-3), 428-434 CODEN: EJPHAZ; ISSN: 0014-2999.
Brullo et al., European Journal of Medicinal Chemistry (2012), 47, 573-579 CODEN: EJMCA5; ISSN: 0223-5234.

(Continued)

*Primary Examiner* — Shawquia Jackson
(74) *Attorney, Agent, or Firm* — Buchanan Ingersoll & Rooney PC

(57) ABSTRACT

We provide compounds given by Formula I, which is shown in FIG. 3, or pharmaceutically acceptable salts thereof, as well as formulations thereof and methods of use of those compounds and formulations for treatment of cancer.

20 Claims, 3 Drawing Sheets

(56) References Cited

U.S. PATENT DOCUMENTS

| | | |
|---|---|---|
| 2012/0122834 A1 | 5/2012 | Sodroski et al. |
| 2012/0178915 A1 | 7/2012 | Xu |
| 2012/0295845 A1 | 11/2012 | Mascitti et al. |
| 2014/0038989 A1 | 2/2014 | Alvarez-Ruiz et al. |
| 2014/0100211 A1 | 4/2014 | Fleck et al. |
| 2014/0179662 A1 | 6/2014 | Ruehter et al. |
| 2014/0294805 A1 | 10/2014 | Bair et al. |
| 2015/0050592 A1 | 2/2015 | Ueda et al. |

FOREIGN PATENT DOCUMENTS

| | | |
|---|---|---|
| EP | 520423 A2 | 12/1992 |
| FR | 3014687 A1 | 6/2015 |
| IN | 2011DE00091 A | 8/2013 |
| JP | 5341430 A | 12/1993 |
| JP | 2003222985 A | 8/2003 |
| JP | 2003327860 A | 11/2003 |
| JP | 2004091369 A | 3/2004 |
| JP | 2004207224 A | 7/2004 |
| JP | 2004-277337 A | 10/2004 |
| JP | 2004319202 A | 11/2004 |
| JP | 2004319309 A | 11/2004 |
| JP | 2004355960 A | 12/2004 |
| JP | 2005035932 A | 2/2005 |
| JP | 2005239611 A | 9/2005 |
| JP | 2006248195 A | 9/2006 |
| JP | 2009282350 A | 12/2009 |
| JP | 2009282351 A | 12/2009 |
| JP | 2010026048 A | 2/2010 |
| WO | 2003004497 A1 | 1/2003 |
| WO | 2004035563 A1 | 4/2004 |
| WO | 2004035564 A1 | 4/2004 |
| WO | 2006026433 A1 | 3/2006 |
| WO | WO 2007/121578 A1 | 11/2007 |
| WO | 2008019309 A1 | 2/2008 |
| WO | WO 2010/019796 A1 | 2/2010 |
| WO | 2011156632 A2 | 12/2011 |
| WO | 2013036994 A1 | 3/2013 |
| WO | 2014173289 A1 | 10/2014 |
| WO | 2014189947 A1 | 11/2014 |
| WO | 2015179615 A1 | 11/2015 |

OTHER PUBLICATIONS

Bruno et al., Bioorganic & Medicinal Chemistry Letters (2007), 17(13), 3696-3701 CODEN: BMCLE8; ISSN: 0960-894.

Seneci et al., Synthetic Communications (1999), 29(2), 311-341 CODEN: SYNCAV; ISSN: 0039-7911.

Vanotti et al., Journal of Heterocyclic Chemistry (1994), 31(4), 737-43 CODEN: JHTCAD; ISSN: 0022-152X.

Wood et al., Journal of ORganic Chemistry (1984), 49(19), 3534-40 CODEN: JOCEAH; ISSN: 0022-3263.

Drev et al., Tetrahedron (2014), 70(44), 8267-8279 CODEN: TETRAB; ISSN:0040-4020.

International Search Report (PCT/ISA/210) dated Jan. 18, 2017, by the European Patent Office as the International Searching Authority for International Application No. PCT/US2016/057135.

Written Opinion (PCT/ISA/237) dated Jan. 18, 2017, by the European Patent Office as the International Searching Authority for International Application No. PCT/US2016/057135.

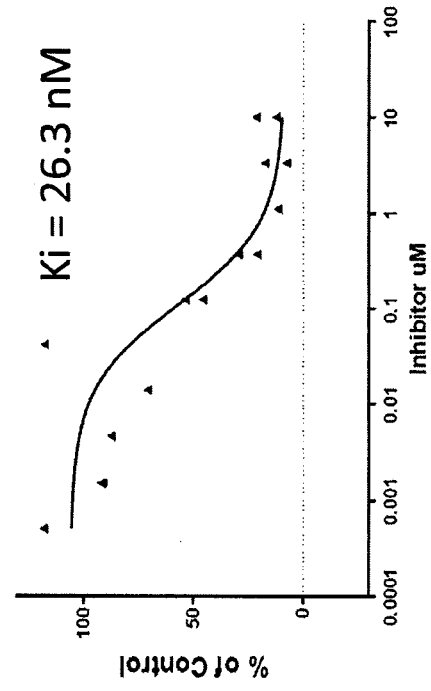
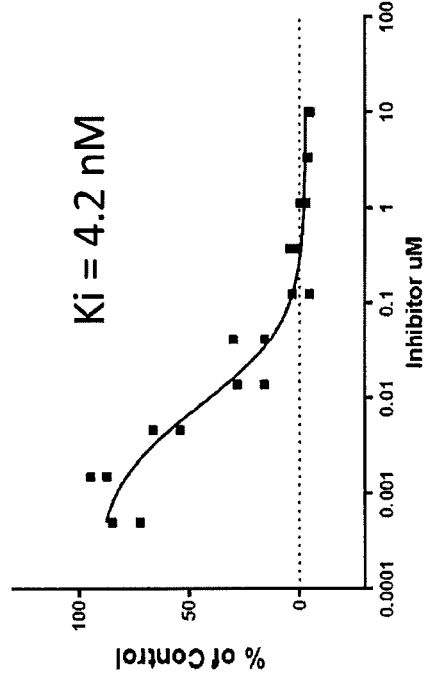
FIG. 1A and FIG. 1B: Inhibition of Compound 1 in the binding of radioligand to EP₄

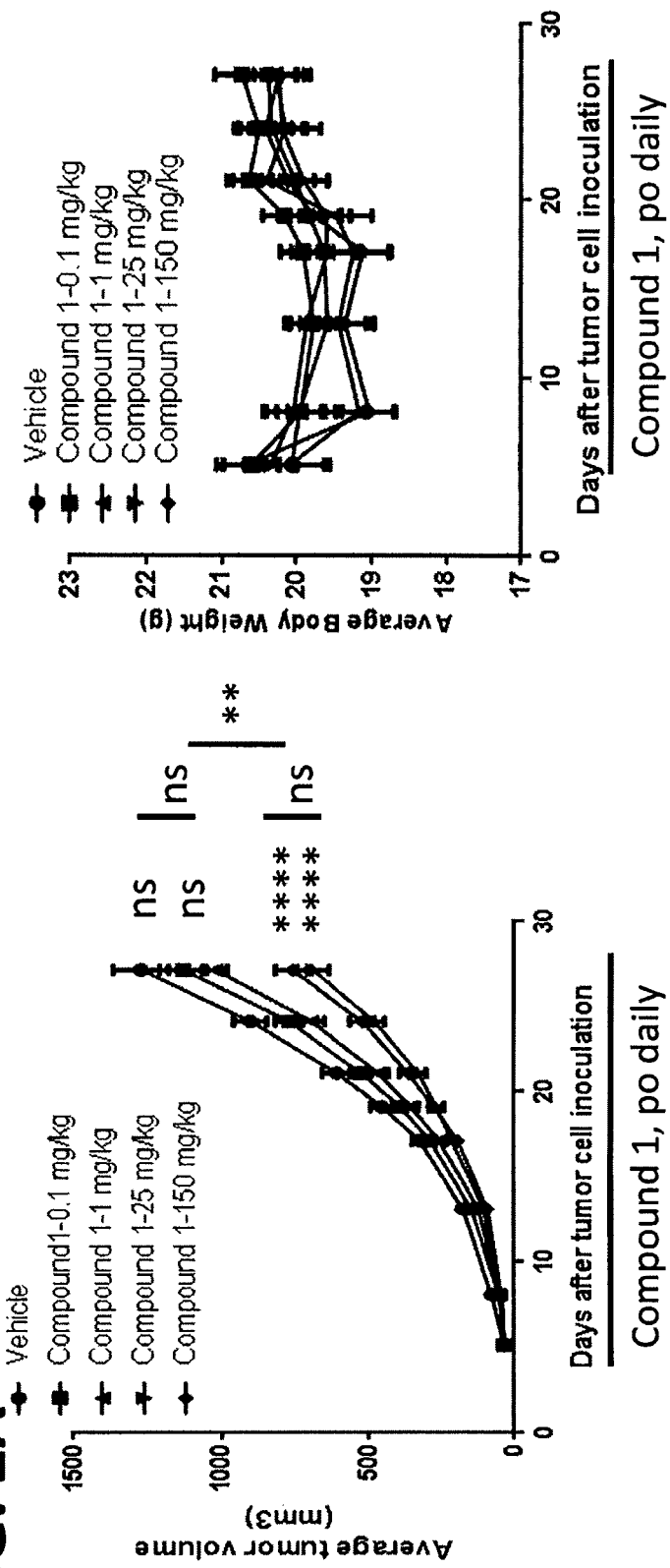
FIG. 2A and FIG. 2B Antitumor Effect of Compound 1 in Mouse 4T1 syngeneic tumors.

Formula (I)

EP4 ANTAGONISTS

CROSS-REFERENCE TO RELATED APPLICATIONS

This application claims priority to U.S. Provisional Patent Application No. 62/242,734, filed on Oct. 16, 2015, and to U.S. Provisional Patent Application No. 62/242,748, filed on Oct. 16, 2015. Those applications are incorporated by reference herein.

BACKGROUND

Prostaglandin E2 ($PGE_2$) is a major mediator of inflammation. Acutely, $PGE_2$ favors a pro-inflammatory immune response; but, sustained levels in tumor microenvironment promote the accumulation and enhance the activity of multiple immunosuppressor cells, including tumor associated macrophages (TAM), Treg cells, and myeloid-derived suppressor cells (MDSCs), and consequently promote tumor immune escape (Kaidi A, et al. Direct transcriptional up-regulation of cyclooxygenase-2 by hypoxia-inducible factor (HIF)-1 promotes colorectal tumor cell survival and enhances HIF-1 transcriptional activity during hypoxia. *Cancer Res*, 2006, 66:6683-6691; Nakanishi Y et al. COX-2 inhibition alters the phenotype of tumor-associated macrophages from M2 to M1 in APCmin/+ mouse polyps. *Carcinogenesis*, 2011, 32:1333-1339; Mahic M et al. FOXP3+CD4+CD25+ adaptive regulatory T cells express cyclooxygenase-2 and suppress effector T cells by a prostaglandin E2-dependent mechanism. *J Immunol*, 2011, 177: 246-254; Adams J L et al. Big opportunities for small molecules in immune-oncology. *Nat Rev Drug Disc*, 2015, dol:10.1038/nrd4596).

Signaling of $PGE_2$ is mediated by a set of four EP receptors ($EP_1$, $EP_2$, $EP_3$ and $EP_4$), which are coupled to different signal transduction pathways in different cell lineages. Accumulating evidence has demonstrated that elevated cAMP levels through $EP_4$ are the primary signal leading to immunosuppression in immune cells (Yokoyama U et al. The prostanoid EP4 receptor and its signaling pathway. *Pharmacol Rev*, 2013, 65:1010-1052). Knockout of $EP_4$ in mice showed delayed tumorigenesis compared to wild-type animals in the background of $APC^{min}$ mutation, indicating a tumor-promoting activity of $PGE_2$-$EP_4$ signaling in host immune cells (Mutoh M et al. Involvement of prostaglandin E receptor subtype EP(4) in colon carcinogenesis. *Cancer Res*, 2002, 62:28-32). Consistently, selective $EP_4$ receptor antagonists have been shown to slow tumor progression in various preclinical tumor models without affecting the cancer cell proliferation in vitro (Yang et al. Host and direct anti-tumor effects of profound reduction in tumor metastasis with selective EP4 receptor antagonism. *Cancer Res*, 2006, 66:9665-9672; Mao Y et al. Inhibition of tumor-derived prostaglandin e2-blocks the induction of myeloid-derived suppressor cells and recovers natural killer cell activity. *Clin Cancer Res*, 2014, 20:4096-4106).

These results suggest that suppression of PGE2/EP4 signaling may have therapeutic value in cancer and other chronically inflammatory diseases such as multiple sclerosis and rheumatoid arthritis. Hence, there is a need for novel compounds capable of suppressing PGE2/EP4 signalling.

BRIEF SUMMARY

Described herein are novel $EP_4$ antagonists. The $EP_4$ antagonists described herein may be applicable for further development to treat $EP_4$ signaling-related diseases including cancer or chronically inflammatory diseases such as multiple sclerosis and rheumatoid arthritis.

By way of example and without being limiting, the compounds described herein may be used for cancer immune therapy targeting host immunosuppressive cells in the tumor microenvironment that can be of either myeloid or lymphoid lineage. In an embodiment, the compounds described herein may be used to treat patients with a variety of tumor types, including those that harbor high levels of myeloid infiltrate. Such levels of myeloid infiltrate may be identified, for example, based on the Cancer Genome Atlas (TCGA) and other sources. Such tumor types may also be identified based on protein or genetic (e.g., mRNA) expression analysis.

Tumor types may include but are not limited to pancreatic adenocarcinoma, renal clear cell carcinoma, squamous cell carcinoma of head and neck (SCCHN), non-small cell lung cancer (NSCLC), colorectal cancer (CRC), hepatocellular carcinoma (HCC), serous epithelial ovarian cancer, cervical cancer, transitional cell bladder cancer, and triple-negative breast cancer (TNBC). One embodiment includes a compound given by formula (I):

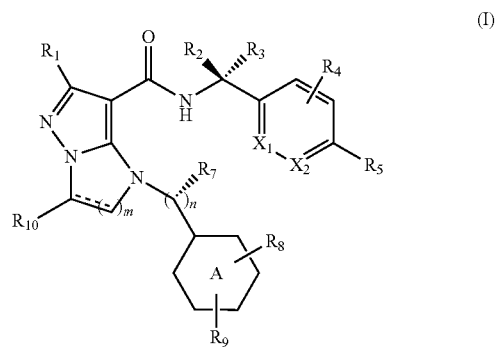

or a pharmaceutically acceptable salt thereof,
wherein
$R_1$ is —$CH_3$, —$CF_3$, —$CH_2CH_3$, —$CH_2F$, $CF_2CH_2OH$, —$CHF_2$, —CH=$CH_2$, —$CH_2OH$, or phenyl;
$R_2$ is —H, —$CH_2OH$, or —$CH_3$;
$R_3$ is —H;
or $R_2$ and $R_3$ taken together form a cyclopropyl with the carbon to which they are attached;
$R_4$ is —H, —F, or —$CH_3$;
$R_5$ is —C(O)OH, —C(O)O$CH_3$, —$CH_2$C(O)OH, cyclopropyl, —C(O)NHCN,

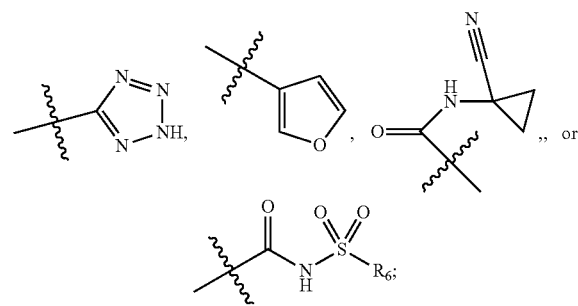

wherein $R_6$ is phenyl, —$CH_3$, cyclopropyl,

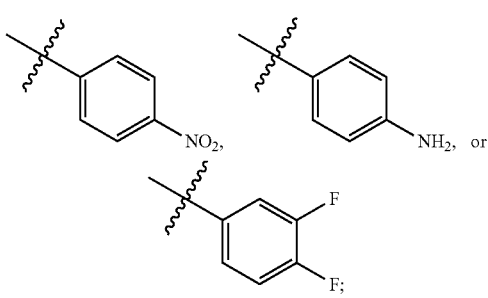

n is 0-1;
m is 1-2;
R$_7$ is —H, —CH$_3$, or absent when n is 0;
R$_8$ is —CF$_3$, —H, —Cl, —F, —CH$_2$CH$_3$, —OCH$_3$, —CH$_3$, —SCH$_3$, —CH$_2$OH, —CH$_2$F, —CH$_2$Cl, —I, —Br, —NH$_2$, —CH$_2$OCH$_2$CH$_2$F, —OCH$_2$F, —CH$_2$CH$_2$CH$_2$F, —OH, —OCF$_3$, —N(CH$_3$)$_2$, —CF$_2$CH$_2$OH,

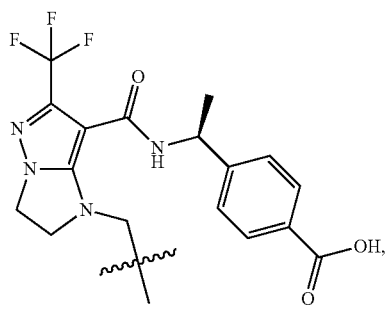 [SMILES: *CN1CCn2nc(C(F)(F)F)c(C(=O)N[C@@H](C)c3ccc(C(=O)O)cc3)c21]

or the bond connecting R$_8$ and ring A is a double bond and R$_8$ is CH$_2$;
R$_9$ is —H, —Cl, or —CF$_3$;
R$_{10}$ is —H, —CH$_3$, —CH$_2$F, —CH$_2$OH, or —CH$_2$OCH$_2$-phenyl;
X$_1$ and X$_2$ are either both C, or one is C and the other is N;
----- represents a single bond or a double bond; and
ring A is phenyl or cyclohexyl.

One embodiment includes a compound given by formula (II):

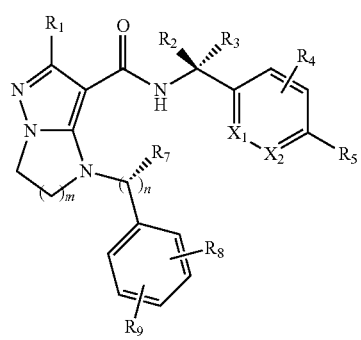

(II)

or pharmaceutically acceptable salts thereof,
wherein R$_1$ is —CH$_3$, —CF$_3$, —CH$_2$CH$_3$, or phenyl;
R$_2$ is —H, or —CH$_3$;
R$_3$ is —H;
or R$_2$ and R$_3$ taken together form a cyclopropyl with the carbon to which they are attached;

R$_4$ is —H, —F, or —CH$_3$;
R$_5$ is —C(O)OH, —C(O)OCH$_3$, —CH$_2$C(O)OH, cyclopropyl, —C(O)NHCN,

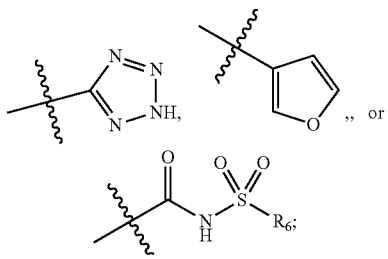

wherein R$_6$ is phenyl, —CH$_3$, cyclopropyl, or

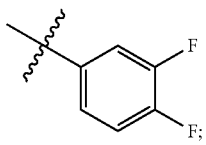

m is 1-2;
n is 0-1;
R$_7$ is —H, —CH$_3$, or absent when n is 0;
R$_8$ is —CF$_3$, —H, —Cl, —F, —CH$_2$CH$_3$, —OCH$_3$, —CH$_3$, or —OCF$_3$;
R$_9$ is —H, —Cl, or —CF$_3$; and
X$_1$ and X$_2$ are either both C, or one is C and the other is N.

In some embodiments, R$_1$ is —CF$_3$. In some embodiments, m is 1. In further embodiments, R$_2$ is methyl and R$_3$ is —H. In still further embodiments X$_1$ and X$_2$ are both C. In some embodiments, R$_4$ is —H. In some embodiments, n is 1. In some embodiments, R$_7$ is —H. In some embodiments, R$_9$ is —H. In further embodiments, R$_8$ is —CF$_3$. In some embodiments, R$_5$ is —C(O)OH. In still further embodiments, R$_4$ is —F. In further embodiments, R$_8$ is —Cl. In some embodiments, ----- represents a single bond. In further embodiments, R$_{10}$ is —H. In still further embodiments, ring A is phenyl. In further embodiments, X$_1$ and X$_2$ are both carbon.

In some embodiments, R$_5$ is —C(O)OH, —C(O)OCH$_3$, —CH$_2$C(O)OH, —C(O)NHCN,

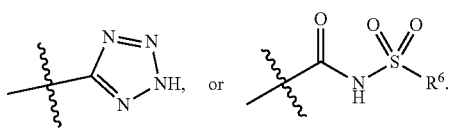

In some embodiments, m is 2, and wherein R$_8$ and R$_9$, if present, are in a meta position or a para position. In one embodiment the compound is (S)-4-(1-(1-(3-chloro-5-(trifluoromethyl)benzyl)-6-(trifluoromethyl)-2,3-dihydro-1H-imidazo[1,2-b]pyrazole-7-carboxamido)ethyl)benzoic acid. In another embodiment the compound is (S)-4-(1-(6-(trifluoromethyl)-1-(3-(trifluoromethyl)benzyl)-2,3-dihydro-1H-imidazo[1,2-b]pyrazole-7-carboxamido)ethyl)benzoic acid.

Embodiments may provide a pharmaceutical composition comprising a compound as reported above and a pharmaceutically acceptable excipient. Embodiments may provide a method of treating cancer comprising administering to a patient a pharmaceutical composition reported herein. In some embodiments, the cancer is pancreatic cancer, renal cell carcinoma, squamous cell carcinoma of head and neck, non-small cell lung cancer, colorectal cancer, hepatocellular carcinoma, ovarian cancer, cervical cancer, bladder cancer, or breast cancer. In some embodiments, the breast cancer is triple-negative breast cancer.

Embodiments may provide use of a compound reported herein for the manufacture of a medicament for treating cancer. In some embodiments the cancer is pancreatic cancer, renal cell carcinoma, squamous cell carcinoma of head and neck, non-small cell lung cancer, colorectal cancer, hepatocellular carcinoma, ovarian cancer, cervical cancer, bladder cancer, or breast cancer.

Certain embodiments may provide a compound selected from the following group:

(S)-4-(1-(6-(trifluoromethyl)-1-(3-(trifluoromethyl)benzyl)-2,3-dihydro-1H-imidazo[12-b]pyrazole-7-carboxamido) ethyl)benzoic acid;

(S)-4-(1-(6-(trifluoromethyl)-1-(4-(trifluoromethyl)benzyl)-2,3-dihydro-1H-imidazo[1,2-b]pyrazole-7-carboxamido) ethyl)benzoic acid;

Methyl (S)-4-(1-(6-(trifluoromethyl)-1-(4-(trifluoromethyl) benzyl)-2,3-dihydro-1H-imidazo[1,2-b]pyrazole-7-carboxamido)ethyl)benzoate;

(S)-4-(1-(6-(trifluoromethyl)-1-(2-(trifluoromethyl)benzyl)-2,3-dihydro-1H-imidazo[1,2-b]pyrazole-7-carboxamido) ethyl)benzoic acid;

(S)-4-(1-(1-(3,5-bis(trifluoromethyl)benzyl)-6-(trifluoromethyl)-2,3-dihydro-1H-imidazo[12-b]pyrazole-7-carboxamido)ethyl)benzoic acid;

(S)-4-(1-(1-(3-chloro-5-(trifluoromethyl)benzyl)-6-(trifluoromethyl)-2,3-dihydro-1H-imidazo[1,2-b]pyrazole-7-carboxamido)ethyl)benzoic acid;

(S)-4-(1-(1-(3,5-dichlorobenzyl)-6-(trifluoromethyl)-2,3-dihydro-1H-imidazo[1,2-b]pyrazole-7-carboxamido)ethyl) benzoic acid;

(S)-4-(1-(1-(4-methoxybenzyl)-6-(trifluoromethyl)-2,3-dihydro-1H-imidazo[1,2-b]pyrazole-7-carboxamido)ethyl) benzoic acid;

(S)-4-(1-(1-(3-methoxybenzyl)-6-(trifluoromethyl)-2,3-dihydro-1H-imidazo[1,2-b]pyrazole-7-carboxamido)ethyl) benzoic acid;

(S)-4-(1-(1-(4-(trifluoromethoxy)benzyl)-6-(trifluoromethyl)-2,3-dihydro-1H-imidazo[1,2-b]pyrazole-7-carboxamido)ethyl)benzoic acid;

(S)-4-(1-(1-(3-(trifluoromethoxy)benzyl)-6-(trifluoromethyl)-2,3-dihydro-H-imidazo[1,2-b]pyrazole-7-carboxamido)ethyl)benzoic acid;

(S)-4-(1-(1-(3-chlorobenzyl)-6-(trifluoromethyl)-2,3-dihydro-1H-imidazo[1,2-b]pyrazole-7-carboxamido)ethyl) benzoic acid;

(S)-4-(1-(1-(3,4-dichlorobenzyl)-6-(trifluoromethyl)-2,3-dihydro-1H-imidazo[1,2-b]pyrazole-7-carboxamido)ethyl) benzoic acid;

(S)-4-(1-(1-(4-fluorobenzyl)-6-(trifluoromethyl)-2,3-dihydro-1H-imidazo[1,2-b]pyrazole-7-carboxamido)ethyl) benzoic acid;

(S)-4-(1-(1-(3-fluorobenzyl)-6-(trifluoromethyl)-2,3-dihydro-1H-imidazo[1,2-b]pyrazole-7-carboxamido)ethyl) benzoic acid;

(S)-4-(1-(1-(2-fluorobenzyl)-6-(trifluoromethyl)-2,3-dihydro-1H-imidazo[1,2-b]pyrazole-7-carboxamido)ethyl) benzoic acid;

(S)-4-(1-(1-(4-methylbenzyl)-6-(trifluoromethyl)-2,3-dihydro-H-imidazo[1,2-b]pyrazole-7-carboxamido)ethyl) benzoic acid;

(S)-4-(1-(1-(3-methylbenzyl)-6-(trifluoromethyl)-2,3-dihydro-1H-imidazo[1,2-b]pyrazole-7-carboxamido)ethyl) benzoic acid;

(S)-4-(1-(1-(2-methylbenzyl)-6-(trifluoromethyl)-2,3-dihydro-1H-imidazo[1,2-b]pyrazole-7-carboxamido)ethyl) benzoic acid;

(S)-4-(1-(1-(4-ethylbenzyl)-6-(trifluoromethyl)-2,3-dihydro-1H-imidazo[1,2-b]pyrazole-7-carboxamido)ethyl) benzoic acid;

(S)-2-fluoro-4-(1-(6-(trifluoromethyl)-1-(4-(trifluoromethyl)benzyl)-2,3-dihydro-1H-imidazo[1,2-b]pyrazole-7-carboxamido)ethyl)benzoic acid;

(S)-3-fluoro-4-(1-(6-(trifluoromethyl)-1-(4-(trifluoromethyl)benzyl)-2,3-dihydro-1H-imidazo[1,2-b]pyrazole-7-carboxamido)ethyl)benzoic acid;

(S)-3-fluoro-4-(1-(6-(trifluoromethyl)-1-(3-(trifluoromethyl)benzyl)-2,3-dihydro-1H-imidazo[1,2-b]pyrazole-7-carboxamido)ethyl)benzoic acid;

(S)-2-fluoro-4-(1-(6-(trifluoromethyl)-1-(3-(trifluoromethyl)benzyl)-2,3-dihydro-1H-imidazo[1,2-b]pyrazole-7-carboxamido)ethyl)benzoic acid;

Methyl (S)-2-fluoro-4-(1-(6-(trifluoromethyl)-1-(3-(trifluoromethyl)benzyl)-2,3-dihydro-1H-imidazo[1,2-b]pyrazole-7-carboxamido)ethyl)benzoate;

(S)-2-(4-(1-(6-(trifluoromethyl)-1-(3-(trifluoromethyl)benzyl)-2,3-dihydro-1H-imidazo[1,2-b]pyrazole-7-carboxamido)ethyl)phenyl)acetic acid;

(S)-2-(4-(1-(6-(trifluoromethyl)-1-(4-(trifluoromethyl)benzyl)-2,3-dihydro-1H-imidazo[1,2-b]pyrazole-7-carboxamido)ethyl)phenyl)acetic acid;

4-(1-(6-methyl-1-(4-(trifluoromethyl)benzyl)-2,3-dihydro-1H-imidazo[1,2-b]pyrazole-7-carboxamido)cyclopropyl) benzoic acid;

4-(1-(6-(trifluoromethyl)-1-(4-(trifluoromethyl)benzyl)-2,3-dihydro-1H-imidazo[12-b]pyrazole-7-carboxamido)cyclopropyl)benzoic acid;

4-(1-(1-(4-chlorobenzyl)-6-(trifluoromethyl)-2,3-dihydro-1H-imidazo[1,2-b]pyrazole-7-carboxamido)cyclopropyl) benzoic acid;

(S)-4-(1-(1-(4-chlorobenzyl)-6-(trifluoromethyl)-2,3-dihydro-1H-imidazo[1,2-b]pyrazole-7-carboxamido)ethyl) benzoic acid;

(S)-4-(1-(1-(4-chlorobenzyl)-6-methyl-2,3-dihydro-1H-imidazo[1,2-b]pyrazole-7-carboxamido)ethyl)benzoic acid;

4-((1-(4-chlorobenzyl)-6-methyl-2,3-dihydro-1H-imidazo [1,2-b]pyrazole-7-carboxamido)methyl)benzoic acid;

(R)-4-(1-(6-methyl-1-(1-(4-(trifluoromethyl)phenyl)ethyl)-2,3-dihydro-1H-imidazo[1,2-b]pyrazole-7-carboxamido) cyclopropyl)benzoic acid;

4-((S)-1-(6-methyl-1-((R)-1-(4-(trifluoromethyl)phenyl) ethyl)-2,3-dihydro-1H-imidazo[1,2-b]pyrazole-7-carboxamido)ethyl)benzoic acid;

(S)—N-(1-(4-(2H-tetrazol-5-yl)phenyl)ethyl)-6-(trifluoromethyl)-1-(3-(trifluoromethyl)benzyl)-2,3-dihydro-1H-imidazo[1,2-b]pyrazole-7-carboxamide;

(S)—N-(1-(4-(2H-tetrazol-5-yl)phenyl)ethyl)-6-(trifluoromethyl)-1-(4-(trifluoromethyl)benzyl)-2,3-dihydro-1H-imidazo[1,2-b]pyrazole-7-carboxamide;

(S)-5-(1-(6-(trifluoromethyl)-1-(3-(trifluoromethyl)benzyl)-2,3-dihydro-1H-imidazo[1,2-b]pyrazole-7-carboxamido) ethyl)picolinic acid;

(S)-6-(1-(6-(trifluoromethyl)-1-(3-(trifluoromethyl)benzyl)-2,3-dihydro-1H-imidazo[12-b]pyrazole-7-carboxamido) ethyl)nicotinic acid;

(S)-4-(1-(4-(4-chlorobenzyl)-2-(trifluoromethyl)-4,5,6,7-tetrahydropyrazolo[1,5-a]pyrimidine-3-carboxamido)ethyl)benzoic acid;

(S)-4-(1-(4-(3-chlorobenzyl)-2-(trifluoromethyl)-4,5,6,7-tetrahydropyrazolo[1,5-a]pyrimidine-3-carboxamido)ethyl)benzoic acid;

(S)-4-(1-(4-(2-chlorobenzyl)-2-(trifluoromethyl)-4,5,6,7-tetrahydropyrazolo[1,5-a]pyrimidine-3-carboxamido)ethyl)benzoic acid;

(S)-4-(1-(2-(trifluoromethyl)-4-(3-(trifluoromethyl)benzyl)-4,5,6,7-tetrahydropyrazolo[1,5-a]pyrimidine-3-carboxamido)ethyl)benzoic acid;

(S)-4-(1-(2-(trifluoromethyl)-4-(4-(trifluoromethyl)benzyl)-4,5,6,7-tetrahydropyrazolo[1,5-a]pyrimidine-3-carboxamido)ethyl)benzoic acid;

(S)-4-(1-(2-(trifluoromethyl)-4-(2-(trifluoromethyl)benzyl)-4,5,6,7-tetrahydropyrazolo[1,5-a]pyrimidine-3-carboxamido)ethyl)benzoic acid;

(S)-4-(1-(6-(trifluoromethyl)-1-(4-(trifluoromethyl)phenyl)-2,3-dihydro-1H-imidazo[12-b]pyrazole-7-carboxamido)ethyl)benzoic acid;

(S)-4-(1-(6-(trifluoromethyl)-1-(3-(trifluoromethyl)phenyl)-2,3-dihydro-H-imidazo[1,2-b]pyrazole-7-carboxamido)ethyl)benzoic acid;

(S)-4-(1-(1-(3-chlorophenyl)-6-(trifluoromethyl)-2,3-dihydro-H-imidazo[1,2-b]pyrazole-7-carboxamido)ethyl)benzoic acid;

(S)-4-(1-(1-(4-chlorophenyl)-6-(trifluoromethyl)-2,3-dihydro-1H-imidazo[1,2-b]pyrazole-7-carboxamido)ethyl)benzoic acid;

(S)-4-(1-(2-(trifluoromethyl)-4-(4-(trifluoromethyl)phenyl)-4,5,6,7-tetrahydropyrazol[1,5-a]pyrimidine-3-carboxamido)ethyl)benzoic acid;

(S)—N-(1-(4-(cyanocarbamoyl)phenyl)ethyl)-6-(trifluoromethyl)-1-(3-(trifluoromethyl)benzyl)-2,3-dihydro-1H-imidazo[1,2-b]pyrazole-7-carboxamide;

(S)—N-(1-(4-(((3,4-difluorophenyl)sulfonyl)carbamoyl)phenyl)ethyl)-6-(trifluoromethyl)-1-(3-(trifluoromethyl)benzyl)-2,3-dihydro-1H-imidazo[1,2-b]pyrazole-7-carboxamide;

(S)—N-(1-(4-((phenylsulfonyl)carbamoyl)phenyl)ethyl)-1-(3-(trifluoromethoxy)benzyl)-6-(trifluoromethyl)-2,3-dihydro-1H-imidazo[1,2-b]pyrazole-7-carboxamide;

(S)—N-(1-(4-((methylsulfonyl)carbamoyl)phenyl)ethyl)-6-(trifluoromethyl)-1-(3-(trifluoromethyl)benzyl)-2,3-dihydro-1H-imidazo[1,2-b]pyrazole-7-carboxamide;

(S)—N-(1-(4-((cyclopropylsulfonyl)carbamoyl)phenyl)ethyl)-6-(trifluoromethyl)-1-(3-(trifluoromethyl)benzyl)-2,3-dihydro-1H-imidazo[1,2-b]pyrazole-7-carboxamide;

(S)—N-(1-(4-(furan-3-yl)phenyl)ethyl)-6-(trifluoromethyl)-1-(4-(trifluoromethyl)benzyl)-2,3-dihydro-1H-imidazo[1,2-b]pyrazole-7-carboxamide;

(S)—N-(1-(4-cyclopropylphenyl)ethyl)-6-(trifluoromethyl)-1-(4-(trifluoromethyl)benzyl)-2,3-dihydro-1H-imidazo[1,2-b]pyrazole-7-carboxamide;

(S)—N-(1-(3-methyl-4-(2H-tetrazol-5-yl)phenyl)ethyl)-6-(trifluoromethyl)-1-(4-(trifluoromethyl)benzyl)-2,3-dihydro-1H-imidazo[1,2-b]pyrazole-7-carboxamide;

(S)-4-(1-(6-ethyl-1-(3-(trifluoromethyl)benzyl)-2,3-dihydro-1H-imidazo[1,2-b]pyrazole-7-carboxamido)ethyl)benzoic acid;

(S)-4-(1-(1-(2-chlorobenzyl)-6-(trifluoromethyl)-2,3-dihydro-1H-imidazo[1,2-b]pyrazole-7-carboxamido)ethyl)benzoic acid;

(S)-4-(1-(6-phenyl-1-(3-(trifluoromethyl)benzyl)-2,3-dihydro-1H-imidazo[1,2-b]pyrazole-7-carboxamido)ethyl)benzoic acid;

(S)-4-(1-(1-(3-(methylthio)-5-(trifluoromethyl)benzyl)-6-(trifluoromethyl)-2,3-dihydro-1H-imidazo[1,2-b]pyrazole-7-carboxamido)ethyl)benzoic acid;

(S)-4-(1-(1-(3-(hydroxymethyl)benzyl)-6-(trifluoromethyl)-2,3-dihydro-1H-imidazo[1,2-b]pyrazole-7-carboxamido)ethyl)benzoic acid;

(S)-4-(1-(1-(3-(fluoromethyl)benzyl)-6-(trifluoromethyl)-2,3-dihydro-1H-imidazo[1,2-b]pyrazole-7-carboxamido)ethyl)benzoic acid;

(S)-4-(1-(1-(3-(chloromethyl)benzyl)-6-(trifluoromethyl)-2,3-dihydro-1H-imidazo[1,2-b]pyrazole-7-carboxamido)ethyl)benzoic acid;

4,4'-((1S,1'S)-((1,1'-(1,3-phenylenebis(methylene))bis(6-(trifluoromethyl)-2,3-dihydro-1H-imidazo[1,2-b]pyrazole-1,7-diyl-7-carbonyl))bis(azanediyl))bis(ethane-1,1-diyl))dibenzoic acid;

(S)-4-(1-(1-(4-iodo-3-(trifluoromethyl)benzyl)-6-(trifluoromethyl)-2,3-dihydro-1H-imidazo[1,2-b]pyrazole-7-carboxamido)ethyl)benzoic acid;

(S)-4-(1-(1-(3-iodobenzyl)-6-(trifluoromethyl)-2,3-dihydro-1H-imidazo[1,2-b]pyrazole-7-carboxamido)ethyl)benzoic acid;

(S)-4-(1-(1-benzyl-6-(trifluoromethyl)-2,3-dihydro-1H-imidazo[1,2-b]pyrazole-7-carboxamido)ethyl)benzoic acid;

(S)—N-(1-(4-(((4-nitrophenyl)sulfonyl)carbamoyl)phenyl)ethyl)-6-(trifluoromethyl)-1-(3-(trifluoromethyl)benzyl)-2,3-dihydro-1H-imidazo[1,2-b]pyrazole-7-carboxamide;

(S)-4-(1-(1-(4-aminobenzyl)-6-(trifluoromethyl)-2,3-dihydro-1H-imidazo[1,2-b]pyrazole-7-carboxamido)ethyl)benzoic acid;

(S)—N-(1-(4-(((4-aminophenyl)sulfonyl)carbamoyl)phenyl)ethyl)-6-(trifluoromethyl)-1-(3-(trifluoromethyl)benzyl)-2,3-dihydro-1H-imidazo[1,2-b]pyrazole-7-carboxamide;

(S)-4-(1-(1-(3-((2-fluoroethoxy)methyl)benzyl)-6-(trifluoromethyl)-2,3-dihydro-1H-imidazo[1,2-b]pyrazole-7-carboxamido)ethyl)benzoic acid;

(S)-4-(1-(1-(3-(2-fluoroethoxy)benzyl)-6-(trifluoromethyl)-2,3-dihydro-1H-imidazo[1,2-b]pyrazole-7-carboxamido)ethyl)benzoic acid;

7-(((S)-1-(4-carboxyphenyl)ethyl)carbamoyl)-1-(3-iodobenzyl)-6-(trifluoromethyl)-2,3-dihydro-1H-imidazo[1,2-b]pyrazole 1-oxide;

(S)-4-(1-(1-(3-hydroxy-5-(trifluoromethyl)benzyl)-6-(trifluoromethyl)-2,3-dihydro-1H-imidazo[1,2-b]pyrazole-7-carboxamido)ethyl)benzoic acid;

(S)-4-(1-(1-(3-fluoro-5-(trifluoromethyl)benzyl)-6-(trifluoromethyl)-2,3-dihydro-1H-imidazo[1,2-b]pyrazole-7-carboxamido)ethyl)benzoic acid;

(S)-4-(1-(1-((4-(fluoromethyl)cyclohexyl)methyl)-6-(trifluoromethyl)-2,3-dihydro-1H-imidazo[1,2-b]pyrazole-7-carboxamido)ethyl)benzoic acid;

(S)-4-(1-(1-((4-methylenecyclohexyl)methyl)-6-(trifluoromethyl)-2,3-dihydro-1H-imidazo[1,2-b]pyrazole-7-carboxamido)ethyl)benzoic acid;

(S)-4-(1-(1-(3-(3-fluoropropyl)benzyl)-6-(trifluoromethyl)-2,3-dihydro-1H-imidazo[1,2-b]pyrazole-7-carboxamido)ethyl)benzoic acid;

(S)-4-(1-(1-(4-(3-fluoropropyl)benzyl)-6-(trifluoromethyl)-2,3-dihydro-1H-imidazo[1,2-b]pyrazole-7-carboxamido)ethyl)benzoic acid;

(S)-4-(1-(1-(3-(3-fluoropropyl)-5-(trifluoromethyl)benzyl)-6-(trifluoromethyl)-2,3-dihydro-1H-imidazo[1,2-b]pyrazole-7-carboxamido)ethyl)benzoic acid;

(S)-4-(1-(1-(4-(3-fluoropropyl)-3-(trifluoromethyl)benzyl)-6-(trifluoromethyl)-2,3-dihydro-1H-imidazo[1,2-b]pyrazole-7-carboxamido)ethyl)benzoic acid;

(S)-4-(1-(6-(fluoromethyl)-1-(3-(trifluoromethyl)benzyl)-2,3-dihydro-1H-imidazo[1,2-b]pyrazole-7-carboxamido)ethyl)benzoic acid;
(S)-4-(1-(1-(4-chloro-3-(trifluoromethyl)benzyl)-6-(trifluoromethyl)-2,3-dihydro-1H-imidazo[1,2-b]pyrazole-7-carboxamido)ethyl)benzoic acid;
(S)-4-(1-(3-methyl-6-(trifluoromethyl)-1-(3-(trifluoromethyl)benzyl)-1H-imidazo[1,2-b]pyrazole-7-carboxamido)ethyl)benzoic acid;
4-((S)-1-((S)-3-(fluoromethyl)-6-(trifluoromethyl)-1-(3-(trifluoromethyl)benzyl)-2,3-dihydro-1H-imidazo[1,2-b]pyrazole-7-carboxamido)ethyl)benzoic acid;
(S)-4-(1-(1-(4-hydroxybenzyl)-6-(trifluoromethyl)-2,3-dihydro-1H-imidazo[1,2-b]pyrazole-7-carboxamido)ethyl)benzoic acid;
(R)-4-(2-hydroxy-1-(6-(trifluoromethyl)-1-(3-(trifluoromethyl)benzyl)-2,3-dihydro-1H-imidazo[1,2-b]pyrazole-7-carboxamido)ethyl)benzoic acid;
(S)-4-(1-(1-(4-(dimethylamino)benzyl)-6-(trifluoromethyl)-2,3-dihydro-1H-imidazo[1,2-b]pyrazole-7-carboxamido)ethyl)benzoic acid;
(S)-4-(1-(1-(3-(dimethylamino)benzyl)-6-(trifluoromethyl)-2,3-dihydro-1H-imidazo[1,2-b]pyrazole-7-carboxamido)ethyl)benzoic acid;
(S)-4-(1-(1-(3-(dimethylamino)-5-(trifluoromethyl)benzyl)-6-(trifluoromethyl)-2,3-dihydro-1H-imidazo[1,2-b]pyrazole-7-carboxamido)ethyl)benzoic acid;
(S)-4-(1-(6-(1,1-difluoro-2-hydroxyethyl)-1-(3-(trifluoromethyl)benzyl)-2,3-dihydro-1H-imidazo[1,2-b]pyrazole-7-carboxamido)ethyl)benzoic acid;
(S)—N-(1-(4-((1-cyanocyclopropyl)carbamoyl)phenyl)ethyl)-6-(trifluoromethyl)-1-(3-(trifluoromethyl)benzyl)-2,3-dihydro-1H-imidazo[1,2-b]pyrazole-7-carboxamide;
4-((S)-1-((S)-3-(hydroxymethyl)-6-(trifluoromethyl)-1-(3-(trifluoromethyl)benzyl)-2,3-dihydro-1H-imidazo[1,2-b]pyrazole-7-carboxamido)ethyl)benzoic acid;
4-((S)-1-((S)-3-((benzyloxy)methyl)-6-(trifluoromethyl)-1-(3-(trifluoromethyl)benzyl)-2,3-dihydro-1H-imidazo[1,2-b]pyrazole-7-carboxamido)ethyl)benzoic acid;
(S)-4-(1-(1-(3-bromo-5-(trifluoromethyl)benzyl)-6-(trifluoromethyl)-2,3-dihydro-1H-imidazo[1,2-b]pyrazole-7-carboxamido)ethyl)benzoic acid;
(S)-4-(1-(6-(difluoromethyl)-1-(3-(trifluoromethyl)benzyl)-2,3-dihydro-1H-imidazo[1,2-b]pyrazole-7-carboxamido)ethyl)benzoic acid;
(S)-4-(1-(1-(3-(trifluoromethyl)benzyl)-6-vinyl-2,3-dihydro-1H-imidazo[1,2-b]pyrazole-7-carboxamido)ethyl)benzoic acid;
(S)-4-(1-(6-(hydroxymethyl)-1-(3-(trifluoromethyl)benzyl)-2,3-dihydro-1H-imidazo[1,2-b]pyrazole-7-carboxamido)ethyl)benzoic acid;
(S)-4-(1-(1-(3-(1,1-difluoro-2-hydroxyethyl)benzyl)-6-(trifluoromethyl)-2,3-dihydro-1H-imidazo[1,2-b]pyrazole-7-carboxamido)ethyl)benzoic acid; and
methyl (S)-4-(1-(1-(2-fluorobenzoyl)-6-(trifluoromethyl)-2,3-dihydro-1H-imidazo[1,2-b]pyrazole-7-carboxamido)ethyl)benzoate.

BRIEF DESCRIPTION OF THE DRAWINGS

FIG. 1A and FIG. 1B show inhibition of Compound 1 in the binding of radioligand to $EP_4$. Dose-dependent inhibition in the binding of $^3$H-labelled $PGE_2$ to human (FIG. 1A) and mouse (FIG. 1B) $EP_4$-expressing cell membrane fraction. Ki values are indicated.

FIG. 2A and FIG. 2B respectively show antitumor effect of Compound 1 in mouse 4T1 syngeneic tumors, and effect on animal body weight. FIG. 2A shows tumor growth curves. Data represent the mean±SEM. Statistically significant inhibition of tumor growth was observed following treatment with 25 and 150 mg/kg of Compound 1 on day 27 after tumor cell injection. FIG. 2B shows animal body weight curves. NS, not significant; , p<0.01; **, p<0.0001, one-way ANOVA.

DETAILED DESCRIPTION

Figure 3:
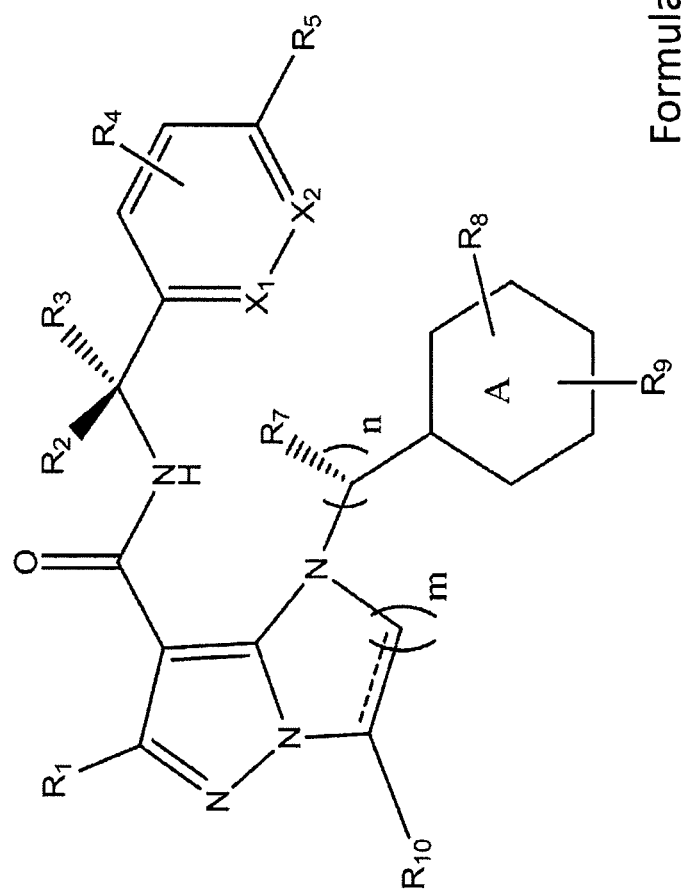
FIG. 3 shows formula (I).

Described herein are novel EP4 antagonists. These compounds may be used in treating cancer.

An embodiment includes a compound given by formula (I):

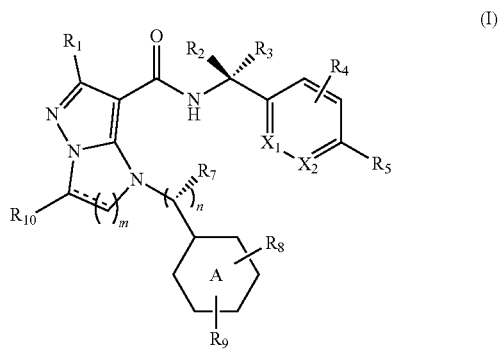

or a pharmaceutically acceptable salt thereof,
wherein
$R_1$ is —$CH_3$, —$CF_3$, —$CH_2CH_3$, —$CH_2F$, $CF_2CH_2OH$, —$CHF_2$, —CH=$CH_2$, —$CH_2OH$, or phenyl;
$R_2$ is —H, —$CH_2OH$, or —$CH_3$;
$R_3$ is —H;
or $R_2$ and $R_3$ taken together form a cyclopropyl with the carbon to which they are attached;
$R_4$ is —H, —F, or —$CH_3$;
$R_5$ is —C(O)OH, —C(O)$OCH_3$, —$CH_2$C(O)OH, cyclopropyl, —C(O)NHCN,

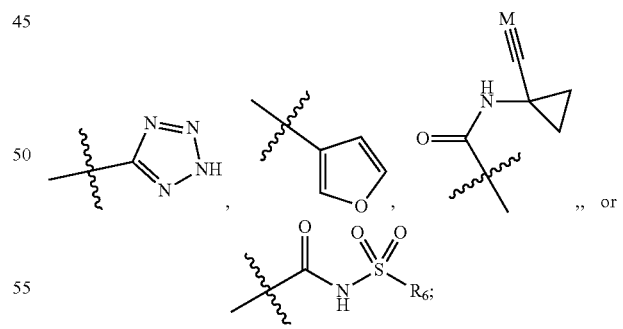

wherein $R_6$ is phenyl, —$CH_3$, cyclopropyl,

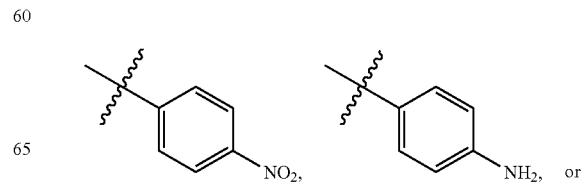

-continued

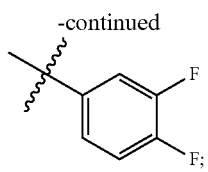

n is 0-1;

m is 1-2;

R$_7$ is —H, —CH$_3$, or absent when n is 0;

R$_8$ is —CF$_3$, —H, —Cl, —F, —CH$_2$CH$_3$, —OCH$_3$, —CH$_3$, —SCH$_3$, —CH$_2$OH, —CH$_2$F, —CH$_2$Cl, —I, —Br, —NH$_2$, —CH$_2$OCH$_2$CH$_2$F, —OCH$_2$CH$_2$F, —CH$_2$CH$_2$CH$_2$F, —OH, —OCF$_3$, —N(CH$_3$)$_2$, —CF$_2$CH$_2$OH, or

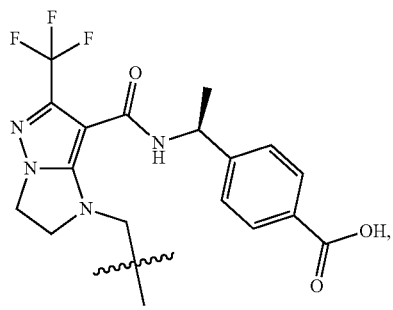 [SMILES: *CN1CCn2nc(C(F)(F)F)c(C(=O)N[C@@H](C)c3ccc(C(=O)O)cc3)c21]

or the bond connecting R$_8$ and ring A is a double bond and R$_8$ is CH$_2$;

R$_9$ is —H, —Cl, or —CF$_3$;

R$_{10}$ is —H, —CH$_3$, —CH$_2$F, —CH$_2$OH, or —CH$_2$OCH$_2$-phenyl;

X$_1$ and X$_2$ are either both C, or one is C and the other is N;

------ represents a single bond or a double bond; and ring A is phenyl or cyclohexyl.

In a further embodiment there is provided a compound having the structure shown in Formula II:

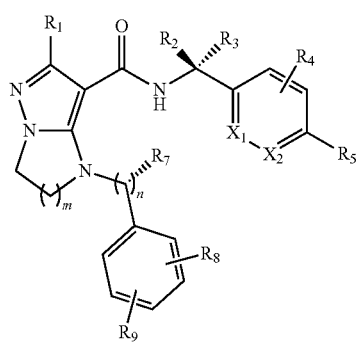

(II)

or pharmaceutically acceptable salts thereof. In typical embodiments R$_1$ is —CH$_3$, —CF$_3$, —CH$_2$CH$_3$, or phenyl; R$_2$ is —H, or —CH$_3$; R$_3$ is —H; or R$_2$ and R$_3$ taken together form a cyclopropyl with the carbon to which they are attached; R$_4$ is —H, —F, or —CH$_3$; R$_5$ is —C(O)OH, —C(O)OCH$_3$, —CH$_2$C(O)OH, cyclopropyl, —C(O)NHCN,

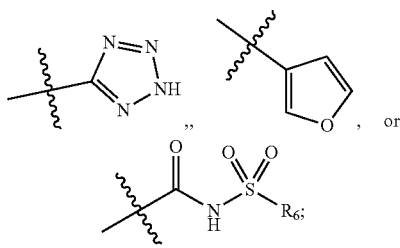

wherein R$_6$ is phenyl, —CH$_3$, cyclopropyl, or

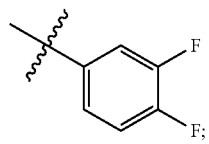 [SMILES: *c1ccc(F)c(F)c1]

m is 1-2; n is 0-1; R$_7$ is —H, —CH$_3$, or absent when n is 0; R$_8$ is —CF$_3$, —Cl, —F, —CH$_2$CH$_3$, —OCH$_3$, —CH$_3$, or —OCF$_3$; R$_9$ is —H, —Cl, or —CF$_3$; and X$_1$ and X$_2$ are either both C, or one is C and the other is N.

Embodiments include a compound having the structure shown in Formula V:

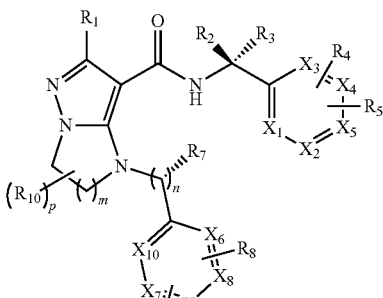

(V)

or pharmaceutically acceptable salts thereof. In typical embodiments R$_1$ is —CF$_3$, C$_1$-C$_6$ alkyl, C$_1$-C$_6$ alkoxy, cyano, aryl, aryloxy, amino, C$_1$-C$_6$ alkylamino, carbonyl, or phenyl; R$_2$ and R$_3$ are independently selected from —H, —CH$_3$, or —CH$_{3-z}$F$_z$, where z is 1 to 3; or R$_2$ and R$_3$ taken together form a cyclopropyl or cyclobutyl with the carbon to which they are attached; R$_4$ is —H, halogen, —CF$_3$C$_1$-C$_3$ alkyl optionally substituted with one or more —F, or C$_1$-C$_3$ alkoxy; R$_5$ is —C(O)OH, —C(O)OCH$_3$, —CH$_2$C(O)OH, cyclopropyl, —C(O)NHCN,

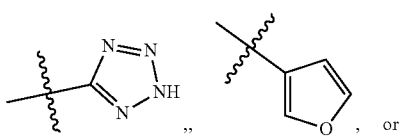

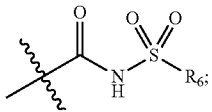

wherein $R_6$ is phenyl, —$CH_3$, cyclopropyl, or

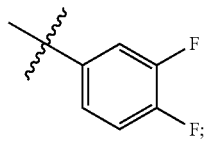 [SMILES: *c1ccc(F)c(F)c1]

m is 1-3; n is 0-5; $R_7$ is —H, —$CH_3$, or absent when n is 0; $R_8$ and $R_9$ are independently selected from —H, —$CF_3$, halogen, amino, $OCH_3$, $C_1$-$C_6$ alkoxy optionally substituted with one or more fluorine, or $C_1$-$C_6$ alkyl, optionally substituted with at least one fluorine and with at least one carbon of the $C_1$-$C_6$ alkyl optionally replaced by O or N; and $X_1$, $X_2$, $X_3$, $X_4$, and $X_5$ are either C or N, where zero, one, or two of $X_1$, $X_2$, $X_3$, $X_4$, and $X_5$ are simultaneously N; wherein $X_6$, $X_7$, $X_8$, $X_9$, and $X_{10}$ are C or N, where zero, one, or two of $X_6$, $X_7$, $X_8$, $X_9$, and $X_{10}$ are simultaneously N; wherein $R_{10}$ is $C_1$-$C_3$ alkyl optionally substituted with one or more fluorine, and wherein p is 0-3.

As used herein, "alkyl", "$C_1$, $C_2$, $C_3$, $C_4$, $C_5$ or $C_6$ alkyl" or "$C_1$-$C_6$ alkyl" is intended to include $C_1$, $C_2$, $C_3$, $C_4$, $C_5$ or $C_6$ straight chain (linear) saturated aliphatic hydrocarbon groups and $C_3$, $C_4$, $C_5$ or $C_6$ branched saturated aliphatic hydrocarbon groups. For example, $C_1$-$C_6$ alkyl is intended to include $C_1$, $C_2$, $C_3$, $C_4$, $C_5$ and $C_6$ alkyl groups. Examples of alkyl include, moieties having from one to six carbon atoms, such as, but not limited to, methyl, ethyl, n-propyl, i-propyl, n-butyl, s-butyl, t-butyl, n-pentyl, s-pentyl or n-hexyl.

In certain embodiments, a straight chain or branched alkyl has six or fewer carbon atoms (e.g., $C_1$-$C_6$ for straight chain, $C_3$-$C_6$ for branched chain), and in another embodiment, a straight chain or branched alkyl has four or fewer carbon atoms.

As used herein, the term "cycloalkyl" refers to a saturated or unsaturated nonaromatic hydrocarbon ring having 3 to 7 carbon atoms (e.g., $C_3$-$C_7$). Examples of cycloalkyl include, but are not limited to, cyclopropyl, cyclobutyl, cyclopentyl, cyclohexyl, cycloheptyl, cyclopentenyl, cyclohexenyl, and cycloheptenyl.

The term "heterocycloalkyl" refers to a saturated or unsaturated nonaromatic 3-8 membered monocyclic, 7-10 membered fused bicyclic having one or more heteroatoms (such as O, N, or S), unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, oxiranyl, azetidinyl, oxetanyl, thietanyl, 1,2,3,6-tetrahydropyridinyl, tetrahydropyranyl, tetrahydrothienyl, dihydropyranyl, pyranyl, morpholinyl, 1,4-diazepanyl, 1,4-oxazepanyl, and the like.

Additional examples of heterocycloalkyl groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuranyl, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol-5-(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl.

The term "optionally substituted alkyl" refers to unsubstituted alkyl or alkyl having designated substituents replacing one or more hydrogen atoms on one or more carbons of the hydrocarbon backbone. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonyl, phosphinyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonyl, sulfamoyl, sulfonamido, nitro, trifluoromethyl, cyano, azido, heterocyclyl, alkylaryl, or an aromatic or heteroaromatic moiety.

An "arylalkyl" or an "aralkyl" moiety is an alkyl substituted with an aryl (e.g., phenylmethyl(benzyl)). An "alkylaryl" moiety is an aryl substituted with an alkyl (e.g., methylphenyl).

"Alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

The term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonyl, phosphinyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonyl, sulfamoyl, sulfonamido, nitro, trifluoromethyl, cyano, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

The term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonyl, phosphinyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonyl, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

"Aryl" includes groups with aromaticity, including "conjugated," or multicyclic systems with at least one aromatic ring and do not contain any heteroatom in the ring structure. Examples include phenyl, benzyl, 1,2,3,4-tetrahydronaphthalenyl, etc.

"Heteroaryl" groups are aryl groups, as defined above, except having from one to four heteroatoms in the ring structure, and may also be referred to as "aryl heterocycles" or "heteroaromatics." As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur. The nitrogen atom may be substituted or unsubstituted (i.e., N or NR' wherein R' is H or other substituents, as defined). The nitrogen and sulfur heteroatoms may optionally be oxidized (i.e., N→O and $S(O)_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., bicyclic. Non-limiting example of such aryl groups include, e.g., naphthalene, benzoxazole, benzodioxazole, benzothiazole, benzoimidazole, benzothiophene, methylenedioxyphenyl, quinoline, isoquinoline, naphthrydine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline).

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonyl, phosphinyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonyl, sulfamoyl, sulfonamido, nitro, trifluoromethyl, cyano, azido, heterocyclyl, alkylaryl, or an aromatic or heteroaromatic moiety. Aryl and heteroaryl groups can also be fused with alicyclic or heterocyclic rings, which are not aromatic so as to form a multicyclic system (e.g., tetralin, methylenedioxyphenyl).

When a bond to a substituent is shown to cross a bond connecting two atoms in a ring (as shown by the examples below with substituent R), then such substituent may be bonded to any atom in the ring.

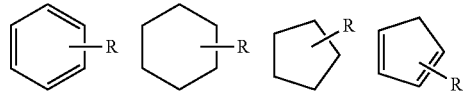

When any variable (e.g., $R_1$) occurs more than one time in any constituent or formula for a compound, its definition at each occurrence is independent of its definition at every other occurrence. Thus, for example, if a group is shown to be substituted with 0-2 $R_1$ moieties, then the group may optionally be substituted with up to two $R_1$ moieties and $R_1$ at each occurrence is selected independently from the definition of $R_1$.

The term "hydroxy" or "hydroxyl" includes groups with an —OH or —O$^-$.

As used herein, "halo" or "halogen" refers to fluoro, chloro, bromo and iodo. The term "perhalogenated" generally refers to a moiety wherein all hydrogen atoms are replaced by halogen atoms. The term "haloalkyl" or "haloalkoxyl" refers to an alkyl or alkoxyl substituted with one or more halogen atoms.

"Alkoxyalkyl," "alkylaminoalkyl," and "thioalkoxyalkyl" include alkyl groups, as described above, wherein oxygen, nitrogen, or sulfur atoms replace one or more hydrocarbon backbone carbon atoms.

The term "alkoxy" or "alkoxyl" includes substituted and unsubstituted alkyl, alkenyl and alkynyl groups covalently linked to an oxygen atom. Examples of alkoxy groups or alkoxyl radicals include, but are not limited to, methoxy, ethoxy, isopropyloxy, propoxy, butoxy and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonyl, phosphinyl, amino (including alkylamino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonyl, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy and trichloromethoxy.

"Isomerism" means compounds that have identical molecular formulae but differ in the sequence of bonding of their atoms or in the arrangement of their atoms in space. Isomers that differ in the arrangement of their atoms in space are termed "stereoisomers." Stereoisomers that are not mirror images of one another are termed "diastereoisomers," and stereoisomers that are non-superimposable mirror images of each other are termed "enantiomers" or sometimes optical isomers. A mixture containing equal amounts of individual enantiomeric forms of opposite chirality is termed a "racemic mixture."

A carbon atom bonded to four nonidentical substituents is termed a "chiral center."

"Chiral isomer" means a compound with at least one chiral center. Compounds with more than one chiral center may exist either as an individual diastereomer or as a mixture of diastereomers, termed "diastereomeric mixture." When one chiral center is present, a stereoisomer may be characterized by the absolute configuration (R or S) of that chiral center. Absolute configuration refers to the arrangement in space of the substituents attached to the chiral center. The substituents attached to the chiral center under consideration are ranked in accordance with the Sequence Rule of Cahn, Ingold and Prelog. (Calm et al., *Angew. Chem. Inter. Edit.* 1966, 5, 385; errata 511; Cahn et al., Angew. Chem. 1966, 78, 413; Cahn and Ingold, *J. Chem. Soc.* 1951 (London), 612; Calm et al., Experientia 1956, 12, 81; Cahn, *J. Chem. Educ.* 1964, 41, 116).

In the present specification, each incidence of a chiral center within a structural formula, such as the non-limiting example shown here:

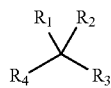

is meant to depict all possible stereoisomers. In contrast, a chiral center drawn with hatches and wedges, such as the non-limiting example shown here:

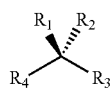

is meant to depict the stereoisomer as indicated (here in this sp³ hybridized carbon chiral center, $R_3$ and $R_4$ are in the plane of the paper, $R_1$ is above the plane of paper, and $R_2$ is behind the plane of paper).

"Geometric isomer" means the diastereomers that owe their existence to hindered rotation about double bonds or a cycloalkyl linker (e.g., 1,3-cyclobutyl). These configurations are differentiated in their names by the prefixes cis and trans, or Z and E, which indicate that the groups are on the same or opposite side of the double bond in the molecule according to the Cahn-Ingold-Prelog rules.

In the present specification, each incidence within a structural formula including a wavy line adjacent to a double bond as shown:

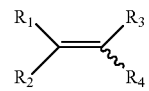

or drawn with all straight bonds, is meant to depict both geometric isomers. In contrast, such structures drawn without a wavy line is meant to depict a compound having the geometric configuration as drawn.

"Tautomer" is one of two or more structural isomers that exist in equilibrium and is readily converted from one isomeric form to another. This conversion results in the formal migration of a hydrogen atom accompanied by a switch of adjacent conjugated double bonds. Tautomers exist as a mixture of a tautomeric set in solution. In solutions where tautomerization is possible, a chemical equilibrium of the tautomers will be reached. The exact ratio of the tautomers depends on several factors, including temperature, solvent and pH. The concept of tautomers that are interconvertable by tautomerizations is called tautomerism.

Where the present specification depicts a compound prone to tautomerization, but only depicts one of the tautomers, it is understood that all tautomers are included as part of the meaning of the chemical depicted. It is to be understood that the compounds of the present disclosure may be depicted as different tautomers. It should also be understood that when compounds have tautomeric forms, all tautomeric forms are intended to be included in the scope of the present disclosure, and the naming of the compounds does not exclude any tautomer form.

Of the various types of tautomerism that are possible, two are commonly observed. In keto-enol tautomerism a simultaneous shift of electrons and a hydrogen atom occurs. Ring-chain tautomerism arises as a result of the aldehyde group (—CHO) in a sugar chain molecule reacting with one of the hydroxy groups (—OH) in the same molecule to give it a cyclic (ring-shaped) form as exhibited by glucose.

Common tautomeric pairs are: ketone-enol, amide-nitrile, lactam-lactim, amide-imidic acid tautomerism in heterocyclic rings (e.g., in nucleobases such as guanine, thymine and cytosine), imine-enamine and enamine-enamine.

Furthermore, the structures and other compounds discussed in this disclosure include all atropic isomers thereof, it being understood that not all atropic isomers may have the same level of activity. "Atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The term "crystal polymorphs", "polymorphs" or "crystal forms" means crystal structures in which a compound (or a salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions. It is understood that the compounds of the present disclosure may exist in crystalline form, crystal form mixture, or anhydride or hydrate thereof.

The compounds disclosed herein include the compounds themselves, as well as their salts and solvates, if applicable. A salt, for example, can be formed between an anion and a positively charged group (e.g., amino) on an aryl- or heteroaryl-substituted benzene compound. Suitable anions include chloride, bromide, iodide, sulfate, bisulfate, sulfamate, nitrate, phosphate, citrate, methanesulfonate, trifluoroacetate, glutamate, glucuronate, glutarate, malate, maleate, succinate, fumarate, tartrate, tosylate, salicylate, lactate, naphthalenesulfonate, and acetate (e.g., trifluoroacetate). The term "pharmaceutically acceptable anion" refers to an anion suitable for forming a pharmaceutically acceptable salt. Likewise, a salt can also be formed between a cation and a negatively charged group (e.g., carboxylate) on an aryl- or heteroaryl-substituted benzene compound. Suitable cations include sodium ion, potassium ion, magnesium ion, calcium ion, and an ammonium cation such as tetramethylammonium ion. The aryl- or heteroaryl-substituted benzene compounds also include those salts containing quaternary nitrogen atoms.

Additionally, compounds of the present disclosure, for example, the salts of the compounds, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

As used herein, "pharmaceutically acceptable salts" refer to derivatives of the compounds as reported herein, wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present disclosure also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. In the salt form, it is understood that the ratio of the compound to the cation or anion of the salt can be 1:1, or any ratio other than 1:1, e.g., 3:1, 2:1, 1:2, or 1:3.

It should be understood that all references to pharmaceutically acceptable salts include solvent addition forms (solvates) or crystal forms (polymorphs) as defined herein, of the same salt.

"Solvate" means solvent addition forms that contain either stoichiometric or non-stoichiometric amounts of solvent. Some compounds have a tendency to trap a fixed molar ratio of solvent molecules in the crystalline solid state, thus forming a solvate. If the solvent is water the solvate formed is a hydrate; and if the solvent is alcohol, the solvate formed is an alcoholate. Hydrates are formed by the combination of one or more molecules of water with one molecule of the substance in which the water retains its molecular state as $H_2O$.

Chemicals as named or depicted are intended to include all naturally occurring isotopes of atoms occurring in the present compounds. Isotopes include those atoms having the same atomic number but different mass numbers. By way of general example and without limitation, isotopes of $^1H$ hydrogen include tritium and deuterium, and isotopes of $^{12}C$ carbon include $^{13}C$ and $^{14}C$.

Compounds of the present invention may also be prepared as radioactive tracers for positron emission tomography (PET). Such PET tracers may incorporate a radioisotope such as $^{11}C$, $^{13}N$, $^{15}O$, or preferably $^{18}F$. Such radioisotopes may be substituted for a corresponding non-radioisotopic C, N, O or F atom already present in the compound, or may be substituted for a hydrogen atom in the compound.

It will be understood that some compounds, and isomers, salts, solvates, and polymorphs thereof, of the present disclosure may exhibit greater in vivo or in vitro activity than others. It will also be appreciated that some diseases or conditions may be treated more effectively than others using the compounds, and isomers, salts, solvates, and polymorphs thereof, of the present disclosure.

As used herein, "treating" means administering to a subject a pharmaceutical composition to ameliorate, reduce or lessen the symptoms of a disease. As used herein, "treating" or "treat" describes the management and care of a subject for the purpose of combating a disease, condition, or disorder and includes the administration of a compound of the present disclosure, or a pharmaceutically acceptable salt, polymorph or solvate thereof, to alleviate the symptoms or complications of a disease, condition or disorder, or to eliminate the disease, condition or disorder. The term "treat" can also include treatment of a cell in vitro or an animal model.

Treating cancer may result in a reduction in size of a tumor. A reduction in size of a tumor may also be referred to as "tumor regression." Preferably, after treatment, tumor size is reduced by 5% or greater relative to its size prior to treatment; more preferably, tumor size is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Size of a tumor may be measured by any reproducible means of measurement. The size of a tumor may be measured as a diameter of the tumor.

Treating cancer may result in a reduction in tumor volume. Preferably, after treatment, tumor volume is reduced by 5% or greater relative to its size prior to treatment; more preferably, tumor volume is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75% or greater. Tumor volume may be measured by any reproducible means of measurement.

Treating cancer may result in a decrease in number of tumors. Preferably, after treatment, tumor number is reduced by 5% or greater relative to number prior to treatment; more preferably, tumor number is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. Number of tumors may be measured by any reproducible means of measurement. The number of tumors may be measured by counting tumors visible to the naked eye or at a specified magnification. Preferably, the specified magnification is 2×, 3×, 4×, 5×, 10×, or 50×.

Treating cancer may result in a decrease in number of metastatic lesions in other tissues or organs distant from the primary tumor site. Preferably, after treatment, the number of metastatic lesions is reduced by 5% or greater relative to number prior to treatment; more preferably, the number of metastatic lesions is reduced by 10% or greater; more preferably, reduced by 20% or greater; more preferably, reduced by 30% or greater; more preferably, reduced by 40% or greater; even more preferably, reduced by 50% or greater; and most preferably, reduced by greater than 75%. The number of metastatic lesions may be measured by any reproducible means of measurement. The number of metastatic lesions may be measured by counting metastatic lesions visible to the naked eye or at a specified magnification. Preferably, the specified magnification is 2×, 3×, 4×, 5×, 10×, or 50×.

As used herein, "subject" or "subjects" refers to any animal, such as mammals including rodents (e.g., mice or rats), dogs, primates, lemurs or humans.

Treating cancer may result in an increase in average survival time of a population of treated subjects in comparison to a population receiving carrier alone. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer may result in an increase in average survival time of a population of treated subjects in comparison to a population of untreated subjects. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer may result in increase in average survival time of a population of treated subjects in comparison to a population receiving monotherapy with a drug that is not a compound of the present disclosure, or a pharmaceutically acceptable salt thereof. Preferably, the average survival time is increased by more than 30 days; more preferably, by more than 60 days; more preferably, by more than 90 days; and most preferably, by more than 120 days. An increase in average survival time of a population may be measured by any reproducible means. An increase in average survival time of a population may be measured, for example, by calculating for a population the average length of survival following initiation of treatment with an active compound. An increase in average survival time of a population may also be measured, for example, by calculating for a population the average length of survival following completion of a first round of treatment with an active compound.

Treating cancer may result in a decrease in the mortality rate of a population of treated subjects in comparison to a population receiving carrier alone. Treating cancer can result in a decrease in the mortality rate of a population of treated subjects in comparison to an untreated population. Treating cancer can result in a decrease in the mortality rate of a population of treated subjects in comparison to a population receiving monotherapy with a drug that is not a compound of the present disclosure, or a pharmaceutically acceptable salt, prodrug, metabolite, analog or derivative thereof. Preferably, the mortality rate is decreased by more than 2%; more preferably, by more than 5%; more preferably, by more than 10%; and most preferably, by more than 25%. A decrease in the mortality rate of a population of treated subjects may be measured by any reproducible means. A decrease in the mortality rate of a population may be measured, for example, by calculating for a population the average number of disease-related deaths per unit time following initiation of treatment with an active compound. A decrease in the mortality rate of a population may also be measured, for example, by calculating for a population the average number of disease-related deaths per unit time following completion of a first round of treatment with an active compound.

Treating cancer may result in a decrease in tumor growth rate. Preferably, after treatment, tumor growth rate is reduced by at least 5% relative to number prior to treatment; more preferably, tumor growth rate is reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Tumor growth rate may be measured by any reproducible means of measurement. Tumor growth rate can be measured according to a change in tumor diameter per unit time.

Treating cancer may result in a decrease in tumor regrowth, for example, following attempts to remove it surgically. Preferably, after treatment, tumor regrowth is less than 5%; more preferably, tumor regrowth is less than 10%; more preferably, less than 20%; more preferably, less than 30%; more preferably, less than 40%; more preferably, less than 50%; even more preferably, less than 50%; and most preferably, less than 75%. Tumor regrowth may be measured by any reproducible means of measurement. Tumor regrowth is measured, for example, by measuring an increase in the diameter of a tumor after a prior tumor shrinkage that followed treatment. A decrease in tumor regrowth is indicated by failure of tumors to reoccur after treatment has stopped.

Treating or preventing a cell proliferative disorder may result in a reduction in the rate of cellular proliferation. Preferably, after treatment, the rate of cellular proliferation is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The rate of cellular proliferation may be measured by any reproducible means of measurement. The rate of cellular proliferation is measured, for example, by measuring the number of dividing cells in a tissue sample per unit time.

Treating or preventing a cell proliferative disorder may result in a reduction in the proportion of proliferating cells. Preferably, after treatment, the proportion of proliferating cells is reduced by at least 5%; more preferably, by at least 10%; more preferably, by at least 20%; more preferably, by at least 30%; more preferably, by at least 40%; more preferably, by at least 50%; even more preferably, by at least 50%; and most preferably, by at least 75%. The proportion of proliferating cells may be measured by any reproducible means of measurement. Preferably, the proportion of proliferating cells is measured, for example, by quantifying the number of dividing cells relative to the number of nondividing cells in a tissue sample. The proportion of proliferating cells can be equivalent to the mitotic index.

Treating or preventing a cell proliferative disorder may result in a decrease in size of an area or zone of cellular proliferation. Preferably, after treatment, size of an area or zone of cellular proliferation is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. Size of an area or zone of cellular proliferation may be measured by any reproducible means of measurement. The size of an area or zone of cellular proliferation may be measured as a diameter or width of an area or zone of cellular proliferation.

Treating or preventing a cell proliferative disorder may result in a decrease in the number or proportion of cells having an abnormal appearance or morphology. Preferably, after treatment, the number of cells having an abnormal morphology is reduced by at least 5% relative to its size prior to treatment; more preferably, reduced by at least 10%; more preferably, reduced by at least 20%; more preferably, reduced by at least 30%; more preferably, reduced by at least 40%; more preferably, reduced by at least 50%; even more preferably, reduced by at least 50%; and most preferably, reduced by at least 75%. An abnormal cellular appearance or morphology may be measured by any reproducible means of measurement. An abnormal cellular morphology can be measured by microscopy, e.g., using an inverted tissue culture microscope. An abnormal cellular morphology can take the form of nuclear pleiomorphism.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions of the disclosure leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein, the term "severity" is meant to describe the potential of cancer to transform from a precancerous, or benign, state into a malignant state. Alternatively, or in addition, severity is meant to describe a cancer stage, for example, according to the TNM system (accepted by the International Union Against Cancer (UICC) and the American Joint Committee on Cancer (AJCC)) or by other art-recognized methods. Cancer stage refers to the extent or severity of the cancer, based on factors such as the location of the primary tumor, tumor size, number of tumors, and lymph node involvement (spread of cancer into lymph nodes). Alternatively, or in addition, severity is meant to describe the tumor grade by art-recognized methods (see, National Cancer Institute, www.cancer.gov). Tumor grade is a system used to classify cancer cells in terms of how abnormal they look under a microscope and how quickly the tumor is likely to grow and spread. Many factors are considered when determining tumor grade, including the structure and growth pattern of the cells. The specific factors used to determine tumor grade vary with each type of cancer. Severity also describes a histologic grade, also called differentiation, which refers to how much the tumor cells resemble normal cells of the same tissue type (see, National Cancer Institute, www.cancer.gov). Furthermore, severity describes a nuclear grade, which refers to the size and shape of the nucleus in tumor cells and the percentage of tumor cells that are dividing (see, National Cancer Institute, www.cancer.gov).

In another aspect as reported herein, severity describes the degree to which a tumor has secreted growth factors, degraded the extracellular matrix, become vascularized, lost adhesion to juxtaposed tissues, or metastasized. Moreover, severity describes the number of locations to which a primary tumor has metastasized. Finally, severity includes the difficulty of treating tumors of varying types and locations. For example, inoperable tumors, those cancers which have greater access to multiple body systems (hematological and immunological tumors), and those which are the most resistant to traditional treatments are considered most severe. In these situations, prolonging the life expectancy of the subject and/or reducing pain, decreasing the proportion of cancerous cells or restricting cells to one system, and improving cancer stage/tumor grade/histological grade/ nuclear grade are considered alleviating a sign or symptom of the cancer.

As used herein the term "symptom" is defined as an indication of disease, illness, injury, or that something is not right in the body. Symptoms are felt or noticed by the individual experiencing the symptom, but may not easily be noticed by non-health-care professionals.

A "pharmaceutical composition" is a formulation containing a compound of the present disclosure in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed compound or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In one embodiment, the active compound is mixed under sterile conditions with a pharmaceutically acceptable carrier, and with any preservatives, buffers, or propellants that are required.

As used herein, the phrase "pharmaceutically acceptable" refers to those compounds, anions, cations, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the specification and claims includes both one and more than one such excipient.

Embodiments reported herein may provide pharmaceutical compositions comprising any compound disclosed herein in combination with at least one pharmaceutically acceptable excipient or carrier.

A pharmaceutical composition as reported herein is typically formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

A compound or pharmaceutical composition can be administered to a subject in many of the well-known methods currently used for chemotherapeutic treatment. For example, for treatment of cancers, a compound as reported herein may be injected directly into tumors, injected into the blood stream or body cavities or taken orally or applied through the skin with patches. The dose chosen should be sufficient to constitute effective treatment but not so high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is cancer. In another aspect, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds as reported herein may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol and sorbitol, and sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primojel® brand cross-linked and carboxymethylated potato starch, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

It is typically advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms as reported herein are dictated by and directly dependent on the unique characteristics of the active compound and the particular therapeutic effect to be achieved.

In therapeutic applications, the dosages of the pharmaceutical compositions used in accordance embodiments reported herein vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. In preferred aspects, dosages can range from about 1 mg/kg per day to about 1000 mg/kg per day. In an aspect, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions can be included in a container, pack, or dispenser together with instructions for administration.

Techniques for formulation and administration of the disclosed compounds can be found in Remington: the Science and Practice of Pharmacy, 19.sup.th edition, Mack Publishing Co., Easton, Pa. (1995). In an embodiment, the compounds described herein, and the pharmaceutically acceptable salts thereof, can be used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

By way of example and without being limiting, the compounds described herein may be used for cancer immune therapy targeting host immunosuppressive cells in the tumor microenvironment that can be of either myeloid or lymphoid lineage. Exemplary cancers that may be treated using one or more compounds of the present disclosure include, but are not limited to, tumor types that harbor high levels of myeloid infiltrate based on the Cancer Genome Atlas (TCGA). Tumor types may include pancreatic adenocarcinoma, renal clear cell carcinoma, squamous cell carcinoma of head and neck (SCCHN), non-small cell lung cancer (NSCLC), colorectal cancer (CRC), hepatocellular carcinoma (HCC), serous epithelial ovarian cancer, cervical cancer, transitional cell bladder cancer, and triple-negative breast cancer (TNBC).

A cancer that is to be treated can be staged according to the American Joint Committee on Cancer (AJCC) TNM classification system, where the tumor (T) has been assigned a stage of TX, T1, T1mic, T1a, T1b, T1c, T2, T3, T4, T4a, T4b, T4c, or T4d; and where the regional lymph nodes (N) have been assigned a stage of NX, N0, N1, N2, N2a, N2b, N3, N3a, N3b, or N3c; and where distant metastasis (M) can be assigned a stage of MX, M0, or M1. A cancer that is to be treated can be staged according to an American Joint Committee on Cancer (AJCC) classification as Stage I, Stage IIA, Stage IIB, Stage IIIA, Stage IIIB, Stage IIIC, or Stage IV. A cancer that is to be treated can be assigned a grade according to an AJCC classification as Grade GX (e.g., grade cannot be assessed), Grade 1, Grade 2, Grade 3 or Grade 4. A cancer that is to be treated can be staged according to an AJCC pathologic classification (pN) of pNX, pN0, PN0 (I−), PN0 (I+), PN0 (mol−), PN0 (mol+), PN1, PN1(mi), PN1a, PN1b, PN1c, pN2, pN2a, pN2b, pN3, pN3a, pN3b, or pN3c.

A cancer that is to be treated can include a tumor that has been determined to be less than or equal to about 2 centimeters in diameter. A cancer that is to be treated can include a tumor that has been determined to be from about 2 to about 5 centimeters in diameter. A cancer that is to be treated can include a tumor that has been determined to be greater than or equal to about 3 centimeters in diameter. A cancer that is to be treated can include a tumor that has been determined to be greater than 5 centimeters in diameter. A cancer that is to be treated can be classified by microscopic appearance as well differentiated, moderately differentiated, poorly differentiated, or undifferentiated. A cancer that is to be treated can be classified by microscopic appearance with respect to mitosis count (e.g., amount of cell division) or nuclear pleiomorphism (e.g., change in cells). A cancer that is to be treated can be classified by microscopic appearance as being associated with areas of necrosis (e.g., areas of dying or degenerating cells). A cancer that is to be treated can be classified as having an abnormal karyotype, having an abnormal number of chromosomes, or having one or more chromosomes that are abnormal in appearance. A cancer that is to be treated can be classified as being aneuploid, triploid, tetraploid, or as having an altered ploidy. A cancer that is to be treated can be classified as having a chromosomal translocation, or a deletion or duplication of an entire chromosome, or a region of deletion, duplication or amplification of a portion of a chromosome.

The compounds, or pharmaceutically acceptable salts thereof are administered orally, nasally, transdermally, pulmonary, inhalationally, buccally, sublingually, intraperitoneally, subcutaneously, intramuscularly, intravenously, rectally, intrapleurally, intrathecally and parenterally. In one embodiment, the compound is administered orally. One skilled in the art will recognize the advantages of certain routes of administration.

The dosage regimen utilizing the compounds is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

By way of example and without being limiting, the compounds described herein may be used for cancer immune therapy targeting host immunosuppressive cells in the tumor microenvironment that can be of either myeloid or lymphoid lineage.

Tumor types may include pancreatic adenocarcinoma, renal clear cell carcinoma, squamous cell carcinoma of head and neck (SCCHN), non-small cell lung cancer (NSCLC), colorectal cancer (CRC), hepatocellular carcinoma (HCC), serous epithelial ovarian cancer, cervix cancer, transitional cell bladder cancer, and triple-negative breast cancer (TNBC).

EXAMPLES

Examples I-LXV

General:

Microwave heating was done using Biotage Emrys Liberator or Initiator microwave. Column chromatography was carried out using Biotage SP4. Solvent removal was carried out using either a Büchii rotary evaporator or a Genevac centrifugal evaporator. Preparative LC/MS was conducted using a Waters autopurifier and 19×100 mm XTerra 5 micron MS C18 column under acidic mobile phase condition. NMR spectra were recorded using Varian 400 MHz spectrometer.

When the term "inerted" is used to describe a reactor (e.g., a reaction vessel, flask, glass reactor, and the like) it is meant that the air in the reactor has been replaced with an essentially moisture-free or dry, inert gas (such as nitrogen, argon, and the like).

General methods and experimental for preparing compounds of the present invention are set forth below. In certain cases, a particular compound is described by way of example. However, it will be appreciated that in each case a series of compounds of the present invention were prepared in accordance with the schemes and experimental described below.

General Experimental Methods:

The following abbreviations are used in the experimental procedures.

AcOH acetic acid
aq. aqueous
tBuOK potassium t-butoxide
Cbz benzyloxycarbonyl
$CDCl_3$ deuterated chloroform
$CH_2Cl_2$ dichloromethane
DCM dichloromethane
DIPEA diisopropylethylamine DMAP dimethylaminopyridine
DMF N,N-dimethylformamide
DMSO dimethylsulfoxide
E ethyl acetate
EDC 1-Ethyl-3-(3-dimethylaminopropyl)carbodiimide
EtOAc ethyl acetate
HCl hydrogen chloride
HPLC high performance liquid chromatography
H heptane
HATU 1-[Bis(dimethylamino)methylene]-1H-1,2,3-triazolo[4,5-b]pyridinium 3-oxid hexafluorophosphate
iPrOH isopropanol
K₂CO₃ potassium carbonate
MgSO₄ magnesium sulfate
MeI methyl iodide
MsCl methanesulfonyl chloride
MS 3 Å 3 Å molecular sieves
MTBE methy tert-butyl ether
NaOH sodium hydroxide
NaHCO₃ sodium hydrogen carbonate
Na₂CO₃ sodium bicarbonate
Na₂SO₄ sodium sulfate
Na₂S₂O₃ Sodium thiosulfate
Pd(OH)₂ palladium dihydroxide
Pd(PPh₃)₄ tetrakis(triphenylphosphine)palladium(0)
PyBOP benzotriazol-1-yl-oxytripyrrolidinophosphonium hexafluorophosphate
PTLC preparative thin layer chromatography
rt room temperature
TBME tert-butylmethylether
TBTU O-(Benzotriazol-1-yl)-N,N,N',N'-tetramethyluronium tetrafluoroborate
TEA triethylamine
TFA trifluoroacetic acid
THF tetrahydrofuran
TLC thin layer chromatography NMR: ¹HNMR spectra were taken using CDCl₃ unless otherwise stated and were recorded at 400 or 500 MHz using a Varian instruments. Multiplicities indicated are s=singlet, d=doublet, t=triplet, q=quartet, quint=quintet, sxt=sextet, m=multiplet, dd=doublet of doublets, dt=doublet of triplets, b=a broad signal. Mass: Waters Acquity Ultra Performance LC.

Example I (S)-4-(1-(6-(trifluoromethyl)-1-(3-(trifluoromethyl)benzyl)-2,3-dihydro-1H-imidazo[1,2-b]pyrazole-7-carboxamido)ethyl)benzoic acid (Compound 1)

Triethylammonium (E)-3-cyano-1,1,1-trifluoro-4-methoxy-4-oxobut-2-en-2-olate (203)

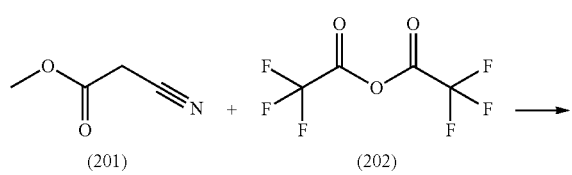

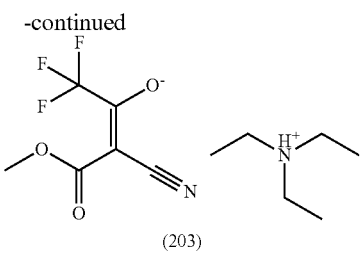

To a solution of methyl 2-cyanoacetate (201) (35.5 mL, 404 mmol) and 2,2,2-trifluoroacetic anhydride (202) (61.7 mL, 444 mmol) in DCM (519 mL) at 0° C. was added slowly TEA (121 mL, 868 mmol) so that the internal reaction temperature was kept below 18° C. Remove the cooling bath and the red clear solution was stirred at rt for overnight. TLC (70% E/H) showed two strong UV active spots at R$_f$=0.1 and 0.2. If the sample was diluted and spotted on TLC, there is only one spot at R$_f$=0.2. LCMS showed only in negative mode for the desired [M−H]=194. The reaction was quenched by addition of sat. NaHCO₃ (400 mL), and the separated aqueous phase was extracted with 6×150 mL DCM until TLC showed no more product. The combined organic phase was dried (Na₂SO₄), filtered and concentrated to give a red colored clear sticky oil as the desired product (120 g, 100% yield). This crude product was used next step without further purification. ¹HNMR (400 MHz): δ ppm 3.65 (s, 3H), 3.18 (q, J=7.4 Hz, 6H), 1.29 (t, J=7.4 Hz, 9H). LCMS (ES) (M−H)=194.1.

Methyl 5-amino-1-(2-hydroxyethyl)-3-(trifluoromethyl)-1H-pyrazole-4-carboxylate (206)

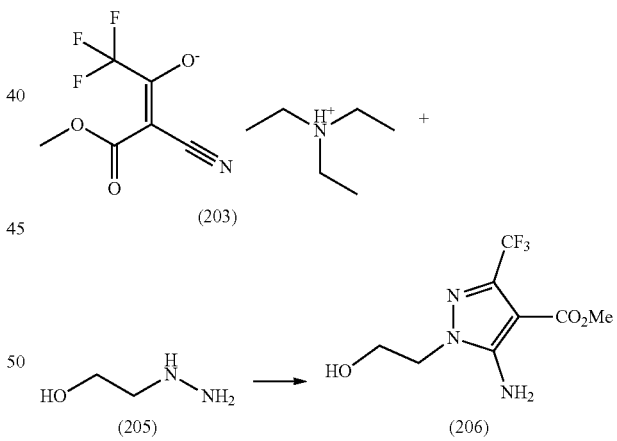

To a solution of 2-hydrazinylethanol (205) (46.2 g, 608 mmol) in 1,4-dioxane (200 mL) at 0° C. was added methanesulfonic acid (47.3 mL, 729 mmol) dropwise (exothermic) followed by TFA (62.4 mL, 810 mmol). After removing the cooling bath, the mixture was stirred for 10 min, and then triethylammonium (E)-3-cyano-1,1,1-trifluoro-4-methoxy-4-oxobut-2-en-2-olate (203) (120 g, 405 mmol) was added rinsing with 1,4-dioxane (280 mL). The resulting mixture was stirred for 10 min at rt, warmed up to 80° C. and stirred for 1 h. TLC (70% E/H) showed mainly trace of SM at R$_f$=0.25 and new spots at R$_f$=0.45 and 0.7 (very minor). LCMS showed desired peak of [M+H]=254. And negative mode of LCMS showed no starting material. The mixture was cooled to rt, concentrated, cooled to 0° C., quenched carefully with sat. NaHCO₃ until no more bubble and pH=8. It was then extracted with 5×150 mL EtOAc until no more product detected by TLC. The combined organic phase was dried (Na₂SO₄), filtered and concentrated to give a yellow oil. Silica gel chromatographic purification (20% to 50% and then 50% isocratic) gave the desired product as a light yellow solid, (12.2 g, 12% yield). ¹HNMR (400 MHz, CD₃OD): δ ppm 4.08 (t, J=5.1 Hz, 2H), 3.86 (t, J=5.1 Hz, 2H), 3.79 (s, 3H). LCMS (ES) (M+H)=254.0.

Methyl 5-amino-1-(2-((methylsulfonyl)oxy)ethyl)-3-(trifluoromethyl)-1H-pyrazole-4-carboxylate (207)

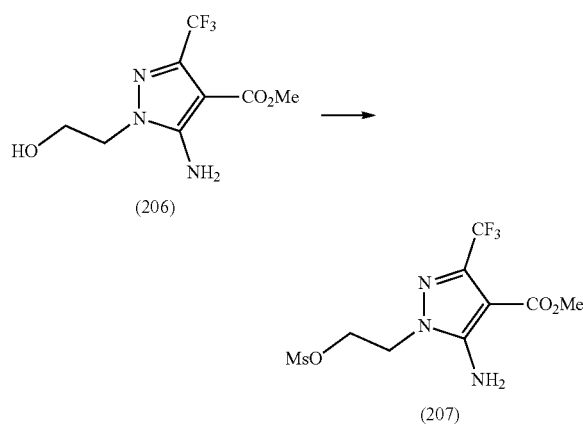

To a solution of methyl 5-amino-1-(2-hydroxyethyl)-3-(trifluoromethyl)-1H-pyrazole-4-carboxylate (206) (14.8 g, 58.5 mmol) and TEA (16.3 mL, 117 mmol) in DCM (100 mL) and THF (100 mL) at 0° C. was added methanesulfonyl chloride (5.02 mL, 64.5 mmol) dropwise during 10 min and stirred for 15 min. TLC (50% E/H) showed no Rf difference between starting material and product. LCMS showed reaction was done shown by [M+H]=332 and no starting material peak of [M+H]=254. The reaction was quenched by addition of sat. NaHCO₃, extracted with 3×50 mL EtOAc, dried (Na₂SO₄), filtered and concentrated to give a yellow oil. Silica gel chromatographic purification (20% to 50% and then 50% isocratic) gave the desired product (18.1 g, 93% yield). ¹HNMR (400 MHz, CD₃OD): δ ppm 4.55 (t, J=5.3 Hz, 2H), 4.32 (t, J=5.3 Hz, 2H), 3.79 (s, 3H), 2.98 (s, 3H). LCMS (ES) (M+H)=332.0.

Methyl 6-(trifluoromethyl)-2,3-dihydro-1H-imidazo[1,2-b]pyrazole-7-carboxylate (208)

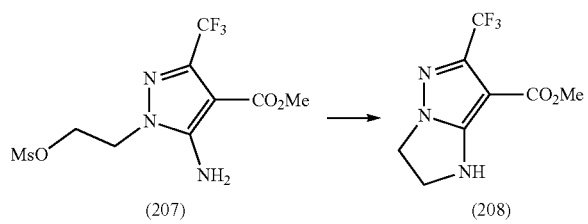 [SMILES: COC(=O)c1c(C(F)(F)F)nn(CCOS(C)(=O)=O)c1N ; COC(=O)c1c(C(F)(F)F)nn2c1NCC2]

An anhydrous suspension of methyl 5-amino-1-(2-((methylsulfonyl)oxy)ethyl)-3-(trifluoromethyl)-1H-pyrazole-4-carboxylate (207) (2.10 g, 6.33 mmol) and potassium carbonate (2.63 g, 19.0 mmol) in DMF (103 mL) was stirred and warmed to 140° C. and stirred for 30 min at 140° C. LCMS showed reaction was completed shown by only [M+H]=236 and trace SM peak of 332 (M+H). TLC (70% E/H) showed new spot at R_f=0.4 and trace starting material spot at R_f=0.42 (almost overlap but the co-spots showed difference). The mixture was cooled to 0° C., quenched by addition of 150 mL sat. NaHCO₃, extracted with 7×80 mL EtOA:ether (2:1) and then 3×50 mL 10% MeOH/EtOAc until TLC showed no product. The combined organic phase was dried (Na₂SO₄), filtered and concentrated to give a crude oil. Silica gel chromatographic purification (10% to 30% E/H and then 30% isocratic) gave the desired product (1.31 g, 88% yield). ¹HNMR (400 MHz, CD₃OD): δ ppm 4.20 (bm, 2H), 4.07 (ddd, J=9.0, 1.6, 0.8 Hz, 2H), 3.75 (s, 3H). LCMS (ES) (M+H)=236.1.

Methyl 2-(trifluoromethyl)-4,5,6,7-tetrahydropyrazolo[1,5-a]pyrimidine-3-carboxylate (212)

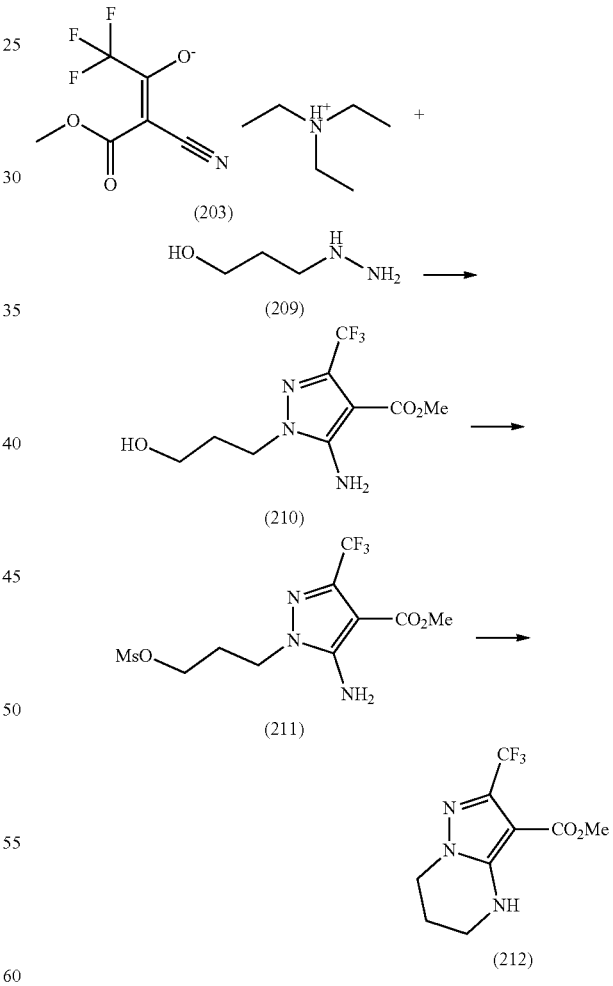

Following the same procedures for the preparation of methyl 6-(trifluoromethyl)-2,3-dihydro-1H-imidazo[1,2-b]pyrazole-7-carboxylate (208), compound 212 was prepared from triethylammonium (E)-3-cyano-1,1,1-trifluoro-4-methoxy-4-oxobut-2-en-2-olate (203) and 3-hydrazinylpropan-1-ol (209).

Methyl 5-amino-1-(3-hydroxypropyl)-3-(trifluoromethyl)-1H-pyrazole-4-carboxylate (210)

¹HNMR (400 MHz): δ ppm 5.78 (bs, 2H), 4.14 (dd, J=6.4, 6.0 Hz, 2H), 3.85 (s, 3H), 3.63 (t, J=5.6 Hz, 2H), 2.04 (m, 2H).

Methyl 5-amino-1-(3-((methylsulfonyl)oxy)propyl)-3-(trifluoromethyl)-1H-pyrazole-4-carboxylate (211)

¹HNMR (400 MHz): δ ppm 5.71 (bs, 2H), 4.27 (dd, J=5.2, 6.0 Hz, 2H), 4.12 (m, 2H), 3.83 (s, 3H), 3.07 (s, 3H), 2.30 (m, 2H).

Methyl 2-(trifluoromethyl)-4,5,6,7-tetrahydropyrazolo[1,5-a]pyrimidine-3-carboxylate (212)

¹HNMR (400 MHz): 6.07 (bs, 1H), 4.12 (dd, J=6.0, 6.4 Hz, 2H), 3.82 (s, 3H), 3.45 (m, 2H), 2.20 (m, 2H).

Methyl 6-(trifluoromethyl)-1-(3-(trifluoromethyl)benzyl)-2,3-dihydro-1H-imidazo[1,2-b]pyrazole-7-carboxylate (213)

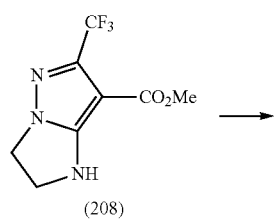

(208)

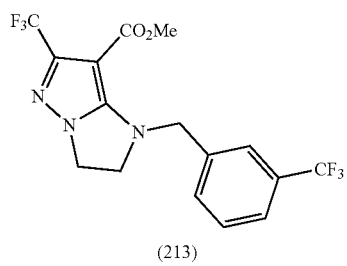

(213)

To a solution of methyl 6-(trifluoromethyl)-2,3-dihydro-1H-imidazo[1,2-b]pyrazole-7-carboxylate (208) (580 mg, 2.47 mmol) and 1-(chloromethyl)-3-(trifluoromethyl)benzene (214) (554 mg, 2.85 mmol) in DMF (15 mL) was added at rt potassium carbonate (1.02 g, 7.40 mmol) and the resulting suspension was stirred at rt overnight. The mixture was then put into a pre-heated oil bath at 140° C. and stirred for 25 min and reaction was completed shown by LCMS with only desired peak of [M+H]=394. TLC (50% E/H) showed one new spot at R$_f$=0.65. The mixture was cooled to rt, diluted with sat. NaHCO$_3$ (50 mL), extracted with 3×50 mL, dried (Na$_2$SO$_4$), filtered and concentrated to give an oil, which after purification by silica gel chromatography (10% to 20% and then 20% isocratic) gave the desired product as a white solid (821 mg, 85% yield). ¹HNMR (400 MHz): δ ppm 7.60-7.45 (m, 4H), 4.99 (s, 2H), 4.20 (dd, J=9.0, 8.2 Hz, 2H), 3.81 (dd, J=9.7, 7.4 Hz, 2H), 3.81 (s, 3H). LCMS (ES) (M+H)=393.9.

6-(trifluoromethyl)-1-(3-(trifluoromethyl)benzyl)-2,3-dihydro-1H-imidazo[1,2-b]pyrazole-7-carboxylic acid (215)

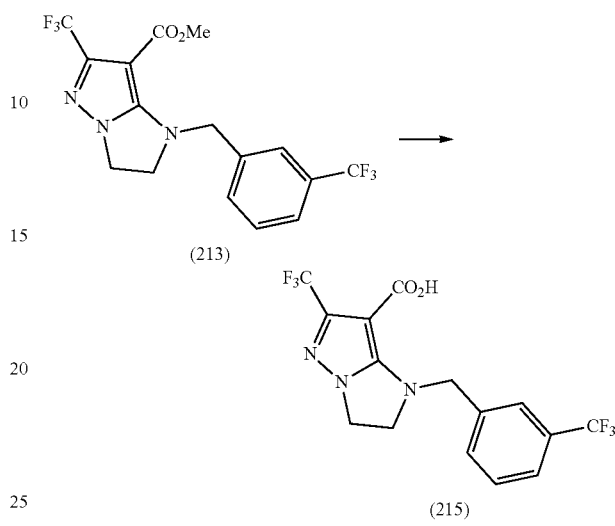

To a solution of methyl 6-(trifluoromethyl)-1-(3-(trifluoromethyl)benzyl)-2,3-dihydro-1H-imidazo[1,2-b]pyrazole-7-carboxylate (213) (821 mg, 2.09 mmol) in methanol (4 mL) and THF (1 mL) at rt was added a solution of lithium hydroxide (500 mg, 20.9 mmol) in water (6 mL) and the mixture was stirred and heated at 45° C. for overnight and TLC (30% E/H) showed reaction was completed. The reaction mixture was cooled to 0° C., neutralized by addition of 1M HCl (20.9 mL, 20.9 mmol) to pH-5, extracted with 3×30 mL EtOAc, dried (Na$_2$SO$_4$), filtered and concentrated to give a white solid desired product as a crude (781 mg, 99% yield). This crude product was used next step directly without further purification. ¹HNMR (400 MHz, CD$_3$OD): δ ppm 7.70-7.50 (m, 4H), 5.01 (s, 2H), 4.18 (dd, J=9.0, 8.2 Hz, 2H), 3.85 (dd, J=8.2, 7.1 Hz, 2H). LCMS (ES) (M+H)=380.2.

Methyl (S)-4-(1-(6-(trifluoromethyl)-1-(3-(trifluoromethyl)benzyl)-2,3-dihydro-1H-imidazo[1,2-b]pyrazole-7-carboxamido)ethyl)benzoate (217)

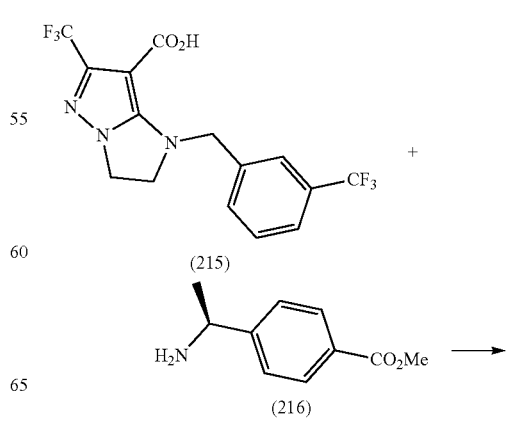

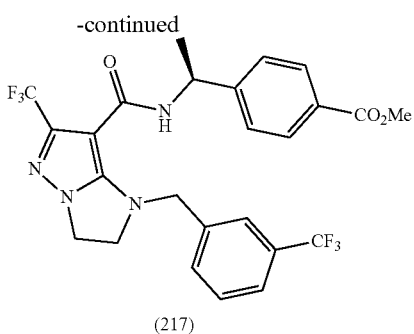

(217)

To a solution of 6-(trifluoromethyl)-1-(3-(trifluoromethyl)benzyl)-2,3-dihydro-1H-imidazo[1,2-b]pyrazole-7-carboxylic acid (215) (781 mg, 2.06 mmol), (S)-methyl 4-(1-aminoethyl)benzoate (216) (443 mg, 2.47 mmol) and HATU (1.18 g, 3.09 mmol) in DCM (10 mL) at rt was added TEA (4.31 mL, 30.9 mmol) and the resulting solution was stirred overnight. LCMS showed reaction was completed shown by only desired peak of [M+H]=541. TLC (50% E/H) showed a new major spot at $R_f$=0.45. The reaction mixture was concentrated and the residue was directly purified by silica gel chromatography (load column with DCM solution and sandwiched with heptane, 10% to 20% E/H and then 20% isocratic) to give the desired product as a white solid (1.05 g, 94% yield). $^1$HNMR (400 MHz): δ ppm 7.98 (d, J=8.2 Hz, 2H), 7.56-7.40 (m, 4H), 7.39 (d, J=8.2 Hz, 2H), 6.26 (bs, 1H), 5.23 (dq, J=7.0, 7.0 Hz, 1H), 4.87 (d, J=14.8 Hz, 1H), 4.80 (d, J=14.8 Hz, 1H), 4.17 (dd, J=8.6, 8.6 Hz, 2H), 3.90 (s, 3H), 3.76 (dd, J=8.6, 8.2 Hz, 2H), 1.53 (J=7.0 Hz, 3H). LCMS (ES) (M+H)=541.2.

(S)-4-(1-(6-(trifluoromethyl)-1-(3-(trifluoromethyl)benzyl)-2,3-dihydro-1H-imidazo[1,2-b]pyrazole-7-carboxamido)ethyl)benzoic acid (Compound 1)

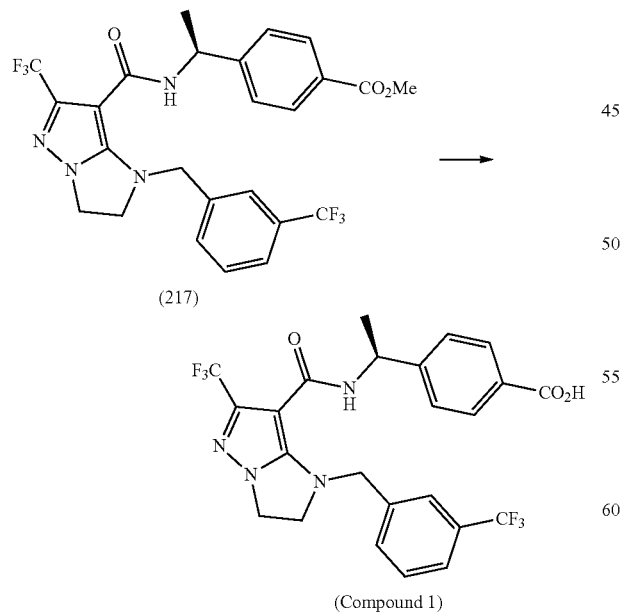

To a solution of (S)-methyl 4-(1-(6-(trifluoromethyl)-1-(3-(trifluoromethyl)benzyl)-2,3-dihydro-1H-imidazo[1,2-b]pyrazole-7-carboxamido)ethyl)benzoate (217) (950 mg, 1.76 mmol) in THF (10 mL), methanol (10 mL) and water (10 mL) at rt was added lithium hydroxise (808 mg, 33.7 mmol) and the resulting mixture was stirred at rt for 2.5 h. LCMS showed only desired peak of [M+H]=527. TLC (50% E/H) showed there is no SM at $R_f$=0.50 and only one new spot at $R_f$=0.05. TLC (5% MeOH/EtOAc) showed that there was only one spot at $R_f$=0.75. The reaction was neutralized by addition of 1M solution HCl (33.7 mL, 33.7 mmol) and concentrated to remove organic solvents. The residue was extracted by 3×50 mL EtOAc until no more product was detected by TLC. The combined organic phase was dried (Na$_2$SO$_4$), filtered and concentrated. The oily colorless residue was purified by silica gel chromatography (EtOAc then 5% MeOH/EtOAc isocratic) to give the desired product as a colorless glassy solid (925 mg, 100% yield). $^1$HNMR (400 MHz): δ ppm 8.04 (d, J=8.2 Hz, 2H), 7.58-7.40 (m, 4H), 7.42 (d, J=8.2 Hz, 2H), 6.30 (bm, 1H), 5.24 (dq, J=7.0, 7.0 Hz, 1H), 4.88 (d, J=14.8 Hz, 1H), 4.81 (d, J=14.8 Hz, 1H), 4.18 (dd, J=8.6, 8.2 Hz, 2H), 3.77 (dd, J=9.0, 8.2 Hz, 2H), 1.54 (J=7.0 Hz, 3H). LCMS (ES) (M+H)=527.2.

Example II

Methyl (S)-4-(1-(6-(trifluoromethyl)-1-(4-(trifluoromethyl)benzyl)-2,3-dihydro-1H-imidazo[1,2-b]pyrazole-7-carboxamido)ethyl)benzoate (Compound 2) and (S)-4-(1-(6-(trifluoromethyl)-1-(4-(trifluoromethyl)benzyl)-2,3-dihydro-1H-imidazo[1,2-b]pyrazole-7-carboxamido)ethyl)benzoic acid (Compound 3)

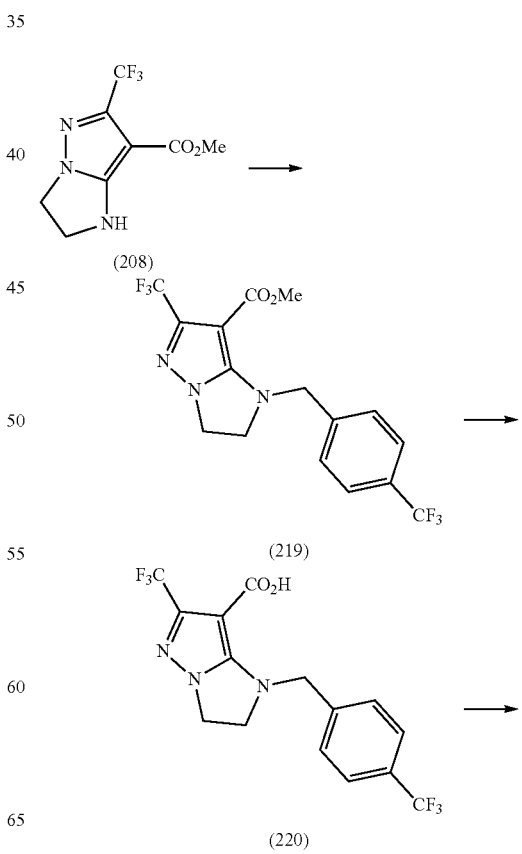

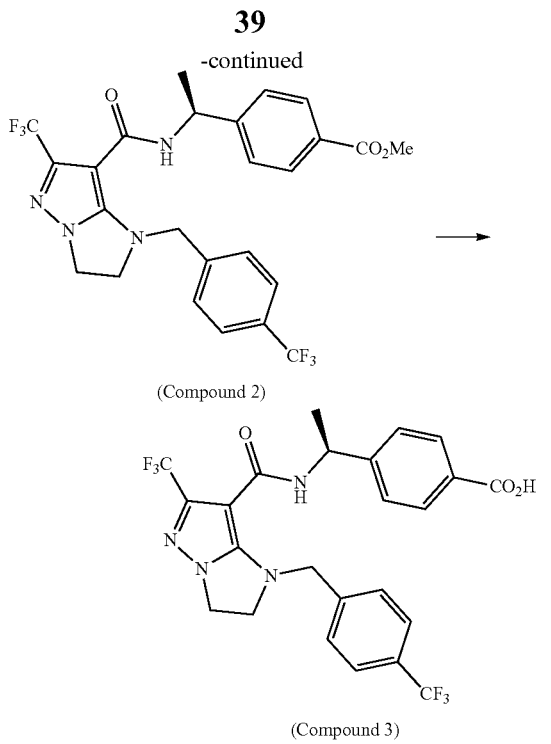

(Compound 2)

(Compound 3)

Following the similar procedure for the preparation of (S)-4-(1-(6-(trifluoromethyl)-1-(3-(trifluoromethyl)benzyl)-2,3-dihydro-1H-imidazo[1,2-b]pyrazole-7-carboxamido)ethyl)benzoic acid (Compound 1) from methyl 6-(trifluoromethyl)-2,3-dihydro-1H-imidazo[1,2-b]pyrazole-7-carboxylate (208) and 1-(chloromethyl)-3-(trifluoromethyl)benzene (214) described in Example I, Compounds 2 and 3 were similarly prepared from methyl 6-(trifluoromethyl)-2,3-dihydro-1H-imidazo[1,2-b]pyrazole-7-carboxylate (208) and 1-(chloromethyl)-4-(trifluoromethyl)benzene (218).

Methyl 6-(trifluoromethyl)-1-(4-(trifluoromethyl)benzyl)-2,3-dihydro-1H-imidazo[1,2-b]pyrazole-7-carboxylate (219)

$^1$HNMR (400 MHz): δ ppm 7.62 (J=8.0 Hz, 2H), 7.46 (d, J=8.0 Hz, 2H), 5.00 (s, 2H), 4.19 (t, J=8.0 Hz, 2H), 3.80 (t, J=8.0 Hz, 2H), 3.80 (s, 3H). LCMS (ES) (M+H)=394.

6-(trifluoromethyl)-1-(4-(trifluoromethyl)benzyl)-2,3-dihydro-1H-imidazo[1,2-b]pyrazole-7-carboxylic acid (220)

$^1$HNMR (400 MHz, CD$_3$OD): δ ppm 7.66 (J=8.0 Hz, 2H), 7.56 (d, J=8.0 Hz, 2H), 5.03 (s, 2H), 4.18 (t, J=8.0 Hz, 2H), 3.86 (t, J=8.0 Hz, 2H). LCMS (ES) (M+H)=380.

Methyl (S)-4-(1-(6-(trifluoromethyl)-1-(4-(trifluoromethyl)benzyl)-2,3-dihydro-1H-imidazo[1,2-b]pyrazole-7-carboxamido)ethyl)benzoate (Compound 2)

$^1$HNMR (400 MHz): δ ppm 7.99 (d, J=8.0 Hz, 2H), 7.56 (d, J=8.0 Hz, 2H), 7.38 (d, J=8.0 Hz, 4H), 6.26 (bs, 1H), 5.22 (m, 1H), 4.86 (d, J=15.0 Hz, 1H), 4.81 (d, J=15.0 Hz, 1H), 4.17 (t, J=8.0 Hz, 2H), 3.90 (s, 3H), 3.77 (t, J=8.0 Hz, 2H), 1.53 (d, J=8.0 Hz, 3H). LCMS (ES) (M+H)=541.

(S)-4-(1-(6-(trifluoromethyl)-1-(4-(trifluoromethyl)benzyl)-2,3-dihydro-1H-imidazo[1,2-b]pyrazole-7-carboxamido)ethyl)benzoic acid (Compound 3)

$^1$HNMR (400 MHz): δ ppm 8.07 (d, J=8.0 Hz, 2H), 7.58 (d, J=8.0 Hz, 2H), 7.44 (d, J=8.0 Hz, 2H), 7.41 (d, J=8.0 Hz, 2H), 6.31 (bs, 1H), 5.26 (m, 1H), 4.88 (dd, J=15.0 Hz, 1H), 4.84 (dd, J=15.0 Hz, 1H), 4.19 (t, J=8.0 Hz, 2H), 3.78 (t, J=8.0 Hz, 2H), 1.56 (d, J=7.0 Hz, 3H). LCMS (ES) (M+H)=527.

Following the similar procedure for the preparation of (S)-4-(1-(6-(trifluoromethyl)-1-(3-(trifluoromethyl)benzyl)-2,3-dihydro-1H-imidazo[1,2-b]pyrazole-7-carboxamido)ethyl)benzoic acid (Compound 1) from methyl 6-(trifluoromethyl)-2,3-dihydro-1H-imidazo[1,2-b]pyrazole-7-carboxylate (208) and 1-(chloromethyl)-3-(trifluoromethyl)benzene (214) described in Example I, Compounds 4-20 were similarly prepared from methyl 6-(trifluoromethyl)-2,3-dihydro-1H-imidazo[1,2-b]pyrazole-7-carboxylate (208) and the corresponding substituted benzyl halide.

Example III

(S)-4-(1-(6-(trifluoromethyl)-1-(2-(trifluoromethyl)benzyl)-2,3-dihydro-1H-imidazo[1,2-b]pyrazole-7-carboxamido)ethyl)benzoic acid (Compound 4)

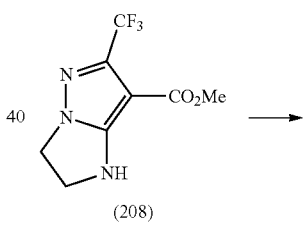

(208)

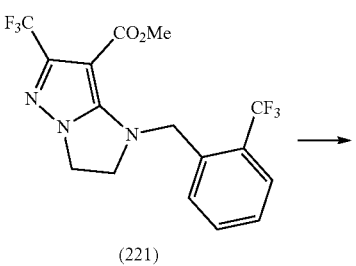

(221)

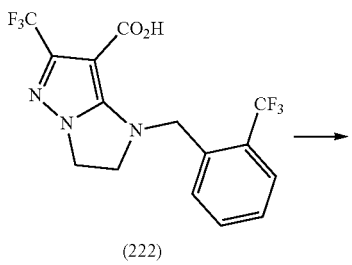

(222)

J=7.6 Hz, 1H), 7.24 (t, J=8.4 Hz, 2H), 5.02 (m, 1H), 4.54 (d, J=16.0 Hz, 1H), 4.46 (d, J=16.0 Hz, 1H), 4.15 (m, 2H), 3.71 (m, 2H), 1.35 (d, J=6.8 Hz, 3H). LCMS (ES) (M+H)=527.3.

Example IV (S)-4-(1-(1-(3,5-bis(trifluoromethyl)benzyl)-6-(trifluoromethyl)-2,3-dihydro-1H-imidazo[1,2-b]pyrazole-7-carboxamido)ethyl)benzoic acid (Compound 5)

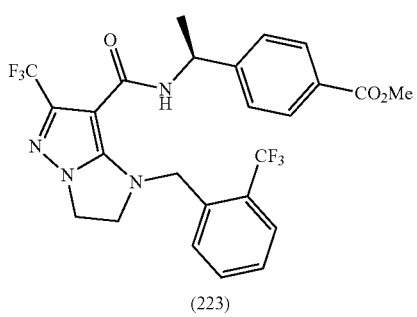
(223)

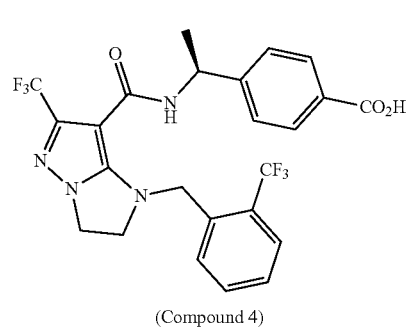
(Compound 4)

Methyl 6-(trifluoromethyl)-1-(2-(trifluoromethyl)benzyl)-2,3-dihydro-1H-imidazo[1,2-b]pyrazole-7-carboxylate (221)

¹HNMR (400 MHz, CD₃OD): δ ppm 7.62 (m, 3H), 7.41 (m, 1H), 5.08 (s, 2H), 4.18 (t, J=8.0 Hz, 2H), 3.85 (dd, J=7.2, 9.2 Hz, 2H), 3.57 (s, 3H). LCMS (ES) (M+H)=394.3.

6-(trifluoromethyl)-1-(2-(trifluoromethyl)benzyl)-2,3-dihydro-1H-imidazo[1,2-b]pyrazole-7-carboxylic acid (222)

¹HNMR (400 MHz, CD₃OD): δ ppm 7.65 (d, J=7.6 Hz, 2H), 7.57 (t, J=7.6 Hz, 1H), 7.40 (t, J=7.6 Hz, 1H), 5.13 (s, 2H), 4.16 (t, J=8.0 Hz, 2H), 3.82 (dd, J=7.2, 9.2 Hz, 2H). LCMS (ES) (M+H)=380.2.

Methyl (S)-4-(1-(6-(trifluoromethyl)-1-(2-(trifluoromethyl)benzyl)-2,3-dihydro-1H-imidazo[1,2-b]pyrazole-7-carboxamido)ethyl)benzoate (223)

¹HNMR (400 MHz): δ ppm 7.90 (d, J=8.0 Hz, 2H), 7.58 (t, J=7.2 Hz, 2H), 7.45 (d, J=8.0 Hz, 1H), 7.31 (m, 3H), 6.17 (bd, J=4.8 Hz, 1H), 5.16 (m, 1H), 4.96 (d, J=16.0 Hz, 1H), 4.89 (d, J=16.0 Hz, 1H), 4.10 (t, J=8.4 Hz, 2H), 3.83 (s, 3H), 3.67 (t, J=8.4 Hz, 2H), 1.45 (d, J=7.2 Hz, 3H). LCMS (ES) (M+H)=541.4.

(S)-4-(1-(6-(trifluoromethyl)-1-(2-(trifluoromethyl)benzyl)-2,3-dihydro-1H-imidazo[1,2-b]pyrazole-7-carboxamido)ethyl)benzoic acid (Compound 4)

¹HNMR (400 MHz, CD₃OD): δ ppm 7.69 (d, J=8.4 Hz, 2H), 7.61 (d, J=8.0 Hz, 2H), 7.53 (t, J=7.6 Hz, 1H), 7.39 (t,

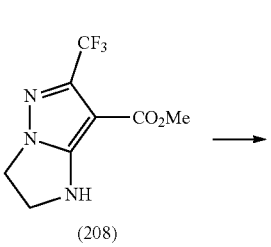
(208)

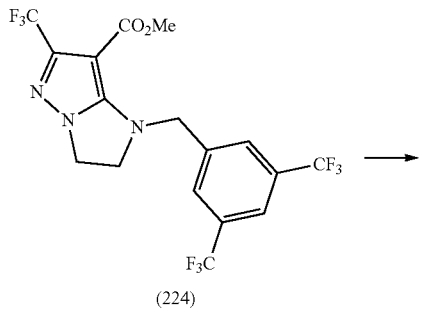
(224)

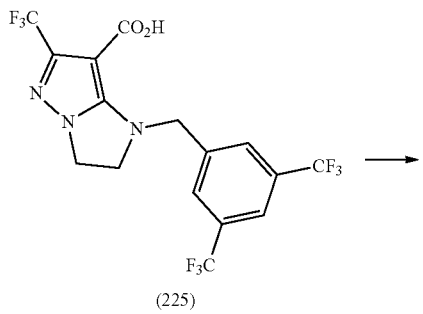
(225)

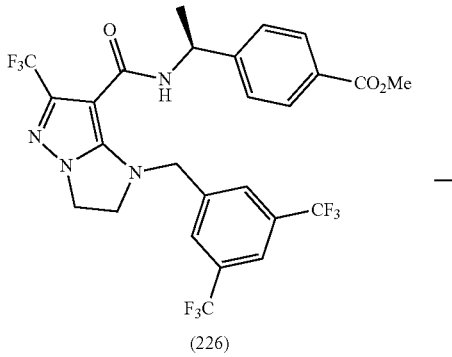
(226)

-continued

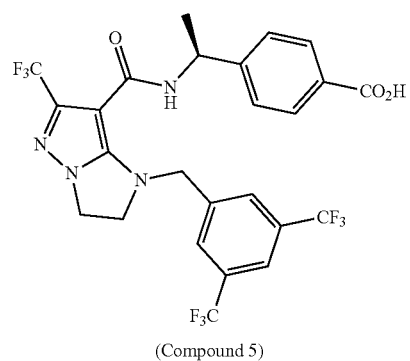

(Compound 5)

Methyl 1-(3,5-bis(trifluoromethyl)benzyl)-6-(trifluoromethyl)-2,3-dihydro-1H-imidazo[1,2-b]pyrazole-7-carboxylate (224)

$^1$HNMR (400 MHz): δ ppm 7.77 (s, 3H), 5.01 (s, 2H), 4.19 (t, J=8.4 Hz, 2H), 3.77 (t, J=8.0 Hz, 2H), 3.74 (s, 3H). LCMS (ES) (M+H)=462.2.

1-(3,5-bis(trifluoromethyl)benzyl)-6-(trifluoromethyl)-2,3-dihydro-1H-imidazo[1,2-b]pyrazole-7-carboxylic acid (225)

$^1$HNMR (400 MHz, CD$_3$OD): δ ppm 7.95 (s, 2H), 7.85 (s, 1H), 5.02 (s, 2H), 4.16 (t, J=8.4 Hz, 2H), 3.84 (dd, J=6.8, 8.8 Hz, 2H). LCMS (ES) (M+H)=448.2.

Methyl (S)-4-(1-(1-(3,5-bis(trifluoromethyl)benzyl)-6-(trifluoromethyl)-2,3-dihydro-1H-imidazo[1,2-b]pyrazole-7-carboxamido)ethyl)benzoate (226)

$^1$HNMR (400 MHz): δ ppm 7.93 (d, J=8.8 Hz, 2H), 7.75 (s, 1H), 7.73 (s, 2H), 7.31 (d, J=8.0 Hz, 1H), 6.25 (bd, J=4.0 Hz, 1H), 5.14 (m, 1H), 4.97 (d, J=14.8 Hz, 1H), 4.80 (d, J=15.2 Hz, 1H), 4.16 (t, J=8.8 Hz, 2H), 3.84 (s, 3H), 3.72 (t, J=8.8 Hz, 2H), 1.47 (d, J=6.8 Hz, 3H). LCMS (ES) (M+H)=609.3.

(S)-4-(1-(1-(3,5-bis(trifluoromethyl)benzyl)-6-(trifluoromethyl)-2,3-dihydro-1H-imidazo[1,2-b]pyrazole-7-carboxamido)ethyl)benzoic acid (Compound 5)

1HNMR (400 MHz, CD$_3$OD): δ ppm 7.84 (s, 2H), 7.81 (s, 1H), 7.72 (d, J=8.0 Hz, 2H), 7.29 (d, J=8.4 Hz, 2H), 5.06 (m, 1H), 4.44 (d, J=15.2 Hz, 1H), 4.35 (d, J=15.2 Hz, 1H), 4.16 (m, 2H), 3.74 (m, 2H), 1.39 (d, J=6.8 Hz, 3H). LCMS (ES) (M+H)=595.3.

Example V (S)-4-(1-(1-(3-chloro-5-(trifluoromethyl)benzyl)-6-(trifluoromethyl)-2,3-dihydro-1H-imidazo[1,2-b]pyrazole-7-carboxamido)ethyl)benzoic acid (Compound 6)

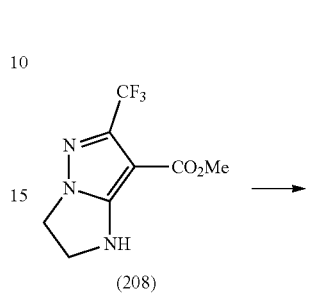

(208)

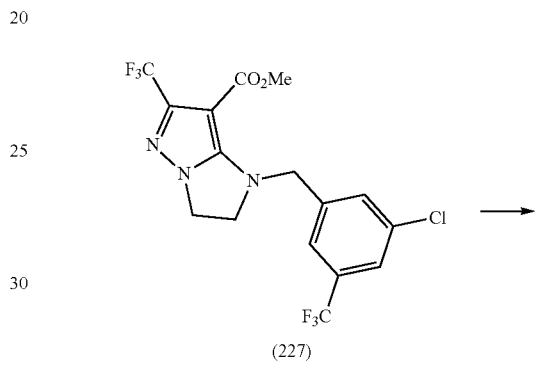

(227)

(228)

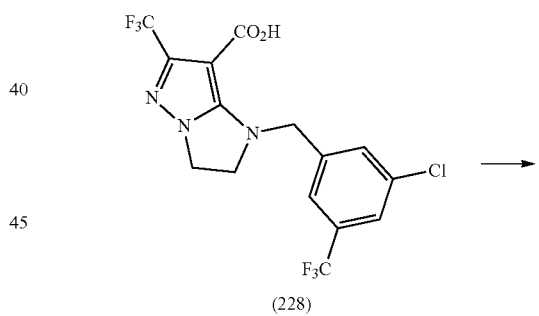

(229)

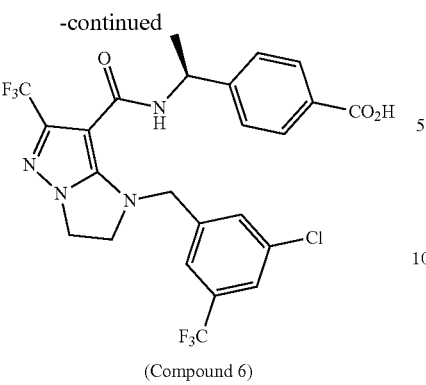

(Compound 6)

Methyl 1-(3-chloro-5-(trifluoromethyl)benzyl)-6-(trifluoromethyl)-2,3-dihydro-1H-imidazo[1,2-b]pyrazole-7-carboxylate (227)

$^1$HNMR (400 MHz): δ ppm 7.50 (bs, 1H), 7.49 (bs, 1H), 7.42 (bs, 1H), 4.92 (s, 2H), 4.17 (t, J=8.4 Hz, 2H), 3.76 (t, J=8.8 Hz, 2H), 3.74 (s, 3H). LCMS (ES) (M+H)=428.2.

1-(3-chloro-5-(trifluoromethyl)benzyl)-6-(trifluoromethyl)-2,3-dihydro-1H-imidazo[1,2-b]pyrazole-7-carboxylic acid (228)

$^1$HNMR (400 MHz): δ ppm 7.64 (bs, 1H), 7.58 (bs, 2H), 4.94 (s, 2H), 4.15 (t, J=8.0 Hz, 2H), 3.82 (t, J=8.0 Hz, 2H). LCMS (ES) (M+H)=414.2.

Methyl (S)-4-(1-(1-(3-chloro-5-(trifluoromethyl)benzyl)-6-(trifluoromethyl)-2,3-dihydro-1H-imidazo[1,2-b]pyrazole-7-carboxamido)ethyl)benzoate (229)

$^1$HNMR (400 MHz): δ ppm 7.94 (d, J=8.4 Hz, 2H), 7.47 (bs, 1H), 7.45 (bs, 1H), 7.38 (bs, 1H), 7.32 (d, J=8.0 Hz, 2H), 6.23 (bd, J=3.6 Hz, 1H), 5.15 (m, 1H), 4.84 (d, J=15.2 Hz, 1H), 4.73 (d, J=14.8 Hz, 1H), 4.17 (t, J=8.4 Hz, 2H), 3.84 (s, 3H), 3.72 (t, J=8.4 Hz, 2H), 1.47 (d, J=6.8 Hz, 3H). LCMS (ES) (M+H)=577.2.

(S)-4-(1-(1-(3-chloro-5-(trifluoromethyl)benzyl)-6-(trifluoromethyl)-2,3-dihydro-1H-imidazo[1,2-b]pyrazole-7-carboxamido)ethyl)benzoic acid (Compound 6)

$^1$HNMR (400 MHz, CD$_3$OD): δ ppm 7.76 (d, J=8.0 Hz, 2H), 7.54 (bs, 1H), 7.51 (bs, 1H), 7.49 (bs, 1H), 7.31 (d, J=8.0 Hz, 2H), 5.07 (m, 1H), 4.38 (d, J=15.2 Hz, 1H), 4.26 (d, J=15.6 Hz, 1H), 4.20 (m, 2H), 3.73 (m, 2H), 1.41 (d, J=7.2 Hz, 3H). LCMS (ES) (M+H)=561.2.

Example VI (S)-4-(1-(1-(3,5-dichlorobenzyl)-6-(trifluoromethyl)-2,3-dihydro-1H-imidazo[1,2-b]pyrazole-7-carboxamido)ethyl)benzoic acid (Compound 7)

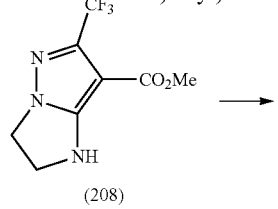

(208)

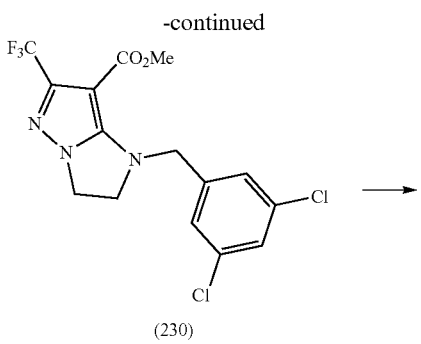

(230)

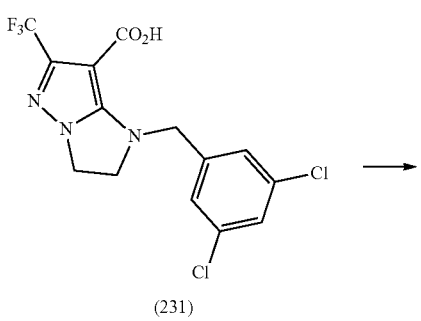

(231)

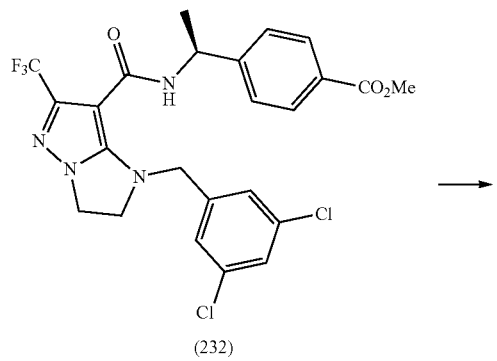

(232)

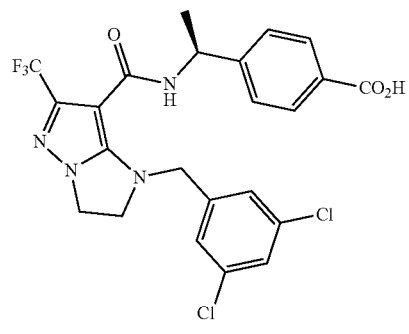

(Compound 7)

Methyl 1-(3,5-dichlorobenzyl)-6-(trifluoromethyl)-2,3-dihydro-1H-imidazo[1,2-b]pyrazole-7-carboxylate (230)

$^1$HNMR (400 MHz): δ ppm 7.25 (t, J=2.0 Hz, 1H), 7.17 (d, J=2.0 Hz, 2H), 4.84 (s, 2H), 4.16 (t, J=8.4 Hz, 2H), 3.76 (t, J=8.4 Hz, 2H), 3.75 (s, 3H). LCMS (ES) (M+H)=394.1.

1-(3,5-dichlorobenzyl)-6-(trifluoromethyl)-2,3-dihydro-1H-imidazo[1,2-b]pyrazole-7-carboxylic acid (231)

¹HNMR (400 MHz, CD₃OD): δ ppm 7.31 (m, 3H), 4.86 (s, 2H), 4.14 (t, J=7.6 Hz, 2H), 3.81 (t, J=8.0 Hz, 2H). LCMS (ES) (M+H)=380.1.

Methyl (S)-4-(1-(1-(3,5-dichlorobenzyl)-6-(trifluoromethyl)-2,3-dihydro-1H-imidazo[1,2-b]pyrazole-7-carboxamido)ethyl)benzoate (232)

¹HNMR (400 MHz): δ ppm 7.93 (d, J=8.4 Hz, 2H), 7.32 (d, J=8.0 Hz, 2H), 7.22 (t, J=1.6 Hz, 1H), 7.12 (d, J=1.6 Hz, 2H), 6.21 (bs, 1H), 5.16 (m, 1H), 4.72 (d, J=14.8, Hz, 1H), 4.65 (d, J=14.8, Hz, 1H), 4.13 (t, J=8.4 Hz, 2H), 3.84 (s, 3H), 3.72 (t, J=8.4 Hz, 2H), 1.47 (d, J=6.8 Hz, 3H). LCMS (ES) (M+H)=541.2.

(S)-4-(1-(1-(3,5-dichlorobenzyl)-6-(trifluoromethyl)-2,3-dihydro-1H-imidazo[1,2-b]pyrazole-7-carboxamido)ethyl)benzoic acid (Compound 7)

¹HNMR (400 MHz, CD₃OD): δ ppm 7.79 (d, J=8.4 Hz, 2H), 7.32 (d, J=8.4 Hz, 2H), 7.27 (s, 1H), 7.17 (bs, 2H), 5.06 (m, 1H), 4.30 (d, J=15.2 Hz, 1H), 4.16 (m, 3H), 3.75 (m, 2H), 1.41 (d, J=7.2 Hz, 3H). LCMS (ES) (M+H)=527.2.

Example VII

(S)-4-(1-(1-(4-methoxybenzyl)-6-(trifluoromethyl)-2,3-dihydro-1H-imidazo[1,2-b]pyrazole-7-carboxamido)ethyl)benzoic acid (Compound 8)

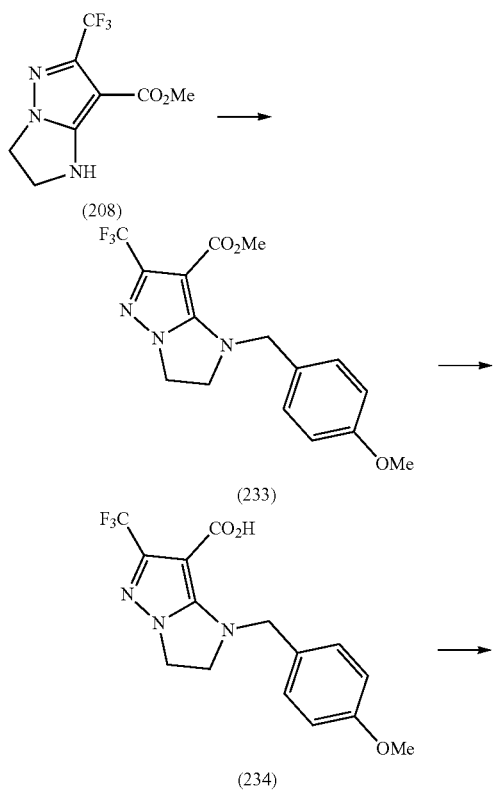

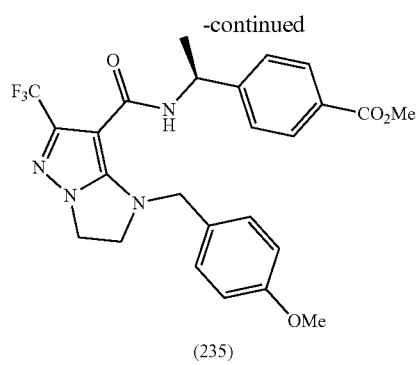

(235)

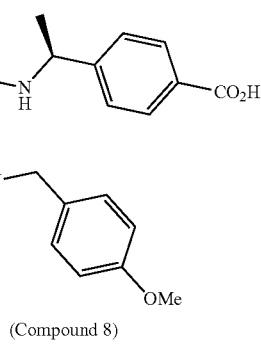

(Compound 8)

Methyl 1-(4-methoxybenzyl)-6-(trifluoromethyl)-2,3-dihydro-1H-imidazo[1,2-b]pyrazole-7-carboxylate (233)

¹HNMR (400 MHz, CD₃OD): δ ppm 7.19 (d, J=8.4 Hz, 2H), 6.84 (d, J=8.8 Hz, 2H), 4.77 (d, J=7.2 Hz, 2H), 4.06 (t, J=8.4 Hz, 2H), 3.75 (t, J=8.4 Hz, 2H), 3.72 (s, 3H), 3.71 (s, 3H). LCMS (ES) (M+H)=356.2.

1-(4-methoxybenzyl)-6-(trifluoromethyl)-2,3-dihydro-1H-imidazo[1,2-b]pyrazole-7-carboxylic acid (234)

¹HNMR (400 MHz, DMSO-d6): δ ppm 7.15 (t, J=8.8 Hz, 2H), 6.82 (dd, J=8.8, 22.0, 2H), 4.72 (s, 2H), 4.32 (d, J=5.2 Hz, 1H), 4.06 (t, J=8.4 Hz, 2H), 3.67 (t, J=8.8 Hz, 2H), 3.65 (s, 3H). LCMS (ES) (M+H)=342.3.

Methyl (S)-4-(1-(1-(4-methoxybenzyl)-6-(trifluoromethyl)-2,3-dihydro-1H-imidazo[1,2-b]pyrazole-7-carboxamido)ethyl)benzoate (235)

¹HNMR (400 MHz): δ ppm 7.93 (d, J=8.0 Hz, 2H), 7.35 (d, J=8.4 Hz, 2H), 7.08 (d, J=8.8 Hz, 2H), 6.74 (d, J=8.8 Hz, 2H), 6.18 (bs, 1H), 5.20 (m, 1H), 4.63 (d, J=14.4 Hz, 1H), 4.56 (d, J=14.4 Hz, 1H), 4.04 (t, J=8.4 Hz, 2H), 3.84 (s, 3H), 3.72 (s, 3H), 3.68 (t, J=8.4 Hz, 2H), 1.46 (bs, 3H). LCMS (ES) (M+H)=503.4.

(S)-4-(1-(1-(4-methoxybenzyl)-6-(trifluoromethyl)-2,3-dihydro-1H-imidazo[1,2-b]pyrazole-7-carboxamido)ethyl)benzoic acid (Compound 8)

¹HNMR (400 MHz, CD₃OD): δ ppm 7.81 (d, J=8.4 Hz, 2H), 7.36 (d, J=8.4 Hz, 2H), 7.04 (d, J=8.8 Hz, 2H), 6.76 (dd, J=2.0, 6.4 Hz, 2H), 5.11 (m, 1H), 4.27 (d, J=14.8 Hz, 1H), 4.12 (d, J=14.8 Hz, 1H), 4.06 (m, 2H), 3.71 (s, 3H), 3.66 (m, 2H), 1.43 (d, J=6.8 Hz, 3H). LCMS (ES) (M+H)=489.3.

Example VIII (S)-4-(1-(1-(3-methoxybenzyl)-6-(trifluoromethyl)-2,3-dihydro-1H-imidazo[1,2-b]pyrazole-7-carboxamido)ethyl)benzoic acid (Compound 9)

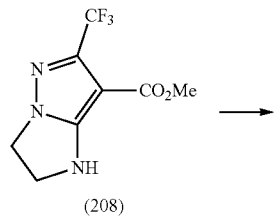

(208)

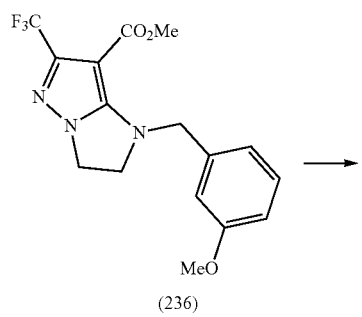

(236)

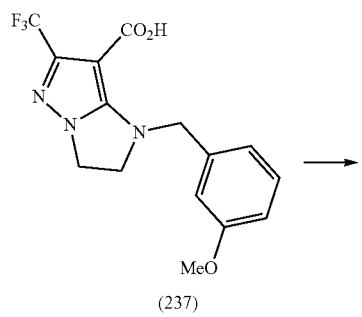

(237)

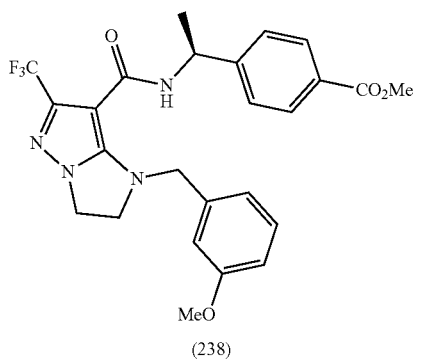

(238)

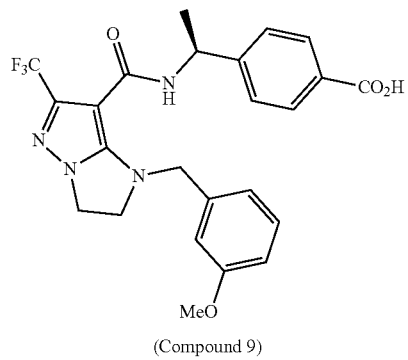

(Compound 9)

Methyl 1-(3-methoxybenzyl)-6-(trifluoromethyl)-2,3-dihydro-1H-imidazo[1,2-b]pyrazole-7-carboxylate (236)

$^1$HNMR (400 MHz, CD$_3$OD): δ ppm 7.18 (m, 1H), 6.83 (m, 3H), 7.08 (m, 2H), 4.80 (s, 2H), 4.08 (t, J=8.0 Hz, 2H), 3.78 (t, J=8.4 Hz, 2H), 3.70 (s, 3H), 3.69 (s, 3H). LCMS (ES) (M+H)=356.2.

1-(3-methoxybenzyl)-6-(trifluoromethyl)-2,3-dihydro-1H-imidazo[1,2-b]pyrazole-7-carboxylic acid (237)

$^1$HNMR (400 MHz, CD$_3$OD): δ ppm 7.18 (m, 1H), 6.84 (m, 2H), 6.77 (m, 1H), 4.83 (s, 2H), 4.08 (t, J=8.4 Hz, 2H), 3.77 (t, J=8.0 Hz, 2H), 3.70 (s, 3H). LCMS (ES) (M+H)=342.3.

Methyl (S)-4-(1-(1-(3-methoxybenzyl)-6-(trifluoromethyl)-2,3-dihydro-1H-imidazo[1,2-b]pyrazole-7-carboxamido)ethyl)benzoate (238)

$^1$HNMR (400 MHz): δ ppm 7.92 (d, J=8.4 Hz, 2H), 7.32 (d, J=8.0 Hz, 2H), 7.14 (m, 1H), 6.75 (m, 3H), 6.18 (bd, J=5.2 Hz, 1H), 5.19 (m, 1H), 4.68 (d, J=15.2 Hz, 1H), 4.63 (d, J=14.4 Hz, 1H), 4.07 (t, J=8.4 Hz, 2H), 3.84 (s, 3H), 3.72 (t, J=8.8 Hz, 2H), 3.69 (s, 3H), 1.47 (d, J=6.4 Hz, 3H). LCMS (ES) (M+H)=503.4.

(S)-4-(1-(1-(3-methoxybenzyl)-6-(trifluoromethyl)-2,3-dihydro-1H-imidazo[1,2-b]pyrazole-7-carboxamido)ethyl)benzoic acid (Compound 9)

$^1$HNMR (400 MHz, CD$_3$OD): δ ppm 7.78 (d, J=8.4 Hz, 2H), 7.33 (d, J=8.0 Hz, 2H), 7.15 (m, 2H), 6.75 (m, 3H), 5.08 (m, 1H), 4.31 (d, J=14.8 Hz, 1H), 4.18 (d, J=14.8 Hz, 1H), 4.10 (m, 2H), 3.72 (m, 2H), 3.70 (s, 3H), 1.42 (d, J=7.2 Hz, 3H). LCMS (ES) (M+H)=489.3.

Example IX (S)-4-(1-(1-(4-(trifluoromethoxy)benzyl)-6-(trifluoromethyl)-2,3-dihydro-1H-imidazo[1,2-b]pyrazole-7-carboxamido)ethyl)benzoic acid (Compound 10)

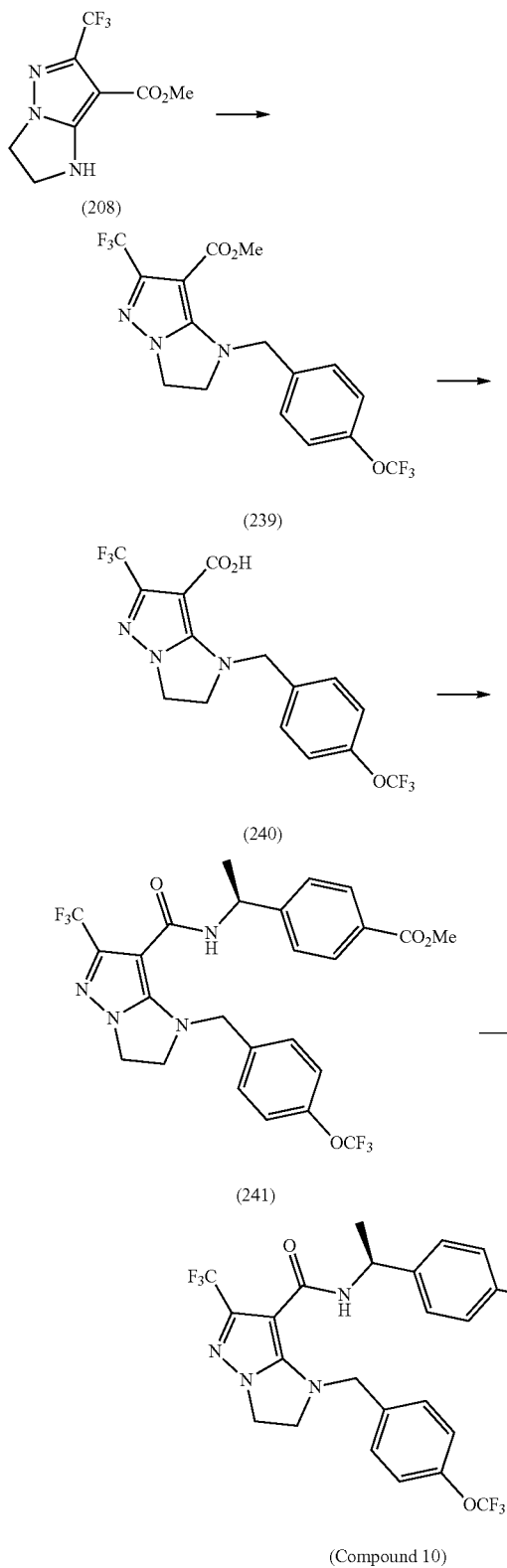

Methyl 1-(4-(trifluoromethoxy)benzyl)-6-(trifluoromethyl)-2,3-dihydro-1H-imidazo[1,2-b]pyrazole-7-carboxylate (239)

$^1$HNMR (400 MHz): δ ppm 7.30 (d, J=8.8 Hz, 2H), 7.15 (d, J=7.6 Hz, 2H), 4.88 (s, 2H), 4.12 (t, J=8.4 Hz, 2H), 3.75 (s, 3H), 3.74 (t, J=8.0 Hz, 2H). LCMS (ES) (M+H)=410.3.

1-(4-(trifluoromethoxy)benzyl)-6-(trifluoromethyl)-2,3-dihydro-1H-imidazo[1,2-b]pyrazole-7-carboxylic acid (240)

$^1$HNMR (400 MHz, CD$_3$OD): δ ppm 7.41 (dd, J=2.0, 6.8 Hz, 2H), 7.21 (d, J=8.0, 2H), 4.91 (s, 2H), 4.11 (t, J=8.4 Hz, 2H), 3.67 (dd, J=6.8, 7.2 Hz, 2H). LCMS (ES) (M+H)=395.3.

Methyl (S)-4-(1-(1-(4-(trifluoromethoxy)benzyl)-6-(trifluoromethyl)-2,3-dihydro-1H-imidazo[1,2-b]pyrazole-7-carboxamido)ethyl)benzoate (241)

$^1$HNMR (400 MHz): δ ppm 7.89 (d, J=8.0 Hz, 2H), 7.29 (d, J=8.4 Hz, 2H), 7.18 (d, J=8.4 Hz, 2H), 7.03 (d, J=7.6 Hz, 2H), 6.16 (bs, 1H), 5.13 (m, 1H), 4.69 (d, J=14.8 Hz, 1H), 4.63 (d, J=14.4 Hz, 1H), 4.06 (t, J=8.0 Hz, 2H), 3.80 (s, 3H), 3.66 (t, J=8.4 Hz, 2H), 1.43 (d, J=6.4 Hz, 3H). LCMS (ES) (M+H)=556.4.

(S)-4-(1-(1-(4-(trifluoromethoxy)benzyl)-6-(trifluoromethyl)-2,3-dihydro-1H-imidazo[1,2-b]pyrazole-7-carboxamido)ethyl)benzoic acid (Compound 10)

$^1$HNMR (400 MHz, CD$_3$OD): δ ppm 7.80 (d, J=8.4 Hz, 2H), 7.35 (d, J=8.0 Hz, 2H), 7.25 (d, J=8.8 Hz, 2H), 7.13 (d, J=8.0 Hz, 2H), 5.08 (m, 1H), 4.35 (d, J=14.8 Hz, 1H), 4.23 (d, J=14.8 Hz, 1H), 4.13 (m, 2H), 3.71 (m, 2H), 1.41 (d, J=7.2 Hz, 3H). LCMS (ES) (M+H)=543.3.

Example X (S)-4-(1-(1-(3-(trifluoromethoxy)benzyl)-6-(trifluoromethyl)-2,3-dihydro-1H-imidazo[1,2-b]pyrazole-7-carboxamido)ethyl)benzoic acid (Compound 11)

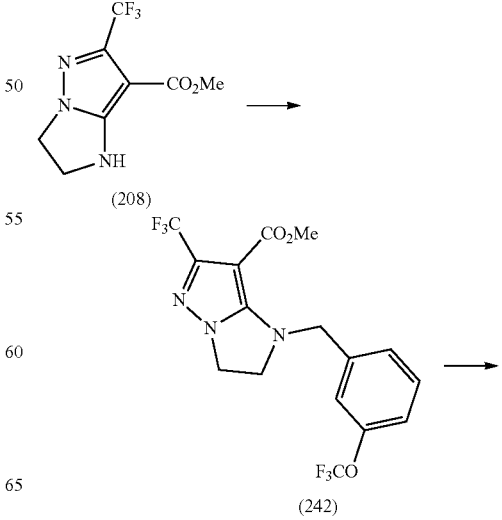

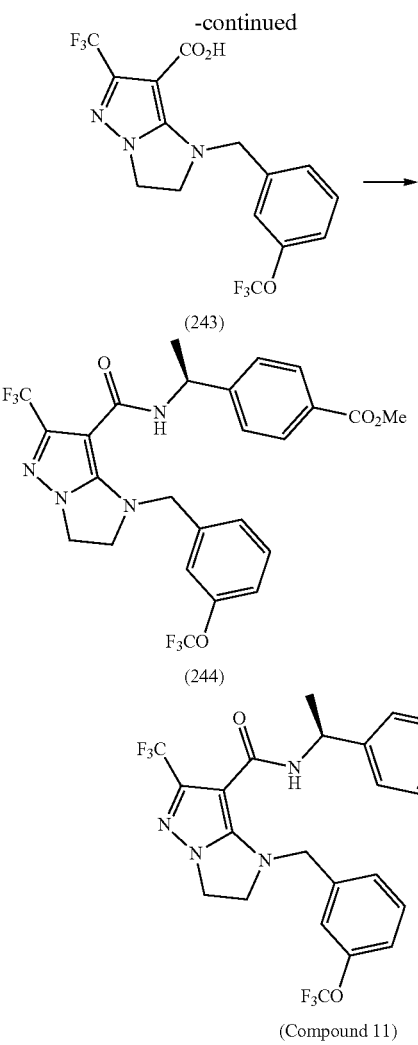

(243)

(244)

(Compound 11)

Methyl 1-(3-(trifluoromethoxy)benzyl)-6-(trifluoromethyl)-2,3-dihydro-1H-imidazo[1,2-b]pyrazole-7-carboxylate (242)

¹HNMR (400 MHz): δ ppm 7.33 (t, J=8.0 Hz, 1H), 7.20 (d, J=8.4 Hz, 1H), 7.13 (bs, 2H), 4.89 (s, 2H), 4.13 (t, J=8.8 Hz, 2H), 3.76 (t, J=8.8 Hz, 2H), 3.75 (s, 3H). LCMS (ES) (M+H)=410.2.

1-(3-(trifluoromethoxy)benzyl)-6-(trifluoromethyl)-2,3-dihydro-1H-imidazo[1,2-b]pyrazole-7-carboxylic acid (243)

¹HNMR (400 MHz, CD₃OD): δ ppm 7.40 (t, J=8.0 Hz, 1H), 7.32 (d, J=7.6 Hz, 1H), 7.25 (s, 1H), 7.15 (d, J=7.6 Hz, 1H), 4.92 (s, 2H), 4.12 (t, J=8.0 Hz, 2H), 3.81 (t, J=8.0 Hz, 2H). LCMS (ES) (M+H)=395.3.

Methyl (S)-4-(1-(1-(3-(trifluoromethoxy)benzyl)-6-(trifluoromethyl)-2,3-dihydro-1H-imidazo[1,2-b]pyrazole-7-carboxamido)ethyl)benzoate (244)

¹HNMR (400 MHz): δ ppm 7.93 (m, 2H), 7.32 (d, J=8.0 Hz, 2H), 7.26 (m, 1H), 7.17 (bd, J=8.0 Hz, 1H), 7.07 (bd, J=6.0 Hz, 2H), 6.20 (bs, 1H), 5.16 (m, 1H), 4.76 (d, J=14.8, Hz, 1H), 4.70 (d, J=15.2, Hz, 1H), 4.11 (t, J=8.0 Hz, 2H), 3.84 (s, 3H), 3.71 (t, J=8.4 Hz, 2H), 1.47 (d, J=6.8 Hz, 3H). LCMS (ES) (M+H)=556.3.

(S)-4-(1-(1-(3-(trifluoromethoxy)benzyl)-6-(trifluoromethyl)-2,3-dihydro-1H-imidazo[1,2-b]pyrazole-7-carboxamido)ethyl)benzoic acid (Compound 11)

¹HNMR (400 MHz, CD₃OD): δ ppm 7.79 (d, J=8.4 Hz, 2H), 7.33 (d, J=8.4 Hz, 2H), 7.36 (m, 1H), 7.15 (m, 3H), 5.07 (m, 1H), 4.36 (d, J=15.2 Hz, 1H), 4.27 (d, J=15.2 Hz, 1H), 4.12 (m, 2H), 3.71 (m, 2H), 1.41 (d, J=7.2 Hz, 3H). LCMS (ES) (M+H)=543.3.

Example XI (S)-4-(1-(1-(3-chlorobenzyl)-6-(trifluoromethyl)-2,3-dihydro-1H-imidazo[1,2-b]pyrazole-7-carboxamido)ethyl)benzoic acid (Compound 12)

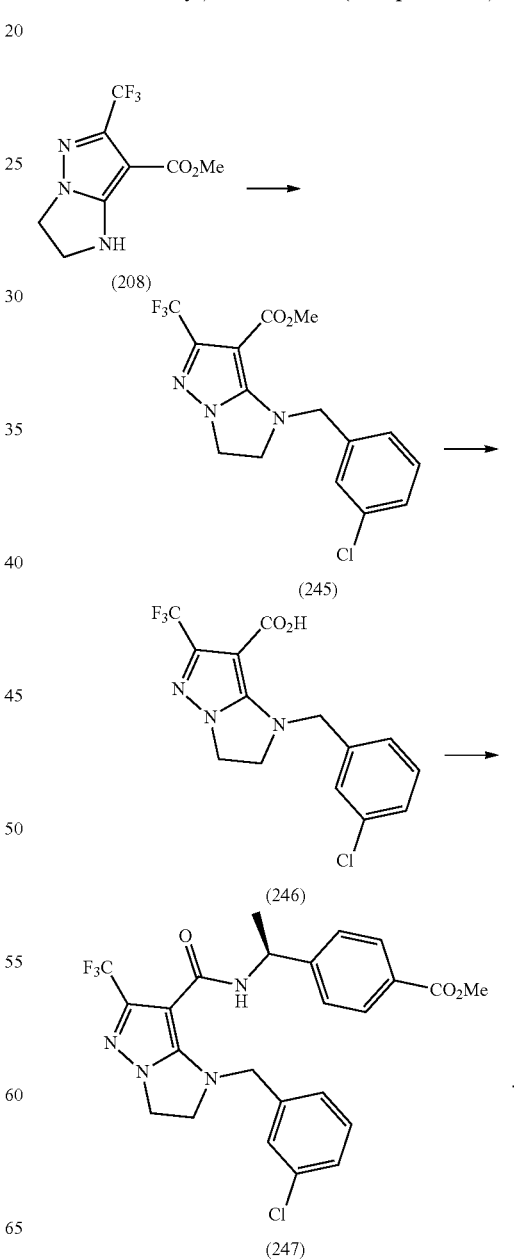

(208)

(245)

(246)

(247)

-continued

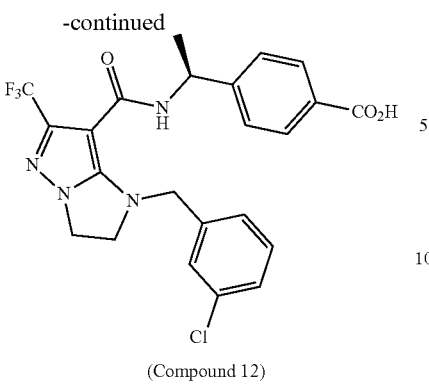

(Compound 12)

Methyl 1-(3-chlorobenzyl)-6-(trifluoromethyl)-2,3-dihydro-1H-imidazo[1,2-b]pyrazole-7-carboxylate (245)

¹HNMR (400 MHz, CD₃OD): δ ppm 7.25 (m, 4H), 4.83 (s, 2H), 4.12 (t, J=8.4 Hz, 2H), 3.80 (t, J=8.4 Hz, 2H), 3.69 (s, 3H). LCMS (ES) (M+H)=360.2.

1-(3-chlorobenzyl)-6-(trifluoromethyl)-2,3-dihydro-1H-imidazo[1,2-b]pyrazole-7-carboxylic acid (246)

¹HNMR (400 MHz, DMSO-d6): δ ppm 7.30 (m, 3H), 7.23 (m, 1H), 4.81 (s, 2H), 4.12 (t, J=8.0 Hz, 2H), 3.74 (t, J=8.0 Hz, 2H). LCMS (ES) (M+H)=346.2.

Methyl (S)-4-(1-(1-(3-chlorobenzyl)-6-(trifluoromethyl)-2,3-dihydro-1H-imidazo[1,2-b]pyrazole-7-carboxamido)ethyl)benzoate (247)

¹HNMR (400 MHz): δ ppm 7.93 (dd, J=2.0, 6.8 Hz, 2H), 7.32 (d, J=8.0 Hz, 2H), 7.18 (m, 3H), 7.07 (bd, J=4.8 Hz, 1H), 6.19 (bs, 1H), 5.17 (m, 1H), 4.68 (s, 2H), 4.10 (t, J=8.0 Hz, 2H), 3.84 (s, 3H), 3.70 (t, J=8.0 Hz, 2H), 1.47 (d, J=6.8 Hz, 3H). LCMS (ES) (M+H)=507.3.

(S)-4-(1-(1-(3-chlorobenzyl)-6-(trifluoromethyl)-2,3-dihydro-1H-imidazo[1,2-b]pyrazole-7-carboxamido)ethyl)benzoic acid (Compound 12)

¹HNMR (400 MHz, CD₃OD): δ ppm 7.80 (d, J=8.4 Hz, 2H), 7.34 (d, J=8.0 Hz, 2H), 7.22 (m, 3H), 7.09 (m, 1H), 5.08 (m, 1H), 4.32 (d, J=14.8 Hz, 1H), 4.21 (d, J=15.2 Hz, 1H), 4.11 (m, 2H), 3.71 (m, 2H), 1.42 (d, J=6.8 Hz, 3H). LCMS (ES) (M+H)=493.3.

Example XII (S)-4-(1-(1-(3,4-dichlorobenzyl)-6-(trifluoromethyl)-2,3-dihydro-1H-imidazo[1,2-b]pyrazole-7-carboxamido)ethyl)benzoic acid (Compound 13)

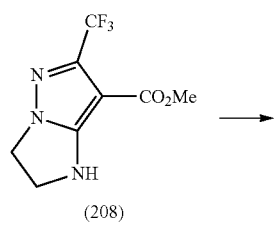

(208)

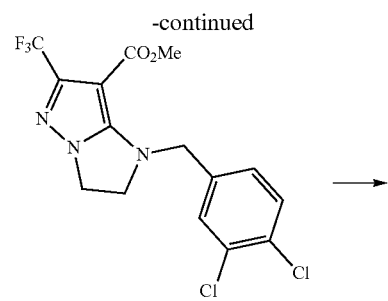

(248)

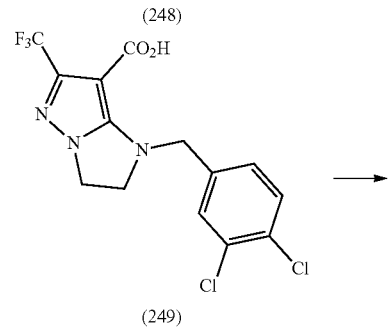

(249)

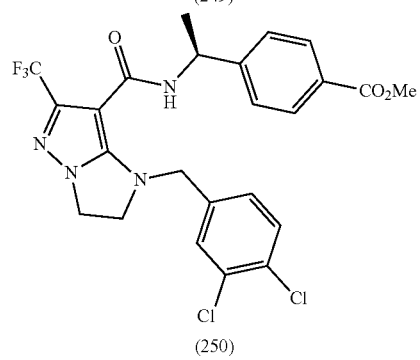

(250)

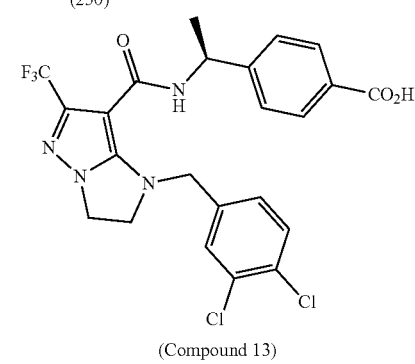

(Compound 13)

Methyl 1-(3,4-dichlorobenzyl)-6-(trifluoromethyl)-2,3-dihydro-1H-imidazo[1,2-b]pyrazole-7-carboxylate (248)

¹HNMR (400 MHz): δ ppm 7.38 (m, 2H), 7.12 (m, 1H), 4.84 (s, 2H), 4.14 (t, J=8.0 Hz, 2H), 3.74 (t, J=8.0 Hz, 2H), 3.75 (s, 3H). LCMS (ES) (M+H)=394.1.

1-(3,4-dichlorobenzyl)-6-(trifluoromethyl)-2,3-dihydro-1H-imidazo[1,2-b]pyrazole-7-carboxylic acid (249)

¹HNMR (400 MHz, CD₃OD): δ ppm 7.45 (m, 2H), 7.21 (ddd, J=2.0, 8.4, 22.0 Hz, 1H), 4.85 (s, 2H), 4.11 (t, J=8.4 Hz, 2H), 3.79 (t, J=8.4 Hz, 2H). LCMS (ES) (M+H)=380.1.

Methyl (S)-4-(1-(1-(3,4-dichlorobenzyl)-6-(trifluoromethyl)-2,3-dihydro-1H-imidazo[1,2-b]pyrazole-7-carboxamido)ethyl)benzoate (250)

¹HNMR (400 MHz): δ ppm 7.85 (d, J=8.0 Hz, 2H), 7.23 (m, 4H), 6.97 (dd, J=2.0, 8.4 Hz, 1H), 6.12 (bs, 1H), 5.08 (m, 1H), 4.59 (s, 2H), 4.03 (t, J=8.0 Hz, 2H), 3.76 (s, 3H), 3.62 (t, J=8.0 Hz, 2H), 1.39 (d, J=6.4 Hz, 3H). LCMS (ES) (M+H)=541.2.

(S)-4-(1-(1-(3,4-dichlorobenzyl)-6-(trifluoromethyl)-2,3-dihydro-1H-imidazo[1,2-b]pyrazole-7-carboxamido)ethyl)benzoic acid (Compound 13)

¹HNMR (400 MHz, CD₃OD): δ ppm 7.79 (d, J=8.4 Hz, 2H), 7.34 (m, 4H), 7.06 (dd, J=3.0, 8.4 Hz, 1H), 5.06 (m, 1H), 4.28 (d, J=14.8 Hz, 1H), 4.16 (d, J=15.2 Hz, 1H), 4.12 (m, 2H), 3.71 (m, 2H), 1.41 (d, J=7.2 Hz, 3H). LCMS (ES) (M+H)=527.2.

Example XIII

(S)-4-(1-(1-(4-fluorobenzyl)-6-(trifluoromethyl)-2,3-dihydro-1H-imidazo[1,2-b]pyrazole-7-carboxamido)ethyl)benzoic acid (Compound 14)

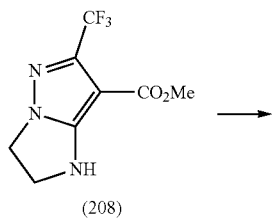

(208)

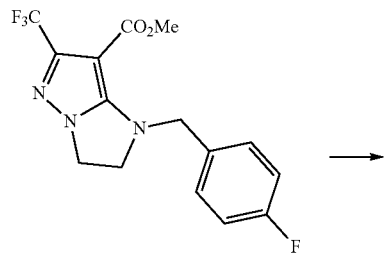

(251)

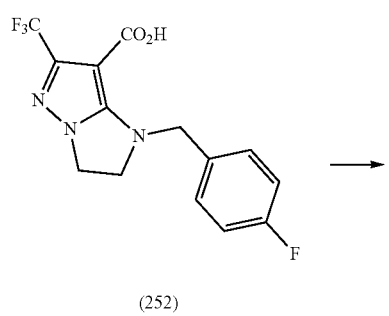

(252)

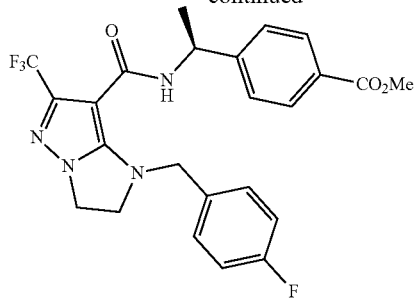

(253)

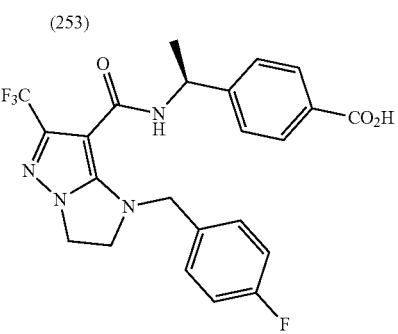

(Compound 14)

Methyl 1-(4-fluorobenzyl)-6-(trifluoromethyl)-2,3-dihydro-1H-imidazo[1,2-b]pyrazole-7-carboxylate (251)

¹HNMR (400 MHz, CD₃OD): δ ppm 7.30 (m, 2H), 7.01 (m, 2H), 4.80 (d, J=17.2 Hz, 2H), 4.10 (t, J=8.0 Hz, 2H), 3.78 (t, J=8.0 Hz, 2H), 3.70 (s, 3H). LCMS (ES) (M+H)=344.2.

1-(4-fluorobenzyl)-6-(trifluoromethyl)-2,3-dihydro-1H-imidazo[1,2-b]pyrazole-7-carboxylic acid (252)

¹HNMR (400 MHz, DMSO-d6): δ ppm 7.29 (dd, J=5.6, 8.8 Hz, 2H), 7.13 (t, J=8.8 Hz, 2H), 4.79 (s, 2H), 4.10 (t, J=8.0 Hz, 2H), 3.71 (t, J=8.4 Hz, 2H). LCMS (ES) (M+H)=330.2.

Methyl (S)-4-(1-(1-(4-fluorobenzyl)-6-(trifluoromethyl)-2,3-dihydro-1H-imidazo[1,2-b]pyrazole-7-carboxamido)ethyl)benzoate (253)

¹HNMR (400 MHz): δ ppm 7.94 (d, J=8.0 Hz, 2H), 7.34 (d, J=8.4 Hz, 2H), 7.18 (dd, J=5.6, 8.8 Hz, 2H), 6.93 (t, J=8.8 Hz, 2H), 6.20 (bd, J=4.4 Hz, 1H), 5.19 (m, 1H), 4.68 (d, J=14.4 Hz, 1H), 4.64 (d, J=14.4 Hz, 1H), 4.08 (t, J=8.4 Hz, 2H), 3.85 (s, 3H), 3.68 (t, J=8.4 Hz, 2H), 1.48 (d, J=6.4 Hz, 3H). LCMS (ES) (M+H)=491.4.

(S)-4-(1-(1-(4-fluorobenzyl)-6-(trifluoromethyl)-2,3-dihydro-1H-imidazo[1,2-b]pyrazole-7-carboxamido)ethyl)benzoic acid (Compound 14)

¹HNMR (400 MHz, CD₃OD): δ ppm 7.82 (d, J=7.6 Hz, 2H), 7.37 (d, J=8.4 Hz, 2H), 7.19 (t, J=6.0 Hz, 2H), 6.97 (t, J=8.4 Hz, 2H), 5.11 (m, 1H), 4.31 (d, J=14.8 Hz, 1H), 4.19 (d, J=14.4 Hz, 1H), 4.11 (m, 2H), 3.68 (m, 2H), 1.44 (d, J=7.2 Hz, 3H). LCMS (ES) (M+H)=477.3.

Example XIV (S)-4-(1-(1-(3-fluorobenzyl)-6-(trifluoromethyl)-2,3-dihydro-1H-imidazo[,2-b]pyrazole-7-carboxamido)ethyl)benzoic acid (Compound 15)

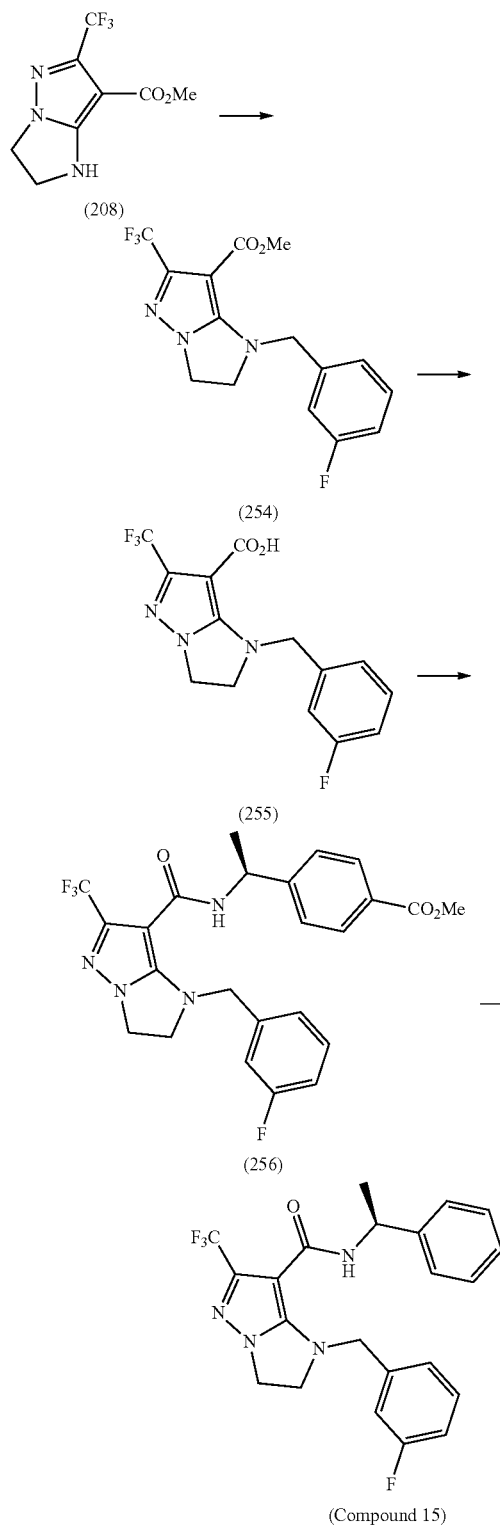

Methyl 1-(3-fluorobenzyl)-6-(trifluoromethyl)-2,3-dihydro-1H-imidazo[1,2-b]pyrazole-7-carboxylate (254)

$^1$HNMR (400 MHz, CD$_3$OD): δ ppm 7.30 (m, 1H), 7.10 (bd, J=7.2 Hz, 1H), 7.04 (bd, J=10.0 Hz, 1H), 6.96 (ddd, J=2.4, 8.4, 17.2 Hz, 1H), 4.78 (s, 2H), 4.17 (t, J=8.8 Hz, 2H), 3.81 (t, J=9.6 Hz, 2H), 3.68 (s, 3H). LCMS (ES) (M+H)=344.2.

1-(3-fluorobenzyl)-6-(trifluoromethyl)-2,3-dihydro-1H-imidazo[1,2-b]pyrazole-7-carboxylic acid (255)

$^1$HNMR (400 MHz, CD$_3$OD): δ ppm δ ppm 7.30 (m, 1H), 7.11 (bd, J=8.0 Hz, 1H), 7.06 (bd, J=9.6 Hz, 1H), 6.96 (ddd, J=2.8, 8.4, 16.8 Hz, 1H), 4.79 (s, 2H), 4.11 (t, J=8.4 Hz, 2H), 3.79 (t, J=8.4 Hz, 2H). LCMS (ES) (M+H)=326.2.

Methyl (S)-4-(1-(1-(3-fluorobenzyl)-6-(trifluoromethyl)-2,3-dihydro-1H-imidazo[1,2-b]pyrazole-7-carboxamido)ethyl)benzoate (256)

$^1$HNMR (400 MHz): δ ppm 7.92 (dd, J=2.0, 6.8 Hz, 2H), 7.32 (d, J=8.0 Hz, 2H), 7.20 (m, 1H), 6.93 (m, 3H), 6.19 (bd, J=4.4 Hz, 1H), 5.17 (m, 1H), 4.70 (s, 2H), 4.09 (t, J=8.0 Hz, 2H), 3.83 (s, 3H), 3.71 (t, J=8.0 Hz, 2H), 1.47 (d, J=6.8 Hz, 3H). LCMS (ES) (M+H)=491.4.

(S)-4-(1-(1-(3-fluorobenzyl)-6-(trifluoromethyl)-2,3-dihydro-H-imidazo[1,2-b]pyrazole-7-carboxamido)ethyl)benzoic acid (Compound 15)

$^1$HNMR (400 MHz, CD$_3$OD): δ ppm 7.78 (d, J=8.0 Hz, 2H), 7.33 (d, J=8.4 Hz, 2H), 7.24 (m, 1H), 6.95 (m, 3H), 5.07 (m, 1H), 4.33 (d, J=15.2 Hz, 1H), 4.22 (d, J=15.2 Hz, 1H), 4.12 (m, 2H), 3.67 (m, 2H), 1.41 (d, J=7.2 Hz, 3H). LCMS (ES) (M+H)=477.3.

Example XV (S)-4-(1-(1-(2-fluorobenzyl)-6-(trifluoromethyl)-2,3-dihydro-1H-imidazo[1,2-b]pyrazole-7-carboxamido)ethyl)benzoic acid (Compound 16)

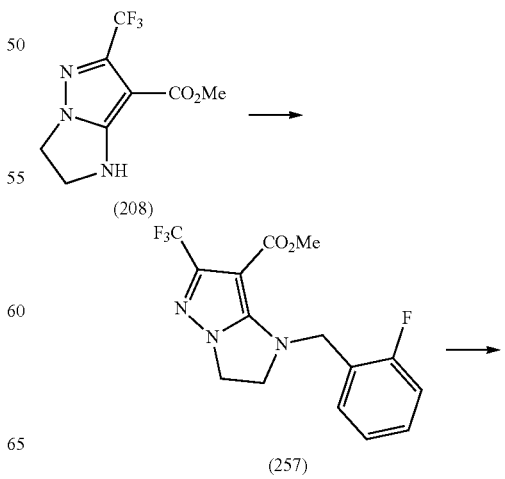

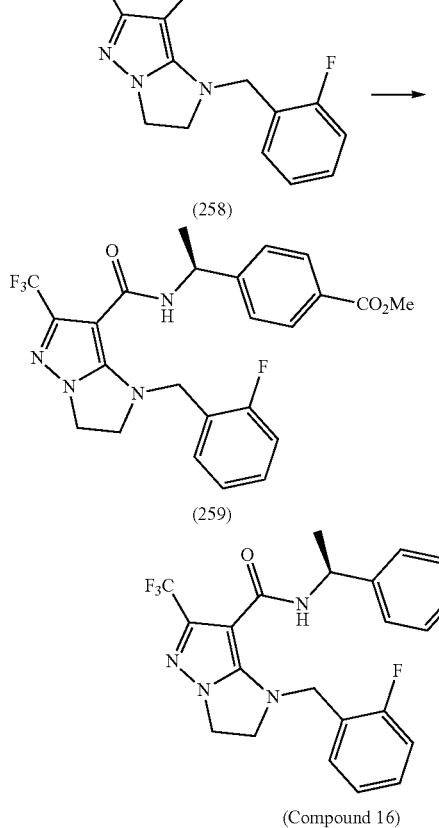

(258)

(259)

(Compound 16)

Methyl 1-(2-fluorobenzyl)-6-(trifluoromethyl)-2,3-dihydro-1H-imidazo[1,2-b]pyrazole-7-carboxylate (257)

¹HNMR (400 MHz): δ ppm 7.36 (m, 1H), 7.27 (m, 1H), 7.08 (m, 2H), 4.95 (s, 2H), 4.11 (t, J=8.4 Hz, 2H), 3.83 (t, J=8.4 Hz, 2H), 3.69 (s, 3H). LCMS (ES) (M+H)=344.2.

1-(2-fluorobenzyl)-6-(trifluoromethyl)-2,3-dihydro-1H-imidazo[1,2-b]pyrazole-7-carboxylic acid (258)

¹HNMR (400 MHz, DMSO-d6): δ ppm 7.31 (m, 2H), 7.13 (m, 2H), 4.90 (s, 2H), 4.10 (t, J=8.0 Hz, 2H), 3.73 (t, J=8.0 Hz, 2H). LCMS (ES) (M+H)=330.2.

Methyl (S)-4-(1-(1-(2-fluorobenzyl)-6-(trifluoromethyl)-2,3-dihydro-1H-imidazo[1,2-b]pyrazole-7-carboxamido)ethyl)benzoate (259)

¹HNMR (400 MHz): δ ppm 7.94 (d, J=8.4 Hz, 2H), 7.35 (d, J=8.0 Hz, 2H), 7.21 (m, 2H), 6.96 (m, 2H), 6.19 (bs, 1H), 5.21 (m, 1H), 4.81 (d, J=15.2 Hz, 1H), 4.74 (d, J=14.8 Hz, 1H), 4.06 (t, J=8.0 Hz, 2H), 3.84 (s, 3H), 3.75 (t, J=8.0 Hz, 2H), 1.48 (d, J=6.4 Hz, 3H). LCMS (ES) (M+H)=491.4.

(S)-4-(1-(1-(2-fluorobenzyl)-6-(trifluoromethyl)-2,3-dihydro-1H-imidazo[1,2-b]pyrazole-7-carboxamido)ethyl)benzoic acid (Compound 16)

¹HNMR (400 MHz, CD₃OD): δ ppm 7.82 (d, J=8.4 Hz, 2H), 7.36 (d, J=8.4 Hz, 2H), 7.22 (m, 2H), 7.02 (m, 2H), 5.10 (m, 1H), 4.43 (d, J=15.2 Hz, 1H), 4.37 (d, J=15.2 Hz, 1H), 4.11 (m, 2H), 3.75 (m, 2H), 1.43 (d, J=6.8 Hz, 3H). LCMS (ES) (M+H)=477.3.

Example XVI (S)-4-(1-(1-(4-methylbenzyl)-6-(trifluoromethyl)-2,3-dihydro-1H-imidazo[1,2-b]pyrazole-7-carboxamido)ethyl)benzoic acid (Compound 17)

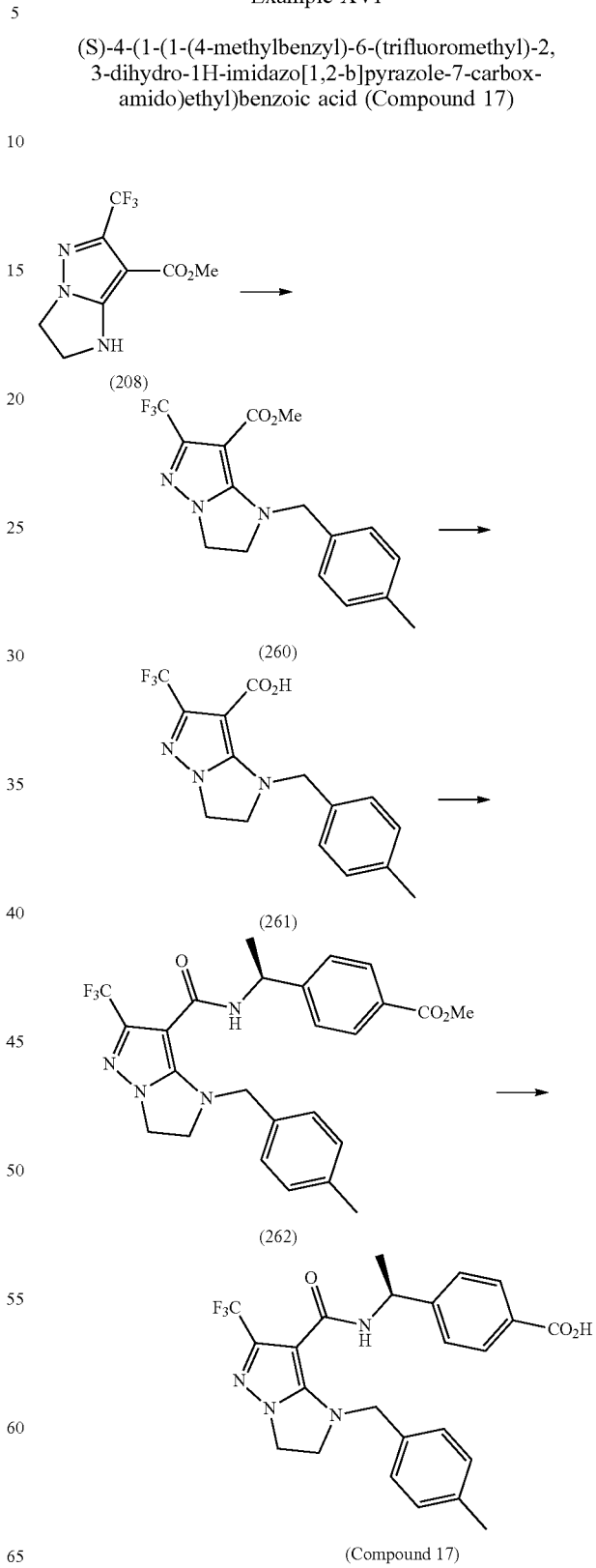

Methyl 1-(4-methylbenzyl)-6-(trifluoromethyl)-2,3-dihydro-1H-imidazo[1,2-b]pyrazole-7-carboxylate (260)

¹HNMR (400 MHz, CD₃OD): δ ppm 7.15 (d, J=8.4 Hz, 2H), 7.10 (d, J=8.0 Hz, 2H), 4.79 (d, J=2.8 Hz, 2H), 4.08 (t, J=8.4 Hz, 2H), 3.77 (t, J=8.0 Hz, 2H), 3.71 (s, 3H), 2.26 (s, 3H). LCMS (ES) (M+H)=340.2.

1-(4-methylbenzyl)-6-(trifluoromethyl)-2,3-dihydro-1H-imidazo[1,2-b]pyrazole-7-carboxylic acid (261)

¹HNMR (400 MHz, DMSO-d6): δ ppm 7.12 (d, J=8.0 Hz, 2H), 7.09 (d, J=8.4 Hz, 2H), 4.75 (s, 2H), 4.08 (t, J=8.8 Hz, 2H), 3.69 (t, J=8.8 Hz, 2H), 2.21 (s, 3H). LCMS (ES) (M+H)=326.2.

Methyl (S)-4-(1-(1-(4-methylbenzyl)-6-(trifluoromethyl)-2,3-dihydro-1H-imidazo[1,2-b]pyrazole-7-carboxamido)ethyl)benzoate (262)

¹HNMR (400 MHz): δ ppm 7.92 (d, J=8.0 Hz, 2H), 7.32 (d, J=8.0 Hz, 2H), 7.05 (d, J=9.6 Hz, 2H), 7.02 (d, J=9.6 Hz, 2H), 6.16 (bd, J=5.6 Hz, 1H), 5.19 (m, 1H), 4.65 (d, J=14.4 Hz, 1H), 4.59 (d, J=14.4 Hz, 1H), 4.04 (t, J=8.4 Hz, 2H), 3.83 (s, 3H), 3.68 (t, J=8.4 Hz, 2H), 2.26 (s, 3H), 1.47 (d, J=7.2 Hz, 3H). LCMS (ES) (M+H)=487.4.

(S)-4-(1-(1-(4-methylbenzyl)-6-(trifluoromethyl)-2,3-dihydro-1H-imidazo[1,2-b]pyrazole-7-carboxamido)ethyl)benzoic acid (Compound 17)

¹HNMR (400 MHz, CD₃OD): δ ppm 7.78 (d, J=8.8 Hz, 2H), 7.34 (d, J=8.0 Hz, 2H), 7.05 (d, J=8.8 Hz, 2H), 7.02 (d, J=8.4 Hz, 2H), 5.09 (m, 1H), 4.29 (d, J=14.4 Hz, 1H), 4.13 (d, J=14.4 Hz, 1H), 4.06 (m, 2H), 3.67 (m, 2H), 2.25 (s, 3H), 1.42 (d, J=6.8 Hz, 3H). LCMS (ES) (M+H)=473.4.

Example XVII (S)-4-(1-(1-(3-methylbenzyl)-6-(trifluoromethyl)-2,3-dihydro-1H-imidazo[1,2-b]pyrazole-7-carboxamido)ethyl)benzoic acid (Compound 18)

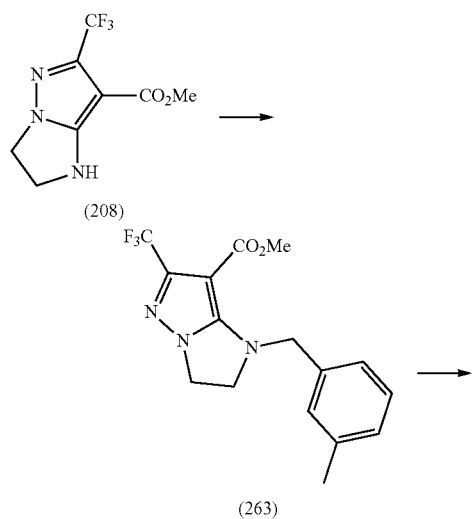

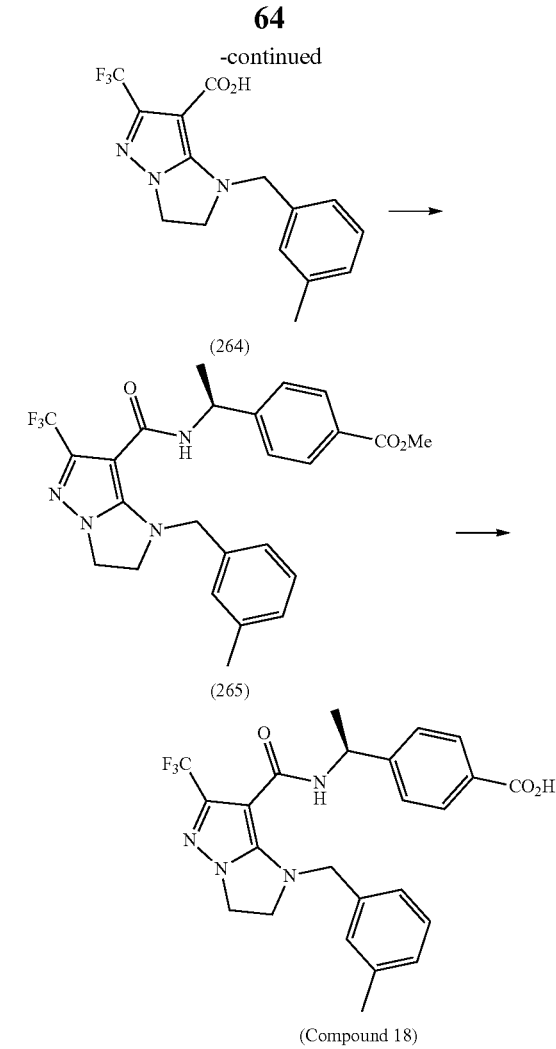

Methyl 1-(3-methylbenzyl)-6-(trifluoromethyl)-2,3-dihydro-1H-imidazo[1,2-b]pyrazole-7-carboxylate (263)

¹HNMR (400 MHz, CD₃OD): δ ppm 7.15 (m, 2H), 7.06 (m, 3H), 4.78 (d, J=6.0 Hz, 2H), 4.08 (t, J=8.0 Hz, 2H), 3.77 (t, J=8.8 Hz, 2H), 3.70 (s, 3H), 2.26 (s, 3H). LCMS (ES) (M+H)=340.2.

1-(3-methylbenzyl)-6-(trifluoromethyl)-2,3-dihydro-1H-imidazo[1,2-b]pyrazole-7-carboxylic acid (264)

¹HNMR (400 MHz, DMSO-d6): δ ppm 7.10 (m, 5H), 4.83 (s, 2H), 4.49 (s, 1H), 4.07 (t, J=8.4 Hz, 2H), 3.75 (t, J=8.4 Hz, 2H), 2.26 (s, 3H). LCMS (ES) (M+H)=326.2.

Methyl (S)-4-(1-(1-(3-methylbenzyl)-6-(trifluoromethyl)-2,3-dihydro-1H-imidazo[1,2-b]pyrazole-7-carboxamido)ethyl)benzoate (265)

¹HNMR (400 MHz): δ ppm 7.91 (d, J=8.4 Hz, 2H), 7.32 (d, J=8.0 Hz, 2H), 7.12 (t, J=7.6 Hz, 1H), 7.00 (m, 2H), 6.20 (bd, J=5.2 Hz, 1H), 5.19 (m, 1H), 4.63 (s, 2H), 4.06 (t, J=8.0 Hz, 2H), 3.83 (s, 3H), 3.69 (t, J=8.4 Hz, 2H), 2.24 (s, 3H), 1.47 (d, J=6.4 Hz, 3H). LCMS (ES) (M+H)=487.4.

(S)-4-(1-(1-(3-methylbenzyl)-6-(trifluoromethyl)-2,3-dihydro-1H-imidazo[1,2-b]pyrazole-7-carboxamido)ethyl)benzoic acid (Compound 18)

¹HNMR (400 MHz, CD₃OD): δ ppm 7.77 (d, J=8.0 Hz, 2H), 7.33 (d, J=8.4 Hz, 2H), 7.12 (t, J=8.0 Hz, 2H), 6.97 (t, J=8.0 Hz, 2H), 5.09 (m, 1H), 4.28 (d, J=15.2 Hz, 1H), 4.13 (d, J=14.4 Hz, 1H), 4.09 (m, 2H), 3.68 (m, 2H), 2.24 (s, 3H), 1.42 (d, J=6.8 Hz, 3H). LCMS (ES) (M+H)=473.4.

Example XVIII (S)-4-(1-(1-(2-methylbenzyl)-6-(trifluoromethyl)-2,3-dihydro-1H-imidazo[1,2-b]pyrazole-7-carboxamido)ethyl)benzoic acid (Compound 19)

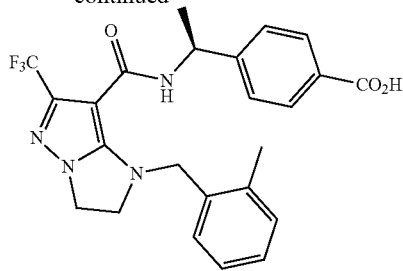

(Compound 19)

Methyl 1-(2-methylbenzyl)-6-(trifluoromethyl)-2,3-dihydro-1H-imidazo[1,2-b]pyrazole-7-carboxylate (266)

¹HNMR (400 MHz, CD₃OD): δ ppm 7.20 (d, J=6.8 Hz, 1H), 7.11 (m, 3H), 4.88 (s, 2H), 4.09 (t, J=8.4 Hz, 2H), 3.69 (t, J=8.0 Hz, 2H), 3.66 (s, 3H), 2.31 (s, 3H). LCMS (ES) (M+H)=340.2.

1-(2-methylbenzyl)-6-(trifluoromethyl)-2,3-dihydro-1H-imidazo[1,2-b]pyrazole-7-carboxylic acid (267)

¹HNMR (400 MHz, CD₃OD): δ ppm 7.17 (d, J=30.0 Hz, 1H), 7.11 (m, 3H), 4.93 (s, 2H), 4.09 (t, J=8.0 Hz, 2H), 3.67 (t, J=8.4 Hz, 2H), 2.32 (s, 3H). LCMS (ES) (M+H)=326.2.

Methyl (S)-4-(1-(1-(2-methylbenzyl)-6-(trifluoromethyl)-2,3-dihydro-1H-imidazo[1,2-b]pyrazole-7-carboxamido)ethyl)benzoate (268)

¹HNMR (400 MHz): δ ppm 7.91 (d, J=8.0 Hz, 2H), 7.29 (d, J=8.4 Hz, 2H), 7.10 (m, 4H), 6.13 (bd, J=5.6 Hz, 1H), 5.16 (m, 1H), 4.69 (s, 2H), 4.07 (t, J=8.4 Hz, 2H), 3.83 (s, 3H), 3.61 (t, J=8.0 Hz, 2H), 2.25 (s, 3H), 1.44 (d, J=6.8 Hz, 3H). LCMS (ES) (M+H)=487.4.

(S)-4-(1-(1-(2-methylbenzyl)-6-(trifluoromethyl)-2,3-dihydro-1H-imidazo[1,2-b]pyrazole-7-carboxamido)ethyl)benzoic acid (Compound 19)

¹HNMR (400 MHz, CD₃OD): δ ppm 7.78 (d, J=8.4 Hz, 2H), 7.30 (d, J=8.0 Hz, 2H), 7.21 (d, J=8.0 Hz, 1H), 7.10 (m, 3H), 5.06 (m, 1H), 4.32 (d, J=14.8 Hz, 1H), 4.27 (d, J=14.8 Hz, 1H), 4.12 (t, J=8.4 Hz, 2H), 3.66 (m, 2H), 2.11 (s, 3H), 1.39 (d, J=6.8 Hz, 3H). LCMS (ES) (M+H)=473.4.

Example XIX (S)-4-(1-(1-(4-ethylbenzyl)-6-(trifluoromethyl)-2,3-dihydro-1H-imidazo[1,2-b]pyrazole-7-carboxamido)ethyl)benzoic acid (Compound 20)

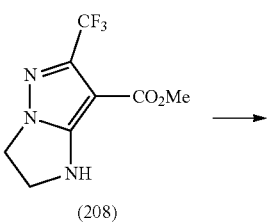

(208)

-continued

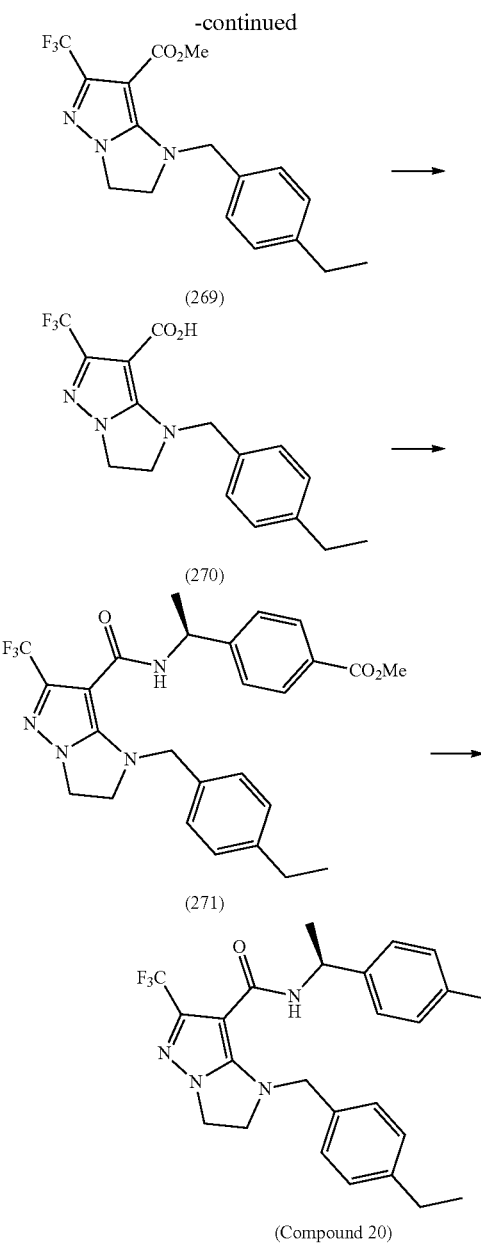

(269)

(270)

(Compound 20)

Methyl 1-(4-ethylbenzyl)-6-(trifluoromethyl)-2,3-dihydro-1H-imidazo[1,2-b]pyrazole-7-carboxylate (269)

¹HNMR (400 MHz, CD₃OD): δ ppm 7.17 (d, J=8.0 Hz, 2H), 7.13 (d, J=8.0 Hz, 2H), 4.79 (d, J=6.4 Hz, 2H), 4.07 (t, J=8.4 Hz, 2H), 3.76 (t, J=8.0 Hz, 2H), 3.70 (s, 3H), 2.56 (q, J=8.0 Hz, 2H), 1.15 (t, J=8.0 Hz, 3H). LCMS (ES) (M+H)=354.3.

1-(4-ethylbenzyl)-6-(trifluoromethyl)-2,3-dihydro-1H-imidazo[1,2-b]pyrazole-7-carboxylic acid (270)

¹HNMR (400 MHz, DMSO-d6)
δ ppm 7.13 (m, 4H), 4.76 (s, 2H), 4.09 (t, J=8.4 Hz, 2H), 3.70 (t, J=9.2 Hz, 2H), 2.49 (q, J=7.6 Hz, 2H), 1.09 (t, J=7.6 Hz, 3H). LCMS (ES) (M+H)=340.3.

Methyl (S)-4-(1-(1-(4-ethylbenzyl)-6-(trifluoromethyl)-2,3-dihydro-1H-imidazo[1,2-b]pyrazole-7-carboxamido)ethyl)benzoate (271)

¹HNMR (400 MHz): δ ppm 7.93 (dd, J=2.0, 6.8 Hz, 2H), 7.34 (bt, J=8.8 Hz, 4H), 6.17 (bd, J=4.8 Hz, 1H), 5.19 (m, 1H), 4.66 (d, J=14.4 Hz, 1H), 4.60 (d, J=14.4 Hz, 1H), 4.05 (t, J=8.0 Hz, 2H), 3.84 (s, 3H), 3.70 (t, J=8.0 Hz, 2H), 2.56 (q, J=7.6 Hz, 2H), 1.47 (d, J=6.8 Hz, 3H), 1.15 (t, J=7.2 Hz, 3H). LCMS (ES) (M+H)=501.4.

(S)-4-(1-(1-(4-ethylbenzyl)-6-(trifluoromethyl)-2,3-dihydro-1H-imidazo[1,2-b]pyrazole-7-carboxamido)ethyl)benzoic acid (Compound 20)

¹HNMR (400 MHz, CD₃OD): δ ppm 7.79 (d, J=8.4 Hz, 2H), 7.35 (d, J=8.0 Hz, 2H), 7.07 (d, J=8.8 Hz, 2H), 7.05 (d, J=8.8 Hz, 2H), 5.10 (m, 1H), 4.31 (d, J=14.4 Hz, 1H), 4.11 (d, J=14.4 Hz, 1H), 4.08 (m, 2H), 3.68 (m, 2H), 2.56 (q, J=7.6 Hz, 2H), 1.42 (d, J=6.8 Hz, 3H), 1.15 (t, J=7.6 Hz, 3H). LCMS (ES) (M+H)=487.3.

Example XX (S)-2-fluoro-4-(1-(6-(trifluoromethyl)-1-(4-(trifluoromethyl)benzyl)-2,3-dihydro-1H-imidazo[1,2-b]pyrazole-7-carboxamido)ethyl)benzoic acid (Compound 21)

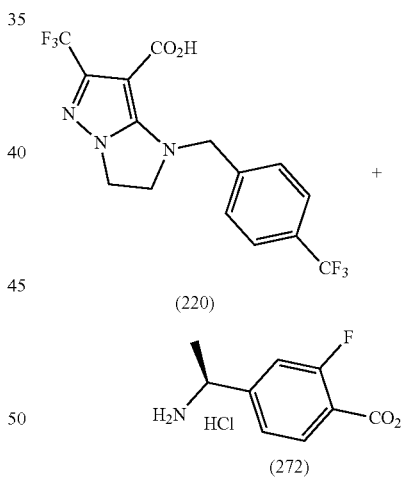

(220)

+

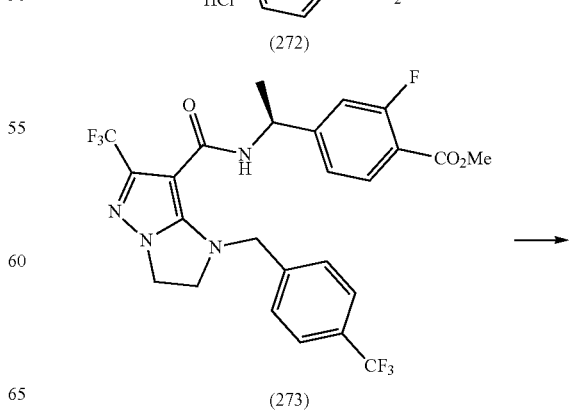

(272)

(273)

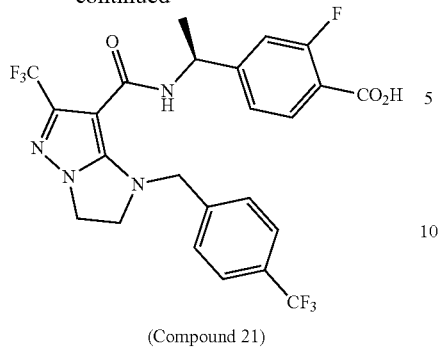

(Compound 21)

Following the procedure for the preparation of (S)-4-(1-(6-(trifluoromethyl)-1-(3-(trifluoromethyl)benzyl)-2,3-dihydro-1H-imidazo[1,2-b]pyrazole-7-carboxamido)ethyl)benzoic acid (Compound 1) from 6-(trifluoromethyl)-1-(3-(trifluoromethyl)benzyl)-2,3-dihydro-1H-imidazo[1,2-b]pyrazole-7-carboxylic acid (215) described in Example I, Compound 21 was prepared from 6-(trifluoromethyl)-1-(4-(trifluoromethyl)benzyl)-2,3-dihydro-1H-imidazo[1,2-b]pyrazole-7-carboxylic acid (220) and methyl (S)-4-(1-aminoethyl)-2-fluorobenzoate hydrochloride (272).

Methyl (S)-2-fluoro-4-(1-(6-(trifluoromethyl)-1-(4-(trifluoromethyl)benzyl)-2,3-dihydro-1H-imidazo[1,2-b]pyrazole-7-carboxamido)ethyl)benzoate (273)

$^1$HNMR (400 MHz): δ ppm 7.89 (dd, J=7.8, 7.4 Hz, 1H), 7.57 (d, J=7.8 Hz, 2H), 7.39 (d, J=7.8 Hz, 2H), 7.15 (dd, J=8.2, 1.5 Hz 1H), 7.09 (dd, J=11.8, 1.5 Hz, 1H), 6.25 (bs, 1H), 5.17 (dq, J=7.0, 7.0 Hz, 1H), 4.84 (s, 2H), 4.18 (dd, J=8.6, 8.2 Hz, 2H), 3.91 (s, 3H), 3.77 (dd, J=9.0, 8.2 Hz, 2H), 1.52 (J=7.1 Hz, 3H). LCMS (ES) (M+H)=559.2.

(S)-2-fluoro-4-(1-(6-(trifluoromethyl)-1-(4-(trifluoromethyl)benzyl)-2,3-dihydro-1H-imidazo[1,2-b]pyrazole-7-carboxamido)ethyl)benzoic acid (Compound 21)

$^1$HNMR (400 MHz): δ ppm 7.89 (dd, J=7.8, 7.4 Hz, 1H), 7.56 (d, J=7.4 Hz, 2H), 7.39 (d, J=7.4 Hz, 2H), 7.14 (dd, J=8.9, 1.5 Hz, 1H), 7.08 (dd, J=11.5, 1.5 Hz, 1H), 6.27 (bs, 1H), 5.15 (dq, J=7.0, 7.0 Hz, 1H), 4.88 (d, J=15.0, 1H), 4.78 (d, J=15.0 Hz, 1H), 4.17 (dd, J=9.4, 7.8 Hz, 2H), 3.75 (dd, J=8.4, 8.2 Hz, 2H), 1.50 (J=7.0 Hz, 3H). LCMS (ES) (M+H)=543.3.

Example XXI (S)-3-fluoro-4-(1-(6-(trifluoromethyl)-1-(4-(trifluoromethyl)benzyl)-2,3-dihydro-1H-imidazo[1,2-b]pyrazole-7-carboxamido)ethyl)benzoic acid (Compound 22)

Methyl (S)-4-(1-aminoethyl)-3-fluorobenzoate hydrochloride (275)

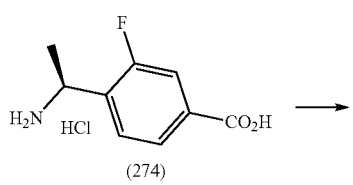

(274)

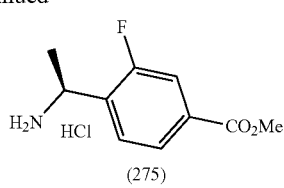

(275)

A solution of (S)-4-(1-aminoethyl)-3-fluorobenzoic acid hydrochloride (274) (500 mg, 2.28 mmol) in methanol (20 mL, 494 mmol) and 4 M hydrochloric acid (2.5 mL, 10.0 mmol) in 1,4-dioxane was heated at reflux for 1.5 h. LCMS after 1 h showed reaction was completed shown by strong peak of [M-NH$_3$+H]=181 and small peak of [M+H]=198. The mixture was concentrated to a pinky gum-like residue. It was then dissolved in EtOAc and concentrated to a glassy solid. Repeat this twice and it resulted in the desired product as a pinky solid (538 mg, 100% yield). $^1$HNMR (400 MHz, CD$_3$OD): δ ppm 7.93 (dd, dd, J=7.8, 1.4 Hz, 1H), 7.81 (dd, J=11.0, 1.5 Hz, 1H), 7.63 (dd, J=7.8, 7.8 Hz, 1H), 4.78 (q, J=7.0 Hz, 1H), 3.93 (s, 3H), 1.66 (d, J=6.6 Hz, 3H), LCMS (ES) (M+H)=198.0 and (M-NH$_3$+H)=181.0.

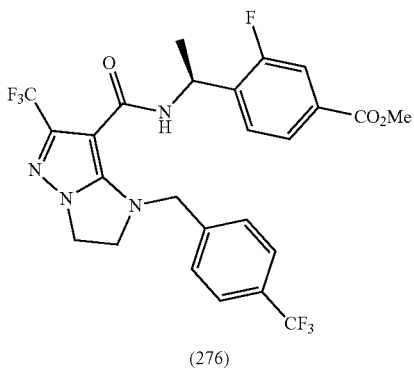

(220)

(275)

(276)

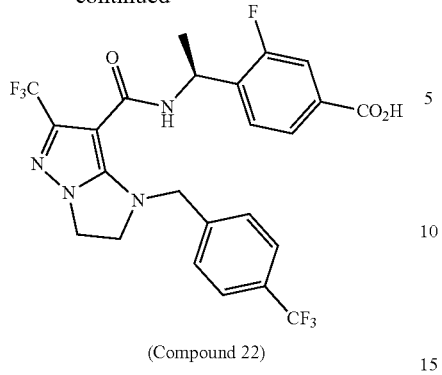

(Compound 22)

Following the procedure for the preparation of (S)-4-(1-(6-(trifluoromethyl)-1-(3-(trifluoromethyl)benzyl)-2,3-dihydro-1H-imidazo[1,2-b]pyrazole-7-carboxamido)ethyl)benzoic acid (Compound 1) from 6-(trifluoromethyl)-1-(3-(trifluoromethyl)benzyl)-2,3-dihydro-1H-imidazo[1,2-b]pyrazole-7-carboxylic acid (215) as described in Example 1, Compound 22 was prepared from 6-(trifluoromethyl)-1-(4-(trifluoromethyl)benzyl)-2,3-dihydro-1H-imidazo[1,2-b]pyrazole-7-carboxylic acid (220) and methyl (S)-4-(1-aminoethyl)-3-fluorobenzoate hydrochloride (275).

Methyl (S)-3-fluoro-4-(1-(6-(trifluoromethyl)-1-(4-(trifluoromethyl)benzyl)-2,3-dihydro-1H-imidazo[1,2-b]pyrazole-7-carboxamido)ethyl)benzoate (276)

¹HNMR (400 MHz, CD₃OD): δ ppm 7.62 (dd, J=8.2, 1.3 Hz, 1H), 7.59 (d, J=7.8 Hz, 2H), 7.52 (dd, J=10.9, 1.5 Hz 1H), 7.45-7.40 (m, 3H), 5.33 (q, J=7.0 Hz, 1H), 4.53 (d, J=14.8 Hz, 1H), 4.36 (d, J=14.8 Hz, 1H), 4.20 (dd, J=7.8, 7.8 Hz, 2H), 3.87 (s, 3H), 3.79 (m 2H), 1.46 (d, J=7.0 Hz, 3H). LCMS (ES) (M+H)=559.0.

(S)-3-fluoro-4-(1-(6-(trifluoromethyl)-1-(4-(trifluoromethyl)benzyl)-2,3-dihydro-1H-imidazo[1,2-b]pyrazole-7-carboxamido)ethyl)benzoic acid (Compound 22)

¹HNMR (400 MHz, CD₃OD): δ ppm 8.36 (bd, J=7.9 Hz, 1H), 7.65 (dd, J=7.8, 1.5 Hz, 1H), 7.60 (d, J=8.2 Hz, 2H), 7.53 (dd, J=10.9, 1.5 Hz 1H), 7.43 (J=8.2 Hz, 2H), 7.42 (dd, J=7.8, 7.8 Hz 1H), 5.34 (dq, J=7.4, 7.1 Hz, 1H), 4.53 (d, J=15.8 Hz, 1H), 4.39 (d, J=15.8 Hz, 1H), 4.19 (m, 2H), 3.80 (m, 2H), 1.46 (J=7.0 Hz, 3H). LCMS (ES) (M+H)=545.2.

Example XXII (S)-3-fluoro-4-(1-(6-(trifluoromethyl)-1-(3-(trifluoromethyl)benzyl)-2,3-dihydro-1H-imidazo[1,2-b]pyrazole-7-carboxamido)ethyl)benzoic acid (Compound 23)

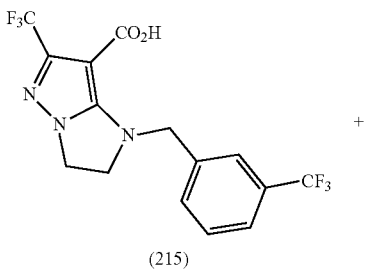

(215)

+

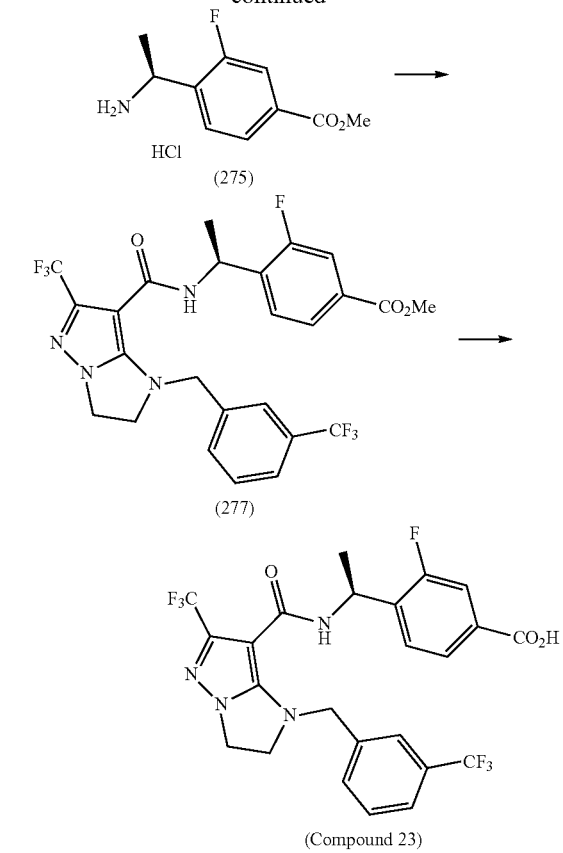

(275)

(277)

(Compound 23)

Following the procedure for the preparation of (S)-4-(1-(6-(trifluoromethyl)-1-(3-(trifluoromethyl)benzyl)-2,3-dihydro-1H-imidazo[1,2-b]pyrazole-7-carboxamido)ethyl)benzoic acid (Compound 1) from 6-(trifluoromethyl)-1-(3-(trifluoromethyl)benzyl)-2,3-dihydro-1H-imidazo[1,2-b]pyrazole-7-carboxylic acid (215) described in Example I, Compound 23 was prepared from 6-(trifluoromethyl)-1-(3-(trifluoromethyl)benzyl)-2,3-dihydro-1H-imidazo[1,2-b]pyrazole-7-carboxylic acid (215) and methyl (S)-4-(1-aminoethyl)-3-fluorobenzoate hydrochloride (275).

Methyl (S)-3-fluoro-4-(1-(6-(trifluoromethyl)-1-(3-(trifluoromethyl)benzyl)-2,3-dihydro-1H-imidazo[1,2-b]pyrazole-7-carboxamido)ethyl)benzoate (277)

¹HNMR (400 MHz, CD₃OD): δ ppm 7.64-7.56 (m, 3H), 7.55-7.47 (m, 3H), 7.43 (dd, J=7.9, 7.4 Hz 1H), 5.34 (q, J=7.0 Hz, 1H), 4.49 (d, J=14.8 Hz, 1H), 4.36 (d, J=14.8 Hz, 1H), 4.20 (ddd, J=8.6, 8.2, 7.4 Hz, 2H), 3.87 (s, 3H), 3.77 (ddd, J=9.4, 9.0, 8.2 Hz, 2H), 1.47 (d, J=7.0 Hz, 3H). LCMS (ES) (M+H)=558.9.

(S)-3-fluoro-4-(1-(6-(trifluoromethyl)-1-(3-(trifluoromethyl)benzyl)-2,3-dihydro-1H-imidazo[1,2-b]pyrazole-7-carboxamido)ethyl)benzoic acid (Compound 23)

¹HNMR (400 MHz, CD₃OD): δ ppm 8.42 (d, J=7.9 Hz, 1H), 7.66-7.56 (m, 3H), 7.55-7.47 (m, 3H), 7.42 (dd, J=7.8, 7.8 Hz, 1H), 5.35 (dq, J=7.5, 7.0 Hz, 1H), 4.50 (d, J=15.1 Hz, 1H), 4.39 (d, J=15.1 Hz, 1H), 4.20 (ddd, J=8.2, 7.1, 7.0 Hz, 2H), 3.78 (m, 2H), 1.47 (d, J=7.0 Hz, 3H). LCMS (ES) (M+H)=543.3.

Example XXIII

Methyl (S)-2-fluoro-4-(1-(6-(trifluoromethyl)-1-(3-(trifluoromethyl)benzyl)-2,3-dihydro-1H-imidazo[1,2-b]pyrazole-7-carboxamido)ethyl)benzoate (Compound 24), and (S)-2-fluoro-4-(1-(6-(trifluoromethyl)-1-(3-(trifluoromethyl)benzyl)-2,3-dihydro-1H-imidazo[1,2-b]pyrazole-7-carboxamido)ethyl)benzoic acid (Compound 25)

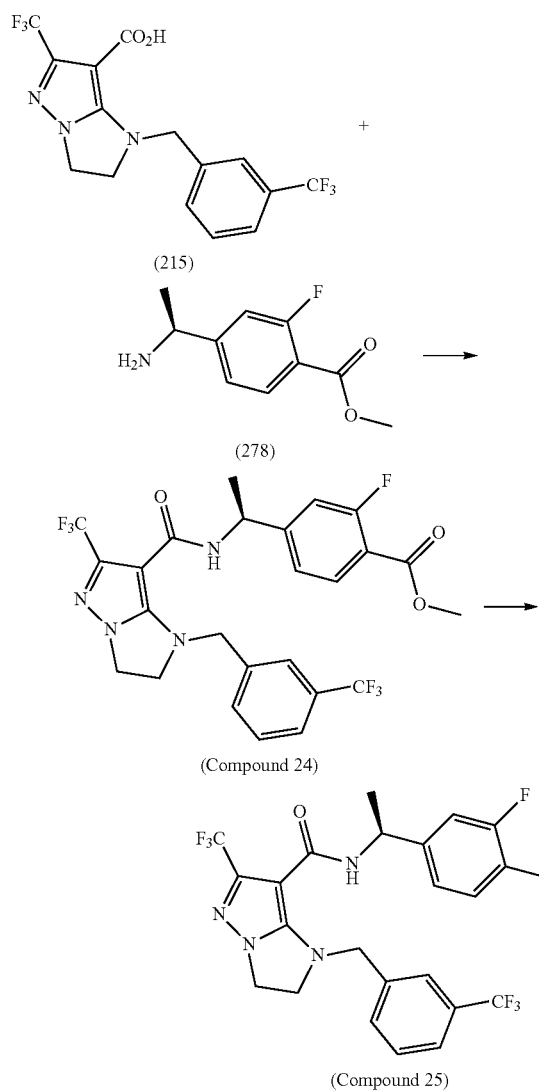

Following the procedure for the preparation of (S)-4-(1-(6-(trifluoromethyl)-1-(3-(trifluoromethyl)benzyl)-2,3-dihydro-1H-imidazo[1,2-b]pyrazole-7-carboxamido)ethyl)benzoic acid (Compound 1) from 6-(trifluoromethyl)-1-(3-(trifluoromethyl)benzyl)-2,3-dihydro-1H-imidazo[1,2-b]pyrazole-7-carboxylic acid (215) described in Example I, Compounds 24 and 25 were prepared from 6-(trifluoromethyl)-1-(3-(trifluoromethyl)benzyl)-2,3-dihydro-1H-imidazo[1,2-b]pyrazole-7-carboxylic acid (215) and methyl (S)-4-(1-aminoethyl)-2-fluorobenzoate (278).

Methyl (S)-2-fluoro-4-(1-(6-(trifluoromethyl)-1-(3-(trifluoromethyl)benzyl)-2,3-dihydro-1H-imidazo[1,2-b]pyrazole-7-carboxamido)ethyl)benzoate (Compound 24)

$^1$HNMR (400 MHz,): δ ppm 7.89 (t, J=7.8 Hz, 1H), 7.55 (d, J=9.8 Hz, 2H), 7.49 (d, J=9.8 Hz, 1H), 7.45 (d, J=7.4 Hz, 1H), 7.16 (dd, J=6.64, 1.6 Hz, 1H), 7.09 (dd, J=10.2, 1.6 Hz, 1H), 6.26 (bs, 1H), 5.21-5.14 (m, 1H), 4.88 (d, J=14.9 Hz, 1H), 4.80 (d, J=14.9 Hz, 1H), 4.18 (t, J=8.6 Hz, 2H), 3.91 (s, 3H), 3.76 (dd, J=7.4, 7.8 Hz, 2H), 1.52 (d, J=7.0 Hz, 3H). LCMS (ES) (M+H)=559.

(S)-2-fluoro-4-(1-(6-(trifluoromethyl)-1-(3-(trifluoromethyl)benzyl)-2,3-dihydro-1H-imidazo[1,2-b]pyrazole-7-carboxamido)ethyl)benzoic acid (Compound 25)

$^1$HNMR (400 MHz): δ ppm 7.95 (dd, J=7.4, 7.0 Hz, 1H), 7.54 (d, J=9.0 Hz, 2H), 7.49 (d, J=7.4 Hz, 1H), 7.45 (d, J=7.4 Hz, 1H), 7.18 (d, J=7.8 Hz, 1H), 7.11 (d, J=11.3 Hz, 1H), 6.28 (bs, 1H), 5.22-5.15 (m, 1H), 4.88 (d, J=14.9 Hz, 1H), 4.80 (d, J=14.9 Hz, 1H), 4.19 (t, J=9.0 Hz, 2H), 3.77 (t, J=8.2 Hz, 2H), 1.52 (d, J=7.0 Hz, 3H). LCMS (ES) (M+H)=545.

Example XXIV (S)-2-(4-(1-(6-(trifluoromethyl)-1-(3-(trifluoromethyl)benzyl)-2,3-dihydro-1H-imidazo[1,2-b]pyrazole-7-carboxamido)ethyl)phenyl)acetic acid (Compound 26)

(S)-methyl 2-(4-(1-aminoethyl)phenyl)acetate (284)

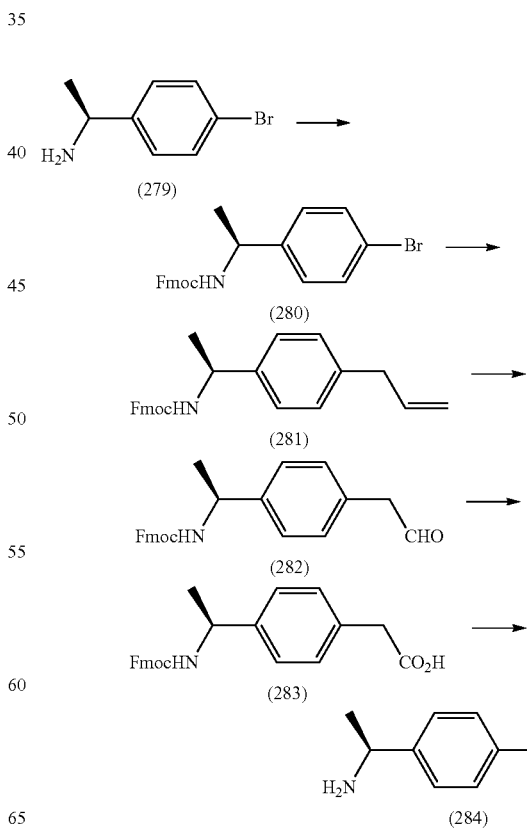

(S)-(9H-fluoren-9-yl)methyl(1-(4-bromophenyl)ethyl)carbamate (280)

To a solution of N-(9-Fluorenylmethoxycarbonyloxy)-succinimide (1.69 g, 5.00 mmol) and (S)-1-(4-bromophenyl)ethanamine (279) (1.00 g, 5.00 mmol) in acetonitrile (52.2 mL) was added water (18.0 mL) and sodium bicarbonate (1.01 g, 12.0 mmol) at 20° C. The mixture was stirred for 1 h. TLC (50% H/E) indicated that the reaction was completed. The suspension reaction mixture was filtered through filter paper. The filter cake was washed with water and dried under vacuum to give the desired product. (2.10 g, 99% yield). ¹HNMR (500 MHz): δ ppm 7.77 (d, J=7.5 Hz, 2H), 7.58 (bs, 2H), 7.46 (d, J=7.5 Hz, 2H), 7.41 (t, J=8.0 Hz, 2H), 7.31 (bs, 2H), 7.16 (bs, 2H), 4.98 (bs, 1H), 4.80 (bs, 1H), 4.44 (bs, 2H), 4.20 (bs, 1H), 1.46 (bs, 3H).

(S)-(9H-fluoren-9-yl)methyl (1-(4-allylphenyl)ethyl)carbamate (281)

To a mixture of Pd(PPh$_3$)$_4$ (0.58 g, 0.50 mmol) and (S)-(9H-fluoren-9-yl)methyl (1-(4-bromophenyl)ethyl)carbamate (280) (2.10 g, 4.97 mmol) in toluene (63.6 mL) was added allyltri-n-butyltin (3.08 mL, 9.95 mmol) at 20° C. The mixture was stirred at 110° C. for 16 h. TLC (50% H/E) and LCMS indicated that the reaction was completed. The reaction was quenched with sat. NaHCO$_3$ and brine and extracted with EtAOc. The organic layer was dried (Na$_2$SO$_4$), filtered and concentrated. The residue was purified with silica gel column chromatography (E/H 0% to 40% and then 40% isocratic) to give the desired product (1.10 g, 58% yield). ¹HNMR (500 MHz): δ ppm 7.79 (J=7.5 Hz, 2H), 7.61 (bs, 2H), 7.42 (t, J=8.0 Hz, 2H), 7.32 (bs, 2H), 7.25 (bs, 2H), 7.19 (d, J=7.5 Hz, 2H), 6.03-5.95 (m, 1H), 5.15-5.09 (m, 2H), 5.06 (bs, 1H), 4.88 (bs, 1H), 4.44 (d, J=6.5, 2H), 4.23 (t, J=7.0, 1H), 3.41 (d, J=7.0, 2H), 1.51 (bs, 3H).

(S)-(9H-fluoren-9-yl)methyl (1-(4-(2-oxoethyl)phenyl)ethyl)carbamate (282)

To a solution of (S)-(9H-fluoren-9-yl)methyl (1-(4-allylphenyl)ethyl)carbamate (281) (1.00 g, 2.61 mmol) in DCM (101 mL) was bubbled through O$_3$ at −78° C. until it became blue color. The mixture was stirred at −78° C. for 10 min before triphenylphosphine (1.37 g, 5.22 mmol) was added. The reaction was warmed to rt. TLC (33% E/H) and LCMS indicated that the reaction was completed. The reaction mixture was concentrated and residue was purified with silica gel column chromatography (E/H 0% to 40% and then 40% isocratic) to give the desired product (950 mg, 95% yield). ¹HNMR (500 MHz): δ ppm 9.76 (t, J=2.5, 1H), 7.77 (d, J=8.0 Hz, 2H), 7.59 (bs, 2H), 7.41 (t, J=7.5, 2H), 7.31 (bs, 4H), 7.20 (d, J=8.0 Hz, 2H), 5.04 (bs, 1H), 4.87 (bs, 1H), 4.43 (d, J=6.5 Hz, 2H), 4.21 (bs, 1H), 3.69 (d, J=2.5, 2H), 1.49 (bs, 3H). LCMS (ES) (M+H)=386.

(S)-2-(4-(1-((((9H-fluoren-9-yl)methoxy)carbonyl)amino)ethyl)phenyl) acetic acid (283)

To a solution of (S)-(9H-fluoren-9-yl)methyl (1-(4-(2-oxoethyl)phenyl)ethyl) carbamate (282) (1.10 g, 2.85 mmol) in THF (19.6 mL) and tert-butanol (98 mL) was added a solution of potassium permanganate (0.451 g, 2.85 mmol) in water (47.6 mL) at 20° C. The mixture was stirred at 20° C. for 1 h. TLC (EtOAc) and LCMS indicated that the reaction was completed. The reaction was diluted with sat. Na$_2$S$_2$O$_3$ and brine and extracted with EtAOc. The organic layer was dried over (Na$_2$SO$_4$), filtered and concentrated. The residue was purified with silica gel column chromatography (E/H 0% to 100% and then MeOH/DCM=1:9) to give the desired product (1.14 g, 100% yield). LCMS (ES) (M+H)=402.

(S)-methyl 2-(4-(1-aminoethyl)phenyl)acetate (284)

To a solution of (S)-2-(4-(1-((((9H-fluoren-9-yl)methoxy)carbonyl)amino)ethyl)phenyl)acetic acid (283) (1.00 g, 2.49 mmol) in methanol (40.3 mL) and toluene (37.1 mL) was added 2.0 M trimethylsilyldiazomethane in hexane (3.74 mL, 7.47 mmol) at 20° C. The mixture was stirred at 20° C. for 5 h. TLC (50% E/H) and LCMS indicated that the reaction was completed. The reaction mixture was concentrated and the residue purified with silica gel column chromatography (E/H 10% to 50%, and then 50% isocratic, and then DCM/MeOH/Et$_3$N=6:1:0.1) to give the desired product (420 mg, 87% yield). ¹HNMR (400 MHz): δ ppm 7.29 (d, J=8.2 Hz, 2H), 7.22 (d, J=8.2 Hz, 2H), 4.08 (q=6.8 Hz, 1H), 3.66 (s, 3H), 3.59 (s, 2H), 2.21 (bs, 2H), 1.36 (d, J=6.6 Hz, 3H). LCMS (ES) (M+H)=194.

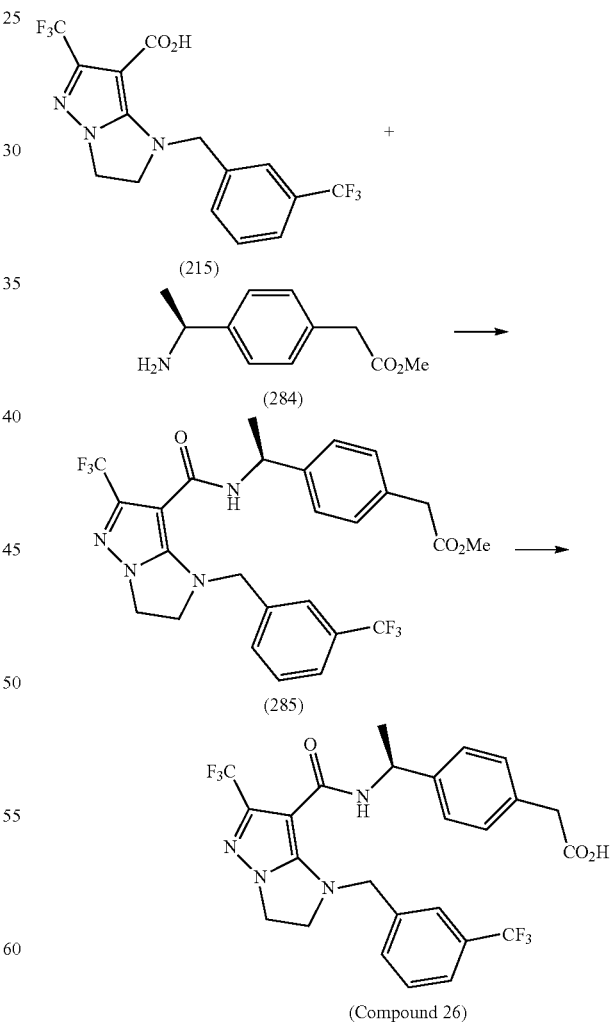

Following the procedure for the preparation of (S)-4-(1-(6-(trifluoromethyl)-1-(3-(trifluoromethyl)benzyl)-2,3-dihydro-1H-imidazo[1,2-b]pyrazole-7-carboxamido)ethyl)

benzoic acid (Compound 1) from 6-(trifluoromethyl)-1-(3-(trifluoromethyl)benzyl)-2,3-dihydro-1H-imidazo[1,2-b]pyrazole-7-carboxylic acid (215) described in Example I, Compound 26 was prepared from 6-(trifluoromethyl)-1-(3-(trifluoromethyl)benzyl)-2,3-dihydro-1H-imidazo[1,2-b]pyrazole-7-carboxylic acid (215) and (S)-methyl 2-(4-(1-aminoethyl)phenyl)acetate (284).

Methyl (S)-2-(4-(1-(6-(trifluoromethyl)-1-(3-(trifluoromethyl)benzyl)-2,3-dihydro-1H-imidazo[1,2-b]pyrazole-7-carboxamido)ethyl)phenyl)acetate (285)

$^1$HNMR (500 MHz): δ ppm 7.57 (s, 1H), 7.56 (d, J=6.9 Hz, 1H), 7.52 (d, J=7.8 Hz, 1H), 7.45 (t, J=7.3 Hz, 1H), 7.30 (d, J=8.3 Hz, 2H), 7.25 (d, J=8.3 Hz, 2H), 6.26 (bd, J=4.9 Hz, 1H), 5.24-5.18 (m, 1H), 4.90 (d, J=14.7 Hz, 1H), 4.82 (d, J=14.7 Hz, 1H), 4.17 (t, J=8.8 Hz, 2H), 3.76 (dt, J=7.8, 2.5 Hz, 2H), 3.69 (s, 3H), 3.61 (s, 2H), 1.53 (d, J=6.9 Hz, 3H). LCMS (ES) (M+H)=555.

(S)-2-(4-(1-(6-(trifluoromethyl)-1-(3-(trifluoromethyl)benzyl)-2,3-dihydro-1H-imidazo[1,2-b]pyrazole-7-carboxamido)ethyl)phenyl)acetic acid (Compound 26)

$^1$HNMR (400 MHz, CDCl$_3$): δ ppm 7.54 (s, 1H), 7.53 (d, J=6.3 Hz, 1H), 7.48 (d, J=7.8 Hz, 1H), 7.41 (t, J=8.2 Hz, 1H), 7.28 (d, J=8.2 Hz, 2H), 7.23 (d, J=8.2 Hz, 2H), 6.26 (bd, J=5.5, 1H), 5.22-5.15 (m, 1H), 4.86 (d, J=14.9 Hz, 1H), 4.78 (d, J=14.9 Hz, 1H), 4.15 (t, J=8.2 Hz, 2H), 3.74 (dt, J=8.6, 2.0 Hz, 2H), 3.60 (s, 2H), 1.51 (d, J=6.6 Hz, 3H). LCMS (ES) (M+H)=541.

Example XXV (S)-2-(4-(1-(6-(trifluoromethyl)-1-(4-(trifluoromethyl)benzyl)-2,3-dihydro-1H-imidazo[1,2-b]pyrazole-7-carboxamido)ethyl)phenyl)acetic acid (Compound 27)

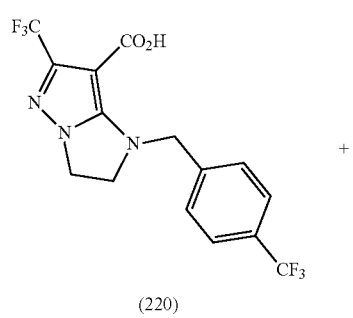
(220)

+

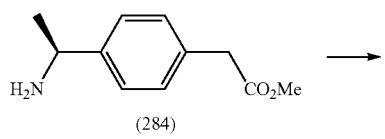
(284)

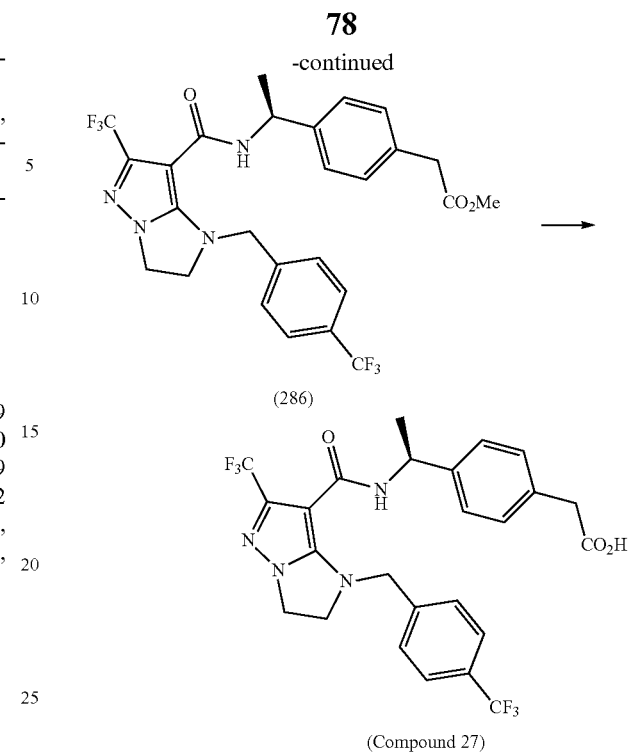
(286)

(Compound 27)

Following the procedure for the preparation of (S)-4-(1-(6-(trifluoromethyl)-1-(3-(trifluoromethyl)benzyl)-2,3-dihydro-1H-imidazo[1,2-b]pyrazole-7-carboxamido)ethyl)benzoic acid (Compound 1) from 6-(trifluoromethyl)-1-(3-(trifluoromethyl)benzyl)-2,3-dihydro-1H-imidazo[1,2-b]pyrazole-7-carboxylic acid (215) described in Example I, Compound 27 was prepared from 6-(trifluoromethyl)-1-(4-(trifluoromethyl)benzyl)-2,3-dihydro-1H-imidazo[1,2-b]pyrazole-7-carboxylic acid (220) and (S)-methyl 2-(4-(1-aminoethyl)phenyl)acetate (284).

Methyl (S)-2-(4-(1-(6-(trifluoromethyl)-1-(4-(trifluoromethyl)benzyl)-2,3-dihydro-1H-imidazo[1,2-b]pyrazole-7-carboxamido)ethyl)phenyl)acetate (286)

$^1$HNMR (500 MHz): δ ppm 7.58 (d, J=8.3 Hz, 2H), 7.42 (d, J=8.3 Hz, 2H), 7.30 (d, J=8.3 Hz, 2H), 7.25 (d, J=8.3 Hz, 2H), 6.25 (bd, J=5.4 Hz, 1H), 5.24-5.18 (m, 1H), 4.88 (d, J=15.2 Hz, 1H), 4.85 (d, J=15.2 Hz, 1H), 4.18 (t, J=8.3 Hz, 2H), 3.78 (td, J=8.3, 2.0 Hz, 2H), 3.69 (s, 3H), 3.61 (s, 2H), 1.53 (d, J=6.9 Hz, 3H). LCMS (ES) (M+H)=555.

(S)-2-(4-(1-(6-(trifluoromethyl)-1-(4-(trifluoromethyl)benzyl)-2,3-dihydro-1H-imidazo[1,2-b]pyrazole-7-carboxamido)ethyl)phenyl)acetic acid (Compound 27)

$^1$HNMR (500 MHz): δ ppm 7.57 (d, J=7.8 Hz, 2H), 7.41 (d, J=7.8 Hz, 2H), 7.30 (d, J=8.3 Hz, 2H), 7.26 (d, J=8.3 Hz, 2H), 6.25 (bd, J=5.4 Hz, 1H), 5.24-5.18 (m, 1H), 4.86 (s, 2H), 4.18 (t, J=8.3 Hz, 2H), 3.78 (td, J=8.8, 2.5 Hz, 2H), 3.63 (s, 2H), 1.53 (d, J=6.9 Hz, 3H). LCMS (ES) (M+H)=541.

Example XXVI 4-(1-(6-methyl-1-(4-(trifluoromethyl)benzyl)-2,3-dihydro-1H-imidazo[1,2-b]pyrazole-7-carboxamido)cyclopropyl)benzoic acid (Compound 28)

Ethyl 5-amino-1-(2-hydroxyethyl)-3-methyl-1H-pyrazole-4-carboxylate (289)

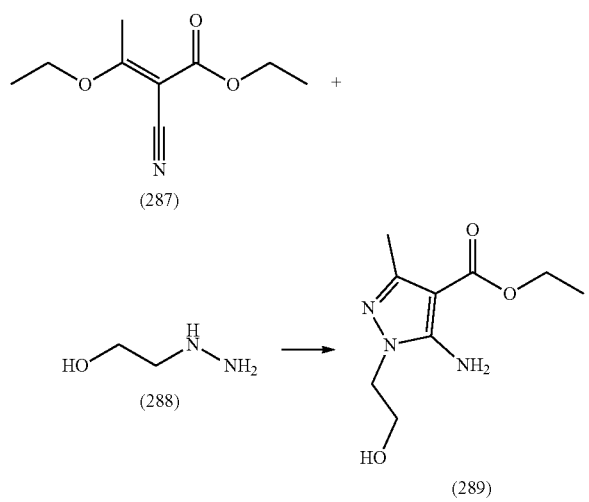

A solution of ethyl (E)-2-cyano-3-ethoxybut-2-enoate (500 mg, 2.73 mmol) and 2-hydroxyethylhydrazine (288) (0.24 mL, 3.51 mmol) in ethanol (4 mL) was heated at 120° C. under microwave for 20 min. The mixture was cooled to rt, poured into water and extracted with EtOAc. The organic layer was washed with brine, dried ($Na_2SO_4$), filtered and concentrated to give the desired product as a white solid (483 mg, 83% yield). This solid was used without further purification for the next step reaction. ¹HNMR (400 MHz): δ ppm 5.33 (bs, 2H), 4.26 (q, J=6.8 Hz, 2H), 3.97 (s, 4H), 2.31 (s, 3H), 1.33 (t, J=6.8 Hz, 3H).

Ethyl 5-amino-3-methyl-1-(2-((methylsulfonyl)oxy)ethyl)-1H-pyrazole-4-carboxylate (290)

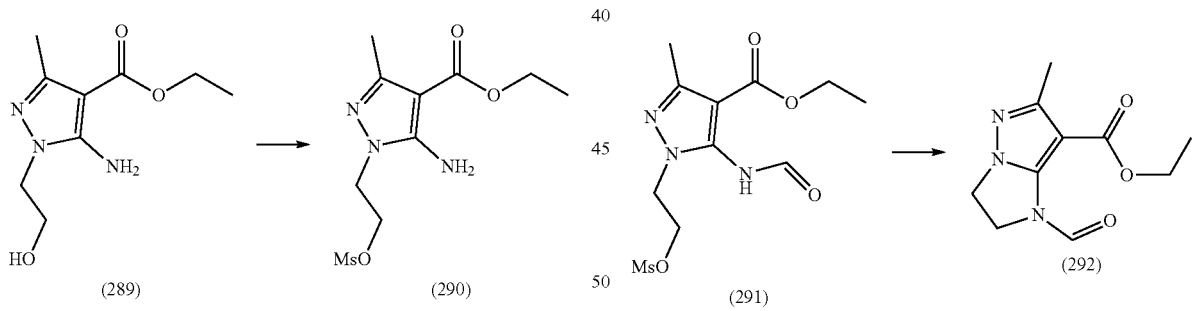

To a solution of Ethyl 5-amino-1-(2-hydroxyethyl)-3-methyl-1H-pyrazole-4-carboxylate (289) (483 mg, 2.27 mmol) and TEA (0.51 mL, 3.66 mmol) in DCM (5 mL) at 0° C. was added methanesulfonyl chloride (0.21 mL, 2.71 mmol) and stirred for 1 h. The reaction mixture was poured into ice water. The separated organic layer was washed with 1N HCl and brine, dried ($MgSO_4$), filtered and concentrated to give the desired compound as a pale yellow solid (358 mg, 54% yield). This solid was used without further purification for the next step reaction. ¹HNMR (400 MHz): δ ppm 5.30 (bs, 2H), 4.57 (t, J=4.8 Hz, 2H), 4.26 (q, J=7.2 Hz, 2H), 4.18 (t, J=4.8 Hz, 2H), 2.95 (s, 3H), 2.32 (s, 3H), 1.33 (t, J=7.0 Hz, 3H).

Ethyl 5-formamido-3-methyl-1-(2-((methylsulfonyl)oxy)ethyl)-1H-pyrazole-4-carboxylate (291)

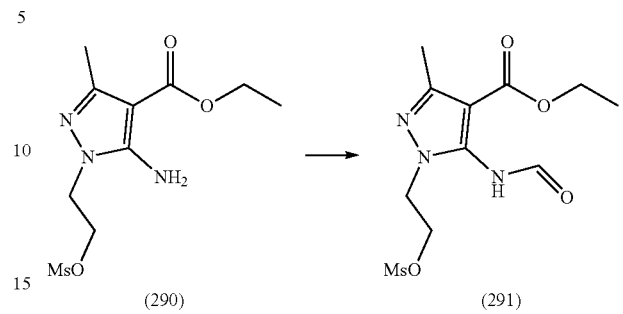

A mixture of acetic anhydride (0.21 mL, 2.18 mmol) and formic acid (0.10 mL, 2.65 mmol) was stirred at rt for 30 min and then cooled to 0° C. This cold mixture was then added to ethyl 5-amino-3-methyl-1-(2-((methylsulfonyl)oxy)ethyl)-1H-pyrazole-4-carboxylate (290) (302 mg. 1.04 mmol) and the resulting mixture was stirred for 2 h at 0° C. and then over weekend at rt. The mixture was then concentrated and the resulting solid was washed with MTBE, dried under vacuum to give the desired compound as a white solid (227 mg, 69% yield). ¹HNMR (400 MHz): δ ppm 8.66 (bs, 1H), 8.34 (s, 1H), 4.62 (t, J=5.6 Hz, 2H), 4.42 (t, J=5.6 Hz, 2H), 4.29 (q, J=7.0 Hz, 2H), 2.95 (s, 3H), 2.38 (s, 3H), 1.35 (t, J=7.0 Hz, 3H).

Ethyl 1-formyl-6-methyl-2,3-dihydro-1H-imidazo[1,2-b]pyrazole-7-carboxylate (292)

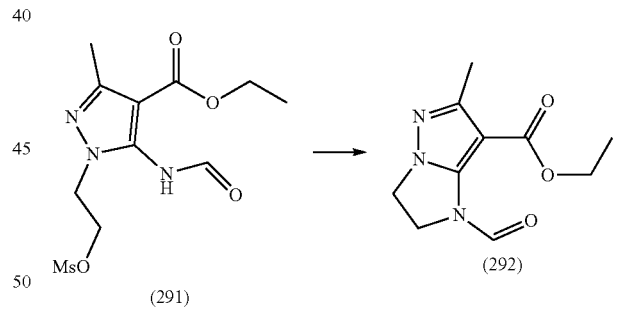

To a solution of ethyl 5-formamido-3-methyl-1-(2-((methylsulfonyl)oxy)ethyl)-1H-pyrazole-4-carboxylate (291) (227 mg, 0.71 mmol) in DMF (2 mL) at 0° C. was added NaH (28.4 mg, 0.71 mmol, 60% in mineral oil) and the resulting mixture was stirred for 3 h. The reaction was quenched by addition of sat. $NH_4Cl$, warmed to rt and extracted with EtOAc. The organic layer was washed with brine, dried ($MgSO_4$), filtered and concentrated. The residue was purified silica gel chromatography (E/H 10% to 80%) to give the desired compound (103 mg, 65% yield). ¹HNMR (400 MHz): δ ppm 9.75 (s, 1H), 4.48 (dd, J=8.8, 7.6 Hz, 2H), 4.32-4.25 (m, 4H), 2.42 (s, 3H), 1.35 (t, J=7.2 Hz, 3H).

Ethyl 6-methyl-2,3-dihydro-1H-imidazo[1,2-b]pyrazole-7-carboxylate (293)

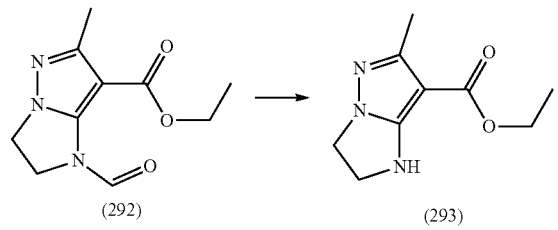 [SMILES: CCOC(=O)c1c(C)nn2c1N(C=O)CC2 ; CCOC(=O)c1c(C)nn2c1NCC2]

To a solution of ethyl 1-formyl-6-methyl-2,3-dihydro-1H-imidazo[1,2-b]pyrazole-7-carboxylate (292) (103 mg, 0.46 mmol) in methanol (2 mL) and THF (2 mL) at 0° C. was added 12 M HCl solution in water (0.082 mL) and the resulting mixture was stirred at rt for 2 h. The reaction mixture was poured into 10 mL of ice/water and neutralized with sat. NaHCO$_3$. The mixture was concentrated down to about 5 mL and extracted with EtOAc twice. The combined organic phase was washed with brine, dried (MgSO$_4$), filtered and concentrated to give the desired compound as a white solid (81 mg, 90% yield). $^1$HNMR (400 MHz): δ ppm 4.52 (bs, 1H), 4.22 (q, J=7.2, Hz, 2H), 4.13 (m, 2H), 4.04 (m, 2H), 2.38 (s, 3H), 1.31 (t, J=7.2 Hz, 3H).

6-methyl-1-(4-(trifluoromethyl)benzyl)-2,3-dihydro-1H-imidazo[1,2-b]pyrazole-7-carboxylic acid (295)

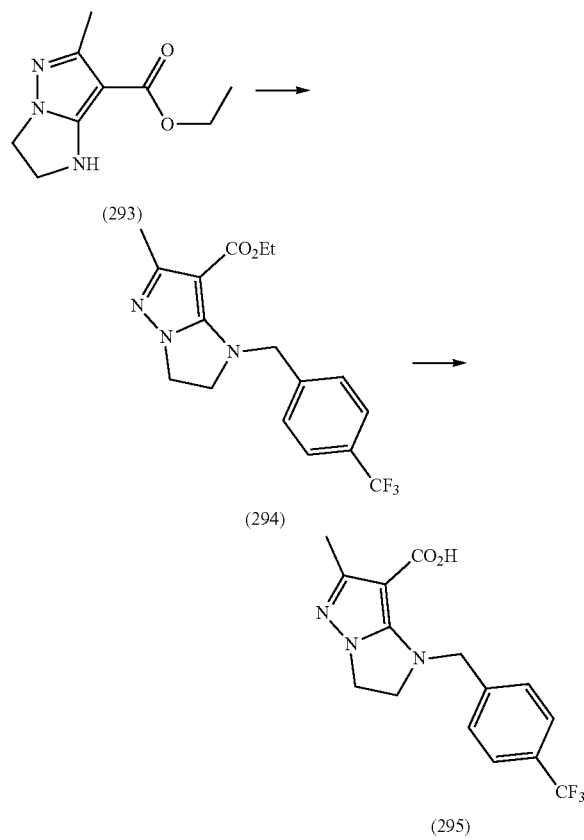

Following similar procedure for the preparation of 6-(trifluoromethyl)-1-(4-(trifluoromethyl)benzyl)-2,3-dihydro-1H-imidazo[1,2-b]pyrazole-7-carboxylic acid (220), compound 295 was prepared from ethyl 6-methyl-2,3-dihydro-1H-imidazo[1,2-b]pyrazole-7-carboxylate (293).

Ethyl 6-methyl-1-(4-(trifluoromethyl)benzyl)-2,3-dihydro-1H-imidazo[1,2-b]pyrazole-7-carboxylate (294)

$^1$HNMR (400 MHz): δ ppm 7.57 (d, J=8.0, Hz, 2H), 7.42 (d, J=8.0, Hz, 2H), 4.95 (s, 2H), 4.22 (q, J=7.2, Hz, 2H), 4.04 (dd, J=8.8, 8.0, Hz, 2H), 3.67 (dd, J=8.8, 8.0, Hz, 2H), 2.39 (s, 3H), 1.27 (t, J=7.2 Hz, 3H).

6-methyl-1-(4-(trifluoromethyl)benzyl)-2,3-dihydro-1H-imidazo[1,2-b]pyrazole-7-carboxylic acid (295)

$^1$HNMR (400 MHz): δ ppm 7.57 (d, J=8.0, Hz, 2H), 7.45 (d, J=8.0, Hz, 2H), 4.96 (s, 2H), 4.05 (dd, J=8.8, 8.0, Hz, 2H), 3.70 (dd, J=8.4, 8.4, Hz, 2H), 2.40 (s, 3H).

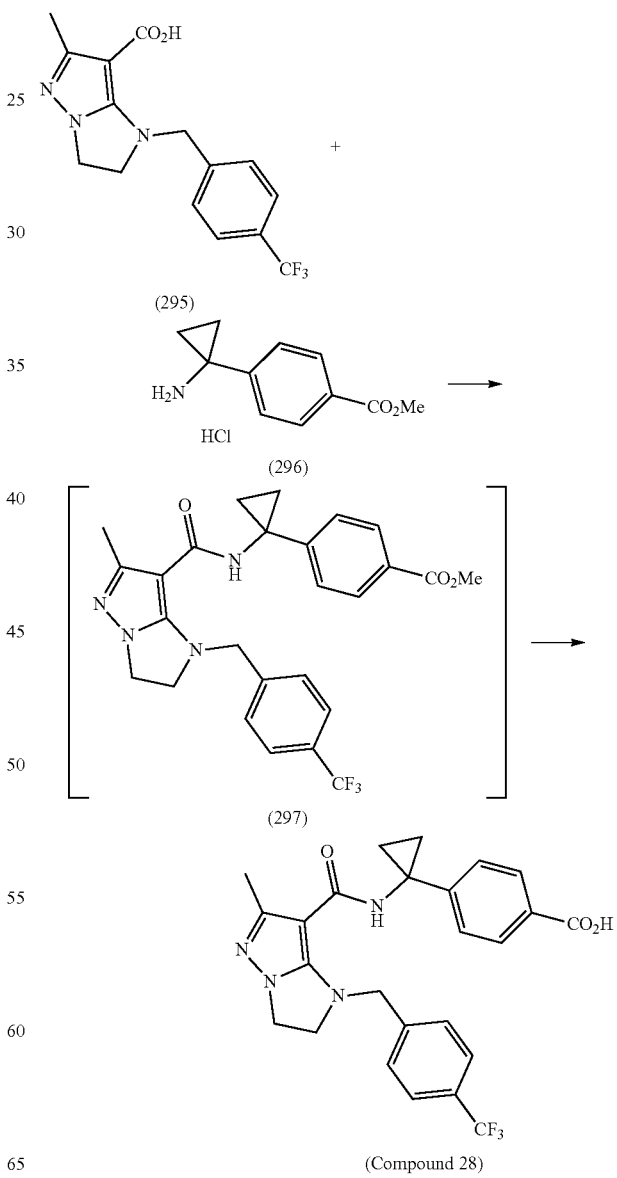

4-(1-(6-methyl-1-(4-(trifluoromethyl)benzyl)-2,3-dihydro-1H-imidazo[1,2-b]pyrazole-7-carboxamido)cyclopropyl)benzoic acid (Compound 28)

Following similar procedure for the preparation of (S)-4-(1-(6-(trifluoromethyl)-1-(3-(trifluoromethyl)benzyl)-2,3-dihydro-1H-imidazo[1,2-b]pyrazole-7-carboxamido)ethyl)benzoic acid (Compound 1) from 6-(trifluoromethyl)-1-(3-(trifluoromethyl)benzyl)-2,3-dihydro-1H-imidazo[1,2-b]pyrazole-7-carboxylic acid (215) described in Example I, Compound 28 was prepared from 6-methyl-1-(4-(trifluoromethyl)benzyl)-2,3-dihydro-1H-imidazo[1,2-b]pyrazole-7-carboxylic acid (295) and methyl 4-(1-aminocyclopropyl)benzoate hydrochloride (296). Compound 28: 1H NMR (400 MHz, CD$_3$OD): δ ppm 7.82 (d, J=8.4 Hz, 2H), 7.58 (d, J=8.4 Hz, 2H), 7.46 (d, J=8.4 Hz, 2H), 7.23 (d, J=8.4 Hz, 2H), 4.69 (s, 2H), 4.01 (dd, J=8.4, 8.0 Hz, 2H), 3.73 (dd, J=8.8, 7.2 Hz, 2H), 2.33 (s, 3H), 1.33 (m, 4H).

Example XXVII

4-(1-(6-(trifluoromethyl)-1-(4-(trifluoromethyl)benzyl)-2,3-dihydro-1H-imidazo[1,2-b]pyrazole-7-carboxamido)cyclopropyl)benzoic acid (Compound 29)

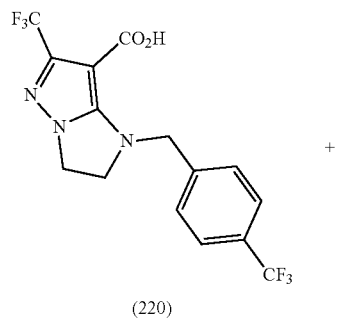

(220)

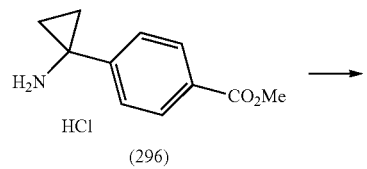

(296)

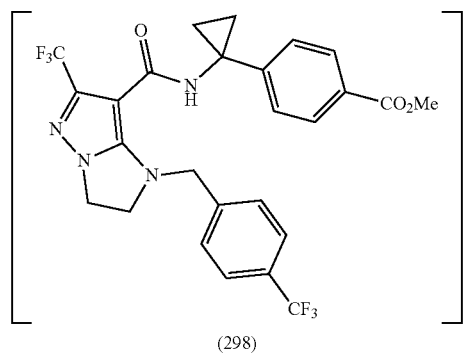

(298)

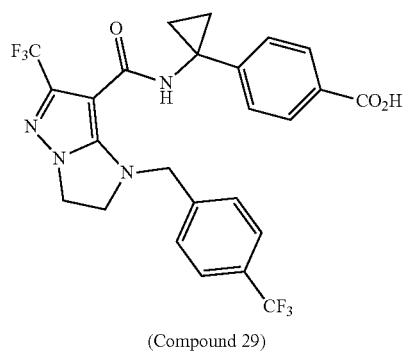

(Compound 29)

Following similar procedure for the preparation of (S)-4-(1-(6-(trifluoromethyl)-1-(3-(trifluoromethyl)benzyl)-2,3-dihydro-1H-imidazo[1,2-b]pyrazole-7-carboxamido)ethyl)benzoic acid (Compound 1) from 6-(trifluoromethyl)-1-(3-(trifluoromethyl)benzyl)-2,3-dihydro-1H-imidazo[1,2-b]pyrazole-7-carboxylic acid (215) described in Example I, Compound 29 was prepared from 6-(trifluoromethyl)-1-(4-(trifluoromethyl)benzyl)-2,3-dihydro-1H-imidazo[1,2-b]pyrazole-7-carboxylic acid (220) and methyl 4-(1-aminocyclopropyl)benzoate hydrochloride (296). $^1$HNMR (400 MHz, CD$_3$OD): δ ppm 7.75 (d, J=8.4 Hz, 2H), 7.62 (d, J=8.0 Hz, 2H), 7.47 (d, J=8.0 Hz, 2H), 7.22 (d, J=8.4 Hz, 2H), 4.53 (s, 2H), 4.20 (dd, J=8.8, 8.4 Hz, 2H), 3.82 (dd, J=8.8, 7.6 Hz, 2H), 1.30 (ddd, J=8.4, 6.0, 4.4 Hz, 2H), 1.19 (ddd, J=8.4, 6.4, 4.4 Hz, 2H).

Example XXVIII

4-(1-(1-(4-chlorobenzyl)-6-(trifluoromethyl)-2,3-dihydro-1H-imidazo[1,2-b]pyrazole-7-carboxamido)cyclopropyl)benzoic acid (Compound 30)

1-(4-chlorobenzyl)-6-(trifluoromethyl)-2,3-dihydro-1H-imidazo[1,2-b]pyrazole-7-carboxylic acid (301)

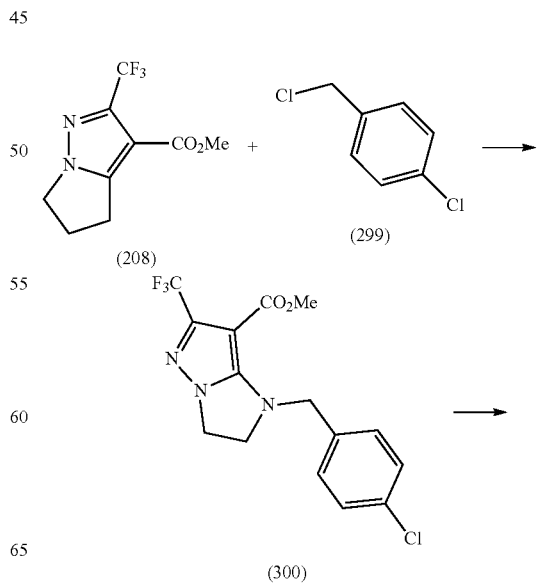

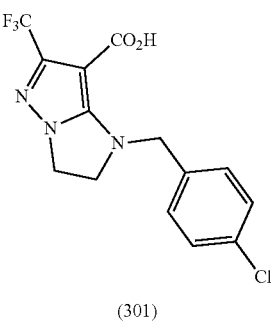

(301)

Following similar procedure for the preparation of 6-(trifluoromethyl)-1-(3-(trifluoromethyl)benzyl)-2,3-dihydro-1H-imidazo[1,2-b]pyrazole-7-carboxylic acid (215), compound 301 was prepared from methyl 6-(trifluoromethyl)-2,3-dihydro-1H-imidazo[1,2-b]pyrazole-7-carboxylate (208) and 1-chloro-4-(chloromethyl)benzene (299).

Methyl 1-(4-chlorobenzyl)-6-(trifluoromethyl)-2,3-dihydro-1H-imidazo[1,2-b]pyrazole-7-carboxylate (300)

¹HNMR (400 MHz): δ ppm 7.32 (d, J=8.4 Hz, 2H), 7.25 (d, J=8.4 Hz, 2H), 4.88 (s, 2H), 4.15 (dd, J=8.8, 8.0 Hz, 2H), 3.80 (s, 3H), 3.77 (dd, J=8.8, 8.4 Hz, 2H).

1-(4-chlorobenzyl)-6-(trifluoromethyl)-2,3-dihydro-1H-imidazo[1,2-b]pyrazole-7-carboxylic acid (301)

¹HNMR (400 MHz, CD₃OD): δ ppm 7.35 (d, J=8.4 Hz, 4H), 4.92 (s, 2H), 4.15 (dd, J=8.8, 8.0 Hz, 2H), 3.82 (dd, J=8.8, 8.4 Hz, 2H).

4-(1-(1-(4-chlorobenzyl)-6-(trifluoromethyl)-2,3-dihydro-1H-imidazo[1,2-b]pyrazole-7-carboxamido)cyclopropyl)benzoic acid (Compound 30)

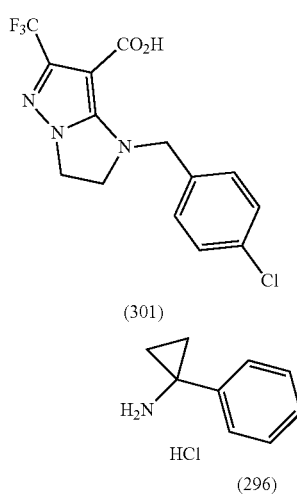

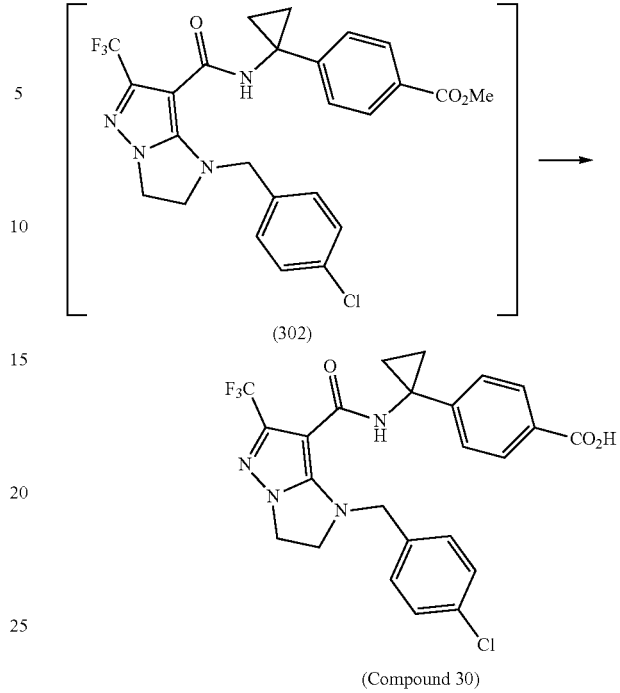

Following similar procedure for the preparation of (S)-4-(1-(6-(trifluoromethyl)-1-(3-(trifluoromethyl)benzyl)-2,3-dihydro-1H-imidazo[1,2-b]pyrazole-7-carboxamido)ethyl)benzoic acid (Compound 1) from 6-(trifluoromethyl)-1-(3-(trifluoromethyl)benzyl)-2,3-dihydro-1H-imidazo[1,2-b]pyrazole-7-carboxylic acid (215) described in Example I, Compound 30 was prepared from 1-(4-chlorobenzyl)-6-(trifluoromethyl)-2,3-dihydro-1H-imidazo[1,2-b]pyrazole-7-carboxylic acid (301) and methyl 4-(1-aminocyclopropyl)benzoate hydrochloride (296). ¹HNMR (400 MHz, CD₃OD): δ ppm 7.81 (d, J=8.0 Hz, 2H), 7.56 (d, J=8.0 Hz, 2H), 7.37 (d, J=8.0 Hz, 2H), 7.36 (d, J=8.0 Hz, 2H), 4.90 (s, 2H), 4.15 (dd, J=8.8, 8.0 Hz, 2H), 3.82 (dd, J=8.8, 8.4 Hz, 2H), 1.30 (ddd, J=8.4, 6.0, 4.4 Hz, 2H), 1.19 (ddd, J=8.4, 6.4, 4.4 Hz, 2H).

Example XXIX (S)-4-(1-(1-(4-chlorobenzyl)-6-(trifluoromethyl)-2,3-dihydro-1H-imidazo[1,2-b]pyrazole-7-carboxamido)ethyl)benzoic acid (Compound 31)

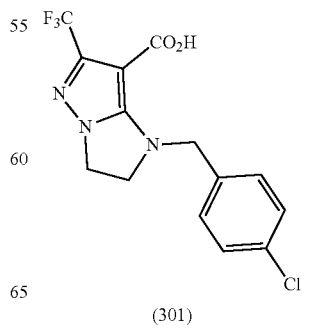

-continued

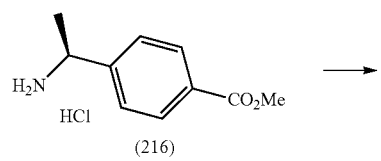

(216)

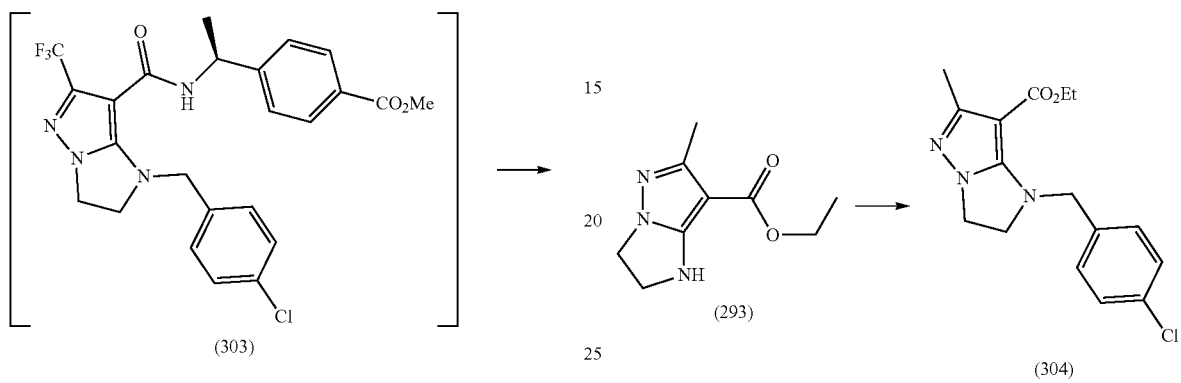

(303)

(Compound 31)

Following similar procedure for the preparation of (S)-4-(1-(6-(trifluoromethyl)-1-(3-(trifluoromethyl)benzyl)-2,3-dihydro-1H-imidazo[1,2-b]pyrazole-7-carboxamido)ethyl) benzoic acid (Compound 1) from 6-(trifluoromethyl)-1-(3-(trifluoromethyl)benzyl)-2,3-dihydro-1H-imidazo[1,2-b] pyrazole-7-carboxylic acid (215) described in Example I, Compound 31 was prepared from 1-(4-chlorobenzyl)-6-(trifluoromethyl)-2,3-dihydro-1H-imidazo[1,2-b]pyrazole-7-carboxylic acid (301) and methyl (S)-4-(1-aminoethyl) benzoate hydrochloride (216). $^1$HNMR (400 MHz, CD$_3$OD): δ ppm 7.83 (d, J=8.0 Hz, 2H), 7.37 (d, J=8.0 Hz, 2H), 7.26 (d, J=8.4 Hz, 2H), 7.17 (d, J=8.4 Hz, 2H), 5.10 (dq, J=7.6, 7.2 Hz, 1H), 4.33 (d, J=15.0 Hz, 1H), 4.21 (d, J=15.0 Hz, 1H), 4.14 (ddd, J=8.8, 8.0, 4.8 Hz, 2H), 3.72 (ddd, J=8.8, 8.4, 2.4 Hz, 2H), 1.44 (d, J=7.2 Hz, 3H).

Example XXX (S)-4-(1-(1-(4-chlorobenzyl)-6-methyl-2,3-dihydro-1H-imidazo[1,2-b]pyrazole-7-carboxamido)ethyl) benzoic acid (Compound 32)

1-(4-chlorobenzyl)-6-methyl-2,3-dihydro-1H-imidazo[1,2-b]pyrazole-7-carboxylic acid (305)

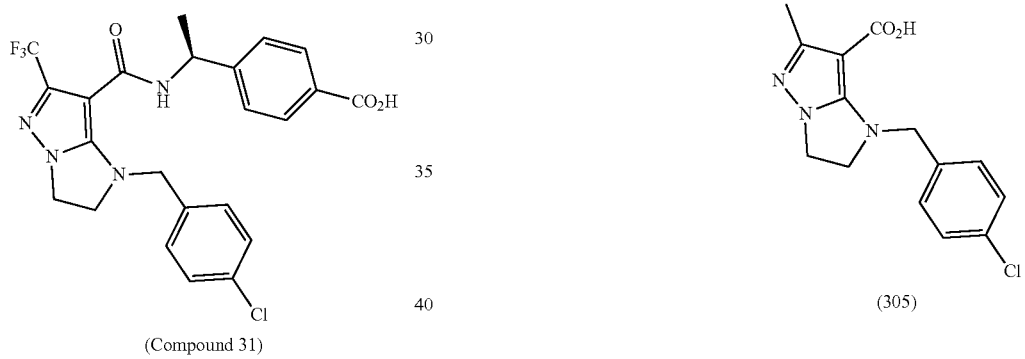

(293)   (304)

(305)

Following similar procedure for the preparation of 6-(trifluoromethyl)-1-(3-(trifluoromethyl)benzyl)-2,3-dihydro-1H-imidazo[1,2-b]pyrazole-7-carboxylic acid (215), compound 305 was prepared from ethyl 6-methyl-2,3-dihydro-1H-imidazo[1,2-b]pyrazole-7-carboxylate (293) and 1-chloro-4-(chloromethyl)benzene (299).

Ethyl 1-(4-chlorobenzyl)-6-methyl-2,3-dihydro-1H-imidazo[1,2-b]pyrazole-7-carboxylate (304)

$^1$HNMR (400 MHz): δ ppm 7.29 (d, J=8.0 Hz, 2H), 7.25 (d, J=8.0 Hz, 2H), 4.86 (s, 2H), 4.23 (q, J=7.2 Hz, 2H), 4.01 (dd, J=8.8, 7.6 Hz, 2H), 3.65 (ddd, J=8.8, 7.6, 1.6 Hz, 2H), 2.38 (s, 3H), 1.28 (t, J=7.2 Hz, 3H).

1-(4-chlorobenzyl)-6-methyl-2,3-dihydro-1H-imidazo[1,2-b]pyrazole-7-carboxylic acid (305)

$^1$HNMR (400 MHz): δ ppm 7.29 (d, J=8.0 Hz, 2H), 7.23 (d, J=8.0 Hz, 2H), 4.86 (s, 2H), 4.02 (dd, J=8.8, 8.0 Hz, 2H), 3.67 (dd, J=8.8, 7.6 Hz, 2H), 2.39 (s, 3H).

89

(S)-4-(1-(1-(4-chlorobenzyl)-6-methyl-2,3-dihydro-1H-imidazo[1,2-b]pyrazole-7-carboxamido)ethyl)benzoic acid (Compound 32)

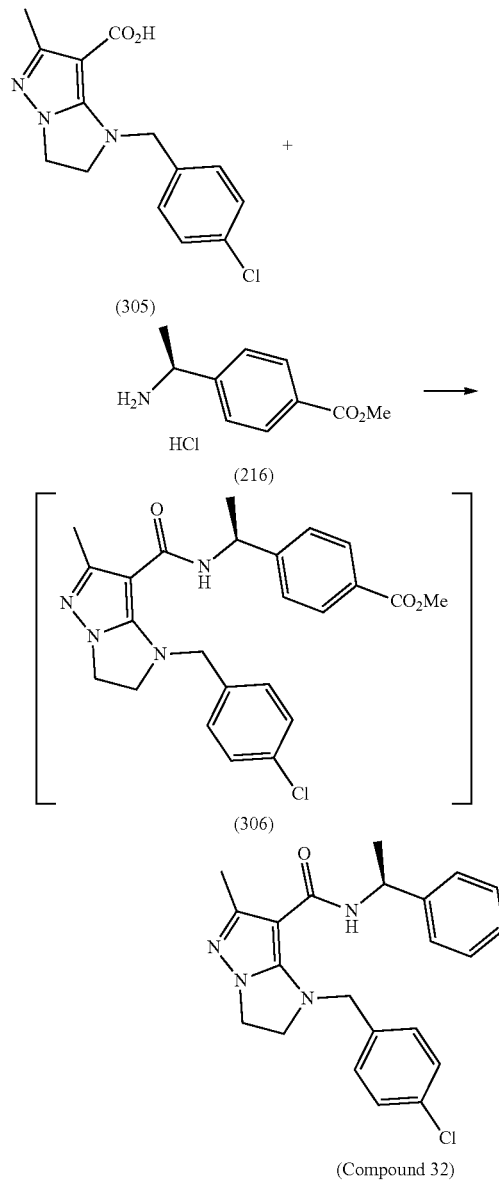

Following similar procedure for the preparation of (S)-4-(1-(6-(trifluoromethyl)-1-(3-(trifluoromethyl)benzyl)-2,3-dihydro-1H-imidazo[1,2-b]pyrazole-7-carboxamido)ethyl)benzoic acid (Compound 1) from 6-(trifluoromethyl)-1-(3-(trifluoromethyl)benzyl)-2,3-dihydro-1H-imidazo[1,2-b]pyrazole-7-carboxylic acid (215) described in Example I, Compound 32 was prepared from 1-(4-chlorobenzyl)-6-methyl-2,3-dihydro-1H-imidazo[1,2-b]pyrazole-7-carboxylic acid (305) and methyl (S)-4-(1-aminoethyl)benzoate hydrochloride (216). ¹HNMR (400 MHz, CD₃OD): δ ppm 7.89 (d, J=8.8 Hz, 2H), 7.41 (d, J=8.8 Hz, 2H), 7.23 (d, J=8.4 Hz, 2H), 7.18 (d, J=8.4 Hz, 2H), 5.13 (q, J=7.4 Hz, 1H), 4.53 (d, J=14.8 Hz, 1H), 4.38 (d, J=14.8 Hz, 1H), 3.96 (ddd, J=8.0, 7.2, 1.8 Hz, 2H), 3.66 (dd, J=9.2, 8.0 Hz, 2H), 2.30 (s, 3H), 1.49 (d, J=7.0 Hz, 3H).

90

Example XXXI 4-((1-(4-chlorobenzyl)-6-methyl-2,3-dihydro-1H-imidazo[1,2-b]pyrazole-7-carboxamido)methyl)benzoic acid (Compound 33)

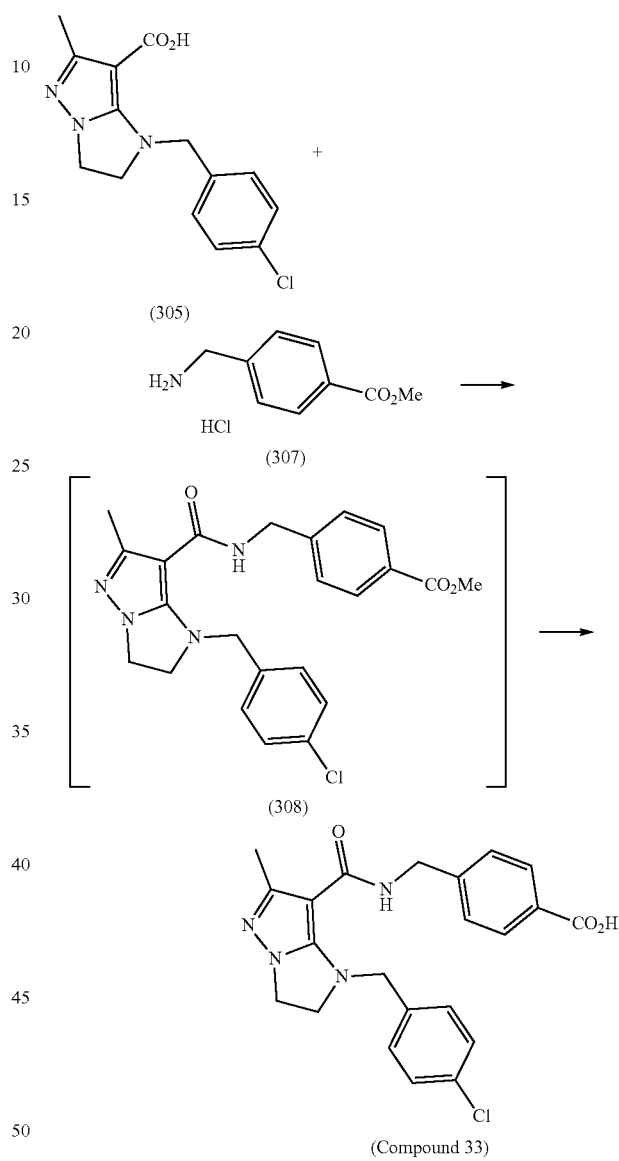

Following similar procedure for the preparation of (S)-4-(1-(6-(trifluoromethyl)-1-(3-(trifluoromethyl)benzyl)-2,3-dihydro-1H-imidazo[1,2-b]pyrazole-7-carboxamido)ethyl)benzoic acid (Compound 1) from 6-(trifluoromethyl)-1-(3-(trifluoromethyl)benzyl)-2,3-dihydro-1H-imidazo[1,2-b]pyrazole-7-carboxylic acid (215) described in Example I, the Compound 33 was prepared from 1-(4-chlorobenzyl)-6-methyl-2,3-dihydro-1H-imidazo[1,2-b]pyrazole-7-carboxylic acid (305) and methyl 4-(aminomethyl)benzoate hydrochloride (307). ¹HNMR (400 MHz, CD₃OD): δ ppm 7.98 (bt, J=6.4 Hz, 1H), 7.89 (d, J=8.0 Hz, 2H), 7.37 (d, J=8.0 Hz, 2H), 7.25 (d, J=8.4 Hz, 4H), 4.56 (s, 2H), 4.52 (d, J=6.4 Hz, 2H), 3.97 (dd, J=8.8, 7.6 Hz, 2H), 3.67 (ddd, J=8.4, 8.0, 2.0 Hz, 2H), 2.31 (s, 3H).

Example XXXII

(R)-4-(1-(6-methyl-1-(1-(4-(trifluoromethyl)phenyl)ethyl)-2,3-dihydro-1H-imidazo[1,2-b]pyrazole-7-carboxamido)cyclopropyl)benzoic acid (Compound 34)

(S)-1-(4-(trifluoromethyl)phenyl)ethyl methanesulfonate (309)

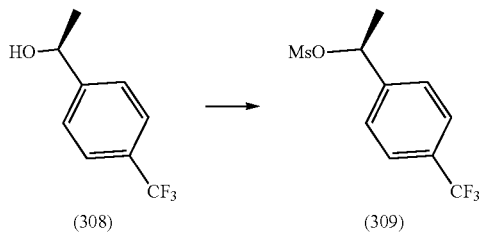 [SMILES: C[C@H](O)c1ccc(C(F)(F)F)cc1 ; C[C@H](OS(C)(=O)=O)c1ccc(C(F)(F)F)cc1]

To a solution of (S)-1-(4-(trifluoromethyl)phenyl)ethan-1-ol (308) (100 mg, 0.53 mmol) and TEA (0.15 mL, xx mmol) in DCM (2 mL) at 0° C. was added methanesulfonyl chloride (0.53 mL, xx mmol) dropwise and the resulting mixture was stirred for 3 h. The reaction was quenched by adding water and extracted with DCM. The organic layer was washed successively with 1N HCl, 10% NaHCO$_3$ and brine, dried (MgSO$_4$) filtered and concentrated to give the desired product as a pale brown oil (125 mg). This crude material was used without further purification for the next step reaction.

(R)-6-methyl-1-(1-(4-(trifluoromethyl)phenyl)ethyl)-2,3-dihydro-1H-imidazo[1,2-b]pyrazole-7-carboxylic acid (312)

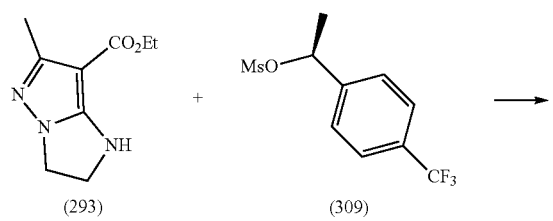

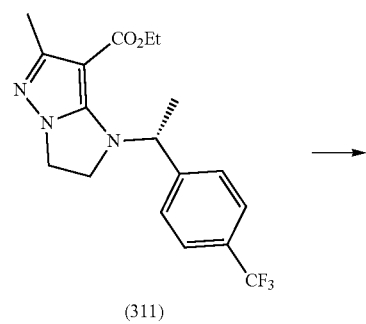

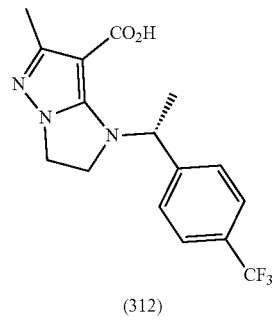

Ethyl (R)-6-methyl-1-(1-(4-(trifluoromethyl)phenyl)ethyl)-2,3-dihydro-1H-imidazo[1,2-b]pyrazole-7-carboxylate (311)

To a solution of ethyl 6-methyl-2,3-dihydro-1H-imidazo[1,2-b]pyrazole-7-carboxylate (293) (77 mg, 0.39 mmol) in DMF (2 mL) at rt was added NaH (20.4 mg, 0.51 mmol, 60% in mineral oil) and stirred for 30 min. The reaction mixture was then cooled to 0° C. and a solution of (S)-1-(4-(trifluoromethyl)phenyl)ethyl methanesulfonate (309) (125 mg) in 1 mL DMF was introduced dropwise. The cooling bath was removed and the reaction mixture was stirred at rt for 2 h. The reaction was quenched by addition of sat. NH$_4$Cl and extracted with EtOAc. The organic layer was washed with brine (×2), dried (MgSO$_4$), filtered and concentrated. The oily residue was purified by silica gel column (20% to 80% E/H) to give the desired compound a white solid (110 mg, 76% yield). $^1$HNMR (400 MHz): δ ppm 7.59 (d, J=8.4 Hz, 2H), 7.47 (d, J=8.4 Hz, 2H), 6.35 (q, J=6.8 Hz, 1H), 4.26 (q, J=7.2 Hz, 2H), 4.00 (ddd, J=7.6, 7.2, 2.4 Hz, 1H), 3.93 (ddd, J=7.2, 6.8, 2.0 Hz, 1H), 3.79 (ddd, J=9.2, 7.2, 2.4 Hz, 1H), 3.37 (ddd, J=9.2, 7.6, 2.0 Hz, 1H), 2.39 (s, 3H), 1.58 (d, J=6.8 Hz, 3H), 1.33 (t, J=7.2 Hz, 3H).

(R)-6-methyl-1-(1-(4-(trifluoromethyl)phenyl)ethyl)-2,3-dihydro-1H-imidazo[1,2-b]pyrazole-7-carboxylic acid (312)

Compound 312 was prepared following similar procedure for the preparation of 6-(trifluoromethyl)-1-(3-(trifluoromethyl)benzyl)-2,3-dihydro-1H-imidazo[1,2-b]pyrazole-7-carboxylic acid (215) from methyl 6-(trifluoromethyl)-2,3-dihydro-1H-imidazo[1,2-b]pyrazole-7-carboxylate (208) but reaction at 140° C. for 1.5 h using microwave. The desired compound was pale pink solid as a crude (45 mg, 44% yield). $^1$HNMR (400 MHz, CD$_3$OD): δ ppm 7.62 (d, J=8.4 Hz, 2H), 7.57 (d, J=8.4 Hz, 2H), 6.35 (q, J=7.2 Hz, 1H), 3.94-3.82 (m, 3H), 3.40 (ddd, J=7.6, 7.2, 2.4 Hz, 1H), 2.30 (s, 3H), 1.57 (d, J=7.6 Hz, 3H).

(R)-4-(1-(6-methyl-1-(1-(4-(trifluoromethyl)phenyl)ethyl)-2,3-dihydro-1H-imidazo[1,2-b]pyrazole-7-carboxamido)cyclopropyl)benzoic acid (Compound 34)

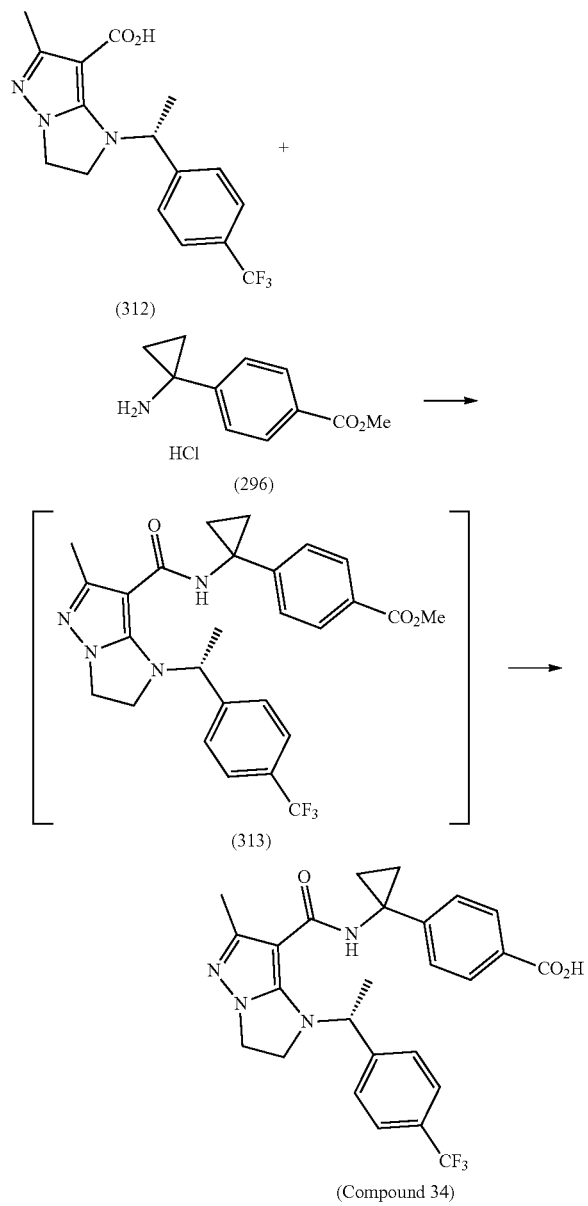

(Compound 34)

Following similar procedure for the preparation of (S)-4-(1-(6-(trifluoromethyl)-1-(3-(trifluoromethyl)benzyl)-2,3-dihydro-1H-imidazo[1,2-b]pyrazole-7-carboxamido)ethyl)benzoic acid (Compound 1) from 6-(trifluoromethyl)-1-(3-(trifluoromethyl)benzyl)-2,3-dihydro-1H-imidazo[1,2-b]pyrazole-7-carboxylic acid (215) described in Example I, Compound 34 was prepared from (R)-6-methyl-1-(1-(4-(trifluoromethyl)phenyl)ethyl)-2,3-dihydro-1H-imidazo[1,2-b]pyrazole-7-carboxylic acid (312) and methyl 4-(1-aminocyclopropyl)benzoate hydrochloride (296). $^1$HNMR (400 MHz, CD$_3$OD): δ ppm 7.86 (d, J=8.4 Hz, 2H), 7.57 (d, J=8.4 Hz, 2H), 7.47 (d, J=8.4 Hz, 2H), 7.28 (d, J=8.4 Hz, 2H), 5.63 (q, J=7.6 Hz, 1H), 3.95-3.84 (m, 3H), 3.49 (ddd, J=9.6, 7.2, 6.8 Hz, 1H), 2.31 (s, 3H), 1.54 (d, J=7.6 Hz, 3H), 1.40-1.28 (m, 4H).

Example XXXIII

4-((S)-1-(6-methyl-1-((R)-1-(4-(trifluoromethyl)phenyl)ethyl)-2,3-dihydro-1H-imidazo[1,2-b]pyrazole-7-carboxamido)ethyl)benzoic acid (Compound 35)

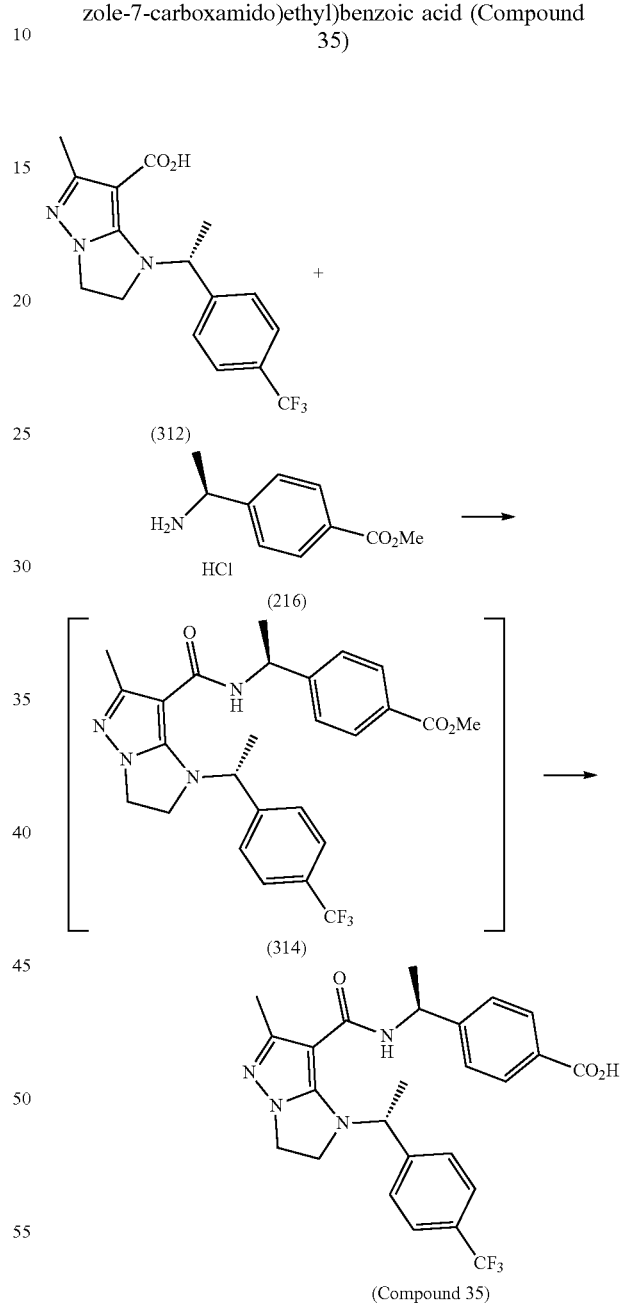

(Compound 35)

Following similar procedure for the preparation of (S)-4-(1-(6-(trifluoromethyl)-1-(3-(trifluoromethyl)benzyl)-2,3-dihydro-1H-imidazo[1,2-b]pyrazole-7-carboxamido)ethyl)benzoic acid (Compound 1) from 6-(trifluoromethyl)-1-(3-(trifluoromethyl)benzyl)-2,3-dihydro-1H-imidazo[1,2-b]pyrazole-7-carboxylic acid (215) described in Example I, Compound 35 was prepared from (R)-6-methyl-1-(1-(4-(trifluoromethyl)phenyl)ethyl)-2,3-dihydro-1H-imidazo[1, 2-b]pyrazole-7-carboxylic acid (312) and methyl (S)-4-(1-aminoethyl)benzoate hydrochloride (216). ¹HNMR (400 MHz, CD₃OD): δ ppm 7.90 (d, J=8.0 Hz, 2H), 7.46 (d, J=8.0 Hz, 4H), 7.31 (d, J=8.0 Hz, 2H), 5.41 (q, J=7.2 Hz, 1H), 5.15 (ddd, J=8.0, 8.0, 7.2 Hz, 1H), 3.94-3.82 (m, 3H), 3.50 (ddd, J=8.8, 8.0, 8.0 Hz, 1H), 2.30 (s, 3H), 1.52 (d, J=7.2 Hz, 3H), 1.49 (d, J=7.2 Hz, 3H).

Example XXXIV (S)—N-(1-(4-(2H-tetrazol-5-yl)phenyl)ethyl)-6-(trifluoromethyl)-1-(3-(trifluoromethyl)benzyl)-2,3-dihydro-1H-imidazo[1,2-b]pyrazole-7-carboxamide (Compound 36)

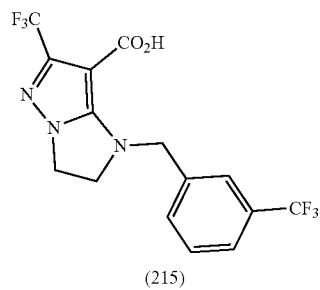

(215)

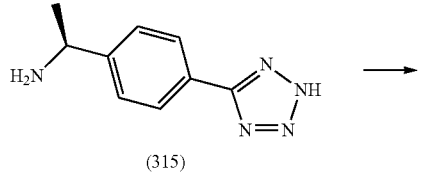

(315)

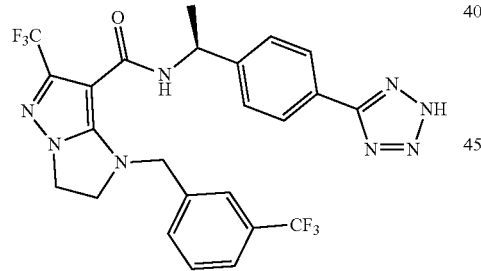

(Compound 36)

Following the procedure for the preparation of (S)-4-(1-(6-(trifluoromethyl)-1-(3-(trifluoromethyl)benzyl)-2,3-dihydro-1H-imidazo[1,2-b]pyrazole-7-carboxamido)ethyl)benzoic acid (Compound 1) from 6-(trifluoromethyl)-1-(3-(trifluoromethyl)benzyl)-2,3-dihydro-1H-imidazo[1,2-b]pyrazole-7-carboxylic acid (215) described in Example I, Compound 36 was prepared from 6-(trifluoromethyl)-1-(3-(trifluoromethyl)benzyl)-2,3-dihydro-1H-imidazo[1,2-b]pyrazole-7-carboxylic acid (215) and (S)-1-(4-(2H-tetrazol-5-yl)phenyl)ethan-1-amine (315). ¹HNMR (500 MHz, CD₃OD): δ ppm 7.87 (d, J=8.3 Hz, 2H), 7.60 (bs, 1H), 7.52 (d, J=7.83 Hz, 2H), 7.51 (d, J=7.83 Hz, 2H), 7.45 (t, J=7.83 Hz, 1H), 5.17 (q, J=7.0 Hz, 1H), 4.46 (d, J=15.2 Hz, 1H), 4.39 (d, J=15.2 Hz, 1H), 4.24-4.16 (m, 2H), 3.81-3.73 (m, 2H), 1.51 (d, J=7.3 Hz, 3H). LCMS (ES) (M+H)=551.

Example XXXV (S)—N-(1-(4-(2H-tetrazol-5-yl)phenyl)ethyl)-6-(trifluoromethyl)-1-(4-(trifluoromethyl)benzyl)-2,3-dihydro-1H-imidazo[1,2-b]pyrazole-7-carboxamide (Compound 37)

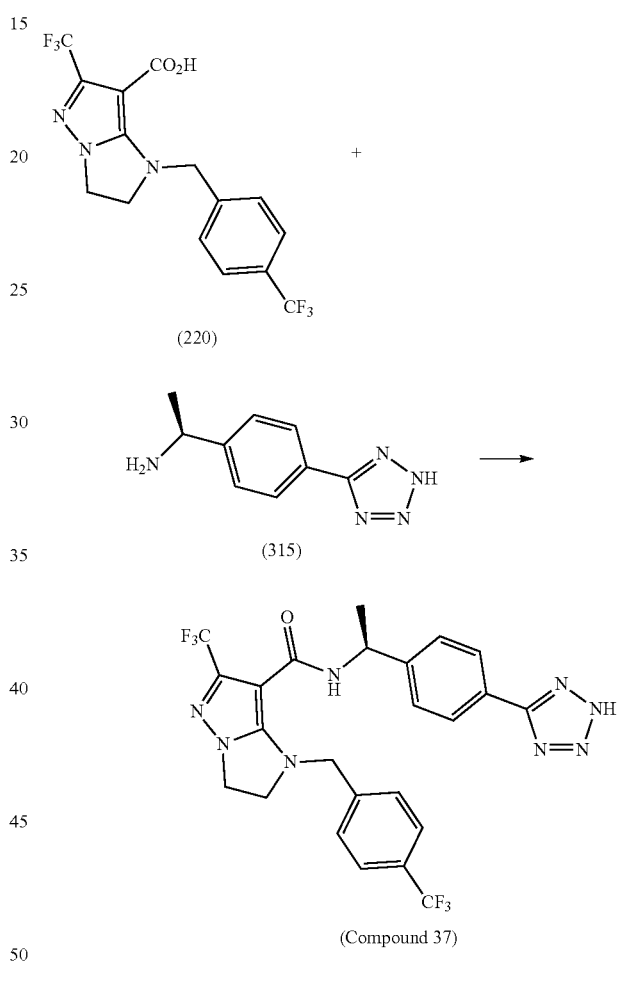

Following the procedure for the preparation of (S)-4-(1-(6-(trifluoromethyl)-1-(3-(trifluoromethyl)benzyl)-2,3-dihydro-1H-imidazo[1,2-b]pyrazole-7-carboxamido)ethyl)benzoic acid (Compound 1) from 6-(trifluoromethyl)-1-(3-(trifluoromethyl)benzyl)-2,3-dihydro-1H-imidazo[1,2-b]pyrazole-7-carboxylic acid (215) described in Example I, Compound 37 was prepared from 6-(trifluoromethyl)-1-(4-(trifluoromethyl)benzyl)-2,3-dihydro-1H-imidazo[1,2-b]pyrazole-7-carboxylic acid (220) and (S)-1-(4-(2H-tetrazol-5-yl)phenyl)ethan-1-amine (315). ¹HNMR (500 MHz, CD₃OD): δ ppm 7.93 (d, J=8.3 Hz, 2H), 7.53 (d, J=8.3 Hz, 2H), 7.50 (d, J=8.3 Hz, 2H), 7.40 (d, J=8.3 Hz, 2H), 5.20-5.15 (m, 1H), 4.62 (d, J=14.7 Hz, 1H), 4.57 (d, J=14.7 Hz, 1H), 4.22-4.14 (m, 2H), 3.81 (t, J=8.3 Hz, 2H), 1.52 (d, J=7.3 Hz, 3H). LCMS (ES) (M+H)=551.

Example XXXVI (S)-5-(1-(6-(trifluoromethyl)-1-(3-(trifluoromethyl)benzyl)-2,3-dihydro-1H-imidazo[1,2-b]pyrazole-7-carboxamido)ethyl)picolinic acid (Compound 38)

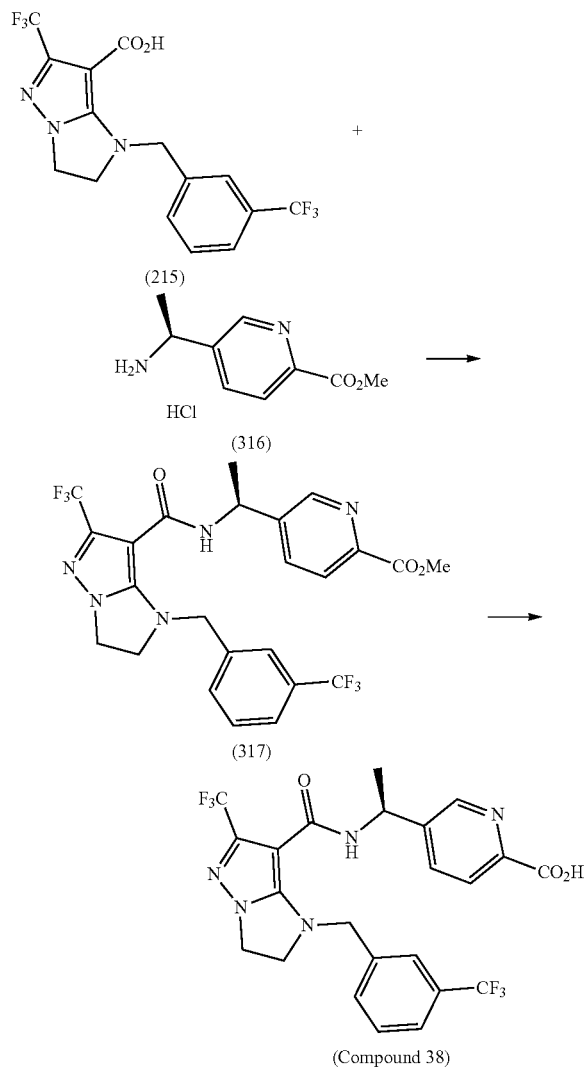

(215)

(316)

(317)

(Compound 38)

Methyl (S)-5-(1-(6-(trifluoromethyl)-1-(3-(trifluoromethyl)benzyl)-2,3-dihydro-1H-imidazo[1,2-b]pyrazole-7-carboxamido)ethyl)picolinate (317)

To a solution of 6-(trifluoromethyl)-1-(3-(trifluoromethyl)benzyl)-2,3-dihydro-1H-imidazo[1,2-b]pyrazole-7-carboxylic acid (215) (30 mg, 0.079 mmol) and methyl (S)-5-(1-aminoethyl)picolinate hydrochloride (316) in DMF (1.07 mL) was added DIPEA (69.1 µL, 0.40 mmol) and HATU (40.6 mg, 0.107 mmol) at rt. The reaction was stirred overnight. The reaction mixture was concentrated to remove DMF and the residue was purified with PTLC (E/H 65%) to give the desired compound (26.9 mg, 63% yield). $^1$HNMR (400 MHz): δ ppm 8.73 (s, 1H), 8.08 (d, J=8.0 Hz, 1H), 7.78 (d, J=8.0 Hz, 1H), 7.56-7.50 (m, 2H), 7.50-7.36 (m, 2H), 6.29 (bs, 1H), 5.25 (dq, J=7.2, 6.4, 6.4 Hz, 1H), 4.87 (d, J=15.0 Hz, 1H), 4.75 (d, J=15.0 Hz, 1H), 4.17 (dd, J=8.4, 8.4 Hz, 2H), 3.98 (s, 3H), 3.76 (dd, J=8.4, 8.4 Hz, 2H), 1.56 (d, J=6.8 Hz, 3H). LCMS (ES) [M+H]=542.3.

(S)-5-(1-(6-(trifluoromethyl)-1-(3-(trifluoromethyl)benzyl)-2,3-dihydro-1H-imidazo[1,2-b]pyrazole-7-carboxamido)ethyl)picolinic acid (Compound 38)

To (S)-methyl 5-(1-(6-(trifluoromethyl)-1-(3-(trifluoromethyl)benzyl)-2,3-dihydro-H-imidazo[1,2-b]pyrazole-7-carboxamido)ethyl)picolinate (317) (22 mg, 0.041 mmol) in methanol (822 µL) was added 1 M LiOH (406 µL, 0.406 mmol) at rt. The reaction mixture was stirred for 4 h. The reaction was neutralized with 1M HCl and extracted with EtOAc (3×15 mL). The combined organic phase was dried (Na$_2$SO$_4$), filtered and concentrated. The residue was purified with PTLC (8% MeOH/EtOAc) to give the desired compound (18.2 mg, 85% yield). $^1$HNMR (400 MHz): δ ppm 8.08 (d, J=8.0 Hz, 1H), 7.78 (d, J=8.0 Hz, 1H), 7.56=7.50 (m, 3H), 7.50-7.36 (m, 2H), 6.29 (bs, 1H), 5.25 (dq, J=7.2, 6.4 Hz, 1H), 5.00 (d, J=15.0 Hz, 1H), 4.42 (d, J=15.0 Hz, 1H), 4.07 (dd, J=8.4, 8.4 Hz, 2H), 3.63 (dd, J=8.4, 8.4 Hz, 2H), 1.25 (d, J=6.8 Hz, 3H). LCMS (ES) [M+H]=528.1.

Example XXXVII (S)-6-(1-(6-(trifluoromethyl)-1-(3-(trifluoromethyl)benzyl)-2,3-dihydro-1H-imidazo[1,2-b]pyrazole-7-carboxamido)ethyl)nicotinic acid (Compound 39)

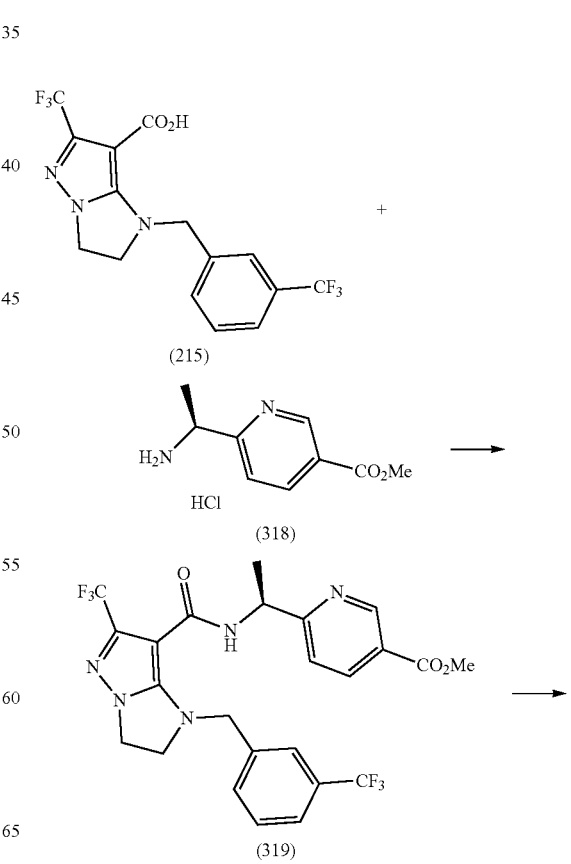

(215)

(318)

(319)

-continued

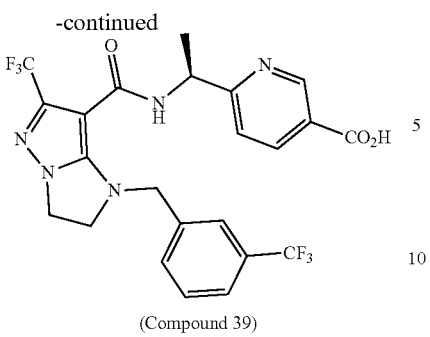

(Compound 39)

Following the procedure for the preparation of (S)-5-(1-(6-(trifluoromethyl)-1-(3-(trifluoromethyl)benzyl)-2,3-dihydro-1H-imidazo[1,2-b]pyrazole-7-carboxamido)ethyl)picolinic acid (Compound 38) as described in Example XXXVI, Compound 39 was prepared from 6-(trifluoromethyl)-1-(3-(trifluoromethyl)benzyl)-2,3-dihydro-1H-imidazo[1,2-b]pyrazole-7-carboxylic acid (215) and methyl (S)-6-(1-aminoethyl)nicotinate hydrochloride (318).

Methyl (S)-6-(1-(6-(trifluoromethyl)-1-(3-(trifluoromethyl)benzyl)-2,3-dihydro-1H-imidazo[1,2-b]pyrazole-7-carboxamido)ethyl)nicotinate (319)

$^1$HNMR (400 MHz): δ ppm 9.13 (s, 1H), 8.27 (d, J=8.0 Hz, 1H), 7.60-7.30 (m, 5H), 5.31 (dq, J=7.2, 6.8 Hz, 1H), 4.82 (d, J=14.8 Hz, 1H), 4.76 (d, J=14.8 Hz, 1H), 4.17 (dd, J=8.2, 8.2 Hz, 2H), 3.94 (s, 3H), 3.76 (dd, J=8.4, 8.2 Hz, 2H), 1.55 (d, J=6.8 Hz, 3H). LCMS (ES) [M+H]=542.2.

(S)-6-(1-(6-(trifluoromethyl)-1-(3-(trifluoromethyl)benzyl)-2,3-dihydro-1H-imidazo[1,2-b]pyrazole-7-carboxamido)ethyl)nicotinic acid (Compound 39)

$^1$HNMR (400 MHz): δ ppm 8.92 (s, 1H), 8.80 (d, J=8.0 Hz, 1H), 7.60-7.30 (m, 5H), 5.36 (dq, J=7.2, 6.8 Hz, 1H), 4.82 (d, J=14.8 Hz, 1H), 4.50 (d, J=14.8 Hz, 1H), 4.06 (dd, J=8.2, 8.2 Hz, 2H), 3.62 (dd, J=8.4, 8.2 Hz, 2H), 1.55 (d, J=6.8 Hz, 3H). LCMS (ES) [M+H]=528.1.

Example XXXVIII (S)—N-(1-(4-(furan-3-yl)phenyl)ethyl)-6-(trifluoromethyl)-1-(4-(trifluoromethyl)benzyl)-2,3-dihydro-1H-imidazo[1,2-b]pyrazole-7-carboxamide (Compound 40)

(S)—N-(1-(4-bromophenyl)ethyl)-6-(trifluoromethyl)-1-(4-(trifluoromethyl)benzyl)-2,3-dihydro-1H-imidazo[1,2-b]pyrazole-7-carboxamide (321)

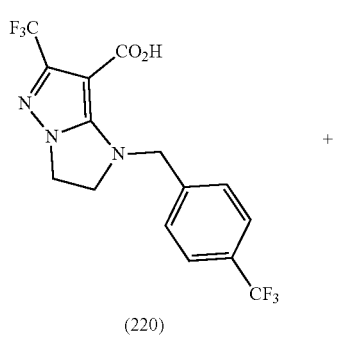

(220)

+

-continued

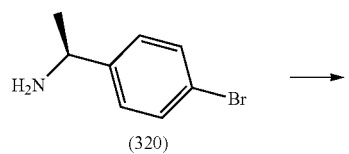

(320)

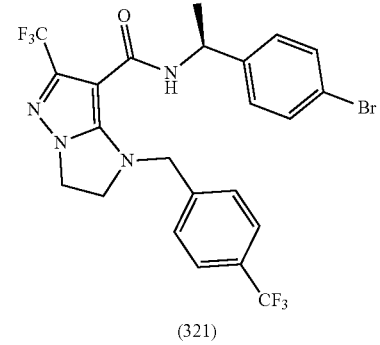

(321)

Following a similar procedure for the preparation of (S)-4-(1-(6-(trifluoromethyl)-1-(3-(trifluoromethyl)benzyl)-2,3-dihydro-1H-imidazo[1,2-b]pyrazole-7-carboxamido)ethyl)benzoic acid (Compound 1), compound 321 was prepared from 6-(trifluoromethyl)-1-(4-(trifluoromethyl)benzyl)-2,3-dihydro-1H-imidazo[1,2-b]pyrazole-7-carboxylic acid (220) and (S)-1-(4-bromophenyl)ethan-1-amine (320). 1HNMR (400 MHz): δ ppm 7.57 (d, J=7.8 Hz, 2H), 7.43 (d, J=7.8 Hz, 2H), 7.39 (d, J=7.8 Hz, 2H), 7.19 (d, J=7.8 Hz, 2H), 6.22 (bs, 1H), 5.16-5.09 (m, 1H), 4.84 (s, 2H), 4.16 (t, J=8.6 Hz, 2H), 3.76 (t, J=8.2 Hz, 2H), 1.50 (d, J=7.0 Hz, 3H). LCMS (ES) [M+H]=561/563.

(S)—N-(1-(4-(furan-3-yl)phenyl)ethyl)-6-(trifluoromethyl)-1-(4-(trifluoromethyl)benzyl)-2,3-dihydro-1H-imidazo[1,2-b]pyrazole-7-carboxamide (Compound 40)

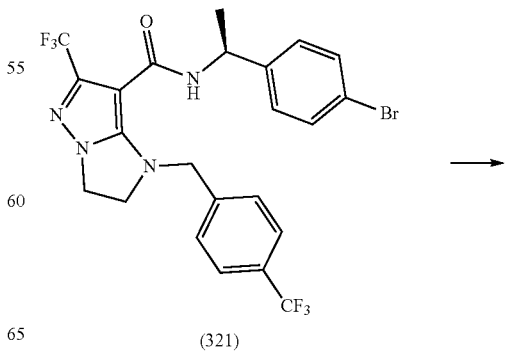

(321)

-continued

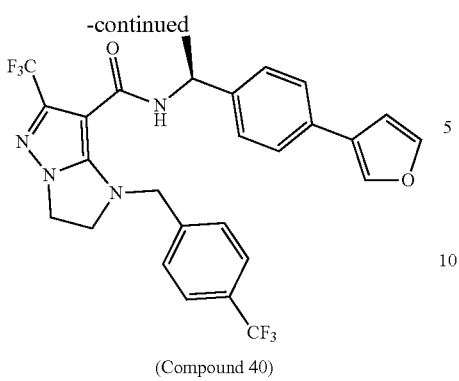

(Compound 40)

To a reaction tube containing furan-3-ylboronic acid (1.3 eq) was added a solution of (S)—N-(1-(4-bromophenyl)ethyl)-6-(trifluoromethyl)-1-(4-(trifluoromethyl)benzyl)-2,3-dihydro-1H-imidazo[1,2-b]pyrazole-7-carboxamide (321) (20 mg, 0.036 mmol) in 1,4-dioxane (0.5 mL), a solution of Pd(PPh$_3$)$_4$ (0.1 eq) in 1,4-dioxane (0.5 mL) and a solution of Na$_2$CO$_3$ (4 eq) in water (0.5 mL). The reaction mixture was degassed by bubbling with N$_2$ and sealed. The reaction was heated at 80° C. for 20 h. After cooling to rt, the reaction mixture was concentrated and the residue was purified by PTLC (50% AcOEt/Heptane) to give Compound 40 (17.2 mg, 88% yield). $^1$HNMR (400 MHz): δ ppm 7.70 (s, 1H), 7.56 (d, J=8.4 Hz, 2H), 7.47-7.20 (m, 3H), 7.39 (d, J=8.0 Hz, 2H), 7.33 (d, J=8.0 Hz, 2H), 6.67 (dd, J=1.6 and 0.8 Hz, 1H), 6.26 (bd, J=5.2 Hz, 1H), 5.20 (dt, J=7.2 and 6.8 Hz, 1H), 4.88 (d, J=14.8 Hz, 1H), 4.82 (d, J=14.8 Hz, 1H), 4.16 (t, J=8.6 Hz, 2H), 3.77 (t, J=8.6 Hz, 2H), 1.54 (d, J=6.4 Hz, 3H). LCMS (ES) [M+H]=549.3.

Example XXXIX (S)-4-(1-(4-(4-chlorobenzyl)-2-(trifluoromethyl)-4,5,6,7-tetrahydropyrazolo[1,5-a]pyrimidine-3-carboxamido)ethyl)benzoic acid (Compound 41)

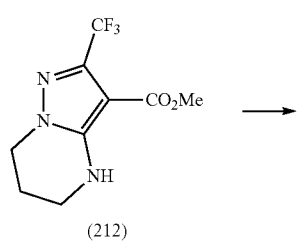

(212)

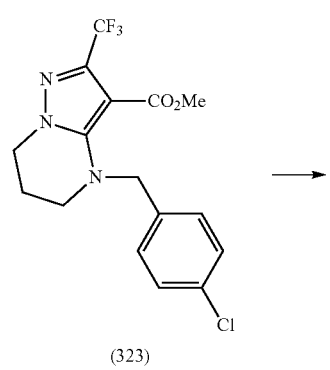

(323)

-continued

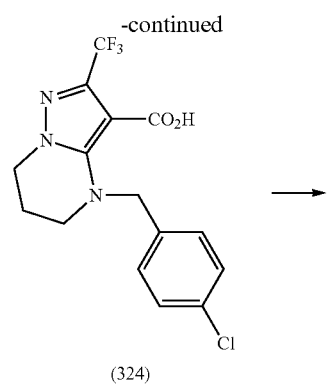

(324)

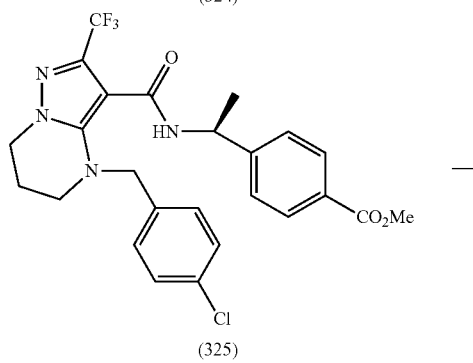

(325)

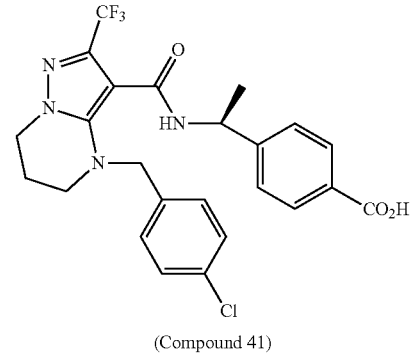

(Compound 41)

Following the similar procedure for the preparation of (S)-4-(1-(6-(trifluoromethyl)-1-(3-(trifluoromethyl)benzyl)-2,3-dihydro-1H-imidazo[1,2-b]pyrazole-7-carboxamido)ethyl)benzoic acid (Compound 1) from methyl 6-(trifluoromethyl)-2,3-dihydro-1H-imidazo[1,2-b]pyrazole-7-carboxylate (208) and 1-(chloromethyl)-3-(trifluoromethyl)benzene (214) described earlier in Example I, Compound 41 was similarly prepared from methyl 2-(trifluoromethyl)-4,5,6,7-tetrahydropyrazolo[1,5-a]pyrimidine-3-carboxylate (212) and 1-chloro-4-(chloromethyl)benzene.

Methyl 4-(4-chlorobenzyl)-2-(trifluoromethyl)-4,5,6,7-tetrahydropyrazolo[1,5-a]pyrimidine-3-carboxylate (323) was used as crude for next step hydrolysis to 4-(4-chlorobenzyl)-2-(trifluoromethyl)-4,5,6,7-tetrahydropyrazolo[1,5-a]pyrimidine-3-carboxylic acid (324): $^1$HNMR (400 MHz, CD$_3$OD): δ ppm 7.31 (d, J=8.6 Hz, 2H), 7.26 (d, J=8.6 Hz, 2H), 4.64 (s, 2H), 4.01 (dd, J=6.0, 5.6 Hz, 2H), 3.10 (dd, J=5.2, 5.6 Hz, 2H), 2.00 (m, 2H).

Methyl (S)-4-(1-(4-(4-chlorobenzyl)-2-(trifluoromethyl)-4,5,6,7-tetrahydropyrazolo[1,5-a]pyrimidine-3-carboxamido)ethyl)benzoate (325)

$^1$HNMR (400 MHz, CD$_3$OD): δ ppm 7.84 (d, J=8.8 Hz, 2H), 7.20 (d, J=8.0 Hz, 2H), 7.17 (d, J=8.8 Hz, 2H), 7.04 (d, J=8.8 Hz, 2H), 5.99 (bd, J=8.0 Hz, 1H), 5.10 (m, 1H), 4.50 (d, J=16.0 Hz, 1H), 4.34 (d, J=16.0 Hz, 1H), 4.05 (m, 2H), 3.84 (s, 3H), 3.11 (m, 2H), 2.05 (m, 2H), 1.38 (d, J=7.2 Hz, 3H). LCMS (ES) (M+H)=521.2.

(S)-4-(1-(4-(4-chlorobenzyl)-2-(trifluoromethyl)-4,5,6,7-tetrahydropyrazolo[15-a]pyrimidine-3-carboxamido)ethyl)benzoic acid (Compound 41)

¹HNMR (400 MHz, CD₃OD): δ ppm 7.74 (d, J=8.4 Hz, 2H), 7.24 (d, J=8.0 Hz, 2H), 7.19 (d, J==8.4 Hz, 2H), 7.07 (d, J=8.4 Hz, 2H), 4.97 (m, 1H), 4.25 (d, J=16.0 Hz, 1H), 4.16 (d, J=16.4 Hz, 1H), 4.02 (m, 2H), 3.06 (m, 2H), 2.04 (m, 2H), 1.31 (d, J=6.8 Hz, 3H). LCMS (ES) (M+H)=507.2.

Following the similar procedure for the preparation of (S)-4-(1-(4-(4-chlorobenzyl)-2-(trifluoromethyl)-4,5,6,7-tetrahydropyrazolo[1,5-a]pyrimidine-3-carboxamido)ethyl)benzoic acid (Compound 41) from methyl 2-(trifluoromethyl)-4,5,6,7-tetrahydropyrazolo[1,5-a]pyrimidine-3-carboxylate (212) and 1-chloro-4-(chloromethyl)benzene described above in Example XXXIX, Compounds 42 and 44-46 were similarly prepared from methyl 2-(trifluoromethyl)-4,5,6,7-tetrahydropyrazolo[1,5-a]pyrimidine-3-carboxylate (212) and corresponding substituted benzyl chloride or benzyl bromide.

Example XL (S)-4-(1-(4-(3-chlorobenzyl)-2-(trifluoromethyl)-4,5,6,7-tetrahydropyrazolo[1,5-a]pyrimidine-3-carboxamido)ethyl)benzoic acid (Compound 42)

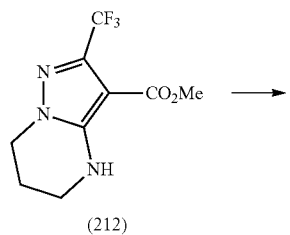
(212)

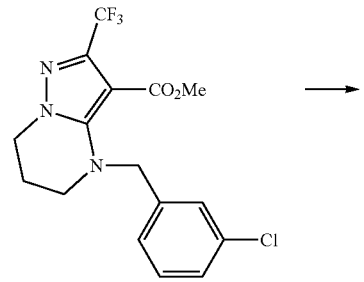
(326)

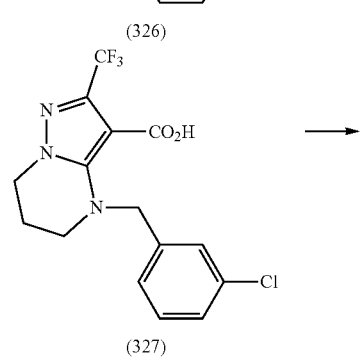
(327)

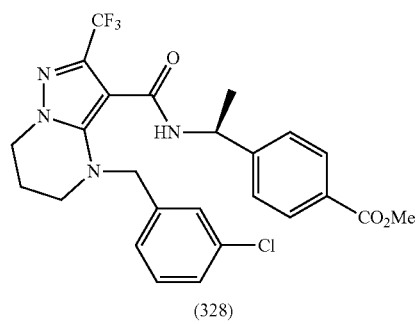
(328)

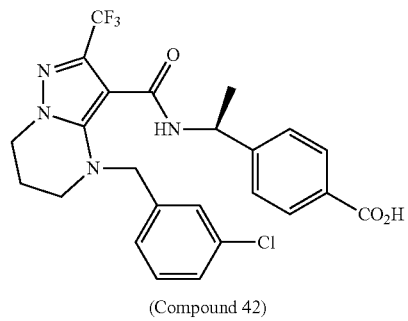
(Compound 42)

4-(3-chlorobenzyl)-2-(trifluoromethyl)-4,5,6,7-tetrahydropyrazolo[1,5-a]pyrimidine-3-carboxylic acid (327)

¹HNMR (400 MHz): δ ppm 7.2-7.45 (m, 4H, m), 4.70 (s, 2H), 4.14 (dd, J=6.0, 6.0 Hz, 2H), 3.18 (dd, J=5.2, 5.6 Hz, 2H), 2.09 (m, 2H).

Methyl (S)-4-(1-(4-(3-chlorobenzyl)-2-(trifluoromethyl)-4,5,6,7-tetrahydropyrazolo[1,5-a]pyrimidine-3-carboxamido)ethyl)benzoate (328)

¹HNMR (400 MHz): δ ppm 7.84 (d, J=8.8 Hz, 2H), 7.20 (d, J=8.0 Hz, 2H), 7.14 (m, 3H), 6.99 (d, J=7.2 Hz, 2H), 5.99 (bd, J=3.6 Hz, 1H), 5.09 (m, 1H), 4.52 (d, J=16.0 Hz, 1H), 4.39 (d, J=16.0 Hz, 1H), 4.05 (m, 2H), 3.84 (s, 3H), 3.13 (m, 2H), 2.06 (m, 2H), 1.37 (d, J=7.2 Hz, 3H). LCMS (ES) (M+H)=521.3.

(S)-4-(1-(4-(3-chlorobenzyl)-2-(trifluoromethyl)-4,5,6,7-tetrahydropyrazolo[1,5-a]pyrimidine-3-carboxamido)ethyl)benzoic acid (Compound 42)

¹HNMR (400 MHz, CD₃OD): δ ppm 7.73 (d, J=8.4 Hz, 2H), 7.24 (d, J=8.8 Hz, 2H), 7.18 (m, 2H), 7.14 (s, 1H), 7.03 (m, 1H), 4.96 (m, 1H), 4.25 (d, J=16.0 Hz, 1H), 4.18 (d, J=16.0 Hz, 1H), 4.02 (t, J=6.0 Hz, 2H), 3.04 (m, 2H), 2.03 (m, 2H), 1.29 (d, J=6.8 Hz, 3H). LCMS (ES) (M+H)=507.2.

Example XLI (S)-4-(1-(1-(2-chlorobenzyl)-6-(trifluoromethyl)-2,3-dihydro-1H-imidazo[1,2-b]pyrazole-7-carboxamido)ethyl)benzoic acid (Compound 43)

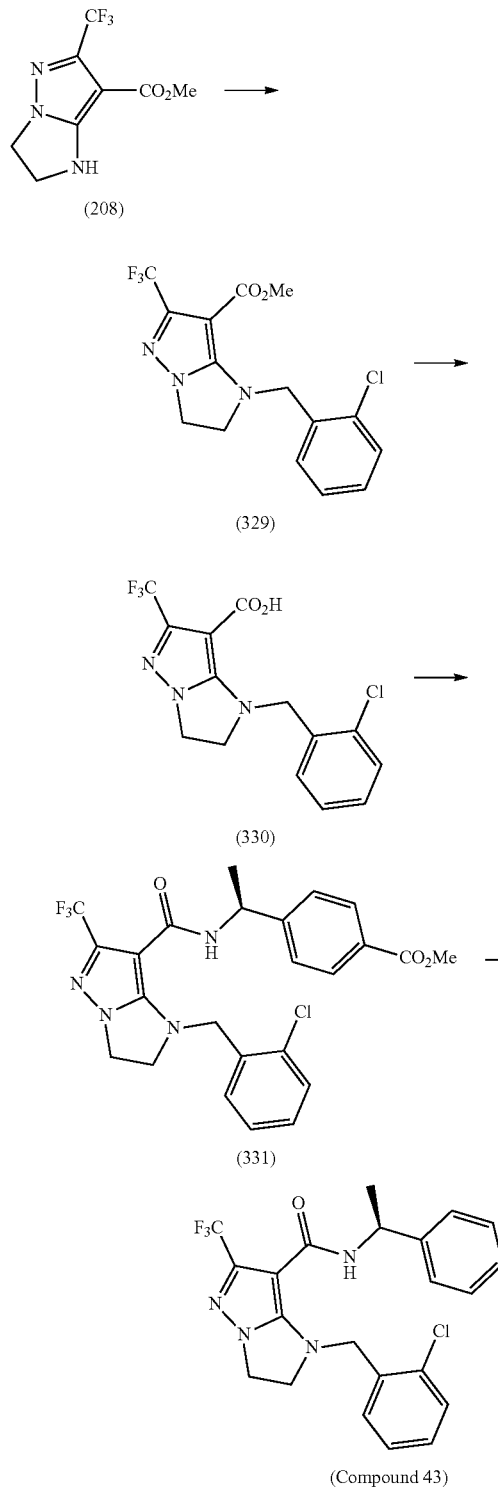

Methyl 1-(2-chlorobenzyl)-6-(trifluoromethyl)-2,3-dihydro-1H-imidazo[1,2-b]pyrazole-7-carboxylate (329)

$^1$HNMR (400 MHz, CD$_3$OD): δ ppm 7.39 (dd, J=7.6, 16.0 Hz, 1H), 7.25 (m, 3H), 5.00 (s, 2H), 4.15 (t, J=8.8 Hz, 2H), 3.87 (t, J=8.0 Hz, 2H), 3.61 (s, 3H). LCMS (ES) (M+H)=360.2.

1-(2-chlorobenzyl)-6-(trifluoromethyl)-2,3-dihydro-1H-imidazo[1,2-b]pyrazole-7-carboxylic acid (330)

$^1$HNMR (400 MHz, DMSO-d6): δ ppm 7.39 (d, J=7.2 Hz, 1H), 7.27 (m, 3H), 4.96 (s, 2H), 4.15 (t, J=8.0 Hz, 2H), 3.78 (t, J=8.4 Hz, 2H). LCMS (ES) (M+H)=346.2.

Methyl (S)-4-(1-(1-(2-chlorobenzyl)-6-(trifluoromethyl)-2,3-dihydro-1H-imidazo[1,2-b]pyrazole-7-carboxamido)ethyl)benzoate (331)

$^1$HNMR (400 MHz): δ ppm 7.92 (d, J=8.8 Hz, 2H), 7.31 (m, 3H), 7.14 (m, 3H), 6.17 (bd, J=5.2 Hz, 1H), 5.19 (m, 1H), 4.90 (d, J=14.8 Hz, 1H), 4.84 (d, J=14.8 Hz, 1H), 4.09 (t, J=8.0 Hz, 2H), 3.84 (s, 3H), 3.74 (t, J=8.4 Hz, 2H), 1.46 (d, J=7.2 Hz, 3H). LCMS (ES) (M+H)=507.3.

(S)-4-(1-(1-(2-chlorobenzyl)-6-(trifluoromethyl)-2,3-dihydro-1H-imidazo[1,2-b]pyrazole-7-carboxamido)ethyl)benzoic acid (Compound 43)

$^1$HNMR (400 MHz, CD$_3$OD): δ ppm 7.78 (d, J=8.4 Hz, 2H), 7.33 (m, 2H), 7.29 (d, J=8.8 Hz, 2H), 7.22 (m, 2H), 5.05 (m, 1H), 4.47 (d, J=15.2 Hz, 1H), 4.43 (d, J=15.2 Hz, 1H), 4.15 (t, J=8.8 Hz, 2H), 3.77 (m, 2H), 1.38 (d, J=7.2 Hz, 3H). LCMS (ES) (M+H)=493.3.

Example XLII (S)-4-(1-(2-(trifluoromethyl)-4-(3-(trifluoromethyl)benzyl)-4,5,6,7-tetrahydropyrazolo[1,5-a]pyrimidine-3-carboxamido)ethyl)benzoic acid (Compound 44)

4.26 (d, J=15.6 Hz, 1H), 4.02 (m, 2H), 3.04 (m, 2H), 2.05 (m, 2H), 1.27 (d, J=7.2 Hz, 3H). LCMS (ES) (M+H)=541.2.

Example XLIII (S)-4-(1-(2-(trifluoromethyl)-4-(4-(trifluoromethyl)benzyl)-4,5,6,7-tetrahydropyrazolo[1,5-a]pyrimidine-3-carboxamido)ethyl)benzoic acid (Compound 45)

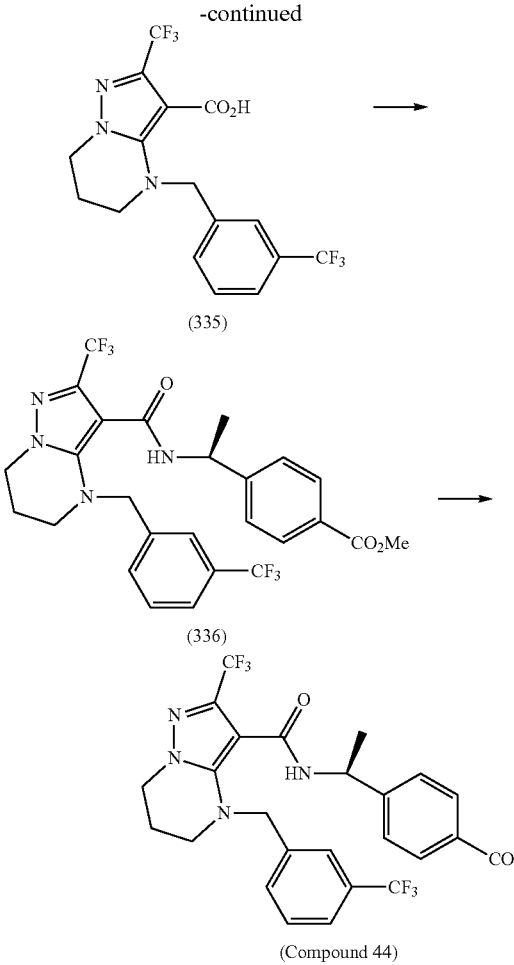

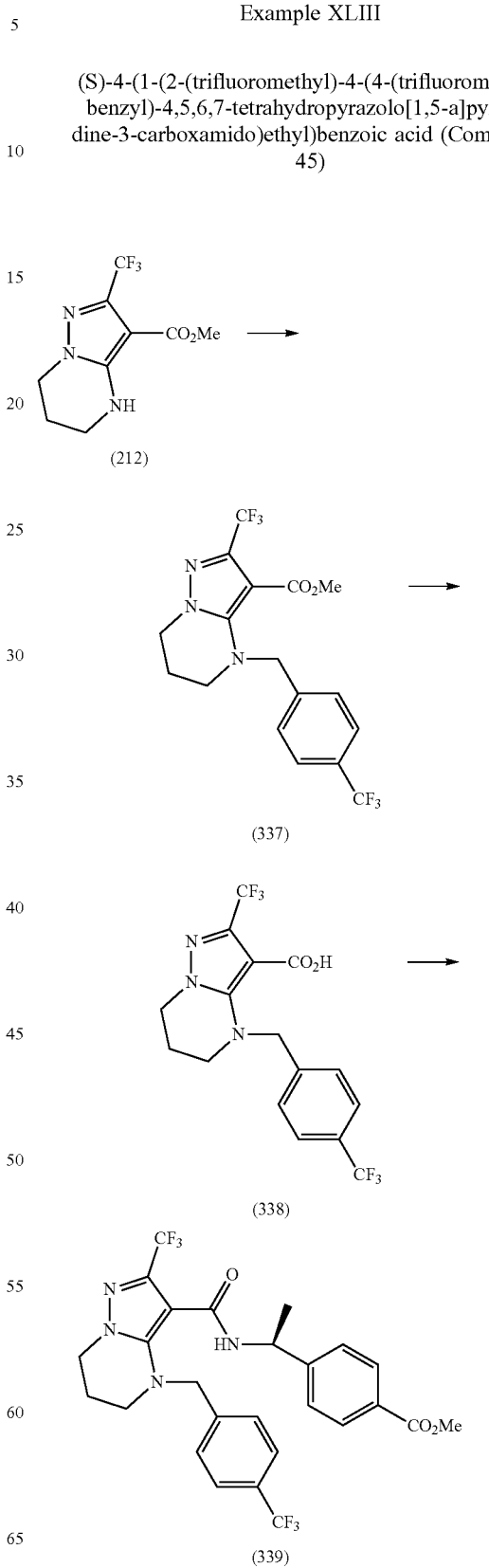

2-(trifluoromethyl)-4-(3-(trifluoromethyl)benzyl)-4,5,6,7-tetrahydropyrazolo[,5-a]pyrimidine-3-carboxylic acid (335)

¹HNMR (400 MHz): δ ppm 7.63 (s, 1H), 7.55 (m, 2H), 7.46 (m, 1H), 4.75 (s, 2H), 4.15 (dd, J=6.0, 6.0 Hz, 2H), 3.17 (dd, J=5.6, 5.2 Hz, 2H), 2.11 (2H, dd, J=6.0, 4.8 Hz, 2H).

Methyl (S)-4-(1-(2-(trifluoromethyl)-4-(3-(trifluoromethyl)benzyl)-4,5,6,7-tetrahydropyrazolo[1,5-a]pyrimidine-3-carboxamido)ethyl)benzoate (336)

¹HNMR (400 MHz): δ ppm 7.81 (d, J=8.4 Hz, 2H), 7.45 (m, 1H), 7.38 (s, 1H), 7.34 (m, 2H), 7.19 (m, 2H), 6.00 (bd, J=7.6 Hz, 1H), 5.07 (m, 1H), 4.55 (d, J=16.0 Hz, 1H), 4.48 (d, J=15.6 Hz, 1H), 4.06 (m, 2H), 3.82 (s, 3H), 3.11 (m, 2H), 2.06 (m, 2H), 1.35 (d, J=6.8 Hz, 3H). LCMS (ES) (M+H)=555.3.

(S)-4-(1-(2-(trifluoromethyl)-4-(3-(trifluoromethyl)benzyl)-4,5,6,7-tetrahydropyrazolo[1,5-a]pyrimidine-3-carboxamido)ethyl)benzoic acid (Compound 44)

¹HNMR (400 MHz, CD₃OD): δ ppm 7.69 (d, J=8.0 Hz, 2H), 7.48 (d, J=6.8 Hz, 1H), 7.44 (s, 1H), 7.38 (m, 2H), 7.23 (d, J=8.4 Hz, 2H), 4.95 (m, 1H), 4.31 (d, J=16.0 Hz, 1H),

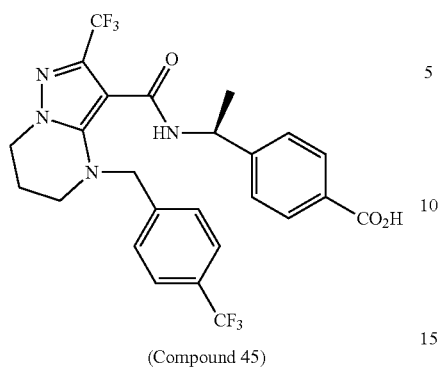

(Compound 45)

Methyl 2-(trifluoromethyl)-4-(4-(trifluoromethyl)benzyl)-4,5,6,7-tetrahydropyrazolo[1,5-a]pyrimidine-3-carboxylate (337)

$^1$HNMR (400 MHz): δ ppm 7.63 (d, J=8.0 Hz, 2H), 7.51 (d, J=8.0 Hz, 2N), 4.76 (s, 2H), 4.15 (t, J=6.0 Hz, 2H), 3.73 (s, 3H), 3.16 (dd, J=5.6, 5.2 Hz, 2H), 2.12 (m, 2H).

2-(trifluoromethyl)-4-(4-(trifluoromethyl)benzyl)-4,5,6,7-tetrahydropyrazolo[1,5-a]pyrimidine-3-carboxylic acid (338)

$^1$HNMR (400 MHz): δ ppm 7.60 (d, J=8.0 Hz, 2H), 7.46 (d, J=8.0 Hz, 2H), 4.78 (s, 2H), 4.15 (dd, J=6.4, 5.6 Hz, 2H), 3.18 (dd, J=5.4, 6.0 Hz, 2H), 2.11 (dd, J=6.0, 6.0 Hz, 2H), 2.12 (H).

Methyl (S)-4-(1-(2-(trifluoromethyl)-4-(4-(trifluoromethyl)benzyl)-4,5,6,7-tetrahydropyrazolo[1,5-a]pyrimidine-3-carboxamido)ethyl)benzoate (339)

$^1$HNMR (400 MHz): δ ppm 7.82 (d, J=8.0 Hz, 2H), 7.46 (d, J=8.4 Hz, 2H), 7.23 (d, J=8.0 Hz, 2H), 7.19 (d, J=8.0 Hz, 2H), 5.99 (bd, J=7.2 Hz, 1H), 5.07 (m, 1H), 4.61 (d, J=16.0 Hz, 1H), 4.44 (d, J=16.0 Hz, 1H), 4.05 (m, 2H), 3.83 (s, 3H), 3.13 (m, 2H), 2.08 (m, 2H), 1.36 (d, J=6.4 Hz, 3H). LCMS (ES) (M+H)=555.3.

(S)-4-(1-(2-(trifluoromethyl)-4-(4-(trifluoromethyl)benzyl)-4,5,6,7-tetrahydropyrazolo[1,5-a]pyrimidine-3-carboxamido)ethyl)benzoic acid (Compound 45)

$^1$HNMR (400 MHz, CD$_3$OD): δ ppm 7.71 (d, J=8.4 Hz, 2H), 7.49 (d, J=8.0 Hz, 2H), 7.27 (d, J=8.0 Hz, 2H), 7.22 (d, J=8.0 Hz, 2H), 4.93 (m, 1H), 4.35 (d, J=16.4 Hz, 1H), 4.27 (d, J=16.4 Hz, 1H), 4.03 (m, 2H), 3.06 (m, 2H), 2.06 (m, 2H), 1.26 (d, J=6.8 Hz, 3H). LCMS (ES) (M+H)=541.2.

Example XLIV

(S)-4-(1-(2-(trifluoromethyl)-4-(2-(trifluoromethyl)benzyl)-4,5,6,7-tetrahydropyrazolo[1,5-a]pyrimidine-3-carboxamido)ethyl)benzoic acid (Compound 46)

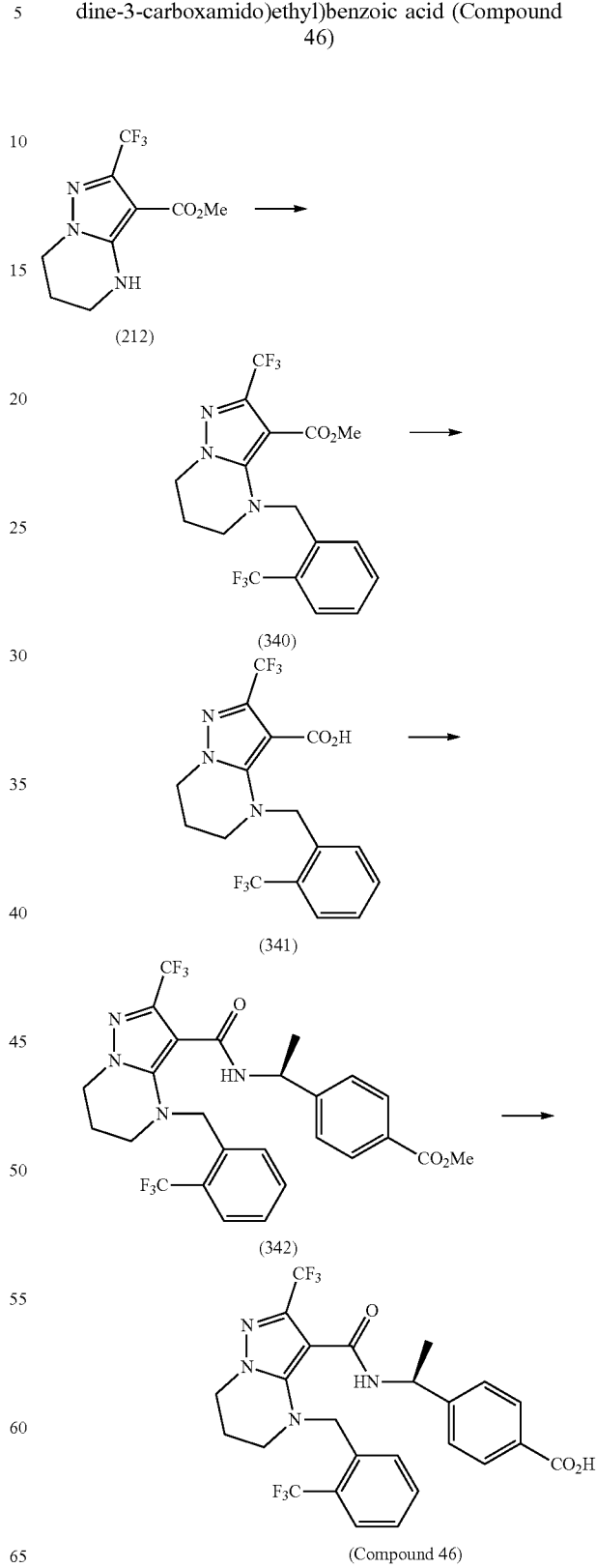

(Compound 46)

2-(trifluoromethyl)-4-(2-(trifluoromethyl)benzyl)-4,
5,6,7-tetrahydropyrazolo[1,5-a]pyrimidine-3-carboxylic acid (341)

¹HNMR (400 MHz): δ ppm 7.72 (d, J=8.0 Hz, 1H), 7.66 (d, J=8.0 Hz, 1H), 7.53 (dd, J=8.0, 8.0 Hz, 1H), 7.32 (dd, J=8.0, 8.0 Hz, 1H), 4.88 (s, 2H), 4.18 (dd, J=5.6, 6.0 Hz, 2H), 3.18 (dd, J=5.2, 5.6 Hz, 2H), 2.16 (m, 2H).

Methyl (S)-4-(1-(2-(trifluoromethyl)-4-(2-(trifluoromethyl)benzyl)-4,5,6,7-tetrahydropyrazolo[1,5-a]pyrimidine-3-carboxamido)ethyl)benzoate (342)

¹HNMR (400 MHz): δ ppm 7.79 (d, J=8.0 Hz, 2H), 7.56 (d, J=8.0 Hz, 1H), 7.48 (d, J=7.6 Hz, 1H), 7.42 (t, J=7.6 Hz, 1H), 7.29 (t, J=7.6 Hz, 1H), 7.14 (d, J=8.0 Hz, 2H), 5.96 (bd, J=8.0 Hz, 1H), 5.07 (m, 1H), 4.68 (d, J=16.8 Hz, 1H), 4.55 (d, J=16.8 Hz, 1H), 4.06 (m, 2H), 3.82 (s, 3H), 3.05 (m, 2H), 2.06 (m, 2H), 1.32 (d, J=6.8 Hz, 3H). LCMS (ES) (M+H) =555.3.

(S)-4-(1-(2-(trifluoromethyl)-4-(2-(trifluoromethyl)benzyl)-4,5,6,7-tetrahydropyrazolo[1,5-a]pyrimidine-3-carboxamido)ethyl)benzoic acid (Compound 46)

¹HNMR (400 MHz, CD₃OD): δ ppm 7.66 (d, J=8.8 Hz, 2H), 7.58 (d, J=8.0 Hz, 1H), 7.48 (m, 2H), 7.35 (m, 1H), 7.13 (d, J=8.4 Hz, 2H), 4.89 (m, 1H), 4.54 (d, J=17.2 Hz, 1H), 4.44 (d, J=17.2 Hz, 1H), 4.05 (m, 2H), 3.08 (m, 2H), 2.09 (m, 2H), 1.17 (d, J=6.8 Hz, 3H). LCMS (ES) (M+H)=541.2.

Example XLV

Intermediates Used in Examples XLVI-L Below

Methyl 6-(trifluoromethyl)-1-(4-(trifluoromethyl)phenyl)-2,3-dihydro-1H-imidazo[1,2-b]pyrazole-7-carboxylate (344)

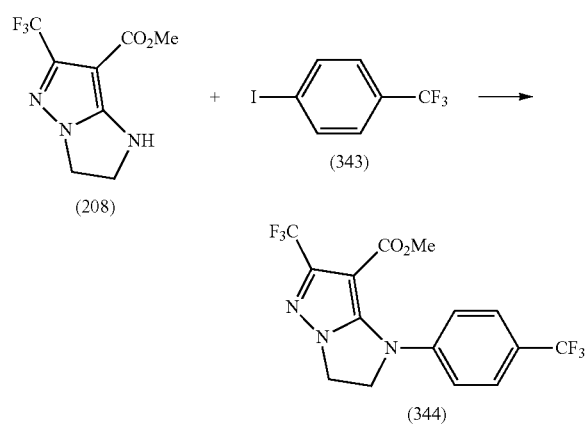

In a microwave vial (50 mL) was charged with methyl 6-(trifluoromethyl)-2,3-dihydro-1H-imidazo[1,2-b]pyrazole-7-carboxylate (208) (2.13 mmol), 1-iodo-4-(trifluoromethyl)benzene (343) (1.4 equiv) and 28 mL of dry toluene under nitrogen atmosphere. Then Pd₂(dba)₃ (65 mg) and DPPF (225 mg) were added followed by sodium tert-butoxide (300 mg, 1.6 equiv). The reaction mixture was capped and heated at 120 C for 30 minutes. The reaction mixture was cooled to rt and filtered. The filtrate was concentrated and purified by column chromatography to give compound 344 (180 mg, 22% yield). ¹HNMR (400 MHz): δ ppm 7.61 (d, J=9.0 Hz, 2H), 7.14 (d, J=9.0 Hz, 2H), 4.59 (dd, J=8.0, 8.8 Hz, 2H), 4.44 (dd, J=8.8, 7.6 Hz, 2H), 3.58 (s, 3H).

Following the same procedures for the preparation of methyl 6-(trifluoromethyl)-1-(4-(trifluoromethyl)phenyl)-2,3-dihydro-1H-imidazo[1,2-b]pyrazole-7-carboxylate (344), the following compounds were prepared from methyl 6-(trifluoromethyl)-2,3-dihydro-1H-imidazo[1,2-b]pyrazole-7-carboxylate (208) and corresponding aryl iodide.

Methyl 6-(trifluoromethyl)-1-(3-(trifluoromethyl)phenyl)-2,3-dihydro-1H-imidazo[1,2-b]pyrazole-7-carboxylate (346)

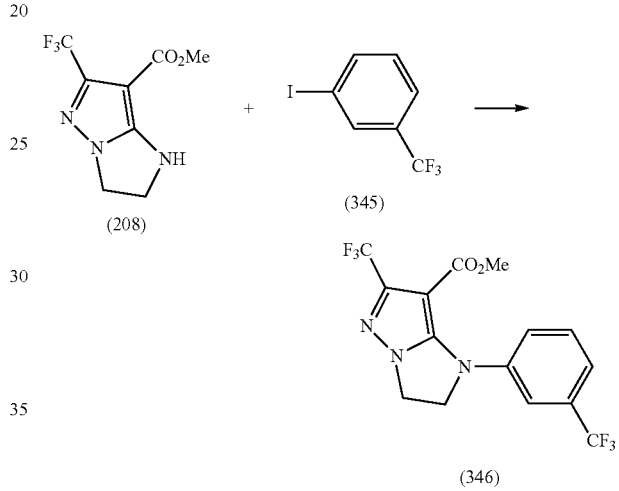

¹HNMR (400 MHz): δ ppm 7.48-7.32 (m, 4H), 4.58-4.43 (m, 4H), 3.52 (s, 3H).

Methyl 1-(3-chlorophenyl)-6-(trifluoromethyl)-2,3-dihydro-1H-imidazo[1,2-b]pyrazole-7-carboxylate (348)

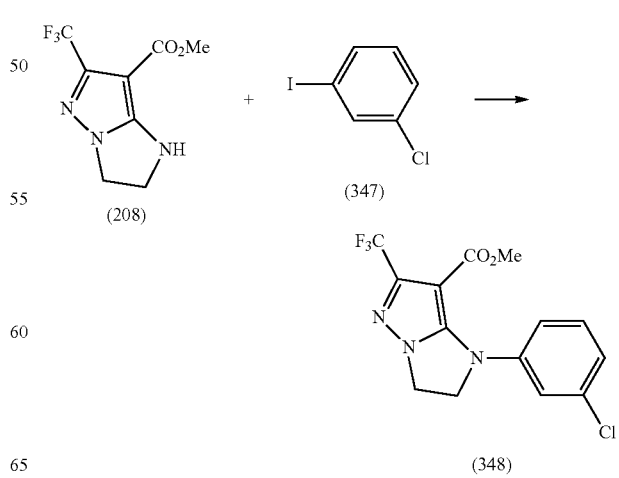

¹HNMR (400 MHz): δ ppm 7.28 (dd, J=8.0, 7.6 Hz, 1H), 7.19-7.17 (m, 1H), 7.09 (dd, J=2.4, 2.0 Hz, 1H), 7.00-6.97 (m, 1H), 4.53-4.48 (m, 2H), 4.43-4.39 (m, 2H), 3.54 (s, 3H).

Methyl 1-(4-chlorophenyl)-6-(trifluoromethyl)-2,3-dihydro-1H-imidazo[1,2-b]pyrazole-7-carboxylate (350)

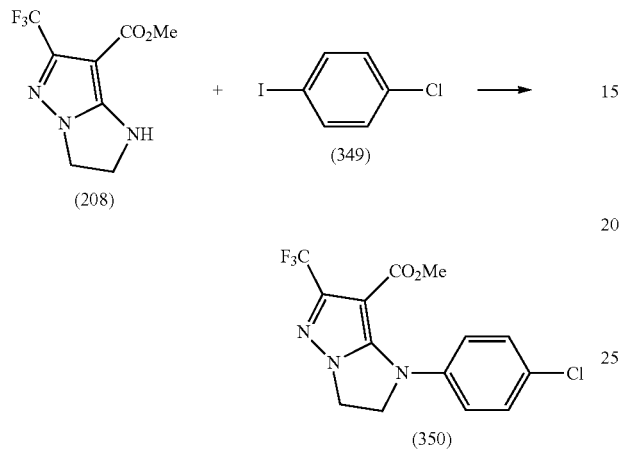

¹HNMR (400 MHz): δ ppm 7.33 (d, J=8.6 Hz, 2H), 7.05 (d, J=8.6 Hz, 2H), 4.48-4.40 (m 4H), 3.52 (s, 3H).

Following the same procedures for the preparation of methyl 6-(trifluoromethyl)-1-(4-(trifluoromethyl)phenyl)-2,3-dihydro-1H-imidazo[1,2-b]pyrazole-7-carboxylate (344), the following compound was prepared from methyl 2-(trifluoromethyl)-4,5,6,7-tetrahydropyrazolo[1,5-a]pyrimidine-3-carboxylate (212) and 1-iodo-4-(trifluoromethyl)benzene (343).

Methyl 2-(trifluoromethyl)-4-(4-(trifluoromethyl)phenyl)-4,5,6,7-tetrahydropyrazolo[1,5-a]pyrimidine-3-carboxylate (351)

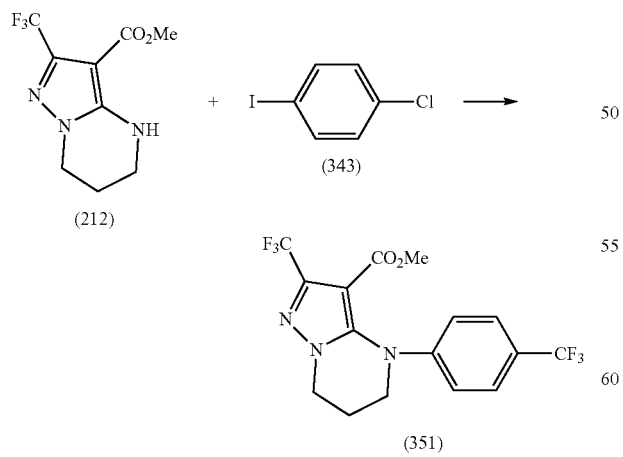

¹HNMR (400 MHz): δ ppm 7.58 (d, J=8.2 Hz, 2H), 7.20 (d, J=8.2 Hz, 2H), 4.31 (dd, J=6.4, 6.0 Hz, 2H), 3.87 (dd, J=5.6, 5.2 Hz, 2H), 3.36 (s, 3H), 2.27 (m, 2H).

Following the same procedure for the hydrolysis of methyl 6-(trifluoromethyl)-1-(3-(trifluoromethyl)benzyl)-2,3-dihydro-1H-imidazo[1,2-b]pyrazole-7-carboxylate (213) to 6-(trifluoromethyl)-1-(3-(trifluoromethyl)benzyl)-2,3-dihydro-1H-imidazo[1,2-b]pyrazole-7-carboxylic acid (215), the following compounds were prepared.

6-(trifluoromethyl)-1-(4-(trifluoromethyl)phenyl)-2,3-dihydro-1H-imidazo[1,2-b]pyrazole-7-carboxylic acid (352)

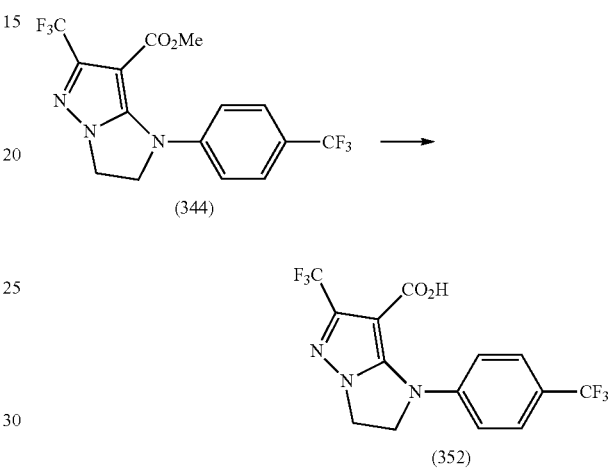

¹HNMR (400 MHz): δ ppm 7.58 (d, J=8.8 Hz, 2H), 7.14 (d, J=8.8 Hz, 2H), 4.60 (m, 2H), 4.47 (m, 2H).

6-(trifluoromethyl)-1-(3-(trifluoromethyl)phenyl)-2,3-dihydro-1H-imidazo[1,2-b]pyrazole-7-carboxylic acid (353)

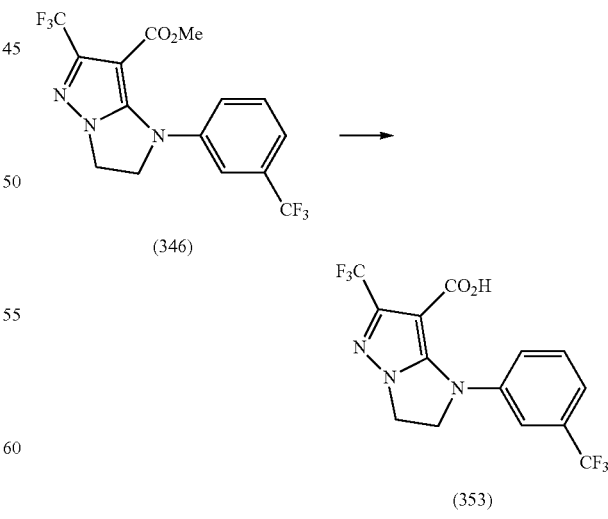

¹HNMR (400 MHz, CD₃OD): δ ppm 7.62-7.48 (m, 4H), 4.95 (s, 2H), 4.12 (dd, J=8.4, 8.4 Hz, 2H), 3.79 (dd, J=9.2, 8.0 Hz, 2H).

1-(3-chlorophenyl)-6-(trifluoromethyl)-2,3-dihydro-1H-imidazo[1,2-b]pyrazole-7-carboxylic acid (354)

2-(trifluoromethyl)-4-(4-(trifluoromethyl)phenyl)-4,5,6,7-tetrahydropyrazolo[1,5-a]pyrimidine-3-carboxylic acid (356)

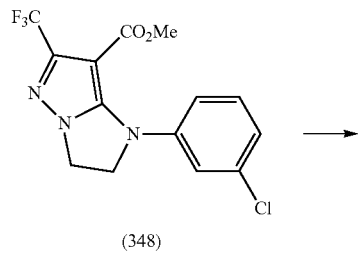

(348)

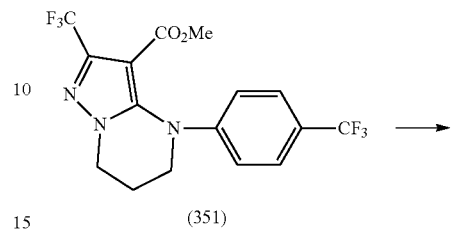

(351)

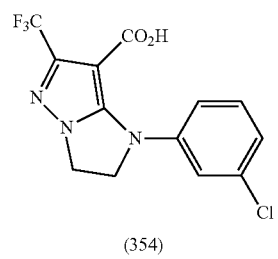

(354)

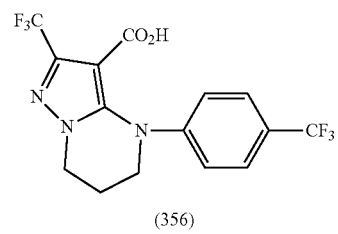

(356)

¹HNMR (400 MHz): δ ppm 7.56 (d, J=8.8 Hz, 2H), 7.19 (d, J=8.8 Hz, 2H), 4.31 (dd, J=6.4, 6.0 Hz, 2H), 3.87 (dd, J=6.0, 5.6 Hz, 2H), 2.26 (m, 2H).

Following the procedure for the preparation of (S)-4-(1-(6-(trifluoromethyl)-1-(3-(trifluoromethyl)benzyl)-2,3-dihydro-1H-imidazo[1,2-b]pyrazole-7-carboxamido)ethyl)benzoic acid (Compound 1) from 6-(trifluoromethyl)-1-(3-(trifluoromethyl)benzyl)-2,3-dihydro-1H-imidazo[1,2-b]pyrazole-7-carboxylic acid (215) described in Example I, Compounds 47-51 were prepared according to each of the corresponding reaction schemes.

¹HNMR (400 MHz): δ ppm 7.24 (d, J=8.0 Hz, 1H), 7.16 (d, J=8.0 Hz, 1H), 7.08 (dd, J=2.0, 2.0 Hz, 1H), 6.97 (dd, J=8.0, 1.6 Hz, 1H), 4.52 (dd, J=1.6, 7.2 Hz, 2H), 4.41 (dd, J=9.2, 1.6 Hz, 2H).

1-(4-chlorophenyl)-6-(trifluoromethyl)-2,3-dihydro-1H-imidazo[1,2-b]pyrazole-7-carboxylic acid (355)

Example XLVI (S)-4-(1-(6-(trifluoromethyl)-1-(4-(trifluoromethyl)phenyl)-2,3-dihydro-1H-imidazo[1,2-b]pyrazole-7-carboxamido)ethyl)benzoic acid (Compound 47)

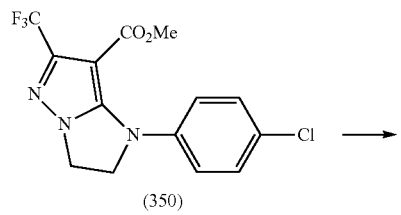

(350)

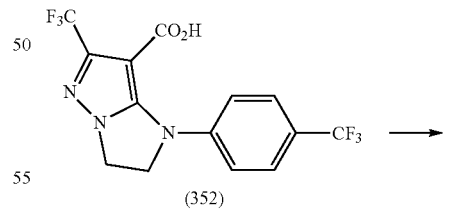

(352)

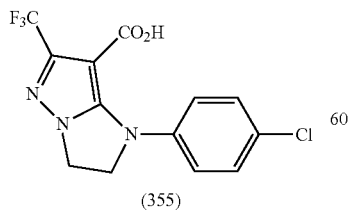

(355)

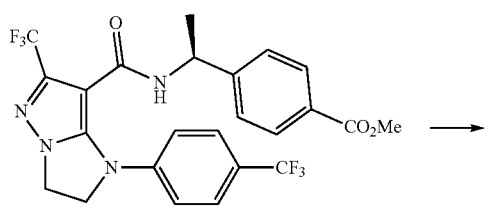

(357)

¹HNMR (400 MHz): δ ppm 7.29 (d, J=8.8 Hz, 2H), 7.03 (d, J=8.8 Hz, 2H), 4.41-4.5 (m, 4H).

-continued

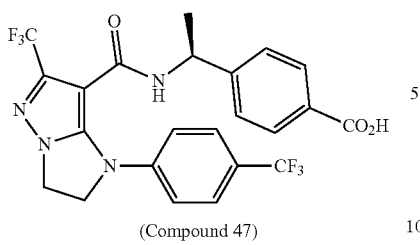

(Compound 47)

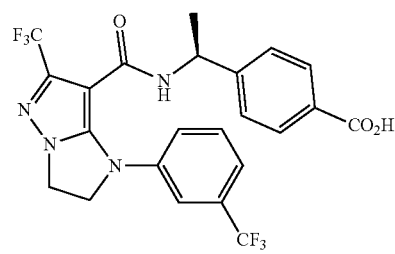

(Compound 48)

Methyl (S)-4-(1-(6-(trifluoromethyl)-1-(4-(trifluoromethyl)phenyl)-2,3-dihydro-1H-imidazo[1,2-b]pyrazole-7-carboxamido)ethyl)benzoate (357)

$^1$HNMR (400 MHz): δ ppm 7.93 (d, J=8.4 Hz, 2H), 7.29 (d, J=8.8 Hz, 2H), 7.25 (d, J=8.0 Hz, 2H), 6.87 (d, J=8.4 Hz, 2H), 6.01 (bd, J=7.2 Hz, 1H), 5.09 (m, 1H), 4.58 (m, 1H), 4.38 (m, 3H), 3.86 (s, 3H), 1.39 (d, J=6.8 Hz, 3H). LCMS (ES) (M+H)=527.2.

(S)-4-(1-(6-(trifluoromethyl)-1-(4-(trifluoromethyl)phenyl)-2,3-dihydro-1H-imidazo[1,2-b]pyrazole-7-carboxamido)ethyl)benzoic acid (Compound 47)

$^1$HNMR (400 MHz, CD$_3$OD): δ ppm 7.83 (d, J=8.4 Hz, 2H), 7.27 (d, J=8.4 Hz, 2H), 7.22 (d, J=8.0 Hz, 2H), 6.99 (d, J=8.8 Hz, 2H), 5.96 (m, 1H), 4.56 (m, 1H), 4.46 (m, 1H), 4.37 (m, 2H), 1.20 (d, J=7.2 Hz, 3H). LCMS (ES) (M+H)=513.2.

Example XLVII (S)-4-(1-(6-(trifluoromethyl)-1-(3-(trifluoromethyl)phenyl)-2,3-dihydro-1H-imidazo[1,2-b]pyrazole-7-carboxamido)ethyl)benzoic acid (Compound 48)

Methyl (S)-4-(1-(6-(trifluoromethyl)-1-(3-(trifluoromethyl)phenyl)-2,3-dihydro-1H-imidazo[1,2-b]pyrazole-7-carboxamido)ethyl)benzoate (358)

$^1$HNMR (400 MHz): δ ppm 7.83 (d, J=8.4 Hz, 2H), 7.15 (m, 4H), 7.07 (bs, 1H), 6.98 (d, J=7.6 Hz, 1H), 5.89 (bd, J=7.2 Hz, 1H), 5.00 (m, 1H), 4.41 (m, 2H), 4.28 (t, J=8.0 Hz, 2H), 3.78 (s, 3H), 1.29 (d, J=7.2 Hz, 3H). LCMS (ES) (M+H)=527.2.

(S)-4-(1-(6-(trifluoromethyl)-1-(3-(trifluoromethyl)phenyl)-2,3-dihydro-1H-imidazo[1,2-b]pyrazole-7-carboxamido)ethyl)benzoic acid (Compound 48)

$^1$HNMR (400 MHz, CD$_3$OD): δ ppm 7.79 (d, J=8.4 Hz, 2H), 7.27 (m, 2H), 7.20 (m, 2H), 7.13 (d, J=8.4 Hz, 2H), 4.89 (m, 1H), 4.52 (m, 2H), 4.37 (t, J=8.4 Hz, 2H), 1.10 (d, J=7.2 Hz, 3H). LCMS (ES) (M+H)=513.2.

Example XLVIII (S)-4-(1-(1-(3-chlorophenyl)-6-(trifluoromethyl)-2,3-dihydro-1H-imidazo[1,2-b]pyrazole-7-carboxamido)ethyl)benzoic acid (Compound 49)

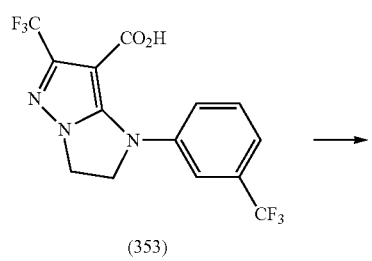

(353)

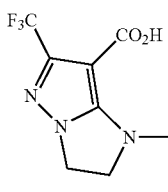

(354)

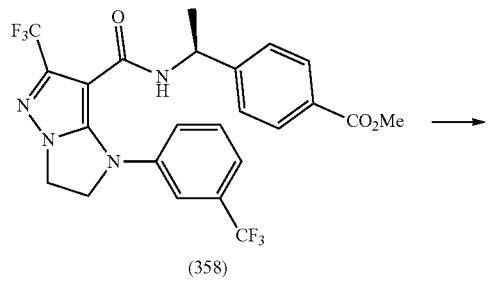

(358)

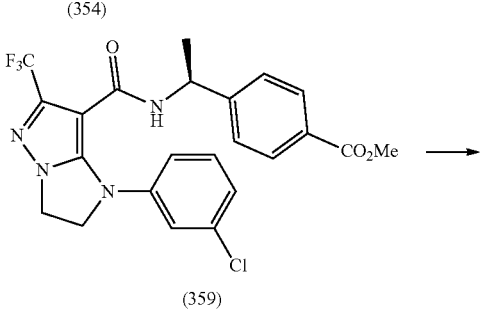

(359)

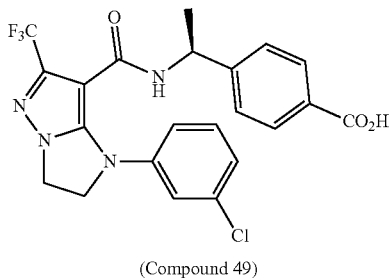

(Compound 49)

Methyl (S)-4-(1-(1-(3-chlorophenyl)-6-(trifluoromethyl)-2,3-dihydro-1H-imidazo[1,2-b]pyrazole-7-carboxamido)ethyl)benzoate (359)

$^1$HNMR (400 MHz): δ ppm 7.89 (d, J=8.0 Hz, 2H), 7.19 (d, J=8.0 Hz, 2H), 7.06 (t, J=8.0 Hz, 1H), 6.98 (d, J=8.0 Hz, 1H), 6.93 (bd, J=4.0 Hz, 1H), 6.80 (dd, J=1.2, 8.0 Hz, 1H), 5.82 (bd, J=7.2 Hz, 1H), 5.09 (m, 1H), 4.43 (m, 2H), 4.34 (m, 2H), 3.85 (s, 3H), 1.34 (d, J=7.2 Hz, 3H). LCMS (ES) (M+H)=493.2.

(S)-4-(1-(1-(3-chlorophenyl)-6-(trifluoromethyl)-2,3-dihydro-1H-imidazo[1,2-b]pyrazole-7-carboxamido)ethyl)benzoic acid (Compound 49)

$^1$HNMR (400 MHz, CD$_3$OD): δ ppm 7.81 (d, J=7.6 Hz, 2H), 7.16 (d, J=8.0 Hz, 2H), 7.06 (t, J=8.0 Hz, 1H), 7.04 (bs, 1H), 6.91 (d, J=8.4 Hz, 2H), 4.94 (m, 1H), 4.47 (t, J=9.2 Hz, 2H), 4.35 (t, J=8.8 Hz, 2H), 1.17 (d, J=7.2 Hz, 3H). LCMS (ES) (M+H)=479.2.

Example XLIX (S)-4-(1-(1-(4-chlorophenyl)-6-(trifluoromethyl)-2,3-dihydro-1H-imidazo[1,2-b]pyrazole-7-carboxamido)ethyl)benzoic acid (Compound 50)

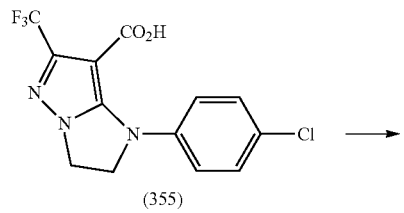

(355)

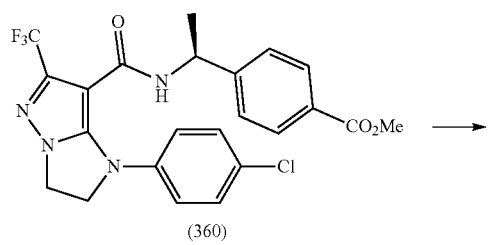

(360)

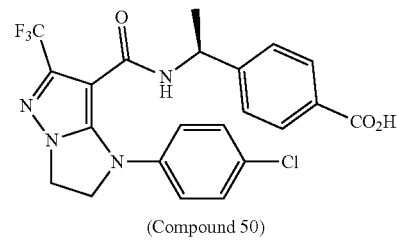

(Compound 50)

Methyl (S)-4-(1-(1-(4-chlorophenyl)-6-(trifluoromethyl)-2,3-dihydro-1H-imidazo[1,2-b]pyrazole-7-carboxamido)ethyl)benzoate (360)

$^1$HNMR (400 MHz): δ ppm 7.90 (d, J=8.0 Hz, 2H), 7.16 (d, J=8.0 Hz, 2H), 7.06 (d, J=8.8 Hz, 2H), 6.83 (d, J=8.8 Hz, 2H), 5.77 (bd, J=7.2 Hz, 1H), 5.06 (m, 1H), 4.38 (m, 2H), 4.34 (m, 2H), 3.85 (s, 3H), 1.31 (d, J=6.8 Hz, 3H). LCMS (ES) (M+H)=493.2.

(S)-4-(1-(1-(4-chlorophenyl)-6-(trifluoromethyl)-2,3-dihydro-1H-imidazo[1,2-b]pyrazole-7-carboxamido)ethyl)benzoic acid (Compound 50)

$^1$HNMR (400 MHz, CD$_3$OD): δ ppm 7.83 (d, J=8.4 Hz, 2H), 7.16 (d, J=8.4 Hz, 2H), 7.02 (d, J=8.4 Hz, 2H), 6.92 (d, J=9.2 Hz, 2H), 4.92 (m, 1H), 4.42 (m, 2H), 4.33 (t, J=8.4 Hz, 2H), 1.17 (d, J=6.8 Hz, 3H). LCMS (ES) (M+H)=479.2.

Example L (S)-4-(1-(2-(trifluoromethyl)-4-(4-(trifluoromethyl)phenyl)-4,5,6,7-tetrahydropyrazolo[1,5-a]pyrimidine-3-carboxamido)ethyl)benzoic acid (Compound 51)

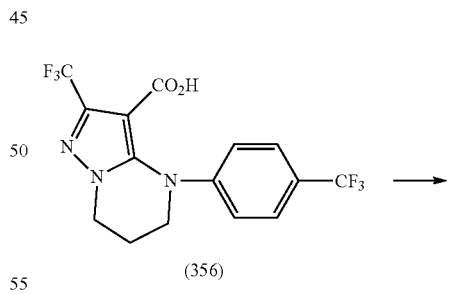

(356)

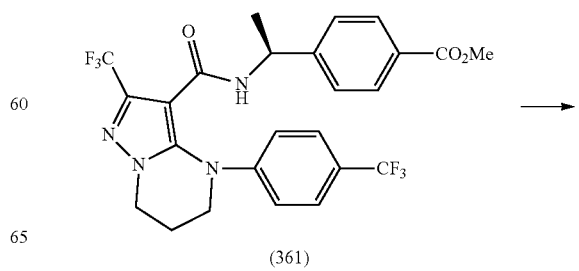

(361)

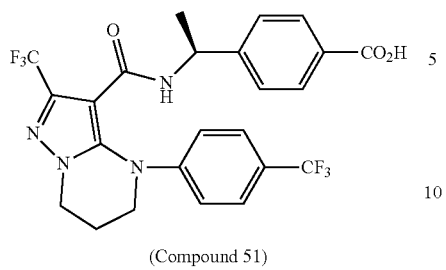

(Compound 51)

Methyl (S)-4-(1-(2-(trifluoromethyl)-4-(4-(trifluoromethyl)phenyl)-4,5,6,7-tetrahydropyrazolo[1,5-a]pyrimidine-3-carboxamido)ethyl)benzoate (361)

$^1$HNMR (400 MHz): δ ppm 7.85 (d, J=8.0 Hz, 2H), 7.39 (d, J=8.8 Hz, 2H), 7.04 (dd, J=6.0, 8.4 Hz, 4H), 5.87 (bd, J=7.6 Hz, 1H), 4.84 (m, 1H), 4.21 (t, J=6.4 Hz, 2H), 3.84 (s, 3H), 3.76 (m, 2H), 2.15 (m, 2H), 1.14 (d, J=6.8 Hz, 3H). LCMS (ES) (M+H)=541.3.

(S)-4-(1-(2-(trifluoromethyl)-4-(4-(trifluoromethyl)phenyl)-4,5,6,7-tetrahydropyrazolo[1,5-a]pyrimidine-3-carboxamido)ethyl)benzoic acid (Compound 51)

$^1$HNMR (400 MHz, CD$_3$OD): δ ppm 7.83 (d, J=8.8 Hz, 2H), 7.43 (d, J=8.4 Hz, 2H), 7.21 (d, J=8.4 Hz, 2H), 7.10 (d, J=8.0 Hz, 2H), 4.58 (m, 1H), 4.20 (t, J=6.4 Hz, 2H), 3.81 (m, 2H), 2.20 (m, 2H), 1.01 (d, J=6.8 Hz, 3H). LCMS (ES) (M+H)=527.2.

Example LI (S)—N-(1-(4-(cyanocarbamoyl)phenyl)ethyl)-6-(trifluoromethyl)-1-(3-(trifluoromethyl)benzyl)-2,3-dihydro-1H-imidazo[1,2-b]pyrazole-7-carboxamide (Compound 52)

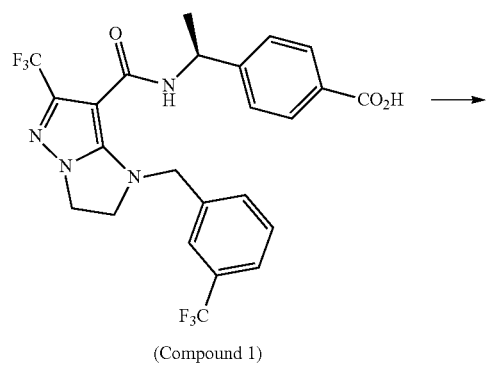

(Compound 1)

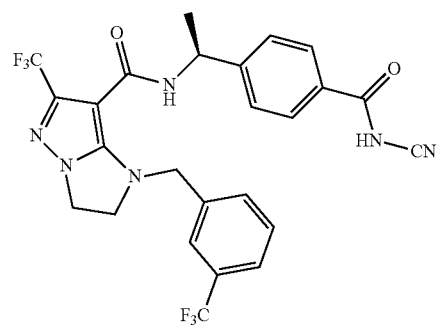

(Compound 52)

To a solution of (S)-4-(1-(6-(trifluoromethyl)-1-(3-(trifluoromethyl)benzyl)-2,3-dihydro-1H-imidazo[1,2-b]pyrazole-7-carboxamido)ethyl)benzoic acid (Compound 1) (22.0 mg, 0.042 mmol) and Cyanamide (3.5 mg, 0.084 mmol) in DCM at rt was added DMAP (10.2 mg, 0.084 mmol), followed by EDC (16.0 mg, 0.084 mmol), the resulting mixture was stirred at rt for 1 h. LCMS showed reaction was completed. The reaction mixture was concentrated and the residue was purified by HPLC (0.1% formic acid, 80% to 100% CH$_3$CN—H$_2$O) to give a colorless glassy solid (15.8 mg, 69% yield). $^1$HNMR (400 MHz, CD$_3$OD): δ ppm 7.73 (d, J=8.0 Hz, 2H), 7.57 (bs, 1H), 7.52 (m, 1H), 7.43 (m, 2H), 7.30 (d, J=8.0 Hz, 2H), 5.06 (m, 1H), 4.36 (d, J=2.0 Hz, 2H), 4.13 (t, J=8.0 Hz, 2H), 3.70 (t, J=8.0 Hz, 2H), 1.39 (d, J=6.8 Hz, 3H). LCMS (ES) (M+H)=551.2.

Example LII (S)—N-(1-(4-(((3,4-difluorophenyl)sulfonyl)carbamoyl)phenyl)ethyl)-6-(trifluoromethyl)-1-(3-(trifluoromethyl)benzyl)-2,3-dihydro-1H-imidazo[1,2-b]pyrazole-7-carboxamide (Compound 53)

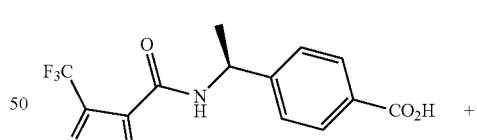

(Compound 1)

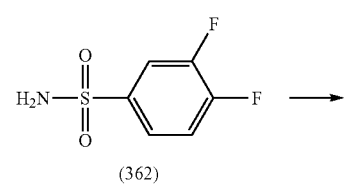

(362)

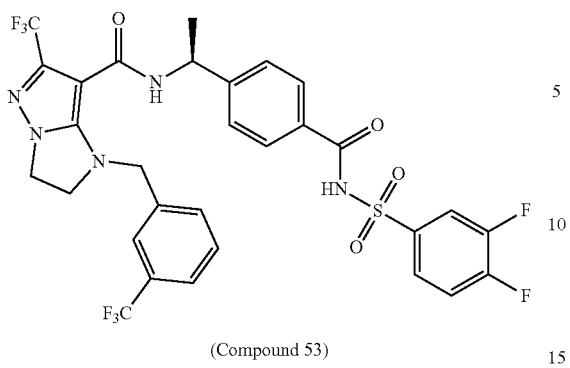

(Compound 53)

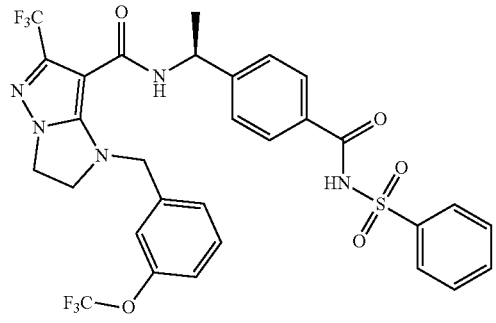

(Compound 54)

To a solution of (S)-4-(1-(6-(trifluoromethyl)-1-(3-(trifluoromethyl)benzyl)-2,3-dihydro-1H-imidazo[1,2-b]pyrazole-7-carboxamido)ethyl)benzoic acid (Compound 1) (22.4 mg, 0.043 mmol) and 3,4-difluorobenzenesulfonamide (16.4 mg, 0.085 mmol) in DCM at rt was added DMAP (10.4 mg, 0.085 mmol), followed by EDC (16.3 mg, 0.085 mmol), the resulting mixture was stirred at rt for 24 h. LCMS showed reaction was completed. The reaction mixture was concentrated and the residue was purified by silica gel prep TLC (1% AcOH-EtOAc) to give a colorless glassy solid (24.4 mg, 82% yield). $^1$HNMR (400 MHz, CD$_3$OD): δ ppm 7.89 (t, J=8.4 Hz, 1H), 7.79 (bd, J=8.8 Hz, 1H), 7.68 (d, J=8.0 Hz, 2H), 7.55 (s, 1H), 7.37 (d, J=4.8 Hz, 1H), 7.38 (m, 3H), 7.28 (d, J=8.4 Hz, 2H), 5.04 (m, 1H), 4.37 (d, J=14.8 Hz, 1H), 4.32 (d, J=14.8 Hz, 1H), 4.12 (t, J=8.4 Hz, 2H), 3.70 (t, J=8.4 Hz, 2H), 1.38 (d, J=6.8 Hz, 3H). LCMS (ES) (M+H)=702.2.

Procedure similar to the synthesis of (S)—N-(1-(4-(((3,4-difluorophenyl)sulfonyl)carbamoyl)phenyl)ethyl)-6-(trifluoromethyl)-1-(3-(trifluoromethyl)benzyl)-2,3-dihydro-1H-imidazo[1,2-b]pyrazole-7-carboxamide (Compound 53) described in Example LII. $^1$HNMR (400 MHz, CD$_3$OD): δ ppm 7.99 (d, J=7.6 Hz, 2H), 7.65 (d, J=8.4 Hz, 2H), 7.57 (m, 1H), 7.49 (m, 2H), 7.29 (m, 2H), 7.25 (d, J=8.4 Hz, 1H), 7.17 (s, 1H), 7.09 (dd, J=7.6, 16.4 Hz, 2H), 5.04 (m, 1H), 4.33 (d, J=15.2 Hz, 1H), 4.27 (d, J=15.2 Hz, 1H), 4.12 (m, 2H), 3.70 (m, 2H), 1.38 (d, J=6.8 Hz, 3H). LCMS (ES) (M+H)=682.6.

Example LIII (S)—N-(1-(4-((phenylsulfonyl)carbamoyl)phenyl)ethyl)-1-(3-(trifluoromethoxy)benzyl)-6-(trifluoromethyl)-2,3-dihydro-1H-imidazo[1,2-b]pyrazole-7-carboxamide (Compound 54)

Example LIV (S)—N-(1-(4-((methylsulfonyl)carbamoyl)phenyl)ethyl)-6-(trifluoromethyl)-1-(3-(trifluoromethyl)benzyl)-2,3-dihydro-1H-imidazo[1,2-b]pyrazole-7-carboxamide (Compound 55)

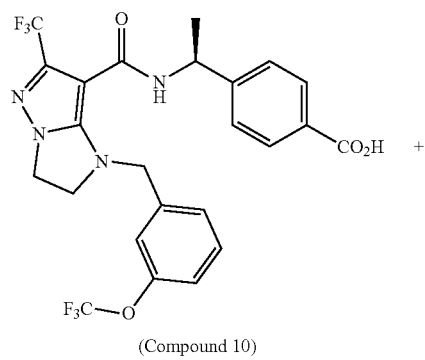

(Compound 10)

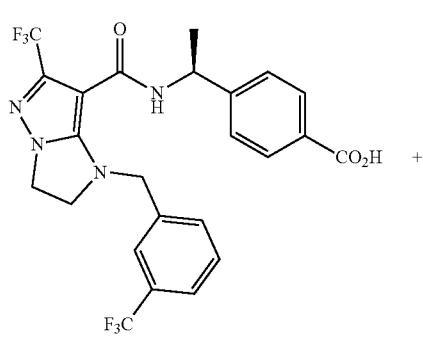

(Compound 1)

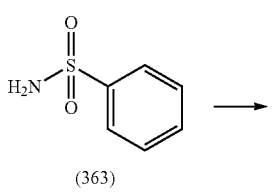

(363)

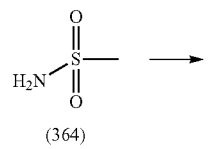

(364)

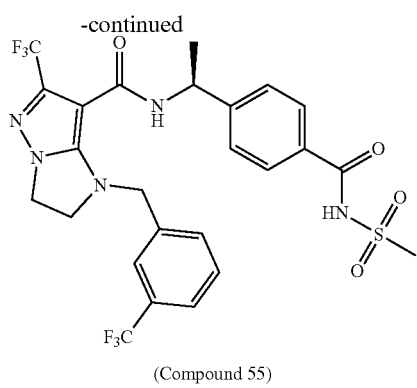

(Compound 55)

Procedure similar to the synthesis of (S)—N-(1-(4-(((3,4-difluorophenyl)sulfonyl)carbamoyl)phenyl)ethyl)-6-(trifluoromethyl)-1-(3-(trifluoromethyl)benzyl)-2,3-dihydro-1H-imidazo[1,2-b]pyrazole-7-carboxamide (Compound 53) described in Example LII. ¹HNMR (400 MHz, CD₃OD): δ ppm 7.71 (d, J=8.4 Hz, 2H), 7.58 (s, 1H), 7.54 (m, 1H), 7.44 (m, 2H), 7.35 (d, J=8.0 Hz, 2H), 5.06 (m, 1H), 4.39 (d, J=16.0 Hz, 1H), 4.34 (d, J=16.0 Hz, 1H), 4.13 (t, J=8.0 Hz, 2H), 3.71 (t, J=8.0 Hz, 2H), 3.22 (s, 3H), 1.39 (d, J=7.2 Hz, 3H). LCMS (ES) (M+H)=605.2.

Example LV (S)—N-(1-(4-((cyclopropylsulfonyl)carbamoyl)phenyl)ethyl)-6-(trifluoromethyl)-1-(3-(trifluoromethyl)benzyl)-2,3-dihydro-1H-imidazo[1,2-b]pyrazole-7-carboxamide (Compound 56)

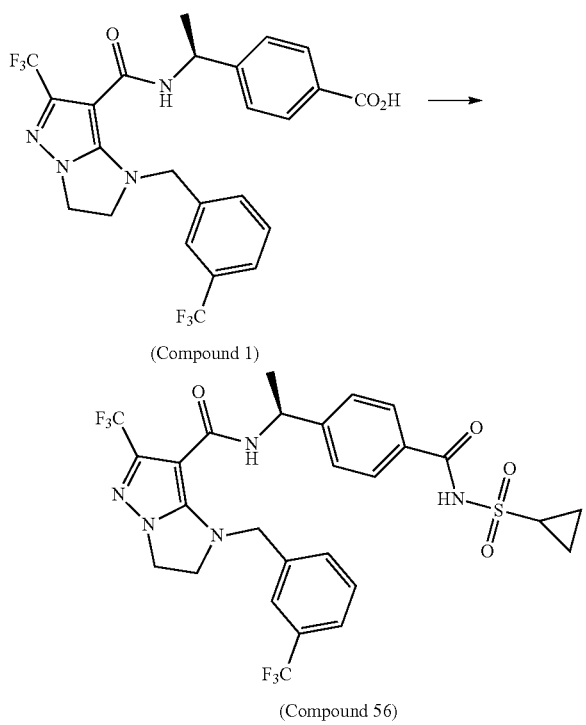

(Compound 1)

(Compound 56)

To a solution of (S)-4-(1-(6-(trifluoromethyl)-1-(3-(trifluoromethyl)benzyl)-2,3-dihydro-1H-imidazo[1,2-b]pyrazole-7-carboxamido)ethyl)benzoic acid (22.6 mg, 0.043 mmol) and cyclopropanesulfonamide (365) (10.4 mg, 0.086 mmol) in DCM at rt was added DMAP (10.5 mg, 0.086 mmol) followed by EDC (16.5 mg, 0.086 mmol). The resulting mixture was stirred at rt for 17 h. The reaction mixture was loaded directly on PTLC, developed with 1% AcOH-EtOAc, the major band was extracted with 20% MeOH-DCM and concentrated to give Compound 56 as a colorless oil (26.1 mg, 97% yield). ¹HNMR (400 MHz, CD₃OD): δ ppm 7.70 (d, J=8.0 Hz, 2H), 7.58 (bs, 1H), 7.53 (m, 1H), 7.45 (m, 2H), 7.36 (d, J=8.0 Hz, 2H), 5.06 (m, 1H), 4.37 (dd, J=15.2, 21.6 Hz, 2H), 4.13 (t, J=8.4 Hz, 2H), 3.70 (t, J=8.0 Hz, 2H), 3.04 (m, 1H), 1.39 (d, J=6.8 Hz, 3H), 1.20 (m, 2H), 1.01 (m, 2H). LCMS (ES) (M+H)=630.3.

Example LVI (S)—N-(1-(4-cyclopropylphenyl)ethyl)-6-(trifluoromethyl)-1-(4-(trifluoromethyl)benzyl)-2,3-dihydro-1H-imidazo[1,2-b]pyrazole-7-carboxamide (Compound 57)

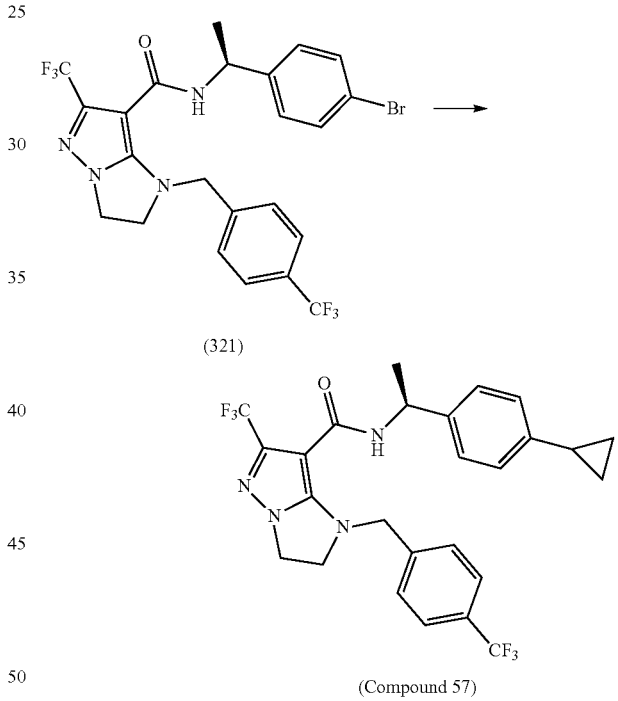

(321)

(Compound 57)

To a reaction tube containing cyclopropylboronic acid (1.3 eq) was added a solution of (S)—N-(1-(4-bromophenyl)ethyl)-6-(trifluoromethyl)-1-(4-(trifluoromethyl)benzyl)-2,3-dihydro-1H-imidazo[1,2-b]pyrazole-7-carboxamide (321) (20 mg, 0.036 mmol) in 1,4-dioxane (0.5 mL), a solution of Pd(PPh₃)₄ (0.1 eq) in 1,4-dioxane (0.5 mL) and a solution of Na₂CO₃ (4 eq) in water (0.5 mL). The reaction mixture was degassed by bubbling with N₂ and sealed. The reaction was heated at 80° C. for 20 h. After cooling to rt, the reaction mixture was concentrated and the residue was purified by PTLC (50% AcOEt/Heptane) to give Compound 57 (9.0 mg, 48% yield). ¹HNMR (400 MHz): δ ppm 7.55 (d, J=8.0 Hz, 2H), 7.38 (d, J=8.0 Hz, 2H), 7.21 (d, J=8.4 Hz, 2H), 7.02 (d, J=8.0 Hz, 2H), 6.22 (bd, J=5.6 Hz, 1H), 5.16 (dt, J=7.2 and 6.8 Hz, 1H), 4.88 (d, J=14.8 Hz, 1H), 4.84 (d, J=14.8 Hz, 1H), 4.16 (t, J=8.4 Hz, 2H), 3.76 (t, J=8.2 Hz, 2H), 1.86 (m, 1H), 1.53 (m, 1H), 1.51 (d, J=6.8 Hz, 3H), 1.24 (m, 1H), 0.94 (m, 1H), 0.65 (m, 1H). LCMS (ES) [M+H]=523.3

Example LVII (S)—N-(1-(3-methyl-4-(2H-tetrazol-5-yl)phenyl)ethyl)-6-(trifluoromethyl)-1-(4-(trifluoromethyl)benzyl)-2,3-dihydro-1H-imidazo[1,2-b]pyrazole-7-carboxamide (Compound 58)

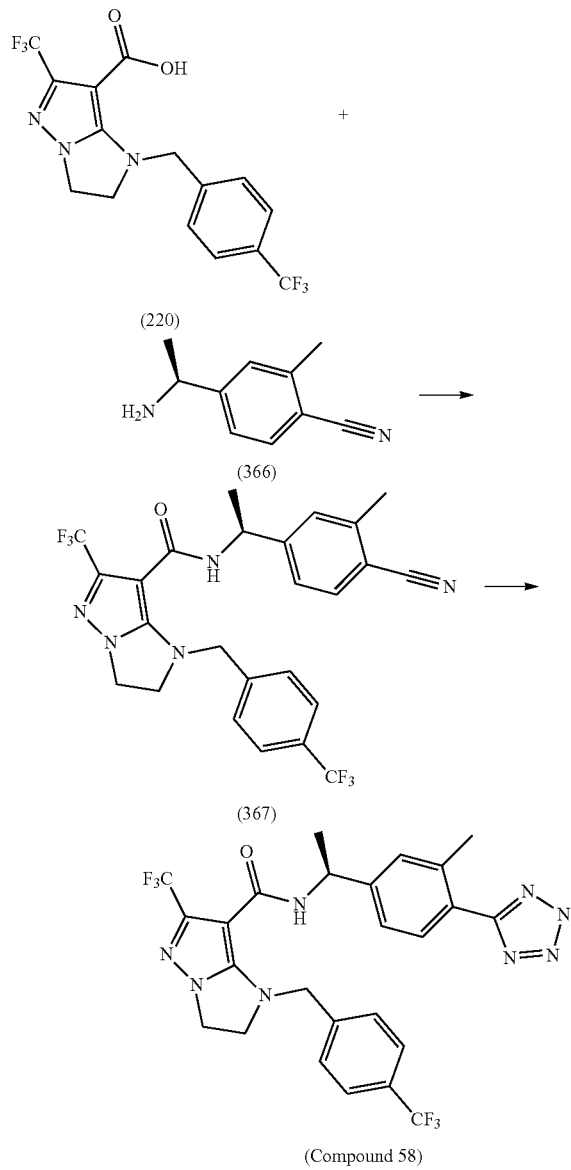

To 6-(trifluoromethyl)-1-(4-(trifluoromethyl)benzyl)-2,3-dihydro-1H-imidazo[1,2-b]pyrazole-7-carboxylic acid (220) (120 mg, 0.32 mmol) and (S)-4-(1-aminoethyl)-2-methylbenzonitrile (366) (60.8 mg, 0.38 mmol) in DMF (4.3 mL, 55.1 mmol) was added Hunig's base (276 µL, 1.6 mmol) and HATU (162 mg, 0.43 mmol) at rt. The reaction mixture was concentrated and the residue was purified by prep PTLC (50% AcOEt/Heptane) to give (S)—N-(1-(4-cyano-3-methylphenyl)ethyl)-6-(trifluoromethyl)-1-(4-(trifluoromethyl)benzyl)-2,3-dihydro-1H-imidazo[1,2-b]pyrazole-7-carboxamide (367) (134 mg, 81% yield). $^1$HNMR (400 MHz): δ ppm 7.57 (d, J=7.2 Hz, 2H), 7.54 (d, J=8.4 Hz, 1H), 7.41 (s 1H), 7.40 (d, J=7.2 Hz, 2H), 7.21 (d, J=8.4 Hz, 1H), 6.26 (bs, 1H), 5.13 (dt, J=7.2 and 6.8 Hz, 1H), 4.87 (d, J=14.8 Hz, 1H), 4.81 (J=14.8 Hz, 1H), 4.18 (dd, J=8.8 and 8.0 Hz, 2H), 3.77 (t, J=8.4 Hz, 2H), 2.51 (s, 3H), 1.49 (d, J=7.6 Hz, 3H). LCMS (ES) [M+Na]=522.3.

A solution of (S)—N-(1-(4-cyano-3-methylphenyl)ethyl)-6-(trifluoromethyl)-1-(4-(trifluoromethyl)benzyl)-2,3-dihydro-1H-imidazo[1,2-b]pyrazole-7-carboxamide (367) (50 mg, 0.10 mmol), sodium azide (59.2 mg, 0.91 mmol) and ammonium chloride (48.7 mg, 0.91 mmol) in DMF (0.9 mL) was heated at 120° C. for 89 h. The reaction mixture was cooled to rt, filtered and rinsed with DMSO (2×0.5 mL). The residue was purified with HPLC to give Compound 58 (30 mg, 55% yield). $^1$HNMR (400 MHz, CD$_3$OD): δ ppm 7.56 (d, J=7.8 Hz, 2H), 7.49 (d, J=8.2 Hz, 1H), 7.44 (d, J=7.8 Hz, 2H), 7.37 (s, 1H), 7.31 (d, J=8.2 Hz, 1H), 5.11 (dt, J=7.2 and 6.8 Hz, 1H), 4.48 (d, J=15.2 Hz, 1H), 4.40 (d, J=15.2 Hz, 1H), 4.19 (t, J=8.4 Hz, 2H), 3.78 (t, J=8.4 Hz, 2H), 2.38 (s, 3H), 1.47 (d, J=6.8 Hz, 3H). LCMS (ES) [M+Na]=565.3.

Example LVII (S)-4-(1-(6-ethyl-1-(3-(trifluoromethyl)benzyl)-2,3-dihydro-1H-imidazo[1,2-b]pyrazole-7-carboxamido)ethyl)benzoic acid (Compound 59)

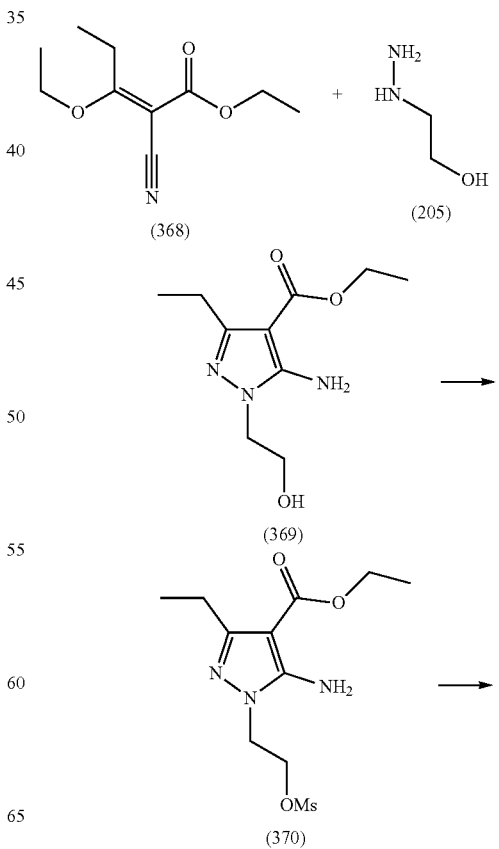

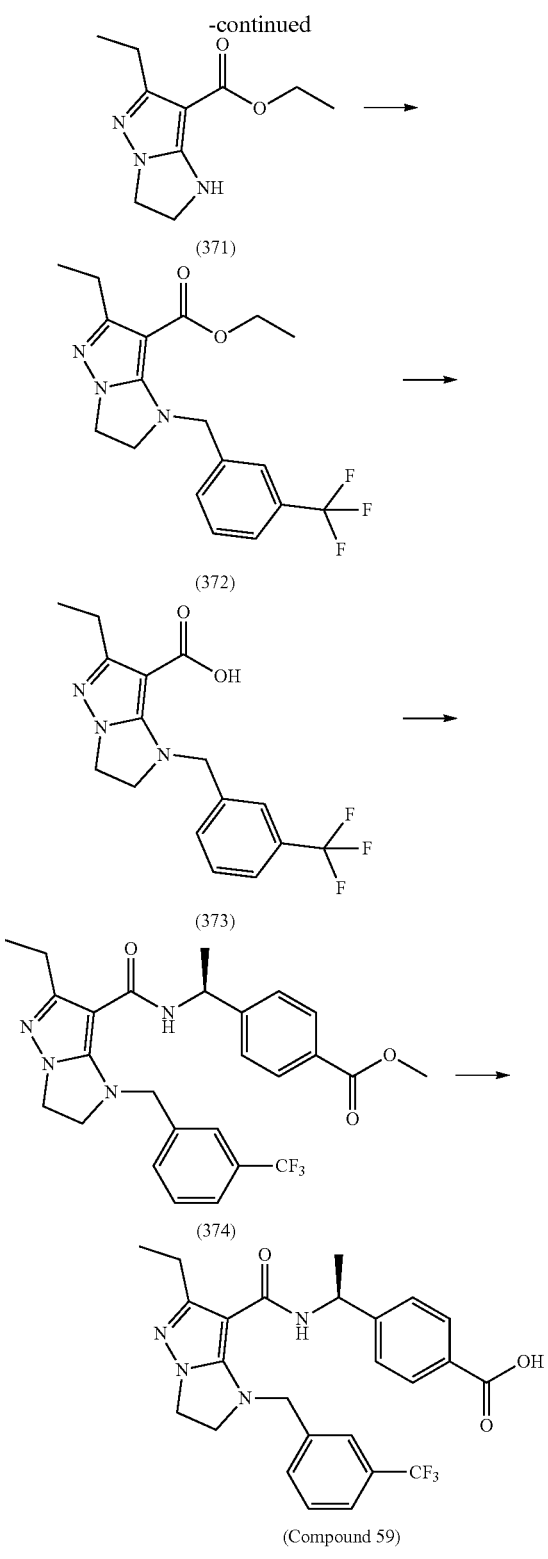

(371)

(372)

(373)

(374)

(Compound 59)

A solution of (E)-ethyl 2-cyano-3-ethoxypent-2-enoate (368) (100 mg, 0.51 mmol), 2-hydrazinylethanol (205) (46.3 mg, 0.61 mmol) and TEA (0.353 mL, 2.5 mmol) in methanol (3 mL, 74.2 mmol) was heated at reflux for 4 h. The mixture was concentrated and chromatography (EtOAc/haptane, 50% to 85%) purification gave ethyl 5-amino-3-ethyl-1-(2-hydroxyethyl)-1H-pyrazole-4-carboxylate (369) (62 mg, 54% yield). $^1$HNMR (400 MHz, CD$_3$OD): δ ppm 4.19 (q, J=7.2 Hz, 2H), 3.90 (t, J=5.5 Hz, 2H), 3.75 (dd, J=5.5 and 5.0 Hz, 2H), 2.65 (q, J=7.6 Hz, 2H), 1.27 (t, J=7.0 Hz, 3H), 1.12 (t, J=7.6 Hz, 3H). LCMS (ES) [M+H]=228.3.

Ethyl 5-amino-3-ethyl-1-(2-((methylsulfonyl)oxy)ethyl)-1H-pyrazole-4-carboxylate (370)

$^1$HNMR (400 MHz): δ ppm 5.26 (bs, 1H), 4.52 (t, J=4.9 Hz, 2H), 4.22 (q, J=7.2 Hz, 2H), 4.14 (t, J=4.9 Hz, 2H), 2.88 (s, 3H), 2.69 (q, J=7.6 Hz, 2H), 1.28 (t, J=7.2 Hz, 3H), 1.15 (t, J=7.4 Hz, 3H). LCMS (ES) [M+H]=306.1.

Ethyl 6-ethyl-2,3-dihydro-1H-imidazo[1,2-b]pyrazole-7-carboxylate (371)

$^1$HNMR (400 MHz): δ ppm 4.24 (q, J=7.2 Hz, 2H), 4.12 (m, 2H), 4.06 (dt, J=7.0 and 2.3 Hz, 2H), 2.83 (q, J=7.4 Hz, 2H), 1.32 (t, J=7.0 Hz, 3H), 1.26 (t, J=7.4 Hz, 3H). LCMS (ES) [M+H]=210.1.

Ethyl 6-ethyl-1-(3-(trifluoromethyl)benzyl)-2,3-dihydro-1H-imidazo[1,2-b]pyrazole-7-carboxylate (372)

$^1$HNMR (400 MHz): δ ppm 7.53 (s, 1H), 7.48 (d, J=7.8 Hz, 2H), 7.40 (t, J=7.6 Hz, 1H), 4.88 (s, 2H), 4.16 (q, J=7.2 Hz, 2H), 3.99 (t, J=8.6 Hz, 2H), 3.61 (t, J=7.8 Hz, 2H), 2.75 (t, J=7.1 Hz, 3H), 1.18 (t, J=7.5 Hz, 3H). LCMS (ES) [M+H]=368.2.

6-ethyl-1-(3-(trifluoromethyl)benzyl)-2,3-dihydro-1H-imidazo[1,2-b]pyrazole-7-carboxylic acid (373)

The material was used as crude for next step reaction. LCMS (ES) [M+H]=340.4.

Methyl (S)-4-(1-(6-ethyl-1-(3-(trifluoromethyl)benzyl)-2,3-dihydro-1H-imidazo[1,2-b]pyrazole-7-carboxamido)ethyl)benzoate (374)

$^1$HNMR (400 MHz, CD$_3$OD): δ ppm 7.81 (d, J=8.2 Hz, 2H), 7.56 (s, 1H), 7.54-7.40 (m, 3H), 7.38 (d, J=7.4 Hz, 2H), 5.11 (q, J=7.0 Hz, 1H), 4.52 (d, J=15.2 Hz, 1H), 4.41 (d, J=15.2 Hz, 1H), 3.98 (m, 2H), 3.82 (s, 3H), 3.64 (m, 2H), 2.70 (q, J=7.6 Hz, 2H), 1.44 (d, J=7.0 Hz, 3H), 1.13 (t, J=7.4 Hz, 3H). LCMS (ES) [M+H]=501.1.

(S)-4-(1-(6-ethyl-1-(3-(trifluoromethyl)benzyl)-2,3-dihydro-1H-imidazo[1,2-b]pyrazole-7-carboxamido)ethyl)benzoic acid (Compound 59)

$^1$HNMR (400 MHz, CD$_3$OD): δ ppm 7.77 (d, J=8.2 Hz, 2H), 7.53 (s, 1H), 7.47 (d, J=7.1 Hz, 1H), 7.40 (m, 2H), 7.30 (d, J=8.6 Hz, 2H), 5.07 (q, m, 1H), 4.47 (d, J=15.2 Hz, 1H), 4.40 (d, J=15.2 Hz, 1H), 3.92 (t, J=7.5 Hz, 2H), 3.59 (t, J=7.6 Hz, 2H), 2.65 (q, J=7.6 Hz, 2H), 1.39 (d, J=7.0 Hz, 3H), 1.13 (t, J=7.0 Hz, 3H). LCMS (ES) [M+H]=486.9.

Example LIX
(S)-4-(1-(6-phenyl-1-(3-(trifluoromethyl)benzyl)-2,3-dihydro-1H-imidazo[1,2-b]pyrazole-7-carboxamido)ethyl)benzoic acid (Compound 60)
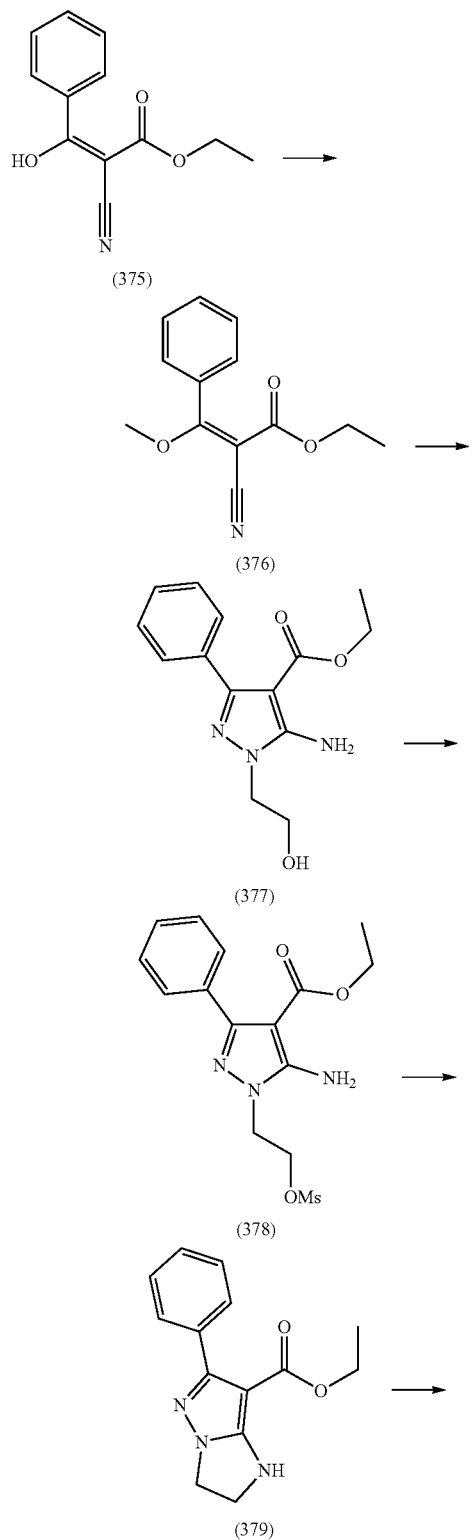
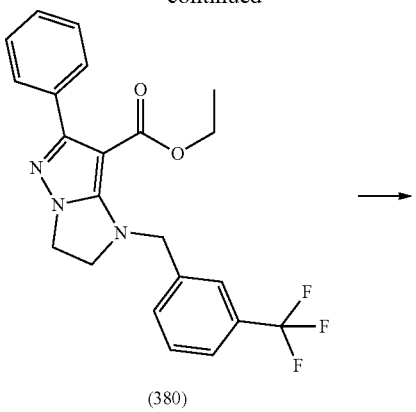
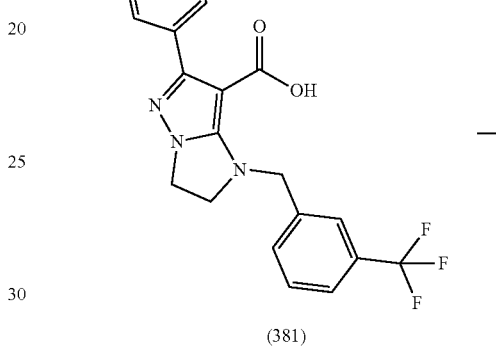
Ethyl (E)-2-cyano-3-methoxy-3-phenylacrylate (376)
To a solution of (E)-ethyl 2-cyano-3-hydroxy-3-phenylacrylate (375) (950 mg, 4.27 mmol) in toluene (15 mL) and methanol (5 mL) at rt was added trimethylsilyldiazomethane (383) (0.276 mL, 0.552 mmol) (2 M solution in hexanes). After 1 h reaction time, both TLC (70% E/H) and LCMS showed that reaction was completed. The mixture was concentrated and the crude ethyl (E)-2-cyano-3-methoxy-3-phenylacrylate (376) was carried on next step directly. LCMS (ES) [M+H]=232.1.

Following the same procedures for the preparation of (S)-4-(1-(6-ethyl-1-(3-(trifluoromethyl)benzyl)-2,3-dihydro-1H-imidazo[1,2-b]pyrazole-7-carboxamido)ethyl) benzoic acid (Compound 59) from (E)-ethyl 2-cyano-3-ethoxypent-2-enoate (368) and 2-hydrazinylethanol (205) (as in Example LIX), Compound 60 was prepared from was prepared from ethyl (E)-2-cyano-3-methoxy-3-phenylacrylate and 2-hydrazinylethanol.

Ethyl 5-amino-1-(2-hydroxyethyl)-3-phenyl-1H-pyrazole-4-carboxylate (377)

$^1$HNMR (400 MHz, CD$_3$OD): δ ppm 7.48 (m, 2H), 7.30 (m, 3H), 4.08 (q, J=7.0 Hz, 2H), 4.02 (t, J=5.1 Hz, 2H), 3.83 (t, J=5.5 and 5.0 Hz, 2H), 1.08 (t, J=7.2 Hz, 3H). LCMS (ES) [M+H]=276.0.

Ethyl 5-amino-1-(2-((methylsulfonyl)oxy)ethyl)-3-phenyl-1H-pyrazole-4-carboxylate (378)

$^1$HNMR (400 MHz, CD$_3$OD): δ ppm 7.45 (m, 2H), 7.28 (m, 3H), 4.50 (dd, J=5.5 and 5.0 Hz, 2H), 4.24 (dd, J=5.5 and 5.0 Hz, 2H), 4.06 (q, J=7.2 Hz, 2H), 2.90 (s, 3H), 1.06 (t, J=7.2 Hz, 3H). LCMS (ES) [M+H]=354.4.

Ethyl 6-phenyl-2,3-dihydro-1H-imidazo[1,2-b]pyrazole-7-carboxylate (379)

$^1$HNMR (400 MHz): δ ppm 7.71 (m, 2H), 7.30 (m, 3H), 4.15 (m, 4H), 4.01 (dd, J=8.1 and 7.8 Hz, 2H), 1.20 (t, J=7.2 Hz, 3H). LCMS (ES) [M+H]=258.1.

Ethyl 6-phenyl-1-(3-(trifluoromethyl)benzyl)-2,3-dihydro-1H-imidazo[1,2-b]pyrazole-7-carboxylate (380)

$^1$HNMR (400 MHz): δ ppm 7.56-7.30 (m, 5H), 4.92 (s, 2H), 4.10 (dd, J=8.4 and 7.1 Hz, 2H), 4.02 (q, J=7.2 Hz, 2H), 3.69 (t, J=8.2 Hz, 2H), 0.96 (t, J=7.2 Hz, 3H). LCMS (ES) [M+H]=416.0.

6-phenyl-1-(3-(trifluoromethyl)benzyl)-2,3-dihydro-1H-imidazo[1,2-b]pyrazole-7-carboxylic acid (381)

The material was used as crude for next step reaction. LCMS (ES) [M+H]=388.1.

Methyl (S)-4-(1-(6-phenyl-1-(3-(trifluoromethyl)benzyl)-2,3-dihydro-1H-imidazo[1,2-b]pyrazole-7-carboxamido)ethyl)benzoate (382)

$^1$HNMR (400 MHz, CD$_3$OD): δ ppm 7.79 (d, J=8.2 Hz, 2H), 7.62 (s, 1H), 7.58-7.43 (m, 5H), 7.37-7.30 (m, 3H), 7.18 (d, J=8.2 Hz, 2H), 5.03 (m, 1H), 4.66 (d, J=15.2 Hz, 1H), 4.60 (d, J=15.2 Hz, 1H), 4.08 (dd, J=8.2 and 7.3 Hz, 2H), 3.83 (s, 3H), 3.71 (dd, J=8.6 and 7.9 Hz, 2H), 1.23 (d, J=7.0 Hz, 3H). LCMS (ES) [M+H]=549.2.

(S)-4-(1-(6-phenyl-1-(3-(trifluoromethyl)benzyl)-2,3-dihydro-1H-imidazo[1,2-b]pyrazole-7-carboxamido)ethyl)benzoic acid (Compound 60)

$^1$HNMR (400 MHz, CD$_3$OD): δ ppm 7.78 (d, J=8.2 Hz, 2H), 7.61 (s, 1H), 7.52 (m, 2H), 7.47-7.38 (m, 3H), 7.36-7.28 (m, 3H), 7.13 (d, J=8.6 Hz, 2H), 5.00 (m, 1H), 4.66 (d, J=14.8 Hz, 1H), 4.60 (d, J=14.8 Hz, 1H), 4.09 (dd, J=8.6 and 7.8 Hz, 2H), 3.70 (dd, J=8.6 and 7.9 Hz, 2H), 1.20 (d, J=7.7 Hz, 3H). LCMS (ES) [M+H]=535.0.

Example LX (S)-4-(1-(4-(2-chlorobenzyl)-2-(trifluoromethyl)-4,5,6,7-tetrahydropyrazolo[1,5-a]pyrimidine-3-carboxamido)ethyl)benzoic acid (Compound 61)

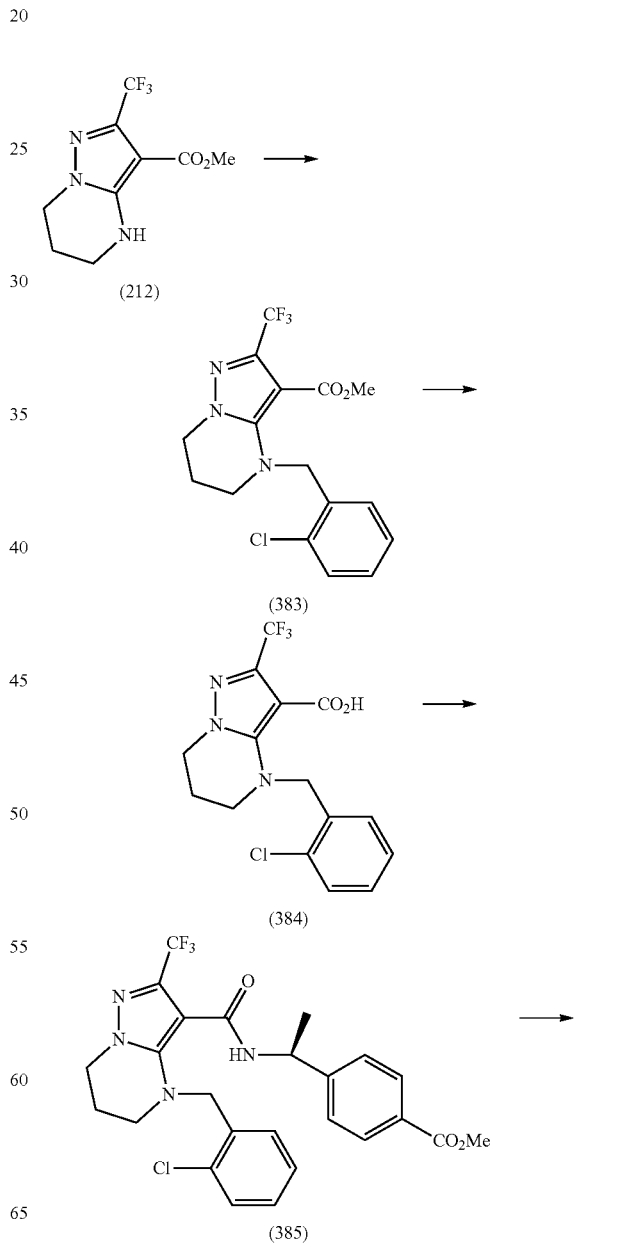

135

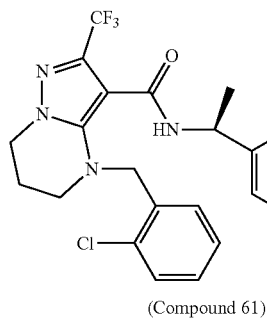

(Compound 61)

Following the similar procedure for the preparation of (S)-4-(1-(6-(trifluoromethyl)-1-(3-(trifluoromethyl)benzyl)-2,3-dihydro-1H-imidazo[1,2-b]pyrazole-7-carboxamido)ethyl)benzoic acid (Compound 1) from methyl 6-(trifluoromethyl)-2,3-dihydro-1H-imidazo[1,2-b]pyrazole-7-carboxylate (208) and 1-(chloromethyl)-3-(trifluoromethyl)benzene (214) described earlier in Example I, Compound 61 was similarly prepared from methyl 2-(trifluoromethyl)-4,5,6,7-tetrahydropyrazolo[1,5-a]pyrimidine-3-carboxylate (212) and 1-chloro-2-(chloromethyl)benzene.

Methyl 4-(2-chlorobenzyl)-2-(trifluoromethyl)-4,5,6,7-tetrahydropyrazolo[1,5-a]pyrimidine-3-carboxylate (compound 383)

Methyl 4-(2-chlorobenzyl)-2-(trifluoromethyl)-4,5,6,7-tetrahydropyrazolo[1,5-a]pyrimidine-3-carboxylate was used as crude for next step hydrolysis to 4-(2-chlorobenzyl)-2-(trifluoromethyl)-4,5,6,7-tetrahydropyrazolo[1,5-a]pyrimidine-3-carboxylic acid (compound 384): $^1$HNMR (400 MHz, CD$_3$OD): δ ppm 7.45 (dd, J=7.6 and 1.2 Hz, 1H), 7.31 (dd, J=7.2 and 1.4 Hz, 1H), 7.23 (dt, J=7.2 and 1.6 Hz, 1H), 7.18 (dt, J=7.6 and 1.6 Hz, 1H), 4.79 (s, 2H), 4.04 (dd, J=6.4 and 6.0 Hz, 2H), 3.15 (dd, J=5.6 and 5.6 Hz, 2H), 2.04 (m, 2H). LCMS (ES) [M+H]=360.07.

Methyl (S)-4-(1-(4-(2-chlorobenzyl)-2-(trifluoromethyl)-4,5,6,7-tetrahydropyrazolo[1,5-a]pyrimidine-3-carboxamido)ethyl)benzoate (compound 385)

$^1$HNMR (400 MHz): δ ppm 7.84 (d, J=8.8 Hz, 2H), 7.18 (m, 4H), 7.04 (d, J=8.8 Hz, 2H), 5.99 (bd, J=8.0 Hz, 1H), 5.10 (m, 1H), 4.50 (d, J=16.0 Hz, 1H), 4.34 (d, J=16.0 Hz, 1H), 4.06 (m, 2H), 3.84 (s, 3H), 3.11 (m, 2H), 2.05 (m, 2H), 1.38 (d, J=7.2 Hz, 3H). LCMS (ES) (M+H)=521.2.

(S)-4-(1-(4-(2-chlorobenzyl)-2-(trifluoromethyl)-4,5,6,7-tetrahydropyrazolo[1,5-a]pyrimidine-3-carboxamido)ethyl)benzoic acid (compound 61)

$^1$HNMR (400 MHz, CD$_3$OD): δ ppm 7.73 (d, J=8.0 Hz, 2H), 7.28 (m, 2H), 7.20 (m, 4H), 4.90 (m, 1H), 4.40 (s, 2H), 4.05 (m, 2H), 3.12 (m, 2H), 2.10 (m, 2H), 1.20 (d, J=7.2 Hz, 3H). LCMS (ES) (M+H)=507.2.

136

Example LXI

(S)-4-(1-(1-(3-(methylthio)-5-(trifluoromethyl)benzyl)-6-(trifluoromethyl)-2,3-dihydro-1H-imidazo[1,2-b]pyrazole-7-carboxamido)ethyl)benzoic acid (Compound 62)

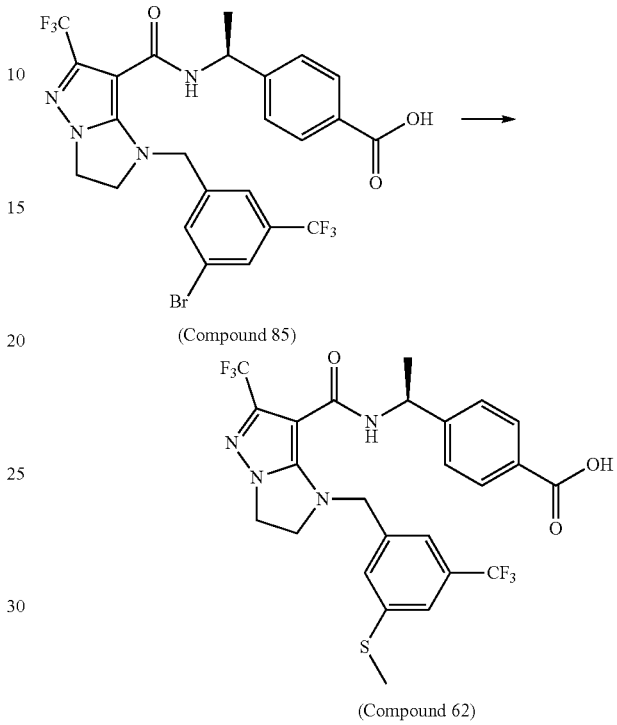

(Compound 85)

(Compound 62)

(S)-4-(1-(1-(3-bromo-5-(trifluoromethyl)benzyl)-6-(trifluoromethyl)-2,3-dihydro-1H-imidazo[1,2-b]pyrazole-7-carboxamido)ethyl)benzoic acid (5 mg, 8.26 μmol) was mixed in DMSO (1 ml) with Cryptand 222 (9.33 mg, 0.025 mmol). CsF (12.55 mg, 0.083 mmol) was added. The resulting suspension was heated to 200° C. with microwave irradiation for 2 h. The resulting crude material was purified by prep HPLC to give Compound 62 (3 mg, 63.4% yield). $^1$HNMR (400 MHz, CDCl$_3$) δ ppm 8.03-8.01 (m, 3H), 7.39-7.36 (m, 4H), 6.3 (br s, 1H), 5.20 (t, J=6.8 Hz, 1H), 4.88 (d, J=15.6 Hz, 1H), 4.75 (d, J=14.8 Hz, 1H), 4.18 (t, J=8.8 Hz, 2H), 3.76 (t, J=8.4 Hz, 2H), 2.46 (s, 3H), 1.53 (d, J=6.8 Hz, 3H). LCMS (ES) (M+H)=573.

Example LXII methyl (S)-4-(1-(6-(trifluoromethyl)-2,3-dihydro-1H-imidazo[1,2-b]pyrazole-7-carboxamido)ethyl)benzoate (387)

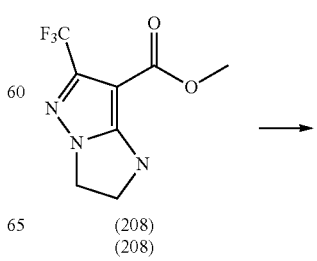

(208)
(208)

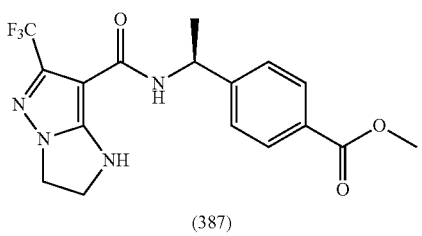

(387)

Methyl 6-(trifluoromethyl)-2,3-dihydro-1H-imidazo[1,2-b]pyrazole-7-carboxylate (208) (0.79 g, 3.359 mmol) was dissolved in a mixture of THF (3.95 ml), MeOH (3.95 ml) and water (3.95 ml). To this solution was added Lithium hydroxide monohydrate (0.705 g, 16.797 mmol) and the mixture was heated to 45° C. for 20 h until the reaction was complete. The mixture was cooled to r.t. and acidified with 1 N HCl (16.80 ml, 16.797 mmol) to pH 4-5 and then extracted with EtOAc (3×20 ml). The organic layers were combined, dried over MgSO$_4$ and concentrated in vacuo. The crude material was mixed with (S)-methyl 4-(1-aminoethyl)benzoate (216) (0.723 g, 4.032 mmol) in CH$_2$Cl$_2$ (14.86 ml), and the mixture was treated with Et$_3$N (1.873 ml, 13.44 mmol) and HATU (1.661 g, 4.368 mmol). The reaction mixture was stirred at rt for 17 h until the reaction was complete. Water (7.43 ml) was added to quenched the reaction. The organic layer was separated and the aqueous layer was extracted with EtOAc (3×15 ml). The organic layers were combined, dried over Na$_2$SO$_4$ and concentrated in vacuo. The residue was purified by column chromatography to give methyl (S)-4-(1-(6-(trifluoromethyl)-2,3-dihydro-1H-imidazo[1,2-b]pyrazole-7-carboxamido)ethyl)benzoate (387) as colorless oil (1.4 g, 100% yield). $^1$HNMR (400 MHz, CDCl$_3$) δ ppm 7.98 (t, J=8.4 Hz, 2H), 7.35 (t, J=8.4 Hz, 2H), 6.21 (br s, 1H), 5.16 (t, J=6.4 Hz, 1H), 4.18 (dd, J=8.0, 8.4 Hz, 2H), 4.08 (q, J=7.2 Hz, 2H), 4.01 (dd, J=8.0, 8.4 Hz, 2H), 1.51 (d, J=6.8 Hz, 3H). LCMS (ES) (M+H)=383

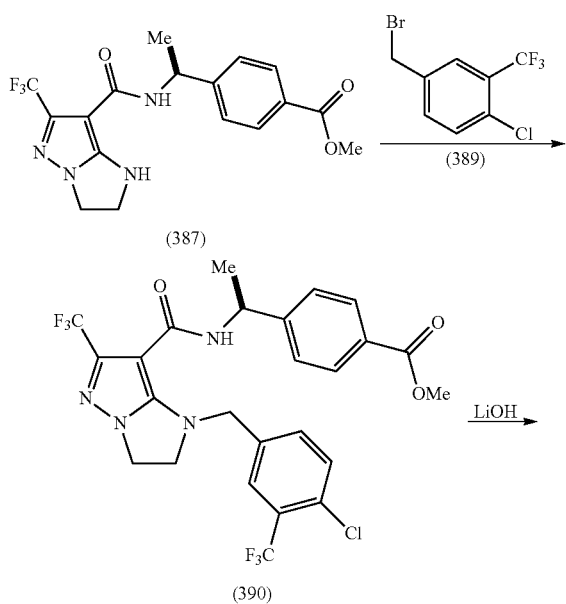

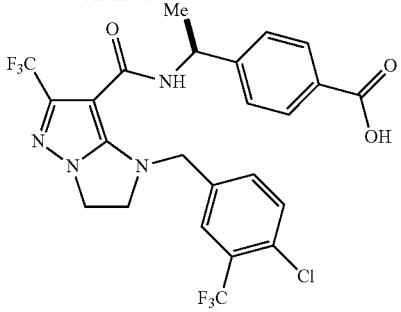

(Compound 63)

(S)-methyl 4-(1-(1-(4-chloro-3-(trifluoromethyl)benzyl)-6-(trifluoromethyl)-2,3-dihydro-1H-imidazo[1,2-b]pyrazole-7-carboxamido)ethyl)benzoate (390)

A mixture of (S)-methyl 4-(1-(6-(trifluoromethyl)-2,3-dihydro-1H-imidazo[1,2-b]pyrazole-7-carboxamido)ethyl)benzoate (387) (238 mg, 0.52 mmol) and 4-chloro-3-(trifluoromethyl)benzyl bromide (389) (172 mg, 0.63 mmol) in DMF (2 ml) was treated with cesium carbonate (511 mg, 1.57 mmol) and stirred at 100° C. for 30 min. After cooling to rt, the mixture was diluted with water (4 ml) and extracted twice with ethyl acetate (4 ml). The organic layers were combined, washed with brine (2 ml), and concentrated in vacuo. The residue was purified by column chromatography (ethyl acetate in n-heptane=10% to 40%) to give (S)-methyl 4-(1-(1-(4-chloro-3-(trifluoromethyl)benzyl)-6-(trifluoromethyl)-2,3-dihydro-1H-imidazo[1,2-b]pyrazole-7-carboxamido)ethyl)benzoate (390) (182 mg, 61%). 1H NMR (400 MHz, CDCl$_3$): δ 8.01 (d, 2H), 7.61 (s, 1H), 7.38-7.45 (m, 4H), 6.28 (m, 1H), 5.21 (m, 1H), 4.82 (d, 1H), 4.78 (d, 2H), 4.19 (m, 2H), 3.91 (s, 3H), 3.76 (m, 2H), 1.56 (d, 3H). LCMS (ES) (M+H)=575.

(S)-4-(1-(1-(4-chloro-3-(trifluoromethyl)benzyl)-6-(trifluoromethyl)-2,3-dihydro-1H-imidazo[1,2-b]pyrazole-7-carboxamido)ethyl)benzoic acid (Compound 63)

A solution of (S)-methyl 4-(1-(1-(4-chloro-3-(trifluoromethyl)benzyl)-6-(trifluoromethyl)-2,3-dihydro-1H-imidazo[1,2-b]pyrazole-7-carboxamido)ethyl)benzoate (390) (0.16 g, 0.28 mmol) in a mixture of THF (1.3 ml), MeOH (1.3 ml) and water (1.3 ml) was treated with LiOH (35 mg, 1.5 mmol), and stirred at rt for 7 h. The reaction mixture was acidified with 1 N HCl (1.5 ml, 1.5 mmol) and extracted three times with ethyl acetate (8 ml). The organic layers were combined, dried over MgSO$_4$ and concentrated in vacuo. The residue was purified by column chromatography (ethyl acetate in hep=10% to 70%) to give (S)-4-(1-(1-(4-chloro-3-(trifluoromethyl)benzyl)-6-(trifluoromethyl)-2,3-dihydro-1H-imidazo[1,2-b]pyrazole-7-carboxamido)ethyl)benzoic acid, compound 63 (102 mg, 65%). $^1$H NMR (400 MHz, CDCl$_3$): δ 8.04 (d, 2H), 7.61 (s, 1H), 7.40-7.43 (m, 4H), 6.32 (m, 1H), 5.23 (m, 1H), 4.86 (d, J=14.8 Hz, 1H), 4.75 (d, J=14.8 Hz, 1H), 4.19 (m, 2H), 4.12 (q, J=7.2 Hz, 1H), 3.75 (m, 2H), 1.54 (d, J=7.2 Hz, 3H). LCMS (ES) (M+H)=561.

(3-(((tert-butyldimethylsilyl)oxy)methyl)phenyl)methanol

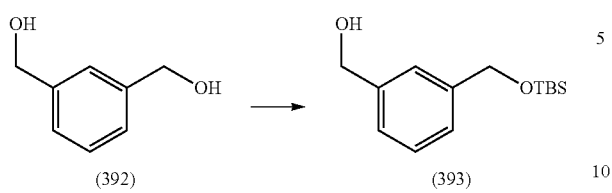

1,3-phenylenedimethanol (2.18 g, 15.778 mmol) was dissolved in DMF (21.80 ml) and cooled to 0° C., Imidazole (2.148 g, 31.557 mmol) was added followed by the addition of tert-Butyldimethylchlorosilane (2.378 g, 15.778 mmol). The mixture was stirred at 0° C. for 1 h and allowed to warm up to r.t. and stirred overnight. Upon completion of the reaction, the mixture was quenched with sat. aq. NH$_4$Cl (10 ml), extracted with EtOAc (2×100 ml). The organic layer was washed with sat. aq. NaHCO$_3$ solution (10 ml), dried over Na$_2$SO$_4$ and concentrated. The residue was purified by flash chromatography to give (3-(((tert-butyldimethylsilyl)oxy)methyl)phenyl)methanol (393) as colorless oil (1.73 g, 43.4% yield). $^1$HNMR (400 MHz, CDCl$_3$) δ ppm 7.35-7.23 (m, 4H), 4.75 (s, 2H), 4.68 (d, J=5.6 Hz, 2H), 0.95 (s, 9H), 0.12 (s, 6H).

((3-(bromomethyl)benzyl)oxy)(tert-butyl)dimethylsilane (395)

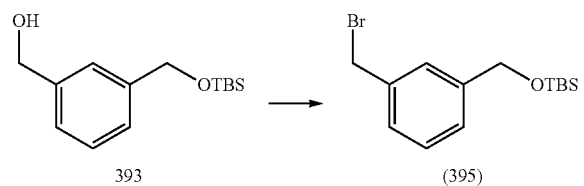 [SMILES: CC(C)(C)[Si](C)(C)OCc1cccc(CO)c1 ; CC(C)(C)[Si](C)(C)OCc1cccc(CBr)c1]

(3-(((tert-butyldimethylsilyl)oxy)methyl)phenyl)methanol (393) (0.293 g, 1.161 mmol) was dissolved in DCM (6.0 ml) and mixed with CBr$_4$ (0.385 g, 1.161 mmol). Ph$_3$P (0.304 g, 1.161 mmol) was added at r.t. and the mixture was continue stirred at r.t. for 2 h until the completion of the reaction. The reaction mixture was directly loaded on silica gel column and purified by flash chromatography to give ((3-(bromomethyl)benzyl)oxy)(tert-butyl)dimethylsilane (395) as colorless oil (319 mg, 87% yield). $^1$HNMR (400 MHz, CDCl$_3$): δ ppm 7.37-7.26 (m, 4H), 4.76 (s, 2H), 4.51 (s, 2H), 0.98 (s, 9H), 0.13 (s, 6H).

Methyl (S)-4-(1-(1-(3-(((tert-butyldimethylsilyl)oxy)methyl)benzyl)-6-(trifluoromethyl)-2,3-dihydro-1H-imidazo[1,2-b]pyrazole-7-carboxamido)ethyl)benzoate (396)

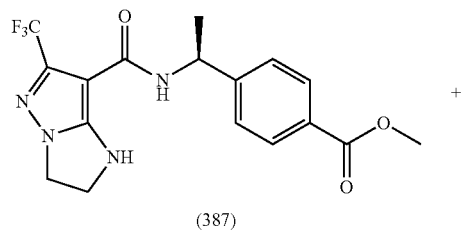
+
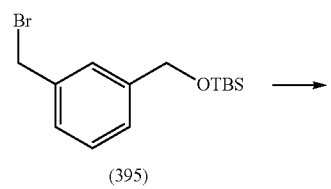
→
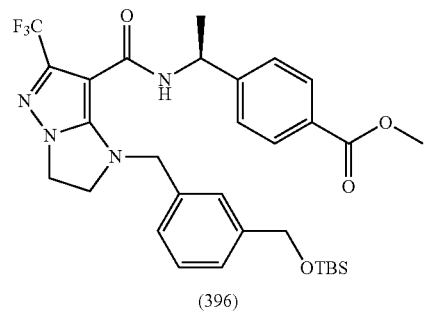

Following the same procedure for the preparation of (S)-methyl 4-(1-(1-(4-chloro-3-(trifluoromethyl)benzyl)-6-(trifluoromethyl)-2,3-dihydro-1H-imidazo[1,2-b]pyrazole-7-carboxamido)ethyl)benzoate (390), compound 396 was prepared (208 mg, 64.5% yield) from methyl (S)-4-(1-(6-(trifluoromethyl)-2,3-dihydro-1H-imidazo[1,2-b]pyrazole-7-carboxamido)ethyl)benzoate (387) and ((3-(bromomethyl)benzyl)oxy)(tert-butyl)dimethylsilane (395) $^1$HNMR (400 MHz, CDCl$_3$): δ ppm 7.98 (d, J=8.0 Hz, 2H), 7.39 (d, J=8.4 Hz, 2H), 7.28-7.21 (m, 3H), 7.11 (d, J=6.4 Hz, 1H), 6.24 (d, J=5.2 Hz, 1H), 5.24 (t, J=7.2 Hz, 1H), 4.75 (s, 2H), 4.70 (s, 2H), 4.11 (t, J=8.4 Hz, 2H), 3.89 (s, 3H), 3.74 (t, J=8.4 Hz, 1H), 1.53 (d, J=6.8 Hz, 3H), 0.90 (s, 9H), 0.07 (s, 6H). LCMS (ES) (M+Na)=639.

Example LXIII

Methyl (S)-4-(1-(1-(3-(hydroxymethyl)benzyl)-6-(trifluoromethyl)-2,3-dihydro-1H-imidazo[1,2-b]pyrazole-7-carboxamido)ethyl)benzoate (397)

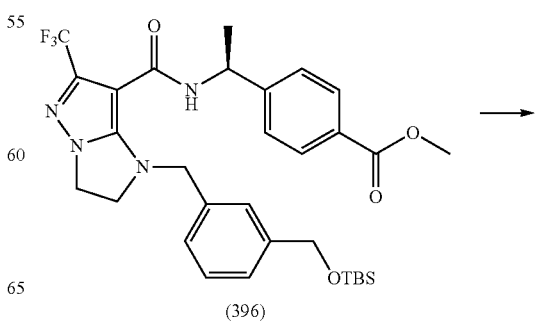

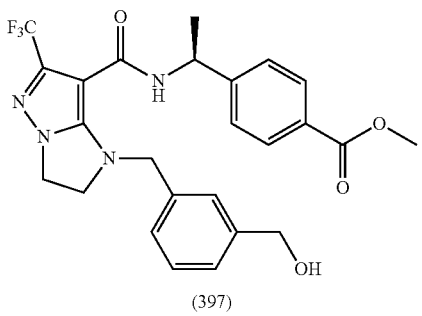

(397)

(S)-methyl 4-(1-(1-(3-(((tert-butyldimethylsilyl)oxy)methyl)benzyl)-6-(trifluoromethyl)-2,3-dihydro-1H-imidazo[1,2-b]pyrazole-7-carboxamido)ethyl)benzoate (396) (0.208 g, 0.337 mmol) was dissolved in THF (4.16 ml) and TBAF (0.506 ml, 0.506 mmol) was added. The resulting solution was stirred at r.t. for 0.5 h. Upon completion of the reaction, the mixture was quenched with NH₄Cl (5 ml), extracted with EtOAc (50 ml). The organic layer was washed with brine (10 ml), dried over Na₂SO₄ and concentrated. The crude material was purified by flash chromatography to give compound 397 as colorless oil (154 mg, 91% yield). ¹HNMR (500 MHz, CDCl₃): δ ppm 7.95 (d, J=8.5 Hz, 2H), 7.37 (d, J=8.5 Hz, 2H), 7.29-7.25 (m, 3H), 7.16 (dd, J=2.0, 3.5 Hz, 1H), 6.25 (d, J=5.0 Hz, 1H), 5.23 (t, J=7.5 Hz, 1H), 4.76 (d, J=14.5 Hz, 2H), 4.68 (d, J=14.5 Hz, 2H), 4.64 (s, 3H), 4.12 (dd, J=8.0, 12.0 Hz, 2H), 3.89 (s, 3H), 3.75 (dd, J=8.0, 9.5 Hz, 2H), 1.53 (d, J=7.0 Hz, 3H). LCMS (ES) (M+Na)=525.

(S)-4-(1-(1-(3-(hydroxymethyl)benzyl)-6-(trifluoromethyl)-2,3-dihydro-1H-imidazo[,2-b]pyrazole-7-carboxamido)ethyl)benzoic acid (Compound 64)

(S)-methyl 4-(1-(1-(3-(hydroxymethyl)benzyl)-6-(trifluoromethyl)-2,3-dihydro-1H-imidazo[1,2-b]pyrazole-7-carboxamido)ethyl)benzoate (397) (10 mg, 0.02 mmol) was dissolved in t-Amyl alcohol (1 ml) and 3M NaOH solution (66.3 µl, 0.199 mmol) was added. The mixture was then stirred at 90° C. for 1 h until the reaction was complete. The mixture was cooled to r.t. and 1N HCl solution (259 µl, 0.259 mmol) was added to make pH<4. The reaction mixture was extracted with EtOAc 3×15 ml. The organic layer was concentrated and purified by flash chromatography to give Compound 64 as white solid (8.4 mg, 86%). ¹HNMR (400 MHz, CDCl₃): δ ppm 7.99 (d, J=8.0 Hz, 2H), 7.39 (d, J=8.0 Hz, 2H), 7.30-7.24 (m, 3H), 7.14 (d, J=6.4 Hz, 1H), 6.30 (d, J=4.8 Hz, 1H), 5.24 (t, J=7.2 Hz, 1H), 4.78 (d, J=14.8 Hz, 1H), 4.68 (d, J=16.4 Hz, 1H), 4.64 (m, 3H), 4.16-4.10 (m, 2H), 3.76 (dd, J=7.6, 9.2 Hz, 2H), 1.54 (d, J=7.2 Hz, 3H). LCMS (ES) (M+H)=489.

Example LXIV

Intermediates Used in Examples LXV-LXVI Below

Methyl (S)-4-(1-(1-(3-(chloromethyl)benzyl)-6-(trifluoromethyl)-2,3-dihydro-1H-imidazo[1,2-b]pyrazole-7-carboxamido)ethyl)benzoate (399) and dimethyl 4,4'-((1S,1'S)-((1,1'-(1,3-phenylenebis(methylene))bis(6-(trifluoromethyl)-2,3-dihydro-1H-imidazo[1,2-b]pyrazole-1,7-diyl-7-carbonyl))bis(azanediyl))bis(ethane-1,1-diyl))dibenzoate (400)

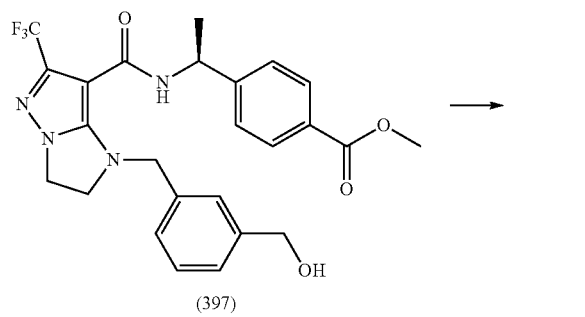

(397)

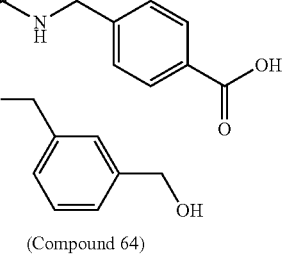

(Compound 64)

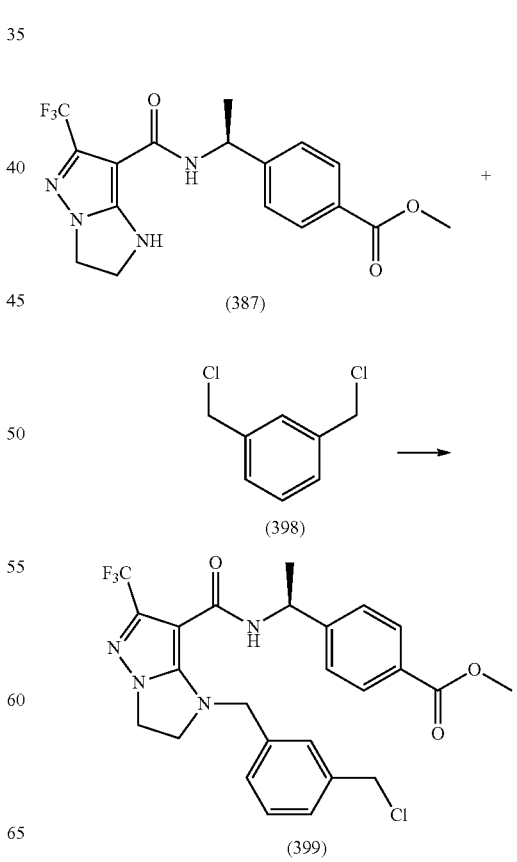

-continued

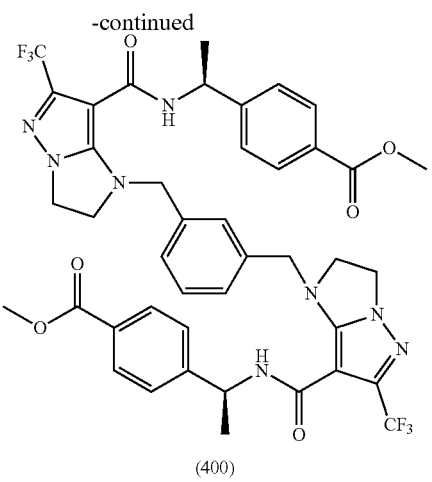

(400)

(S)-methyl 4-(1-(6-(trifluoromethyl)-2,3-dihydro-1H-imidazo[1,2-b]pyrazole-7-carboxamido)ethyl)benzoate (387) (0.048 g, 0.105 mmol) and 1,3-bis(chloromethyl)benzene (398) (0.037 g, 0.211 mmol) were mixed in DMF (0.8 ml), and to this mixture was added $K_2CO_3$ (0.044 g, 0.316 mmol) under $N_2$. The resulting suspension was stirred at 100° C. for 20 min until the fully consumption of SM. The mixture was cooled to r.t., quenched with $NaHCO_3$ solution (5 ml), extracted with EtOAc (2×50 ml). The organic layer was washed with water (2×10 ml), brine (2×10 ml), dried and concentrated. The residue was purified by flash chromatography to give (S)-4-(1-(1-(3-(chloromethyl)benzyl)-6-(trifluoromethyl)-2,3-dihydro-1H-imidazo[1,2-b]pyrazole-7-carboxamido)ethyl)benzoate (399) as white solid (37 mg, 67.4% yield), and Dimethyl 4,4'-((1S,1'S)-((1,1'-(1,3-phenylenebis(methylene))bis(6-(trifluoromethyl)-2,3-dihydro-1H-imidazo[1,2-b]pyrazole-1,7-diyl-7-carbonyl))bis(azanediyl))bis(ethane-1,1-diyl))dibenzoate (400) as white solid (9.8 mg, 10.7% yield).

(S)-4-(1-(1-(3-(chloromethyl)benzyl)-6-(trifluoromethyl)-2,3-dihydro-1H-imidazo[1,2-b]pyrazole-7-carboxamido)ethyl)benzoate (399)

$^1$HNMR (400 MHz, $CDCl_3$): δ ppm 7.99 (d, J=8.4 Hz, 2H), 7.39 (d, J=8.0 Hz, 2H), 7.31-7.26 (m, 3H), 7.22-7.20 (m, 1H), 6.26 (d, J=4.8 Hz, 1H), 5.24 (t, J=7.2 Hz, 1H), 4.76 (s, 2H), 4.54 (s, 2H), 4.15 (dd, J=8.0, 8.8 Hz, 2H), 3.90 (s, 3H), 3.76 (dd, J=8.0, 8.8 Hz, 2H), 1.54 (d, J=7.2 Hz, 3H). LCMS (ES) (M+H)=521.

Dimethyl 4,4'-((1S,1'S)-((1,1'-(1,3-phenylenebis(methylene))bis(6-(trifluoromethyl)-2,3-dihydro-1H-imidazo[1,2-b]pyrazole-1,7-diyl-7-carbonyl))bis(azanediyl))bis(ethane-1,1-diyl))dibenzoate (400)

$^1$HNMR (400 MHz, $CDCl_3$): δ ppm 7.97 (d, J=8.4 Hz, 4H), 7.38 (d, J=8.0 Hz, 4H), 7.25-7.16 (m, 4H), 6.32 (d, J=4.4 Hz, 2H), 5.22 (t, J=7.2 Hz, 2H), 4.67 (s, 4H), 4.10 (dd, J=8.0, 8.8 Hz, 4H), 3.89 (s, 6H), 3.69 (dd, J=8.0, 8.8 Hz, 4H), 1.51 (d, J=7.2 Hz, 6H). LCMS (ES) (M+H)=867.

Example LXV (S)-4-(1-(1-(3-(chloromethyl)benzyl)-6-(trifluoromethyl)-2,3-dihydro-1H-imidazo[1,2-b]pyrazole-7-carboxamido)ethyl)benzoic acid (Compound 65)

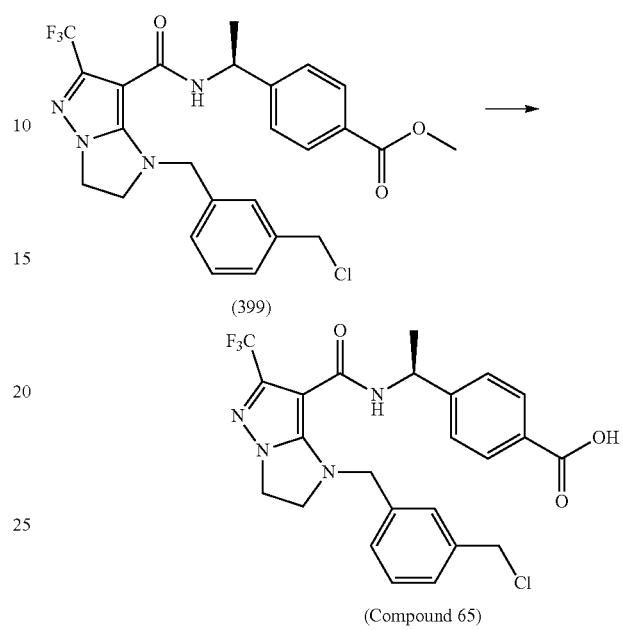

Following the same procedure for the preparation of (S)-4-(1-(1-(3-(hydroxymethyl)benzyl)-6-(trifluoromethyl)-2,3-dihydro-1H-imidazo[1,2-b]pyrazole-7-carboxamido)ethyl)benzoic acid (Compound 64), Compound 65 was prepared (8.3 mg, 32.8% yield) from (S)-4-(1-(1-(3-(chloromethyl)benzyl)-6-(trifluoromethyl)-2,3-dihydro-H-imidazo[1,2-b]pyrazole-7-carboxamido)ethyl)benzoate (399). $^1$HNMR (400 MHz, $CDCl_3$): δ ppm 8.04 (d, J=8.0 Hz, 2H), 7.42 (d, J=8.0 Hz, 2H), 7.31-7.29 (m, 3H), 7.22-7.20 (m, 1H), 6.29 (d, J=4.8 Hz, 1H), 5.26 (t, J=7.2 Hz, 1H), 4.76 (s, 2H), 4.54 (s, 2H), 4.16 (dd, J=8.0, 8.8 Hz, 2H), 3.77 (dd, J=8.0, 8.8 Hz, 2H), 1.55 (d, J=7.2 Hz, 3H). LCMS (ES) (M+H)=507.

Example LXVI 4,4'-((1S,1'S)-((1,1'-(1,3-phenylenebis(methylene))bis(6-(trifluoromethyl)-2,3-dihydro-1H-imidazo[1,2-b]pyrazole-1,7-diyl-7-carbonyl))bis(azanediyl))bis(ethane-1,1-diyl))dibenzoic acid (Compound 66)

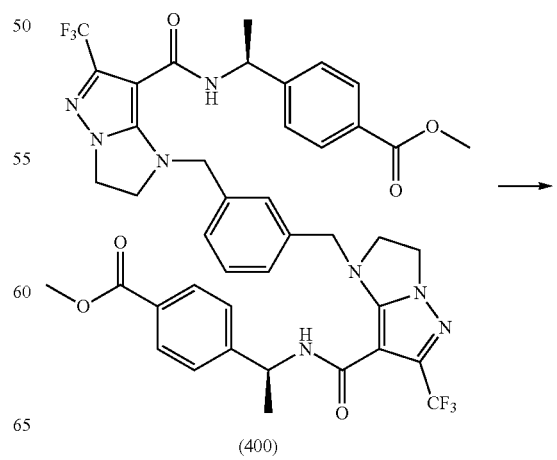

(400)

-continued

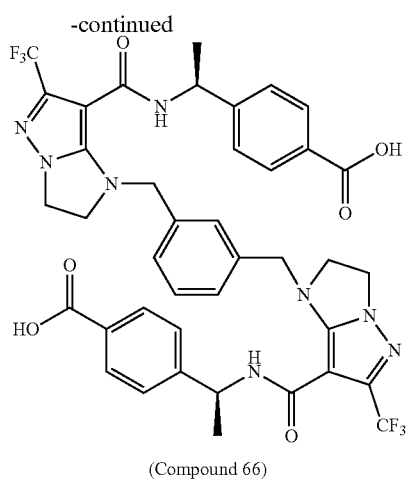

(Compound 66)

Following the same procedure for the preparation of (S)-4-(1-(1-(3-(hydroxymethyl)benzyl)-6-(trifluoromethyl)-2,3-dihydro-1H-imidazo[1,2-b]pyrazole-7-carboxamido)ethyl)benzoic acid (Compound 64), Compound 66 was prepared (7.9 mg, 42.5% yield) from dimethyl 4,4'-((1S,1'S)-((1,1'-(1,3-phenylenebis(methylene)))bis(6-(trifluoromethyl)-2,3-dihydro-1H-imidazo[1,2-b]pyrazole-1,7-diyl-7-carbonyl))bis(azanediyl))bis(ethane-1,1-diyl))dibenzoate (400).

$^1$HNMR (400 MHz, CDCl$_3$): δ ppm 7.89 (d, J=8.0 Hz, 4H), 7.30 (d, J=8.0 Hz, 4H), 7.19-7.09 (m, 4H), 6.48 (d, J=6.8 Hz, 2H), 5.14 (t, J=7.2 Hz, 2H), 4.55 (d, J=14.4 Hz, 2H), 4.50 (d, J=14.8 Hz, 2H), 4.06 (dd, J=8.0, 8.8 Hz, 4H), 3.63 (dd, J=8.0, 8.8 Hz, 4H), 1.45 (d, J=7.2 Hz, 6H). LCMS (ES) (M+Na)=861.

Example LXVII

Methyl (S)-4-(1-(1-(3-(fluoromethyl)benzyl)-6-(trifluoromethyl)-2,3-dihydro-1H-imidazo[1,2-b]pyrazole-7-carboxamido)ethyl)benzoate (401)

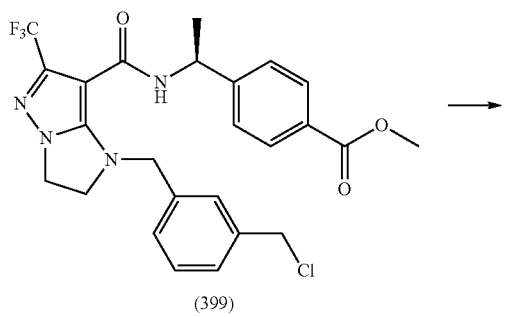
(399)

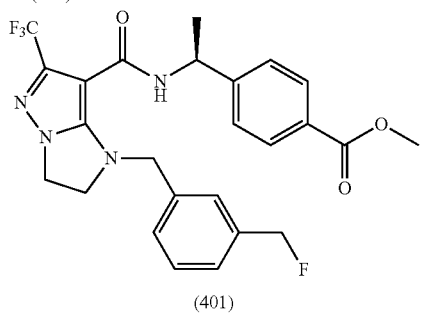
(401)

(S)-methyl 4-(1-(1-(3-(chloromethyl)benzyl)-6-(trifluoromethyl)-2,3-dihydro-1H-imidazo[1,2-b]pyrazole-7-carboxamido)ethyl)benzoate (399) (6 mg, 0.012 mmol) was dissolved in t-Amyl alcohol (300 μl) and 1M TBAF in THF solution (57.6 μl) was added. The mixture was then stirred at 150° C. for 10 min until the reaction was complete. The mixture was cooled to r.t., extracted with EtOAc (3×10 ml), washed with water (5 ml), brine (5 ml), the organic layer was dried and concentrated. The residue was purified by flash chromatography to give compound 401 as white solid (5.4 mg, 93% yield). $^1$HNMR (400 MHz, CDCl$_3$): δ ppm 8.01-7.98 (m, 2H), 7.41-7.26 (m, 6H), 6.26 (d, J=4.8 Hz, 1H), 5.34 (d, J=47.6 Hz, 2H), 5.25 (t, J=6.8 Hz, 1H), 4.78 (s, 2H), 4.15 (dd, J=8.0, 8.8 Hz, 2H), 3.90 (s, 3H), 3.76 (dd, J=8.0, 8.8 Hz, 2H), 1.54 (d, J=6.8 Hz, 3H). LCMS (ES) (M+Na)=527.

(S)-4-(1-(1-(3-(fluoromethyl)benzyl)-6-(trifluoromethyl)-2,3-dihydro-1H-imidazo[1,2-b]pyrazole-7-carboxamido)ethyl)benzoic acid (Compound 67)

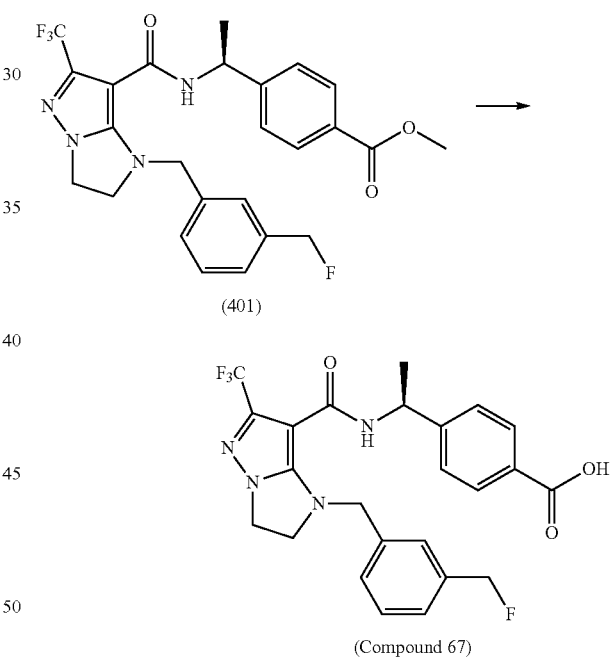

(Compound 67)

Following the same procedure for the preparation of (S)-4-(1-(1-(3-(hydroxymethyl)benzyl)-6-(trifluoromethyl)-2,3-dihydro-1H-imidazo[1,2-b]pyrazole-7-carboxamido)ethyl)benzoic acid (Compound 64), Compound 67 was prepared (54 mg, 79% yield) from methyl (S)-4-(1-(1-(3-(fluoromethyl)benzyl)-6-(trifluoromethyl)-2,3-dihydro-H-imidazo[1,2-b]pyrrazole-7-carboxamido)ethyl)benzoate (401) $^1$HNMR (400 MHz, CDCl$_3$): δ ppm 8.04 (d, J=8.4 Hz, 2H), 7.42 (d, J=8.4 Hz, 2H), 7.33-7.24 (m, 4H), 6.30 (d, J=4.8 Hz, 1H), 5.33 (d, J=47.6 Hz, 2H), 5.28-5.24 (m, 1H), 4.77 (s, 2H), 4.17-4.09 (m, 2H), 3.76 (dd, J=8.0, 8.8 Hz, 2H), 1.55 (d, J=7.2 Hz, 3H). LCMS (ES) (M+H)=491.

Example LXVIII

Methyl (S)-4-(1-(1-(4-iodo-3-(trifluoromethyl)benzyl)-6-(trifluoromethyl)-2,3-dihydro-1H-imidazo[1,2-b]pyrazole-7-carboxamido)ethyl)benzoate (403) and (S)-4-(1-(1-(4-iodo-3-(trifluoromethyl)benzyl)-6-(trifluoromethyl)-2,3-dihydro-1H-imidazo[1,2-b]pyrazole-7-carboxamido)ethyl)benzoic acid (Compound 68)

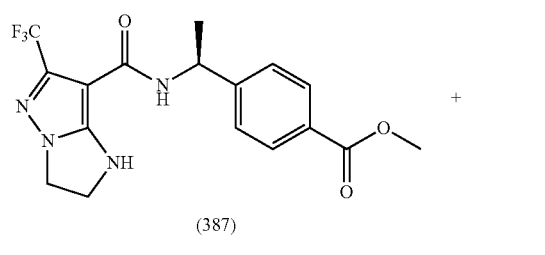

(387)

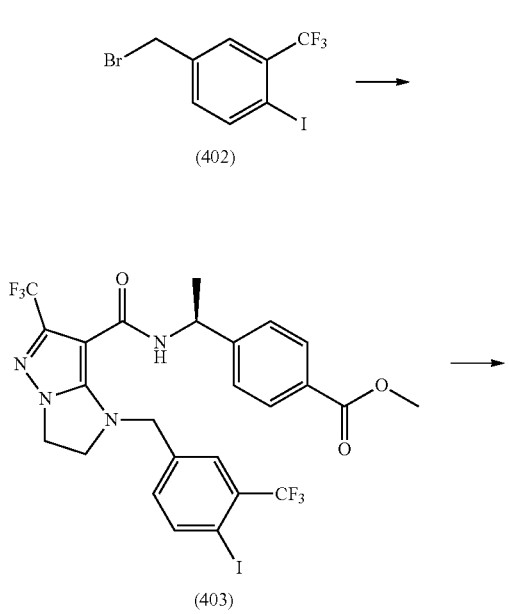

(402)

(403)

(Compound 68)

Following the similar procedure for the preparation of (S)-4-(1-(1-(3-(chloromethyl)benzyl)-6-(trifluoromethyl)-2,3-dihydro-1H-imidazo[1,2-b]pyrazole-7-carboxamido)ethyl)benzoic acid (Compound 65) from (S)-methyl 4-(1-(6-(trifluoromethyl)-2,3-dihydro-1H-imidazo[1,2-b]pyrazole-7-carboxamido)ethyl)benzoate (387) and 1,3-bis(chloromethyl)benzene (398) described in Example LXV, Compounds 403 and 68 were similarly prepared from (S)-methyl 4-(1-(6-(trifluoromethyl)-2,3-dihydro-1H-imidazo[1,2-b]pyrazole-7-carboxamido)ethyl)benzoate (387) and 4-(bromomethyl)-1-iodo-2-(trifluoromethyl)benzene (402).

Methyl (S)-4-(1-(1-(4-iodo-3-(trifluoromethyl)benzyl)-6-(trifluoromethyl)-2,3-dihydro-1H-imidazo[1,2-b]pyrazole-7-carboxamido)ethyl)benzoate (403)

$^1$HNMR (400 MHz, CDCl$_3$): δ ppm 8.02-7.93 (m, 3H), 7.57 (s, 1H), 7.38 (d, J=8.4 Hz, 2H), 7.13 (d, J=8.4 Hz, 1H), 6.29 (d, J=4.0 Hz, 1H), 5.21 (t, J=6.8 Hz, 1H), 4.82 (d, J=14.8 Hz, 1H), 4.75 (d, J=14.8 Hz, 1H), 4.18 (dd, J=8.0, 8.8 Hz, 2H), 3.91 (s, 3H), 3.76 (dd, J=8.0, 8.8 Hz, 2H), 1.53 (d, J=6.8 Hz, 3H). LCMS (ES) (M+H)=667.

(S)-4-(1-(1-(4-iodo-3-(trifluoromethyl)benzyl)-6-(trifluoromethyl)-2,3-dihydro-1H-imidazo[1,2-b]pyrazole-7-carboxamido)ethyl)benzoic acid (Compound 68)

$^1$HNMR (400 MHz, CDCl$_3$): δ ppm 8.04 (d, J=8.4 Hz, 2H), 7.94 (d, J=7.6 Hz, 1H), 7.56 (s, 1H), 7.39 (d, J=8.0 Hz, 2H), 7.15 (d, J=7.2 Hz, 1H), 6.34 (br s, 1H), 5.21 (t, J=6.8 Hz, 1H), 4.85 (d, J=14.8 Hz, 1H), 4.72 (d, J=14.8 Hz, 1H), 4.18 (t, J=8.4 Hz, 2H), 3.79 (t, J=8.4 Hz, 2H), 1.53 (d, J=7.2 Hz, 3H). LCMS (ES) (M+H)=653.

Example LXIX

Methyl (S)-4-(1-(1-(3-iodobenzyl)-6-(trifluoromethyl)-2,3-dihydro-1H-imidazo[1,2-b]pyrazole-7-carboxamido)ethyl)benzoate (405) and (S)-4-(1-(1-(3-iodobenzyl)-6-(trifluoromethyl)-2,3-dihydro-1H-imidazo[1,2-b]pyrazole-7-carboxamido)ethyl)benzoic acid (Compound 69)

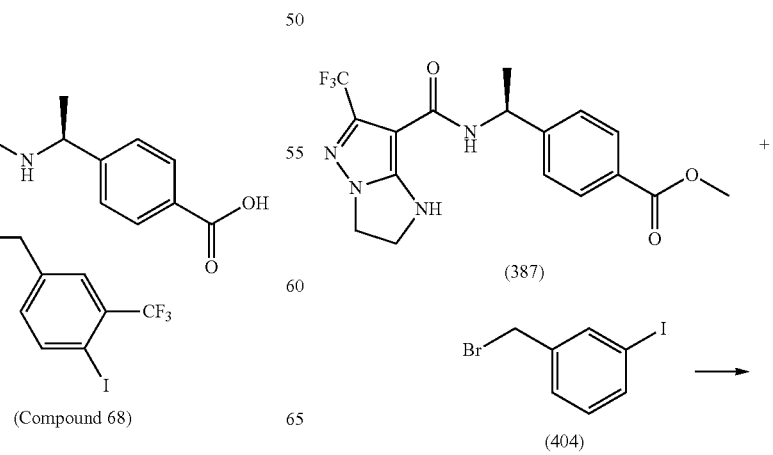

(387)

(404)

Example LXX

Methyl (S)-4-(1-(1-benzyl-6-(trifluoromethyl)-2,3-dihydro-1H-imidazo[1,2-b]pyrazole-7-carboxamido)ethyl)benzoate (407) and (S)-4-(1-(1-benzyl-6-(trifluoromethyl)-2,3-dihydro-1H-imidazo[1,2-b]pyrazole-7-carboxamido)ethyl)benzoic acid (Compound 70)

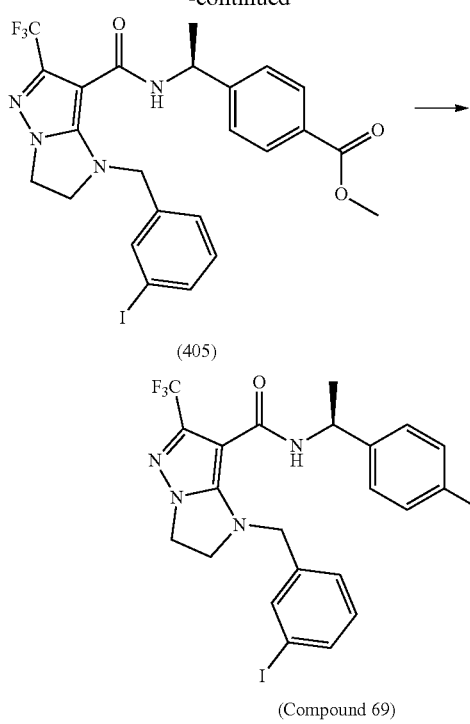

(405)

(Compound 69)

Following the similar procedure for the preparation of (S)-4-(1-(1-(3-(chloromethyl)benzyl)-6-(trifluoromethyl)-2,3-dihydro-1H-imidazo[1,2-b]pyrazole-7-carboxamido)ethyl)benzoic acid (Compound 65) from (S)-methyl 4-(1-(6-(trifluoromethyl)-2,3-dihydro-1H-imidazo[1,2-b]pyrazole-7-carboxamido)ethyl)benzoate (387) and 1,3-bis(chloromethyl)benzene (398) described in Example LXV, Compounds 405 (265 mg, 85%) and 69 (33 mg, 67%) were similarly prepared from methyl (S)-4-(1-(6-(trifluoromethyl)-2,3-dihydro-1H-imidazo[1,2-b]pyrazole-7-carboxamido)ethyl)benzoate (387) and 1-(bromomethyl)-3-iodobenzene (404).

Methyl (S)-4-(1-(1-(3-iodobenzyl)-6-(trifluoromethyl)-2,3-dihydro-1H-imidazo[1,2-b]pyrazole-7-carboxamido)ethyl)benzoate (405)

$^1$HNMR (400 MHz, CDCl$_3$): δ ppm 8.04 (d, J=8.4 Hz, 2H), 7.62 (d, J=8.0 Hz, 2H), 7.41 (d, J=8.4 Hz, 2H), 7.26-7.05 (m, 2H), 6.28 (br s, 1H), 5.23 (t, J=6.8 Hz, 1H), 4.72 (m, 2H), 4.18 (t, J=8.4 Hz, 2H), 3.92 (s, 3H), 3.76 (t, J=8.4 Hz, 2H), 1.57 (d, J=7.2 Hz, 3H). LCMS (ES) (M+H)=599.

(S)-4-(1-(1-(3-iodobenzyl)-6-(trifluoromethyl)-2,3-dihydro-1H-imidazo[1,2-b]pyrazole-7-carboxamido)ethyl)benzoic acid (Compound 69)

$^1$HNMR (400 MHz, CDCl$_3$): δ ppm 7.93 (d, J=8.4 Hz, 2H), 7.57-7.52 (m, 2H), 7.32 (d, J=8.0 Hz, 2H), 7.16 (d, J=7.6 Hz, 1H), 6.98 (dd, J=7.2, 7.6 Hz, 1H), 6.35 (br s, 1H), 5.15 (t, J=6.8 Hz, 1H), 4.59 (d, J=14.8 Hz, 1H), 4.58 (d, J=14.8 Hz, 1H), 4.10 (t, J=8.4 Hz, 2H), 3.71 (t, J=8.4 Hz, 2H), 1.47 (d, J=7.2 Hz, 3H). LCMS (ES) (M+H)=585.

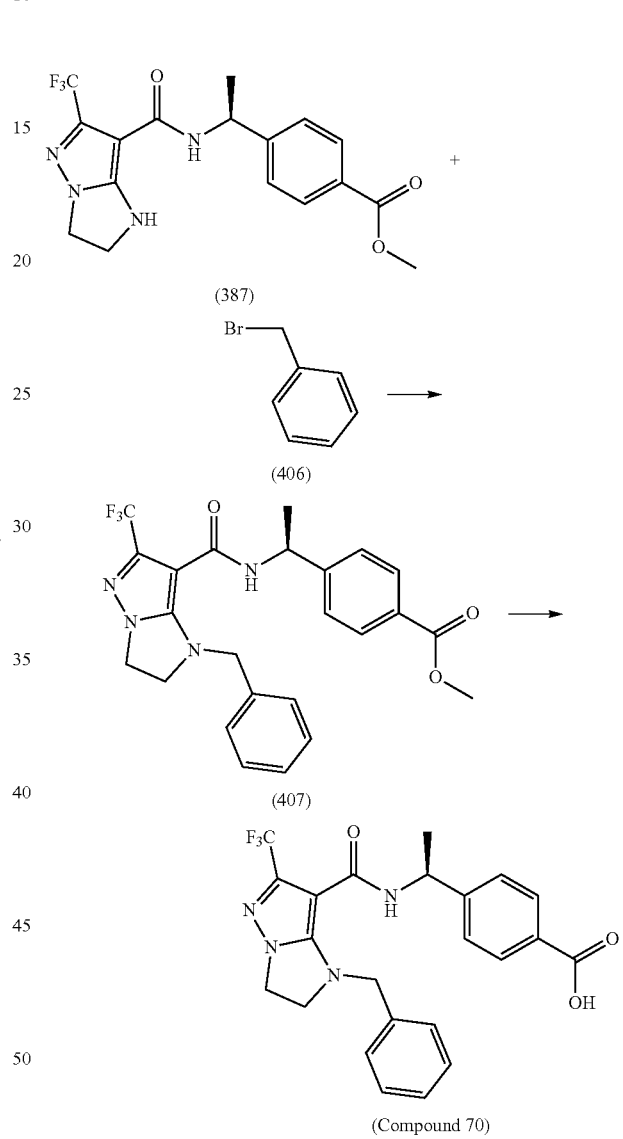

(387)

(406)

(407)

(Compound 70)

Following the similar procedure for the preparation of (S)-4-(1-(1-(3-(chloromethyl)benzyl)-6-(trifluoromethyl)-2,3-dihydro-1H-imidazo[1,2-b]pyrazole-7-carboxamido)ethyl)benzoic acid (Compound 65) from (S)-methyl 4-(1-(6-(trifluoromethyl)-2,3-dihydro-1H-imidazo[1,2-b]pyrazole-7-carboxamido)ethyl)benzoate (387) and 1,3-bis(chloromethyl)benzene (398) described in Example LXV, Compounds 407 (53 mg, 86%) and 70 (36 mg, 84%) were similarly prepared from methyl (S)-4-(1-(6-(trifluoromethyl)-2,3-dihydro-1H-imidazo[1,2-b]pyrazole-7-carboxamido)ethyl)benzoate (387) and (bromomethyl)benzene (406).

151

Methyl (S)-4-(1-(1-benzyl-6-(trifluoromethyl)-2,3-dihydro-1H-imidazo[1,2-b]pyrazole-7-carboxamido)ethyl)benzoate (407)

$^1$HNMR (400 MHz, CDCl$_3$): δ ppm 8.00 (d, J=8.4 Hz, 2H), 7.40 (d, J=8.4 Hz, 2H), 7.31-7.23 (m, 5H), 6.25 (d, J=4.8 Hz, 1H), 5.25 (t, J=7.2 Hz, 1H), 4.77 (d, J=14.8 Hz, 1H), 4.72 (d, J=14.8 Hz, 1H), 4.13 (t, J=8.4 Hz, 2H), 3.90 (s, 3H), 3.76 (t, J=8.4 Hz, 2H), 1.54 (d, J=7.2 Hz, 3H). LCMS (ES) (M+H)=473.

(S)-4-(1-(1-benzyl-6-(trifluoromethyl)-2,3-dihydro-1H-imidazo[1,2-b]pyrazole-7-carboxamido)ethyl)benzoic acid (Compound 70)

$^1$HNMR (400 MHz, CDCl$_3$): δ ppm 8.05 (d, J=8.4 Hz, 2H), 7.42 (d, J=8.4 Hz, 2H), 7.26-6.97 (m, 5H), 6.30 (br s, 1H), 5.27 (t, J=6.8 Hz, 1H), 4.76 (s, 2H), 4.17-4.11 (m, 2H), 3.80-3.76 (m, 2H), 1.54 (d, J=7.2 Hz, 3H). LCMS (ES) (M+H)=459.

Example LXXI (S)—N-(1-(4-(((4-nitrophenyl)sulfonyl)carbamoyl)phenyl)ethyl)-6-(trifluoromethyl)-1-(3-(trifluoromethyl)benzyl)-2,3-dihydro-1H-imidazo[1,2-b]pyrazole-7-carboxamide (Compound 71)

152

(S)-4-(1-(6-(trifluoromethyl)-1-(3-(trifluoromethyl)benzyl)-2,3-dihydro-1H-imidazo[1,2-b]pyrazole-7-carboxamido)ethyl)benzoic acid (Compound 1) (100 mg, 0.19 mmol) was dissolved in DCM (2 ml) and mixed with 4-nitrobenzenesulfonamide (409) (77 mg, 0.38 mmol) and DMAP (46.4 mg, 0.38 mmol). To this mixture was added EDC (72.8 mg, 0.38 mmol) and the mixture was stirred at r.t. for 20 h until the reaction was complete. The reaction was quenched with water (2 ml), extracted with DCM (2×30 ml). The organic layer was washed with brine (5 ml), dried and concentrated, the residue was purified by flash chromatography to give Compound 71 as white solid (93 mg, 68.9% yield). $^1$HNMR (400 MHz, CDCl$_3$): δ ppm 8.20-8.10 (m, 4H), 7.57-7.26 (m, 7H), 7.19 (d, J=8.4 Hz, 2H), 6.33 (br s, 1H), 5.11 (t, J=6.8 Hz, 1H), 4.86-4.83 (m, 1H), 4.72 (d, J=14.8 Hz, 1H), 4.21-4.10 (m, 2H), 3.75 (t, J=8.4 Hz, 2H), 1.42 (d, J=6.8 Hz, 3H). LCMS (ES) (M+H)=711.

Example LXXII (S)—N-(1-(4-(((4-aminophenyl)sulfonyl)carbamoyl)phenyl)ethyl)-6-(trifluoromethyl)-1-(3-(trifluoromethyl)benzyl)-2,3-dihydro-1H-imidazo[1,2-b]pyrazole-7-carboxamide (Compound 72)

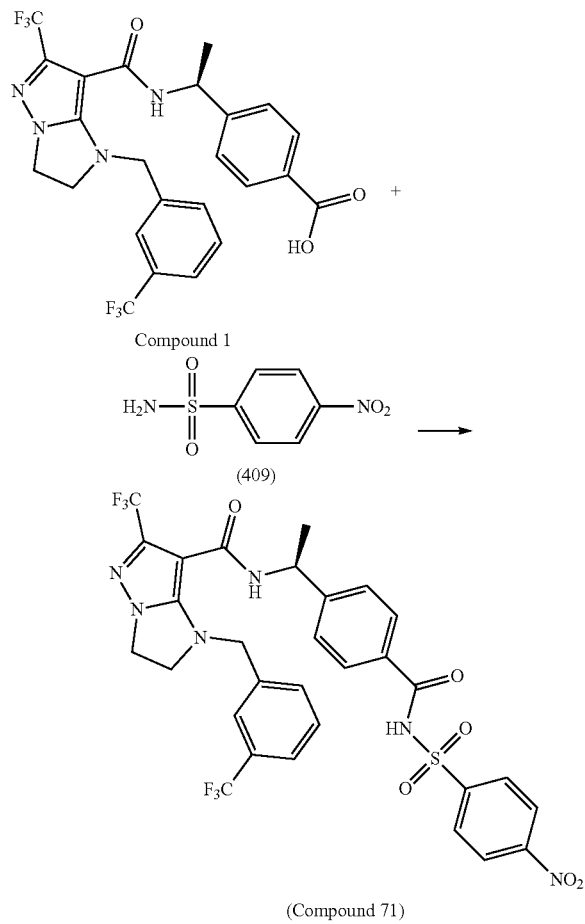

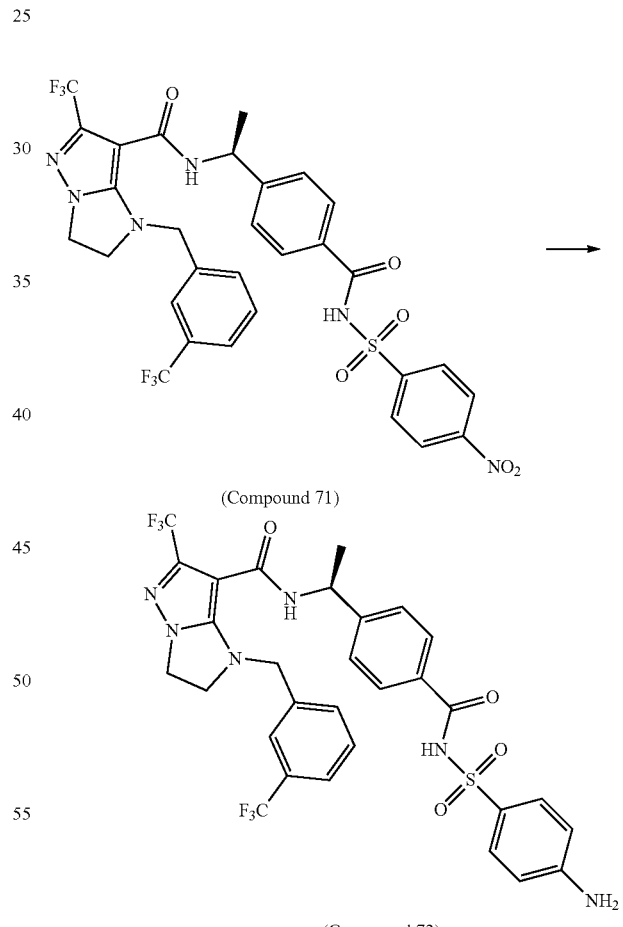

(S)—N-(1-(4-(((4-nitrophenyl)sulfonyl)carbamoyl)phenyl)ethyl)-6-(trifluoromethyl)-1-(3-(trifluoromethyl)benzyl)-2,3-dihydro-1H-imidazo[1,2-b]pyrazole-7-carboxamide (Compound 71) (0.046 g, 0.065 mmol) was dissolved in MeOH (2.3 ml) and mixed with Pd—C (6.89 mg, 6.473 μmol) under N$_2$ atmosphere. The flask was flushed with H$_2$ and the reaction mixture was stirred under H₂ atmosphere for 1 h until the reaction was complete. The mixture was filtered through a pad of celite and the filtrate was concentrated to give Compound 72 as white solid (41 mg, 93% yield). (400 MHz, CDCl₃): δ ppm 7.77 (d, J=7.6 Hz, 2H), 7.63 (d, J=7.6 Hz, 2H), 7.50-7.36 (m, 4H), 7.22 (d, J=7.2 Hz, 2H), 6.54 (d, J=5.2 Hz, 2H), 6.28 (d, J=3.6 Hz, 1H), 5.11 (t, J=6.4 Hz, 1H), 4.83-4.71 (m, 2H), 4.32 (br s, 1H), 4.14 (t, J=8.3 Hz, 2H), 3.73 (t, J=8.4 Hz, 2H), 1.43 (d, J=6.4 Hz, 3H). LCMS (ES) (M+H)=681.

Example LXXIII

Methyl (S)-4-(1-(1-(4-nitrobenzyl)-6-(trifluoromethyl)-2,3-dihydro-1H-imidazo[1,2-b]pyrazole-7-carboxamido)ethyl)benzoate (411)

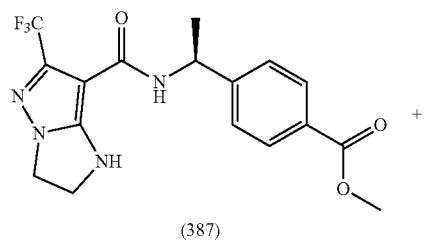

(387)

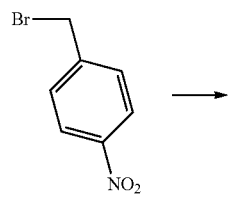

(410)

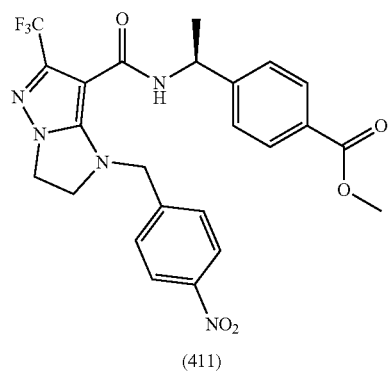

(411)

Following the same procedure for the preparation of (S)-methyl 4-(1-(1-(4-chloro-3-(trifluoromethyl)benzyl)-6-(trifluoromethyl)-2,3-dihydro-1H-imidazo[1,2-b]pyrazole-7-carboxamido)ethyl)benzoate (390), compound 411 was prepared (14 mg, 51.7% yield) from methyl (S)-4-(1-(6-(trifluoromethyl)-2,3-dihydro-1H-imidazo[1,2-b]pyrazole-7-carboxamido)ethyl)benzoate (387) and 1-(bromomethyl)-4-nitrobenzene (410). ¹HNMR (400 MHz, CDCl₃): δ ppm 8.15 (d, J=8.4 Hz, 2H), 7.99 (d, J=8.4 Hz, 2H), 7.44 (d, J=8.0 Hz, 2H), 7.37 (d, J=8.4 Hz, 2H), 6.30 (d, J=4.4 Hz, 1H), 5.20 (t, J=6.8 Hz, 1H), 4.93 (d, J=14.8 Hz, 1H), 4.88 (d, J=14.8 Hz, 1H), 4.20 (t, J=8.4 Hz, 2H), 3.91 (s, 3H), 3.79 (t, J=8.4 Hz, 2H), 1.53 (d, J=6.8 Hz, 3H). LCMS (ES) (M+H)=518.

(S)-4-(1-(1-(4-aminobenzyl)-6-(trifluoromethyl)-2,3-dihydro-1H-imidazo[1,2-b]pyrazole-7-carboxamido)ethyl)benzoic acid (Compound 73)

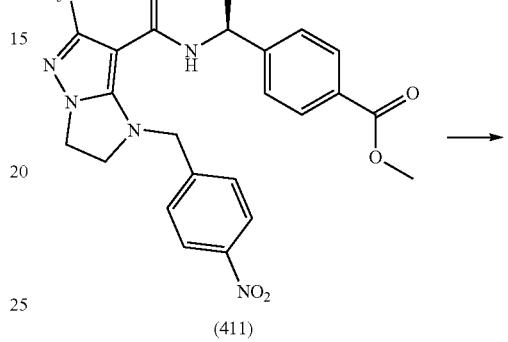

(411)

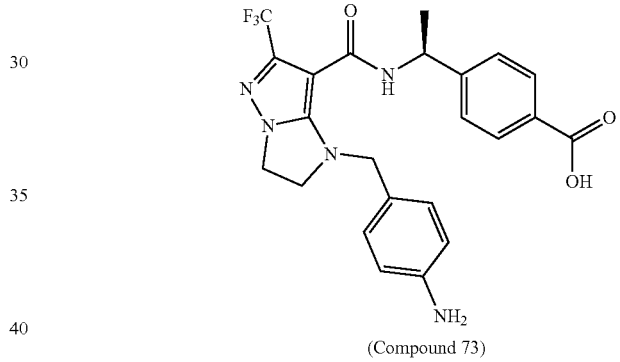

(Compound 73)

(S)-methyl 4-(1-(1-(4-nitrobenzyl)-6-(trifluoromethyl)-2,3-dihydro-1H-imidazo[1,2-b]pyrazole-7-carboxamido)ethyl)benzoate (411) (7 mg, 0.014 mmol) was dissolved in MeOH (1.4 ml) and mixed with Pd—C (1.440 mg, 1.353 μmol) under N₂ atmosphere. The flask was flushed with H₂ and the reaction mixture was stirred under H₂ atmosphere for 30 min until the reaction was complete. The mixture was filled through a celite pad, rinsed with MeOH (3×1 ml). The filtrate was concentrated and redissolved in t-Amyl alcohol (659 μl), 3N NaOH solution (45.1 μl, 0.135 mmol) was added. The mixture was then stirred at 90° C. for 30 min until the reaction was complete. The mixture was then cooled to r.t. and 1N HCl (176 μk, 0.176 mmol) was added to make pH<4. The material was subjected for prep HPLC purification to give Compound 73 as light yellow oil (3.5 mg, 54.7% yield). ¹HNMR (400 MHz, CDCl₃): δ ppm 7.95-7.85 (m, 2H), 7.32-7.24 (m, 2H), 6.98-6.84 (m. 2H), 6.60-6.24 (m, 3H), 5.18-5.09 (m, 1H), 4.62 (br s., 1H), 4.38 (br s, 1H), 4.14 (br s, 1H), 4.03 (s, 2H), 3.69 (t, J=8.4 Hz, 2H), 3.40-3.22 (m, 2H), 1.47 (d, J=7.2 Hz, 3H). LCMS (ES) (M+Na)=496.

Example LXXIV

Methyl (S)-4-(1-(1-(3-((2-hydroxyethoxy)methyl)benzyl)-6-(trifluoromethyl)-2,3-dihydro-1H-imidazo[1,2-b]pyrazole-7-carboxamido)ethyl)benzoate (412)

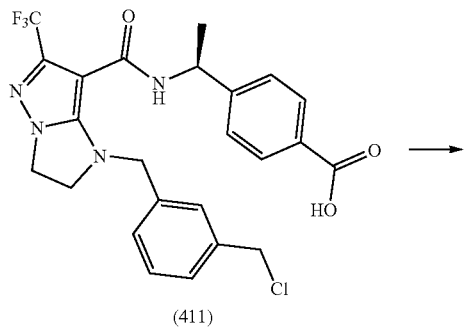
(411)

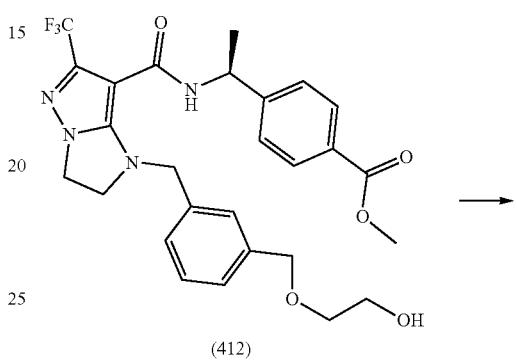
(412)

(S)-4-(1-(1-(3-(chloromethyl)benzyl)-6-(trifluoromethyl)-2,3-dihydro-H-imidazo[1,2-b]pyrazole-7-carboxamido)ethyl)benzoic acid (Compound 65) (0.2 g, 0.395 mmol) was dissolved in polyethylene glycol (1.0 ml) and toluene (2.0 ml). KOH (0.221 g, 3.946 mmol) was added and the resulting mixture was refluxed for 30 min until the reaction was complete. The mixture was cooled to r.t., neutralized to pH=4 with 3N HCl (1.558 ml, 5.129 mmol) and extracted with DCM (3×20 ml). The organic layer was concentrated and the crude product was dissolved in MeOH (2 ml) at rt and then mixed with toluene (3 ml). To this mixture was added Trimethylsilyldiazomethane (0.986 ml, 1.972 mmol) (2M solution in hexanes) until yellow color persist. The mixture was then stirred at r.t. for 1 h. before concentration. The residue was purified by flash chromatography to give compound 412 as light yellow oil (146 mg, 67.7%). $^1$HNMR (400 MHz, CDCl$_3$): δ ppm 7.97 (d, J=8.4 Hz, 2H), 7.39 (d, J=8.4 Hz, 2H), 7.31-7.24 (m, 3H), 7.17 (d, J=6.8 Hz, 1H), 6.30 (d, J=4.2 Hz, 1H), 5.24 (t, J=6.8 Hz, 1H), 4.76 (d, J=14.4 Hz, 1H), 4.70 (d, J=14.8 Hz, 1H), 4.51 (s, 2H), 4.14-4.09 (m, 2H), 3.89 (s, 3H), 3.78-3.58 (m, 4H), 3.56 (d, J=6.4 Hz, 2H), 1.53 (d, J=7.2 Hz, 3H). LCMS (ES) (M+Na)=569.

Methyl (S)-4-(1-(1-(3-((2-((methylsulfonyl)oxy)ethoxy)methyl)benzyl)-6-(trifluoromethyl)-2,3-dihydro-1H-imidazo[1,2-b]pyrazole-7-carboxamido)ethyl)benzoate (413)

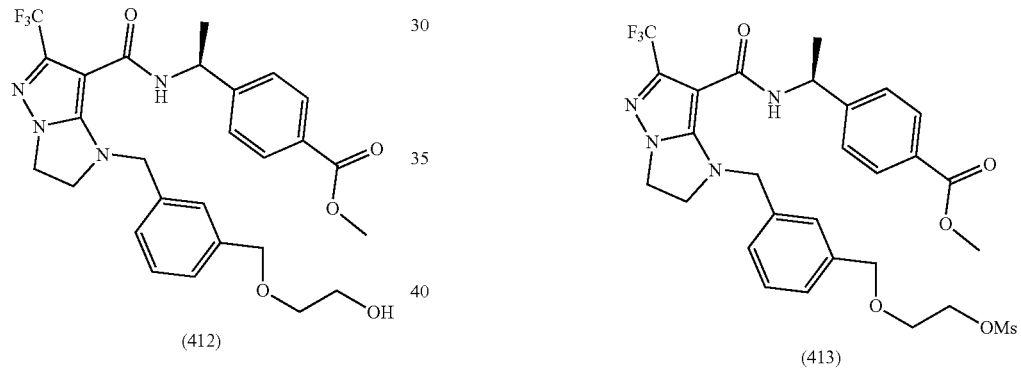
(412) → (413)

(S)-methyl 4-(1-(1-(3-((2-hydroxyethoxy)methyl)benzyl)-6-(trifluoromethyl)-2,3-dihydro-1H-imidazo[1,2-b]pyrazole-7-carboxamido)ethyl)benzoate (412) (0.125 g, 0.229 mmol) was dissolved in DCM (2.84 ml), cooled to −10° C., Et$_3$N (0.080 ml, 0.572 mmol) was added followed by the slow addition of MsCl (0.027 ml, 0.343 mmol). The mixture was stirred at −5° C. for 30 min until the reaction was complete. The reaction was quenched with NaHCO$_3$ (1 ml), extracted with DCM (2×20 ml), washed with brine (3 ml). The organic layer was dried with Na$_2$SO$_4$, concentrated and purified by flash chromatography to give compound 413 as white foam (134 mg, 94% yield). $^1$HNMR (400 MHz, CDCl$_3$): δ ppm 7.97 (d, J=8.2 Hz, 2H), 7.39 (d, J=8.2 Hz, 2H), 7.31-7.23 (m, 3H), 7.18 (d, J=7.2 Hz, 1H), 6.29 (d, J=4.2 Hz, 1H), 5.23 (t, J=7.2 Hz, 1H), 4.76 (d, J=14.4 Hz, 1H), 4.70 (d, J=14.8 Hz, 1H), 4.53 (s, 2H), 4.35 (dd, J=4.4, 8.8 Hz, 2H), 4.16-4.10 (m, 2H), 3.89 (s, 3H), 3.77-3.71 (m, 4H), 3.00 (s, 3H), 1.53 (d, J=6.8 Hz, 3H). LCMS (ES) (M+H)=625.

(S)-4-(1-(1-(3-((2-fluoroethoxy)methyl)benzyl)-6-(trifluoromethyl)-2,3-dihydro-1H-imidazo[1,2-b]pyrazole-7-carboxamido)ethyl)benzoic acid (Compound 74)

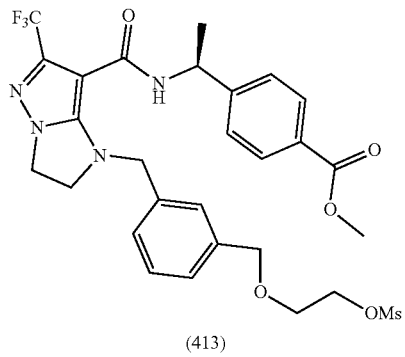
(413)

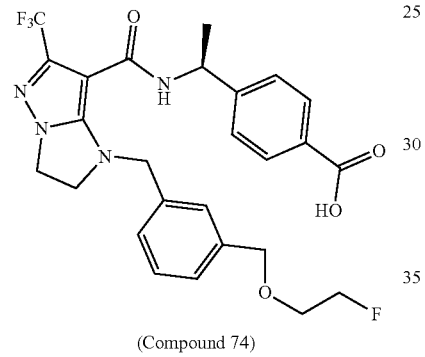
(Compound 74)

(S)-methyl 4-(1-(1-(3-((2-((methylsulfonyl)oxy)ethoxy)methyl)benzyl)-6-(trifluoromethyl)-2,3-dihydro-1H-imidazo[1,2-b]pyrazole-7-carboxamido)ethyl)benzoate (413) (37 mg, 0.059 mmol) was mixed with Cryptand 222 (44.6 mg, 0.118 mmol) and CsF (18.00 mg, 0.118 mmol) in t-Amyl alcohol (1.8 ml). The resulting suspension was stirred at 120° C. for 20 min until the reaction was complete. The mixture was cooled to 90° C., mixed with 3N NaOH (197 µl, 0.592 mmol) and continued stirring at 90° C. for 20 min. The mixture was cooled to r.t., quenched with 1N HCl (889 µl, 0.889 mmol) until pH 4. The mixture was extracted by DCM (3×10 ml), washed with brine (3 ml). The organic layer was dried and concentrated, and the residue was purified by flash chromatography to give Compound 74 as colorless oil (29.8 mg, 94% yield). $^1$HNMR (400 MHz, CDCl$_3$): δ ppm 8.04 (d, J=8.0 Hz, 2H), 7.43 (d, J=8.4 Hz, 2H), 7.32-7.26 (m, 3H), 7.18 (d, J=7.2 Hz, 1H), 6.29 (d, J=4.8 Hz, 1H), 5.26 (t, J=7.2 Hz, 1H), 4.78 (d, J=14.8 Hz, 1H), 4.72 (d, J=14.8 Hz, 1H), 4.63 (dd, J=4.0, 4.4 Hz, 1H), 4.55 (s, 2H), 4.51 (dd, J=4.0, 4.4 Hz, 1H), 4.16-4.10 (m, 2H), 3.79-3.73 (m, 3H), 3.67 (t, J=4.0 Hz, 1H), 1.55 (d, J=7.2 Hz, 3H). LCMS (ES) (M+H)=535.

Example LXXV

Methyl (S)-4-(1-(1-(3-(2-((methylsulfonyl)oxy)ethoxy)benzyl)-6-(trifluoromethyl)-2,3-dihydro-1H-imidazo[1,2-b]pyrazole-7-carboxamido)ethyl)benzoate (416)

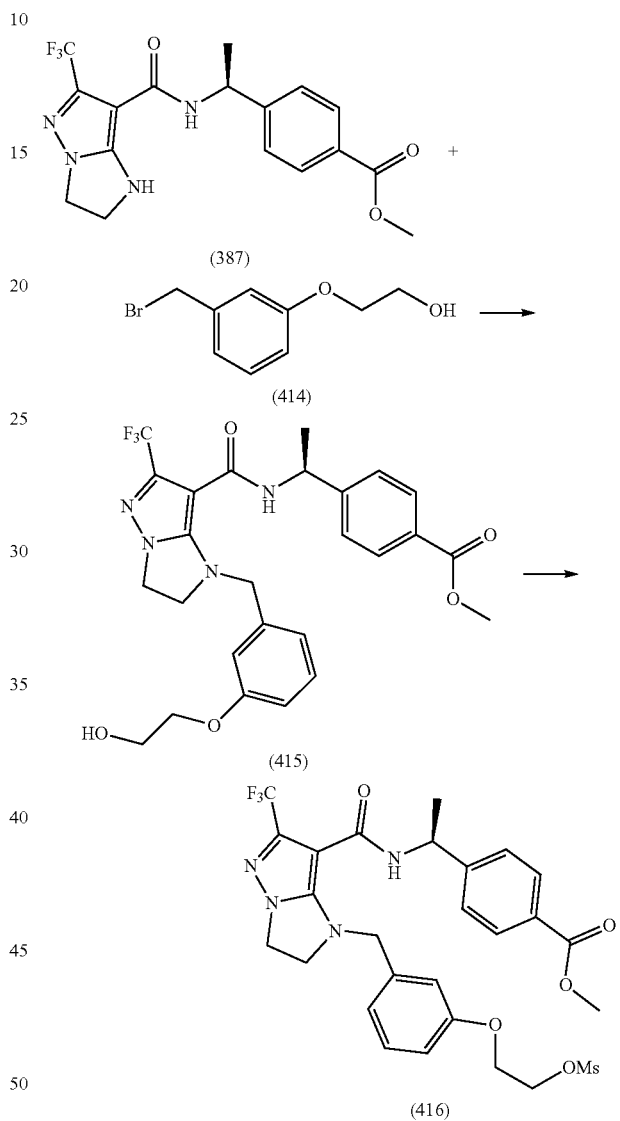

Methyl (S)-4-(1-(1-(3-(2-hydroxyethoxy)benzyl)-6-(trifluoromethyl)-2,3-dihydro-1H-imidazo[1,2-b]pyrazole-7-carboxamido)ethyl)benzoate (415)

Following the same procedure for the preparation of (S)-methyl 4-(1-(1-(4-chloro-3-(trifluoromethyl)benzyl)-6-(trifluoromethyl)-2,3-dihydro-1H-imidazo[1,2-b]pyrazole-7-carboxamido)ethyl)benzoate (390), Compound (415) was prepared (128 mg, 92% yield) from methyl (S)-4-(1-(6-(trifluoromethyl)-2,3-dihydro-1H-imidazo[1,2-b]pyrazole-7-carboxamido)ethyl)benzoate (387) and 2-(3-(bromomethyl)phenoxy)ethan-1-ol (414). LCMS (ES) (M+H)=533.

Methyl (S)-4-(1-(1-(3-(2-((methylsulfonyl)oxy)ethoxy)benzyl)-6-(trifluoromethyl)-2,3-dihydro-1H-imidazo[1,2-b]pyrazole-7-carboxamido)ethyl)benzoate (416)

Following the same procedure for the preparation of (Methyl (S)-4-(1-(1-(3-((2-((methylsulfonyl)oxy)ethoxy)methyl)benzyl)-6-(trifluoromethyl)-2,3-dihydro-1H-imidazo[1,2-b]pyrazole-7-carboxamido)ethyl)benzoate (413), compound 416 was prepared (140 mg, 94% yield) from methyl (S)-4-(1-(1-(3-(2-hydroxyethoxy)benzyl)-6-(trifluoromethyl)-2,3-dihydro-1H-imidazo[1,2-b]pyrazole-7-carboxamido)ethyl)benzoate (415). $^1$HNMR (400 MHz, CDCl$_3$): δ ppm 7.96 (d, J=8.4 Hz, 2H), 7.38 (d, J=8.0 Hz, 2H), 7.22 (t, J=8.4 Hz, 1H), 7.20-6.85 (m, 2H), 6.80 (dd, J=3.6, 8.0 Hz, 1H), 6.28 (d, J=4.8 Hz, 1H), 5.22 (t, J=7.2 Hz, 1H), 4.72 (d, J=14.8 Hz, 1H), 4.66 (d, J=14.8 Hz, 1H), 4.52 (dd, J=4.8, 6.0 Hz, 2H), 4.19-4.11 (m, 4H), 3.88 (s, 3H), 3.75 (t, J=8.8 Hz, 2H), 3.04 (s, 3H), 1.52 (d, J=6.8 Hz, 3H). LCMS (ES) (M+H)=611.

(S)-4-(1-(1-(3-(2-fluoroethoxy)benzyl)-6-(trifluoromethyl)-2,3-dihydro-1H-imidazo[1,2-b]pyrazole-7-carboxamido)ethyl)benzoic acid (Compound 75)

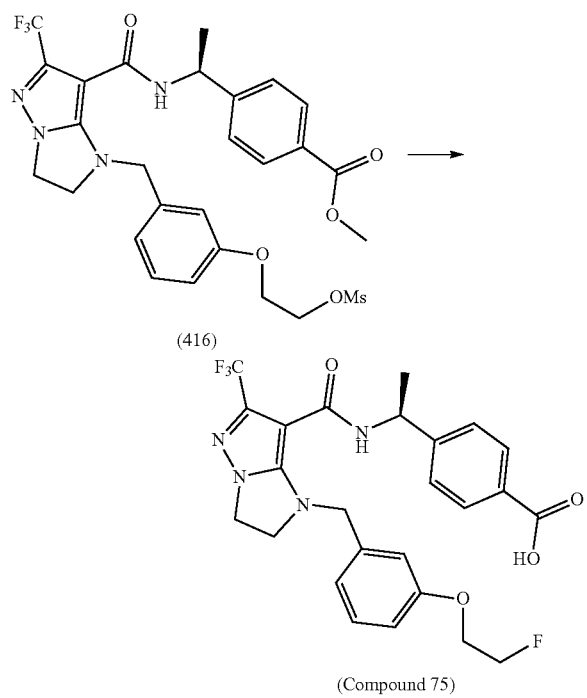

Following the same procedure for the preparation of (S)-4-(1-(1-(3-((2-fluoroethoxy)methyl)benzyl)-6-(trifluoromethyl)-2,3-dihydro-1H-imidazo[1,2-b]pyrazole-7-carboxamido)ethyl)benzoic acid (Compound 74), Compound 75 was prepared (30 mg, 88% yield) from methyl (S)-4-(1-(1-(3-(2-((methylsulfonyl)oxy)ethoxy)benzyl)-6-(trifluoromethyl)-2,3-dihydro-1H-imidazo[1,2-b]pyrazole-7-carboxamido)ethyl)benzoate (416). $^1$HNMR (400 MHz, CDCl$_3$): δ ppm 8.03 (d, J=8.0 Hz, 2H), 7.41 (d, J=7.6 Hz, 2H), 7.23-7.20 (m, 1H), 6.85-6.82 (m, 3H), 6.28 (br s, 1H), 5.27 (t, J=7.2 Hz, 1H), 4.74 (d, J=12.4 Hz, 2H), 4.68 (d, J=12.0 Hz, 2H), 4.19-4.12 (m, 4H), 3.79-3.75 (m, 2H), 1.54 (d, J=6.4 Hz, 3H). LCMS (ES) (M+H)=521.

Example LXXVI 1-(3-iodobenzyl)-7-(((S)-1-(4-(methoxycarbonyl)phenyl)ethyl)carbamoyl)-6-(trifluoromethyl)-2,3-dihydro-1H-imidazo[1,2-b]pyrazole 1-oxide (417)

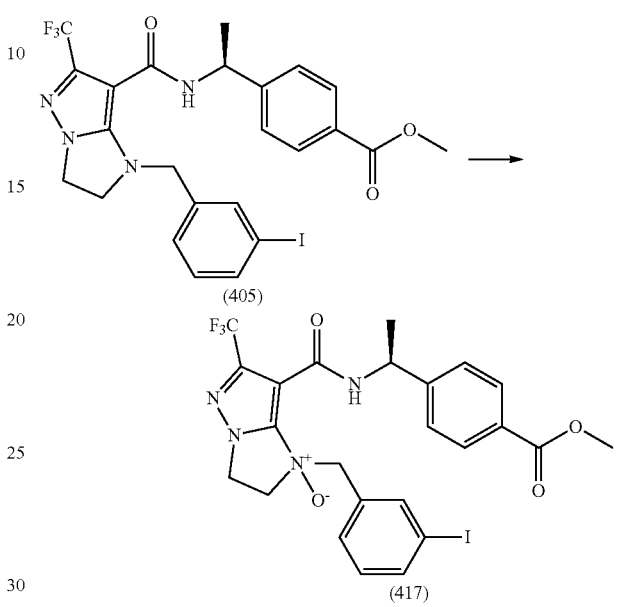

(S)-methyl 4-(1-(1-(3-iodobenzyl)-6-(trifluoromethyl)-2,3-dihydro-1H-imidazo[1,2-b]pyrazole-7-carboxamido)ethyl)benzoate (405) (10 mg, 0.017 mmol) was dissolved in acetic acid (200 μl) and mixed with Sodium perborate tetrahydrate (25.7 mg, 0.167 mmol). The mixture was stirred at 50° C. for 2 h before it was quenched with NaHCO$_3$ solution (pH 7). The mixture was extracted with DCM (3×10 ml), washed with brine (5 ml), the organic layer was concentrated and purified by flash chromatography to give compound 417 as light yellow oil (6.5 mg, 64% yield). $^1$HNMR (400 MHz, CDCl$_3$): δ ppm 10.8 (d, J=11.2 Hz, 1H), 8.00 (d, J=8.4 Hz, 2H), 7.78 (d, J=7.6 Hz, 1H), 7.66-7.55 (m, 2H), 7.42 (d, J=8.4 Hz, 1H), 7.13 (br s, 1H), 7.02 (t, J=8.0 Hz, 1H), 5.30-5.25 (m, 1H), 5.00-4.83 (m, 2H), 4.74-4.58 (m, 2H), 4.38-4.31 (m, 1H), 3.89 (s, 3H), 3.35-3.26 (m, 1H), 1.59 (d, J=7.2 Hz, 3H). LCMS (ES) (M+H)=615.

7-(((S)-1-(4-carboxyphenyl)ethyl)carbamoyl)-1-(3-iodobenzyl)-6-(trifluoromethyl)-2,3-dihydro-1H-imidazo[1,2-b]pyrazole 1-oxide (Compound 76)

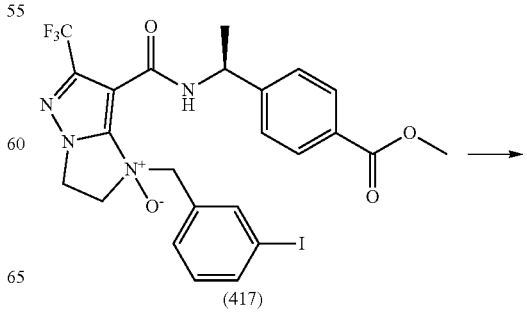

161

-continued

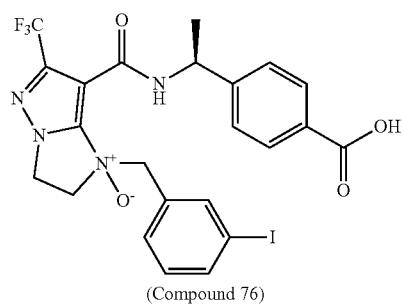

(Compound 76)

Following the same procedure for the preparation of (S)-4-(1-(1-(3-(hydroxymethyl)benzyl)-6-(trifluoromethyl)-2,3-dihydro-1H-imidazo[1,2-b]pyrazole-7-carboxamido)ethyl)benzoic acid (Compound 64), Compound 76 was prepared (4.5 mg, 70.8% yield) from 1-(3-iodobenzyl)-7-(((S)-1-(4-(methoxycarbonyl)phenyl)ethyl)carbamoyl)-6-(trifluoromethyl)-2,3-dihydro-1H-imidazo[1,2-b]pyrazole 1-oxide (417). $^1$HNMR (400 MHz, CDCl$_3$): δ ppm 8.05 (d, J=8.4 Hz, 2H), 7.68 (br s, 2H), 7.44 (d, J=8.0 Hz, 2H), 7.26-7.23 (m, 1H), 7.07 (t, J=8.0 Hz, 1H), 6.57 (d, J=7.2 Hz, 1H), 5.37 (t, J=6.8 Hz, 1H), 4.88 (d, J=11.2 Hz, 1H), 4.84 (d, J=11.6 Hz, 1H), 4.23-4.19 (m, 2H), 3.99 (dd, J=7.2, 8.0 Hz, 2H), 1.54 (d, J=7.2 Hz, 3H). LCMS (ES) (M+Na)=623.

Example LXXVII

Benzyl 3-(benzyloxy)-5-(trifluoromethyl)benzoate (419)

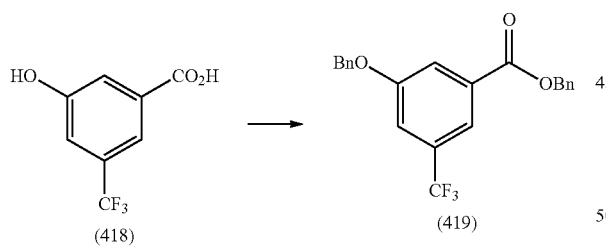

3-hydroxy-5-(trifluoromethyl)benzoic acid (418) (0.5 g, 2.426 mmol) was dissolved in DMF (5.00 ml) and mixed with BENZYL BROMIDE (1.154 ml, 9.703 mmol) and CESIUM CARBONATE (7.90 g, 24.258 mmol). The mixture was stirred at 50° C. for 4 h. Upon completion of the reaction, the mixture was cooled to r.t., quenched with NH$_4$Cl (10 ml), extracted with EtOAc (2×30 ml), washed with brine (10 ml), the organic layer was concentrated and purified by flash chromatography to give compound 419 as white solid (724 mg, 77% yield). $^1$HNMR (400 MHz, CDCl$_3$): δ ppm 7.98 (br s, 1H), 7.86 (br s, 1H), 7.50-7.38 (m, 11H), 5.42 (s, 2H), 5.15 (s, 2H).

162

(3-(benzyloxy)-5-(trifluoromethyl)phenyl)methanol (420)

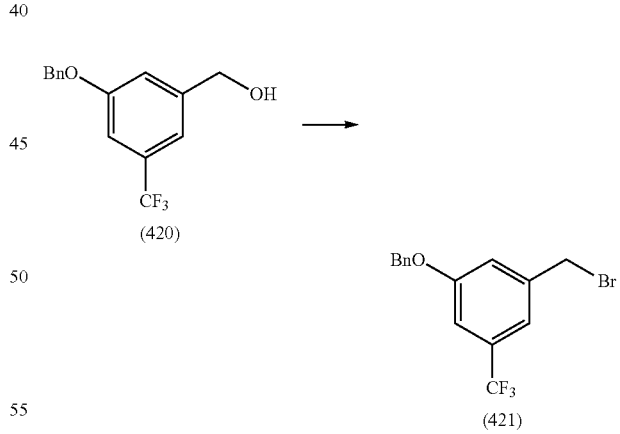

benzyl 3-(benzyloxy)-5-(trifluoromethyl)benzoate (419) (0.72 g, 1.864 mmol) was dissolved in THF (14 ml) and cooled to 0° C. under N2. Lithium borohydride (0.932 ml, 3.727 mmol) was added slowly and the mixture was then stirred at r.t. for 18 h. Upon completion of the reaction, the mixture was quenched by dropwise addition of NH$_4$Cl (5 ml), the mixture was extracted with EtOAc (2×30 ml), washed with NaHCO$_3$ (5 ml), brine (5 ml), the organic layer was concentrated and purified by flash chromatography to give compound 420 as colorless oil (524 mg, quantitative yield). $^1$HNMR (400 MHz, CDCl$_3$): δ ppm 7.45-7.34 (m, 5H), 7.22 (s, 1H), 7.17 (s, 1H), 7.14 (s, 1H), 5.09 (s, 2H), 4.70 (d, J=6.0 Hz, 2H), 1.82 (t, J=6.0 Hz, 1H). LCMS (ES) (M+Na)=306.

1-(benzyloxy)-3-(bromomethyl)-5-(trifluoromethyl)benzene (421)

(3-(benzyloxy)-5-(trifluoromethyl)phenyl)methanol (420) (0.205 g, 0.726 mmol) was dissolved in DCM (4.10 ml) and mixed with CBr$_4$ (0.265 g, 0.799 mmol). Ph$_3$P (0.210 g, 0.799 mmol) was added at r.t. and the mixture was stirred at r.t. for 2 h until the completion of the reaction. The mixture was directly loaded on column and purified by flash chromatography to give compound 421 as colorless oil (155 mg, 61.8% yield). $^1$HNMR (400 MHz, CDCl$_3$): δ ppm 7.45-7.31 (m, 5H), 7.22 (s, 1H), 7.18 (s, 1H), 7.16 (s, 1H), 5.10 (s, 2H), 4.46 (s, 2H).

163

Methyl (S)-4-(1-(1-(3-(benzyloxy)-5-(trifluoromethyl)benzyl)-6-(trifluoromethyl)-2,3-dihydro-1H-imidazo[1,2-b]pyrazole-7-carboxamido)ethyl)benzoate (422)

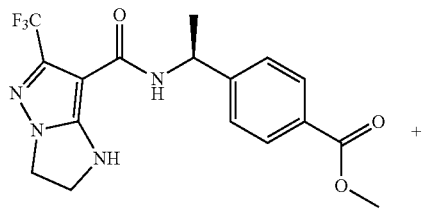

(387)

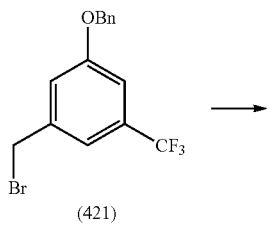

(421)

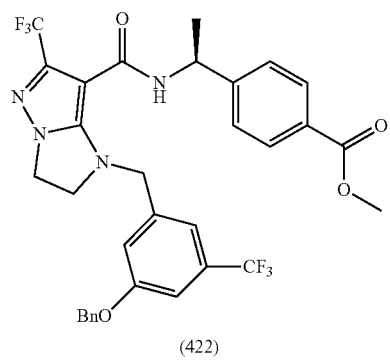

(422)

Following the same procedure for the preparation of (S)-methyl 4-(1-(1-(4-chloro-3-(trifluoromethyl)benzyl)-6-(trifluoromethyl)-2,3-dihydro-1H-imidazo[1,2-b]pyrazole-7-carboxamido)ethyl)benzoate (390), compound 422 was prepared (210 mg, 49.7% yield) from methyl (S)-4-(1-(6-(trifluoromethyl)-2,3-dihydro-1H-imidazo[1,2-b]pyrazole-7-carboxamido)ethyl)benzoate (387) and 1-(benzyloxy)-3-(bromomethyl)-5-(trifluoromethyl)benzene (421). $^1$HNMR (400 MHz, CDCl$_3$): δ ppm 7.99-7.97 (m, 2H), 7.41-7.25 (m, 6H), 7.14 (s, 1H), 7.11 (s, 2H), 6.26 (br s, 1H), 5.22 (t, J=6.8 Hz, 1H), 5.20 (s, 2H), 4.83 (d, J=14.8 Hz, 1H), 4.75 (d, J=14.8 Hz, 1H), 4.74 (d, J=5.2 Hz, 1H), 4.16-4.12 (m, 2H), 3.90 (s, 3H), 3.71 (t, J=8.0 Hz, 2H), 1.53 (d, J=6.8 Hz, 3H). LCMS (ES) (M+H)=647.

164

Methyl (S)-4-(1-(1-(3-hydroxy-5-(trifluoromethyl)benzyl)-6-(trifluoromethyl)-2,3-dihydro-1H-imidazo[1,2-b]pyrazole-7-carboxamido)ethyl)benzoate (423)

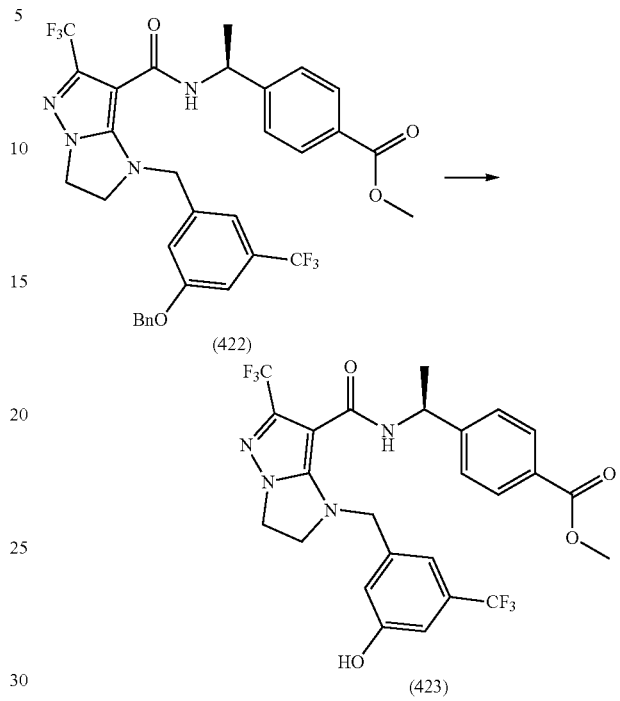

(S)-methyl 4-(1-(1-(3-(benzyloxy)-5-(trifluoromethyl)benzyl)-6-(trifluoromethyl)-2,3-dihydro-1H-imidazo[1,2-b]pyrazole-7-carboxamido)ethyl)benzoate (422) (0.21 g, 0.325 mmol) was dissolved in MeOH (21.00 ml) and mixed with 10% Pd/C (0.035 g, 0.032 mmol) under N$_2$ atmosphere. The H$_2$ gas exchange was performed and the resulting suspension was stirred at r.t. under H$_2$ atmosphere for 30 min. Upon completion of the reaction, the mixture was filtered through celite pad, rinsed with MeOH (3×2 ml). The filtrate was concentrated and purified by flash chromatography to give compound 423 as colorless oil (155 mg, 86% yield). $^1$HNMR (400 MHz, CDCl$_3$): δ ppm 7.96 (d, J=8.4 Hz, 2H), 7.37 (d, J=8.0 Hz, 2H), 6.94 (s, 1H), 6.90 (s, 1H), 6.85 (s, 1H), 6.82 (s, 1H), 6.37 (d, J=4.0 Hz, 1H), 5.18 (t, J=7.2 Hz, 1H), 4.63-4.60 (m, 2H), 4.19-4.13 (m, 2H), 3.89 (s, 3H), 3.76-3.72 (m, 2H), 1.54 (d, J=7.2 Hz, 3H). LCMS (ES) (M+H)=557.

(S)-4-(1-(1-(3-hydroxy-5-(trifluoromethyl)benzyl)-6-(trifluoromethyl)-2,3-dihydro-1H-imidazo[1,2-b]pyrazole-7-carboxamido)ethyl)benzoic acid (Compound 77)

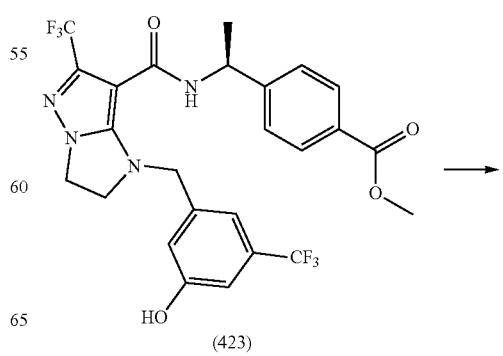

(423)

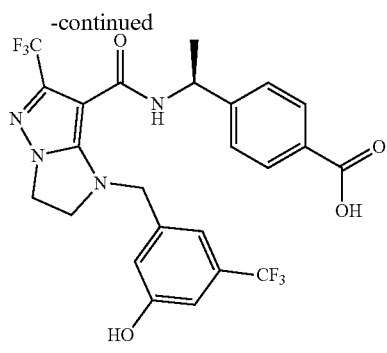

(Compound 77)

Following the same procedure for the preparation of (S)-4-(1-(1-(3-(hydroxymethyl)benzyl)-6-(trifluoromethyl)-2,3-dihydro-1H-imidazo[1,2-b]pyrazole-7-carboxamido)ethyl)benzoic acid (Compound 64), Compound 77 was prepared (11 mg, 81% yield) from (S)-methyl 4-(1-(1-(3-hydroxy-5-(trifluoromethyl)benzyl)-6-(trifluoromethyl)-2,3-dihydro-1H-imidazo[1,2-b]pyrazole-7-carboxamido)ethyl)benzoate (423). $^1$HNMR (400 MHz, CDCl$_3$): δ ppm 7.86 (d, J=4.0 Hz, 2H), 7.38 (d, J=4.0 Hz, 2H), 6.95 (s, 1H), 6.85 (s, 2H), 6.41 (br s, 1H), 5.17 (br s, 1H), 4.65 (d, J=12.0 Hz, 1H), 4.55 (d, J=12.0 Hz, 1H), 4.19-4.11 (m, 3H), 3.76 (br s, 2H), 1.54 (br s, 3H). LCMS (ES) (M+H)=543.

Example LXXVIII

Methyl (S)-4-(1-(1-((4-(bromomethyl)cyclohexyl)methyl)-6-(trifluoromethyl)-2,3-dihydro-1H-imidazo[1,2-b]pyrazole-7-carboxamido)ethyl)benzoate (425)

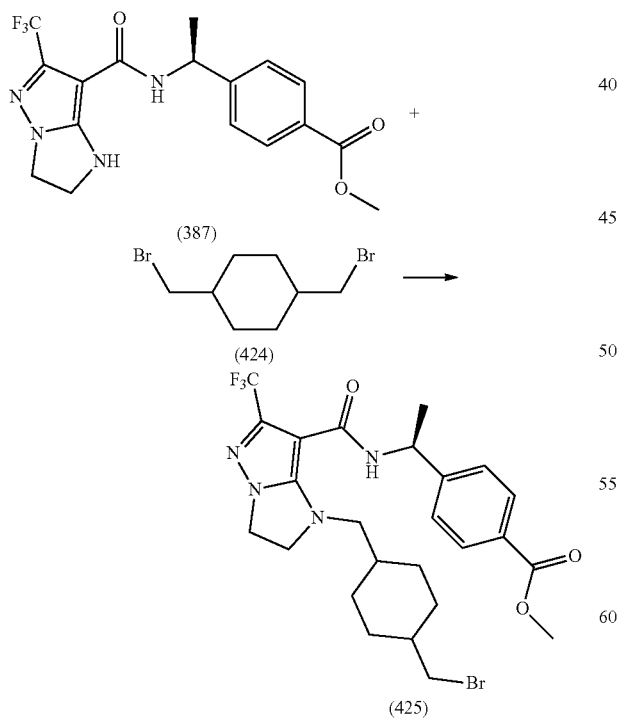

Following the same procedure for the preparation of (S)-methyl 4-(1-(1-(4-chloro-3-(trifluoromethyl)benzyl)-6-(trifluoromethyl)-2,3-dihydro-1H-imidazo[1,2-b]pyrazole-7-carboxamido)ethyl)benzoate (390), compound 425 was prepared (27.5 mg, 36.8% yield) from methyl (S)-4-(1-(6-(trifluoromethyl)-2,3-dihydro-1H-imidazo[1,2-b]pyrazole-7-carboxamido)ethyl)benzoate (387) and 1,4-bis(bromomethyl)cyclohexane (424). $^1$HNMR (400 MHz, CDCl$_3$): δ ppm 8.01 (d, J=8.4 Hz, 2H), 7.41 (d, J=8.4 Hz, 2H), 6.15 (d, J=5.6 Hz, 1H), 5.23 (d, J=7.2 Hz, 1H), 4.17 (t, J=8.4 Hz, 2H), 3.91 (s, 3H), 3.89-3.82 (m, 2H), 3.44 (dd, J=7.6, 13.6 Hz, 2H), 3.24 (dd, J=6.4, 12.4 Hz, 2H), 1.86-1.66 (m, 4H), 1.52 (s, 3H), 1.56-1.42 (m, 2H), 0.99-0.88 (m, 4H). LCMS (ES) (M+H)=571/573.

(S)-4-(1-(1-((4-(fluoromethyl)cyclohexyl)methyl)-6-(trifluoromethyl)-2,3-dihydro-1H-imidazo[1,2-b]pyrazole-7-carboxamido)ethyl)benzoic acid (Compound 78) and (S)-4-(1-(1-((4-methylenecyclohexyl)methyl)-6-(trifluoromethyl)-2,3-dihydro-1H-imidazo[1,2-b]pyrazole-7-carboxamido)ethyl)benzoic acid (Compound 79)

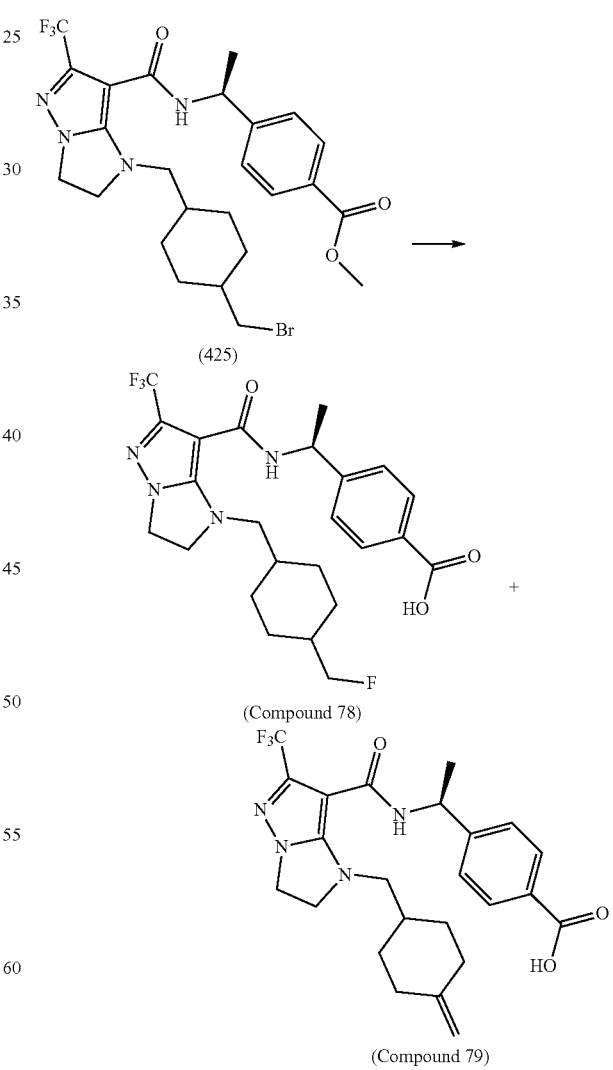

Methyl (S)-4-(1-(1-((4-(bromomethyl)cyclohexyl)methyl)-6-(trifluoromethyl)-2,3-dihydro-1H-imidazo[1,2-b]

pyrazole-7-carboxamido)ethyl)benzoate (425) (27 mg, 0.047 mmol) was mixed with Cryptand 222 (89 mg, 0.236 mmol) and KF (13.73 mg, 0.236 mmol) in t-Amyl alcohol (1.4 ml) in a small vial. The resulting suspension was stirred at 120° C. for 1.5 h until the complete consumption of SM. To this mixture was added 3N NaOH solution (162 µl, 0.486 mmol) and the mixture was continue stirred at 120° C. for 5 min until the complete hydrolysis of ester. Upon completion of the reaction, the mixture was cooled to r.t., quenched with 1 N HCl solution (709 µl, 0.709 mmol), extracted with EtOAc (2×10 ml), washed with brine (5 ml). The organic layer was dried and concentrated and the residue was purified by prep TLC to give (S)-4-(1-(1-((4-(fluoromethyl)cyclohexyl)methyl)-6-(trifluoromethyl)-2,3-dihydro-1H-imidazo[1,2-b]pyrazole-7-carboxamido)ethyl)benzoic acid (Compound 78) (10.5 mg, 44.7% yield) and (S)-4-(1-(1-((4-methylenecyclohexyl)methyl)-6-(trifluoromethyl)-2,3-dihydro-1H-imidazo[1,2-b]pyrazole-7-carboxamido)ethyl)benzoic acid (Compound 79) (1.1 mg, 4.9% yield).

(S)-4-(1-(1-((4-(fluoromethyl)cyclohexyl)methyl)-6-(trifluoromethyl)-2,3-dihydro-1H-imidazo[1,2-b]pyrazole-7-carboxamido)ethyl)benzoic acid (Compound 78) LCMS (ES) (M+H)=497.

(S)-4-(1-(1-((4-methylenecyclohexyl)methyl)-6-(trifluoromethyl)-2,3-dihydro-1H-imidazo[1,2-b]pyrazole-7-carboxamido)ethyl)benzoic acid (Compound 79)

$^1$HNMR (400 MHz, CDCl$_3$): δ ppm 8.07 (d, J=8.0 Hz, 2H), 7.44 (d, J=8.0 Hz, 2H), 6.15 (d, J=5.2 Hz, 1H), 5.25 (t, J=7.2 Hz, 1H), 4.61 (s, 2H), 4.19 (t, J=8.4 Hz, 2H), 3.90 (t, J=8.8 Hz, 2H), 3.43 (dd, J=7.6, 13.6 Hz, 1H), 3.31 (dd, J=7.2, 13.6 Hz, 1H), 2.31-2.24 (m, 2H), 2.04-1.90 (m, 2H), 1.71-1.66 (m, 3H), 1.54 (d, J=7.2 Hz, 3H), 1.10-0.98 (m, 2H). LCMS (ES) (M+H)=477.

Example LXXVIII

Tert-butyl (R)-(3-(benzyloxy)-2-hydroxypropyl)carbamate (429)

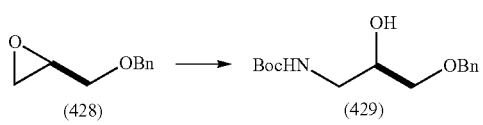 [SMILES: c1ccc(COC[C@H]2CO2)cc1 ; CC(C)(C)OC(=O)NC[C@@H](O)COCc1ccccc1]

(R)-2-((benzyloxy)methyl)oxirane (428) (10 g, 60.901 mmol) was dissolved in 2-PROPANOL (750 ml) and mixed with AMMONIUM HYDROXIDE (750 ml, 19260.511 mmol). The mixture was stirred at r.t. for overnight until the completion of epoxide opening. The organic solvent was evaporated under reduced pressure, the residue (~15 ml) was extracted with DCM (2×30 ml). The combined organic layer was concentrated to give crude material (11.9 g), which was mixed with Et$_3$N (12.69 ml, 91.044 mmol) in DCM (220 ml). Boc$_2$O (18.32 ml, 78.905 mmol) was added at 0° C. under N$_2$ atmosphere and the resulting mixture was allowed to warm up to at r.t. and stirred overnight. Upon completion of the reaction, the reaction was quenched with sat. aq. NH$_4$Cl solution (15 ml), extracted with DCM (100 ml). The organic layer was washed with brine (10 ml), dried and concentrated and the residue was purified by flash chromatography to give compound 429 as colorless oil (13.3 g, 78% yield). $^1$HNMR (400 MHz, CDCl$_3$): δ ppm 7.29-7.20 (m, 5H), 5.12 (br s, 1H), 4.46 (s, 2H), 3.81 (br s, 1H), 3.42 (dd, J=4.0, 9.6 Hz, 1H), 3.35 (dd, J=4.0, 9.6 Hz, 1H), 3.37-3.32 (m, 1H), 3.29-3.25 (m, 1H), 3.09-3.03 (m, 1H), 1.37 (s, 9H). LCMS (ES) (M+Na)=304.

(R)-1-(benzyloxy)-3-((tert-butoxycarbonyl)amino)propan-2-yl 4-methylbenzenesulfonate (430)

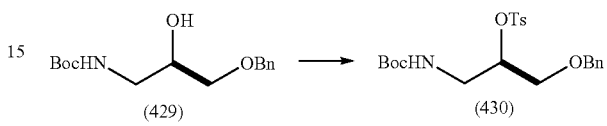

(R)-tert-butyl (3-(benzyloxy)-2-hydroxypropyl)carbamate (429) (5 g, 17.772 mmol) was mixed with Et$_3$N (12.39 ml, 88.858 mmol) and DMAP (0.217 g, 1.777 mmol) in DCM (100 ml) and cooled to 0° C. p-Toluenesulfonyl chloride (3.56 g, 18.66 mmol) was added under N$_2$. The mixture was stirred at r.t. for 3 h until the reaction was complete. The reaction was quenched with sat. aq. NaHCO$_3$ solution (10 ml), extracted with EtOAc (2×50 ml). The organic layer was washed with water (10 ml), brine (10 ml), dried and concentrated and the residue was purified by flash chromatography to give compound 430 as white solid (5.5 g, 71% yield). $^1$HNMR (400 MHz, CDCl$_3$): δ ppm 7.78 (d, J=8.0 Hz, 2H), 7.34-7.26 (m, 5H), 7.21 (d, J=8.0 Hz, 2H), 4.79 (br s, 1H), 4.69 (br s, 1H), 4.41 (d, J=11.6 Hz, 1H), 4.37 (d, J=11.6 Hz, 1H), 3.54-3.31 (m, 4H), 3.42 (s, 3H), 1.42 (s, 9H). LCMS (ES) (M+Na)=458.

1-(tert-butyl) 7-ethyl (S)-3-((benzyloxy)methyl)-6-bromo-2,3-dihydro-1H-imidazo[1,2-b]pyrazole-1,7-dicarboxylate (432)

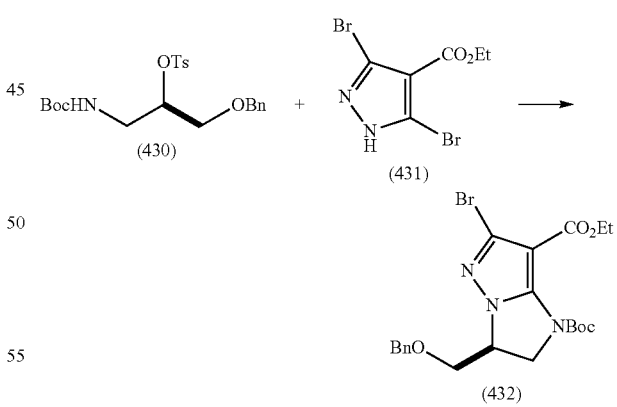

(R)-1-(benzyloxy)-3-((tert-butoxycarbonyl)amino)propan-2-yl 4-methylbenzenesulfonate (430) (5.47 g, 12.553 mmol) was mixed with ethyl 3,5-dibromo-1H-pyrazole-4-carboxylate (431) (3.4 g, 11.412 mmol) in DMF (68.0 ml). Cs$_2$CO$_3$ (4.46 g, 13.694 mmol) was added and the resulting suspension was stirred at 100° C. for 2 h until the complete consumption of (R)-1-(benzyloxy)-3-((tert-butoxycarbonyl)amino)propan-2-yl 4-methylbenzenesulfonate (430). The crude material was cooled to r.t. and filtered through a short cotton plot, rinsed with DMF (3×1 ml). To the filtrate was added Cs$_2$CO$_3$ (4.46 g, 13.694 mmol) and the resulting mixture was stirred at 120° C. for 1 h until complete conversion of intermediate to the desired product. The reaction mixture was then cooled to r.t., quenched with water (10 ml), extracted with EtOAc (2×100 ml). The organic layer was washed with water (20 ml), brine (20 ml), dried and concentrated and the residue was purified by flash chromatography to give compound 432 as colorless oil (1.9 g, 34.7% yield). $^1$HNMR (400 MHz, CDCl$_3$): δ ppm 7.40-7.23 (m, 5H), 4.60-4.57 (m, 1H), 4.51 (s, 2H), 4.47 (d, J=10.8 Hz, 2H), 4.35 (d, J=7.2 Hz, 2H), 3.83 (d, J=10.0 Hz, 1H), 3.78 (d, J=10.0 Hz, 1H), 1.51 (s, 9H), 1.39 (t, J=7.2 Hz, 3H). LCMS (ES) (M+Na)=502/504.

Ethyl (S)-3-((benzyloxy)methyl)-6-bromo-2,3-dihydro-1H-imidazo[1,2-b]pyrazole-7-carboxylate (433)

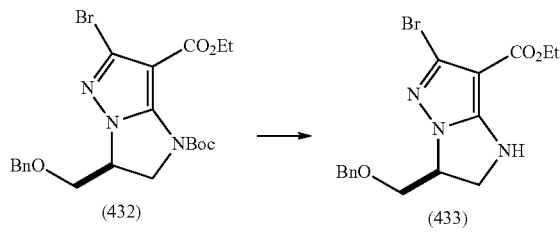 [SMILES: CCOC(=O)c1c(Br)nn2c1N(C(=O)OC(C)(C)C)C[C@H]2COCc1ccccc1 ; CCOC(=O)c1c(Br)nn2c1NC[C@H]2COCc1ccccc1]

(S)-1-tert-butyl 7-ethyl 3-((benzyloxy)methyl)-6-bromo-2,3-dihydro-1H-imidazo[1,2-b]pyrazole-1,7-dicarboxylate (432) (1.9 g, 3.955 mmol) was dissolved in DCM (9.50 ml), and then mixed with TFA (6.09 ml, 79.109 mmol). The mixture was stirred at r.t for 10 min. Upon completion of the reaction, the solvent was removed by evaporation and the residue was diluted with EtOAc (100 ml), washed with sat. aq. NaHCO$_3$ (10 ml). The aqueous layer was back extracted with EtOAc (2×30 ml). The combined organic layer was washed with brine (10 ml), dried and concentrated. The residue was purified by flash chromatography to give compound 433 as colorless oil (1.15 g, 76% yield). $^1$HNMR (400 MHz, CDCl$_3$): δ ppm 7.34-7.23 (m, 5H), 4.69 (m, 1H), 4.58-4.53 (m, 1H), 4.51 (s, 2H), 4.30-4.21 (m, 2H), 4.10 (t, J=9.6 Hz, 1H), 4.01 (dd, J=6.0, 9.2 Hz, 1H), 3.75 (dd, J=7.6, 10.0 Hz, 2H), 1.32 (t, J=6.8 Hz, 3H). LCMS (ES) (M+H)=380/382.

Ethyl (S)-3-((benzyloxy)methyl)-6-bromo-1-(3-(trifluoromethyl)benzyl)-2,3-dihydro-1H-imidazo[1,2-b]pyrazole-7-carboxylate (435)

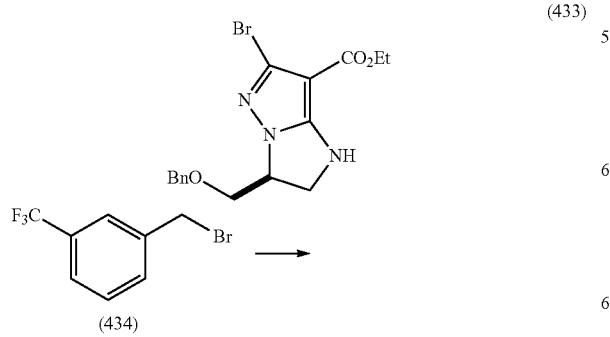

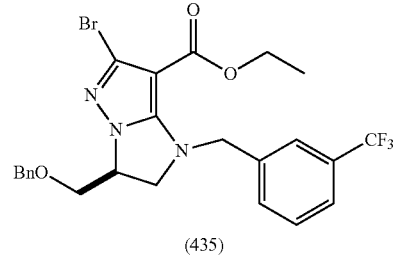

(S)-ethyl 3-((benzyloxy)methyl)-6-bromo-2,3-dihydro-1H-imidazo[1,2-b]pyrazole-7-carboxylate (433) (1.612 g, 4.239 mmol) was mixed with 3-Trifluoromethylbenzyl bromide (434) (0.777 ml, 5.087 mmol) in DMF (16 ml) and Cs$_2$CO$_3$ (4.14 g, 12.718 mmol) was added. The resulting suspension was stirred at 100° C. for 30 min until the reaction was complete. The reaction was quenched with sat. aq. NH$_4$Cl (10 mL), extracted with EtOAc (2×30 ml), washed with brine (5 mL). The organic layer was dried and concentrated and the residue was purified by flash chromatography to give compound 435 as colorless oil (2.22 g, 97% yield). $^1$HNMR (400 MHz, CDCl$_3$): δ ppm 7.57-7.20 (m, 9H), 4.97 (d, J=15.6 Hz, 1H), 4.89 (d, J=15.2 Hz, 1H), 4.48 (s, 2H), 4.51-4.47 (m, 1H), 4.26 (dd, J=6.8, 14.4 Hz, 2H), 3.83 (t, J=10.0 Hz, 1H), 3.77-3.68 (m, 3H), 1.26 (t, J=6.8 Hz, 3H). LCMS (ES) (M+H)=538/540.

Ethyl (S)-3-((benzyloxy)methyl)-6-(trifluoromethyl)-1-(3-(trifluoromethyl)benzyl)-2,3-dihydro-1H-imidazo[1,2-b]pyrazole-7-carboxylate (437)

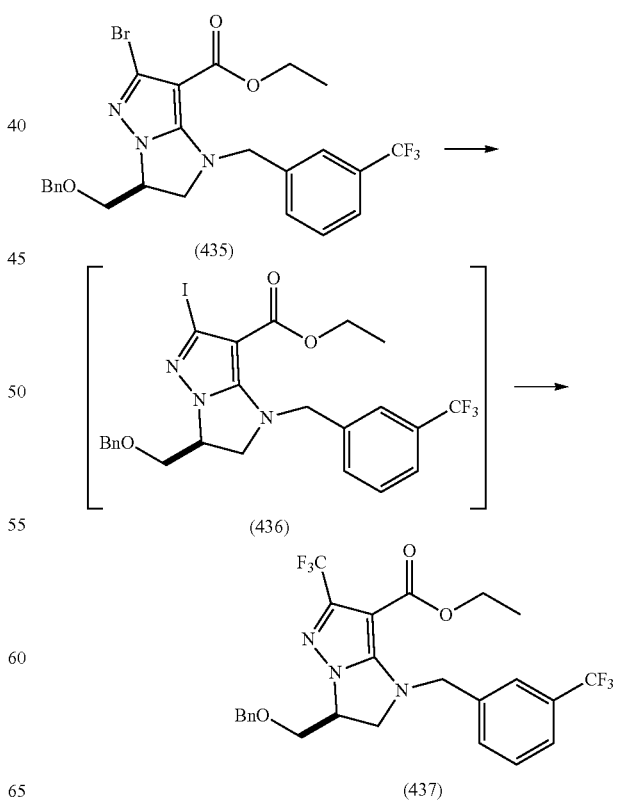

(S)-ethyl 3-((benzyloxy)methyl)-6-bromo-1-(3-(trifluoromethyl)benzyl)-2,3-dihydro-1H-imidazo[1,2-b]pyrazole-7-carboxylate (435) (2.22 g, 4.124 mmol) was dissolved in 1,4-DIOXANE (44.4 ml), NaI (1.545 g, 10.309 mmol), trans-1,2-Bis(methylamino)cyclohexane (0.130 ml, 0.825 mmol) and CuI (0.314 g, 1.649 mmol) were added under N₂. The mixture was stirred at 100° C. to allow iodination of bromide substrate. After 3 h, the reaction was quenched with water (10 mL), extracted with EtOAc (3×50 mL). The combined organic layers was washed with water (10 mL), dried over MgSO₄ and concentrated. The residue was purified by flash chromatography to give the iodinated intermediate (436), which was mixed with CuI (0.696 g, 3.656 mmol) in DMF (64.2 ml). 2,6-LUTIDINE (0.085 ml, 0.731 mmol) was added followed by the addition of Methyl fluorosulfonyldifluoroacetate (0.931 ml, 7.312 mmol). The resulting mixture was then stirred at 100° C. for 1 h until the full consumption of iodinated intermediate (436). The material was cooled to r.t., quenched with sat. aq. NaHCO₃ solution (20 ml), extracted with EtOAc (2×100 ml). The combined organic layers was washed with water (2×20 ml), brine (20 ml), dried over Na₂SO₄ and concentrated. The residue was purified by flash chromatography to give compound 437 as colorless oil (705 mg, 35% yield). ¹HNMR (400 MHz, CDCl₃): δ ppm 7.58-7.18 (m, 9H), 5.01 (d, J=15.2 Hz, 1H), 4.95 (d, J=15.2 Hz, 1H), 4.54 (br s, 1H), 4.49 (s, 2H), 4.26 (dd, J=7.2, 14.4 Hz, 2H), 3.90 (t, J=10.0 Hz, 1H), 3.81-3.76 (m, 2H), 3.70 (dd, J=3.6, 10.0 Hz, 1H), 1.29 (t, J=6.8 Hz, 3H). LCMS (ES) (M+H)=528.

Methyl 4-((S)-1-((S)-3-((benzyloxy)methyl)-6-(trifluoromethyl)-1-(3-(trifluoromethyl)benzyl)-2,3-dihydro-1H-imidazo[1,2-b]pyrazole-7-carboxamido)ethyl)benzoate (439)

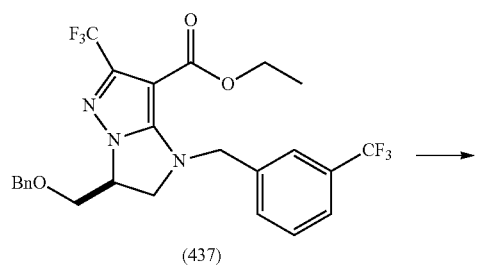

(437)

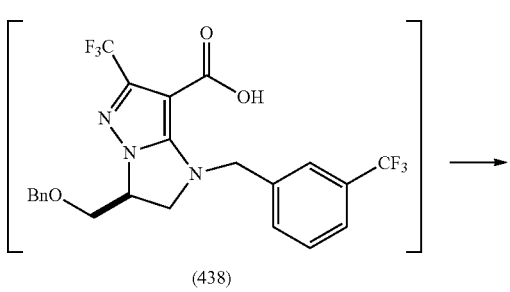

(438)

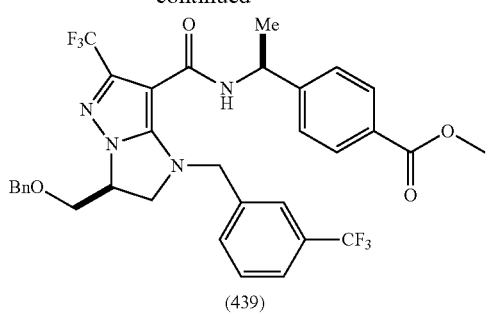

(439)

(S)-ethyl 3-((benzyloxy)methyl)-6-(trifluoromethyl)-1-(3-(trifluoromethyl)benzyl)-2,3-dihydro-1H-imidazo[1,2-b]pyrazole-7-carboxylate (437) (0.705 g, 1.337 mmol) was dissolved in t-Amyl alcohol (3.53 ml) and MeOH (7.05 ml) and mixed with 3N NaOH solution (4.46 ml, 13.366 mmol). The resulting solution was stirred at 90° C. for 1 h until the completion of the hydrolysis. The mixture was cooled to r.t., quenched with 10% HCl (4.87 ml, 16.039 mmol) until pH<4, extracted with EtOAc (2×50 ml). The combined organic layer was washed with water (5 mL), brine (5 mL), dried over Na₂SO₄ and concentrated. The residue was purified by flash chromatography to give the acid (438) (680 mg quantitative yield). The acid (438) was mixed with (S)-methyl 4-(1-aminoethyl)benzoate (216) (0.313 g, 1.744 mmol) in DMF (6.70 ml, 86.53 mmol) and treated with Et₃N (0.748 ml, 5.366 mmol) and HATU (0.765 g, 2.012 mmol). The resulting mixture was stirred at rt for overnight until the reaction was complete. The reaction was then quenched with sat. aq. NH₄Cl solution (10 ml), extracted with EtOAc (2×50 ml). The combined organic layers was washed with water (10 ml), brine (10 ml), dried over Na₂SO₄ and concentrated. The residue was purified by flash chromatography to give compound 439 as white solid (735 mg, 83% yield). ¹HNMR (400 MHz, CDCl₃): δ ppm 7.98 (d, J=8.4 Hz, 2H), 7.53 (d, J=5.6 Hz, 2H), 7.47-7.19 (m, 9H), 6.25 (d, J=4.8 Hz, 1H), 5.22 (t, J=6.8 Hz, 1H), 4.87 (d, J=14.8 Hz, 1H), 4.75 (d, J=15.6 Hz, 1H), 4.55-4.52 (m, 1H), 4.45 (s, 2H), 3.89 (s, 3H), 3.90-3.79 (m, 1H), 3.77-3.69 (m, 3H), 1.53 (d, J=6.8 Hz, 3H). LCMS (ES) (M+H)=661.

4-((S)-1-((S)-3-((benzyloxy)methyl)-6-(trifluoromethyl)-1-(3-(trifluoromethyl)benzyl)-2,3-dihydro-1H-imidazo[1,2-b]pyrazole-7-carboxamido)ethyl)benzoic acid (Compound 80)

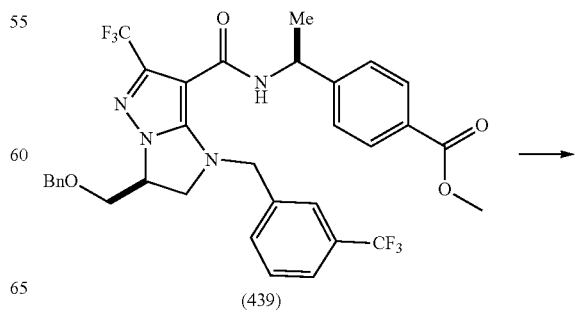

(439)

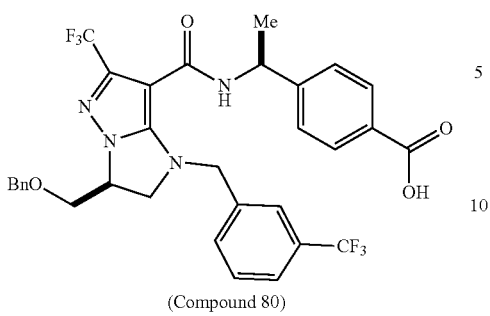

(Compound 80)

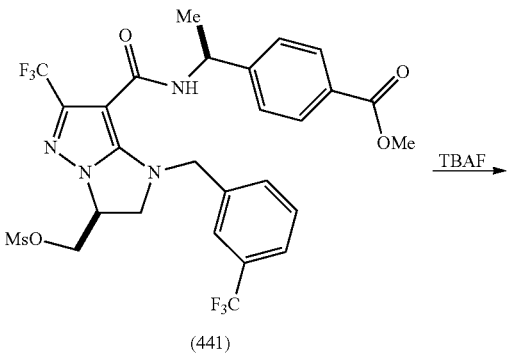

(441)

Following the same procedure for the preparation of (S)-4-(1-(1-(3-(hydroxymethyl)benzyl)-6-(trifluoromethyl)-2,3-dihydro-1H-imidazo[1,2-b]pyrazole-7-carboxamido)ethyl)benzoic acid (Compound 64), Compound 80 was prepared (9.8 mg, 66.8% yield) from methyl 4-((S)-1-((S)-3-((benzyloxy)methyl)-6-(trifluoromethyl)-1-(3-(trifluoromethyl)benzyl)-2,3-dihydro-1H-imidazo[1,2-b]pyrazole-7-carboxamido)ethyl)benzoate (439). $^1$HNMR (400 MHz, CDCl$_3$): δ ppm 8.04 (d, J=8.4 Hz, 2H), 7.54-7.18 (m, 11H), 6.27 (d, J=4.0 Hz, 1H), 5.24 (t, J=6.8 Hz, 1H), 4.88 (d, J=14.8 Hz, 1H), 4.75 (d, J=14.8 Hz, 1H), 4.56-4.53 (m, 1H), 4.48 (s, 2H), 3.88 (t, J=10.0 Hz, 1H), 3.79-3.69 (m, 3H), 1.54 (d, J=6.8 Hz, 3H). LCMS (ES) (M+H)=647.

Example LXXIX

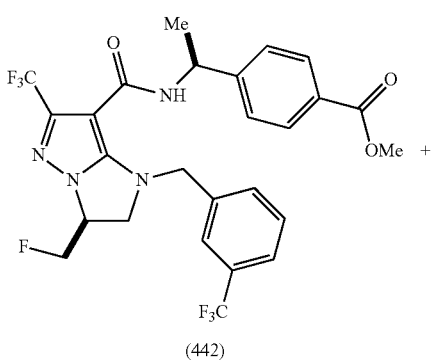

(442)

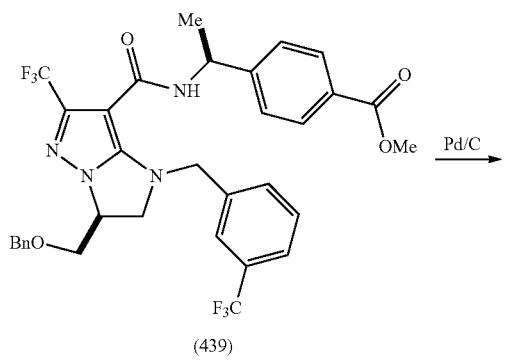

(439)

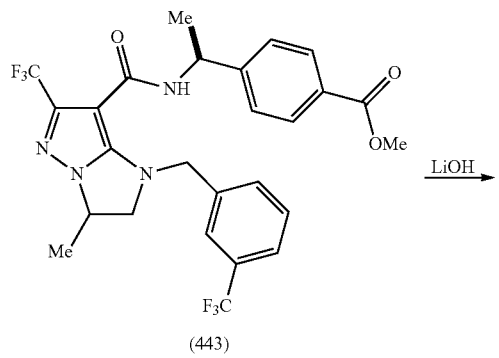

(443)

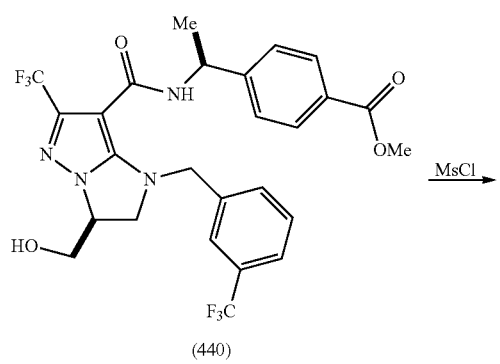

(440)

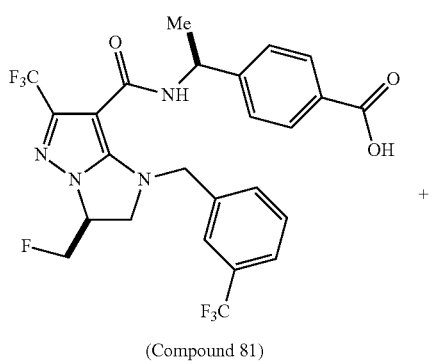

(Compound 81)

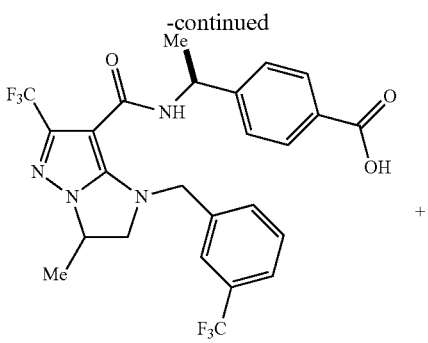

(Compound 82)

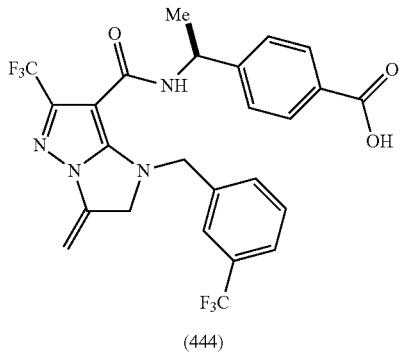

(444)

Methyl 4-((S)-1-((S)-3-(hydroxymethyl)-6-(trifluoromethyl)-1-(3-(trifluoromethyl)benzyl)-2,3-dihydro-1H-imidazo[1,2-b]pyrazole-7-carboxamido)ethyl)benzoate (440)

A solution of methyl 4-((S)-1-((S)-3-((benzyloxy)methyl)-6-(trifluoromethyl)-1-(3-(trifluoromethyl)benzyl)-2,3-dihydro-1H-imidazo[1,2-b]pyrazole-7-carboxamido)ethyl)benzoate (439) (16 mg, 24 µmol) in ethyl acetate (3 mL) was treated with 5% Pd—C (5.2 mg, 1.2 µmol) (Evonik E107 MA/W, 64% water) and stirred under hydrogen gas (balloon) for 17 h. Additional Pd—C (10.4 mg, 2.4 µmol) was added and stirring was continued under hydrogen gas for another 8 h. The mixture was filtered through celite pad and rinsed with ethyl acetate. The filtrate was concentrated in vacuo to give compound 440 (14 mg, quantitative). $^1$H NMR (400 MHz, CDCl$_3$): δ 7.98 (d, 2H), 7.4-7.6 (m, 4H), 7.30 (d, 2H), 6.27 (m, 1H), 5.21 (m, 1H), 4.96 (d, 1H), 4.66 (d, 1H), 4.50 (m, 1H), 4.04 (dd, 1H), 3.88 (s, 3H), 3.87 (dd, 1H), 3.76 (dd, 1H), 3.69 (dd, 1H), 1.52 (d, 3H). LCMS (ES) (M+H)=571.

Methyl 4-((S)-1-((S)-3-(((methylsulfonyl)oxy)methyl)-6-(trifluoromethyl)-1-(3-(trifluoromethyl)benzyl)-2,3-dihydro-1H-imidazo[1,2-b]pyrazole-7-carboxamido)ethyl)benzoate (441)

A solution of methyl 4-((S)-1-((S)-3-(hydroxymethyl)-6-(trifluoromethyl)-1-(3-(trifluoromethyl)benzyl)-2,3-dihydro-H-imidazo[1,2-b]pyrazole-7-carboxamido)ethyl)benzoate (440) (14 mg, 25 µmol) in THF (1 mL) was cooled to 0° C. and treated with MsCl (13 µL, 172 µmol) and Et$_3$N (68 µL, 491 µmol). The mixture was stirred at 0° C. for 30 min and quenched with water (1.4 mL). The mixture was extracted three times with ethyl acetate (1.4 mL). The organic layers were combined, dried over MgSO$_4$ and concentration in vacuo to give compound 441. The product was used for the next step without further purification. $^1$H NMR (400 MHz, CDCl$_3$): δ 7.96 (d, 2H), 7.4-7.6 (m, 4H), 7.36 (d, 2H), 6.28 (m, 1H), 5.20 (m, 1H), 4.90 (d, J=14.8 Hz, 1H), 4.76 (d, J=14.8 Hz, 1H), 4.69 (m, 1H), 4.49 (dd, J=4.0, 11.2 Hz, 1H), 4.40 (dd, J=4.0, 11.2 Hz, 1H), 3.96 (dd, J=9.6, 10.0 Hz, 1H), 3.87 (s, 3H), 3.72 (dd, J=6.4, 10.0 Hz, 1H), 2.93 (s, 3H), 1.51 (d, J=6.8 Hz, 3H). LCMS (ES) (M+H)=649.

Methyl 4-((S)-1-((S)-3-(fluoromethyl)-6-(trifluoromethyl)-1-(3-(trifluoromethyl)benzyl)-2,3-dihydro-1H-imidazo[1,2-b]pyrazole-7-carboxamido)ethyl)benzoate (442)

The above product (441) was dissolved in t-Amyl alcohol (1 mL) and treated with 1M TBAF in THF (74 µL, 74 µmol). The mixture was heated to 60° C. for 30 min and 80° C. for 30 min. Additional 1M TBAF in THF (49 µL, 49 µmol) was added and stirring was continued at 80° C. for another 30 min. After cooling to rt, the mixture was treated with water (1.4 mL) and extracted three times with MTBE (1.4 mL). The organic layers were combined, dried over MgSO$_4$ and concentrated in vacuo to give compound 442 as a mixture with methyl (S)-4-(1-(3-methyl-6-(trifluoromethyl)-1-(3-(trifluoromethyl)benzyl)-1H-imidazo[1,2-b]pyrazole-7-carboxamido)ethyl)benzoate (443). $^1$H NMR (400 MHz, CDCl$_3$): δ 7.98 (d, 2H), 7.4-7.6 (m, 4H), 7.37 (d, 2H), 6.28 (m, 1H), 5.22 (m, 1H), 4.95 (d, J=14.8 Hz, 1H), 4.82 (ddd, J=3.6, 10.4, 47.6 Hz, 1H), 4.72 (d, J=14.8 Hz, 1H), 4.60 (m, 1H), 4.55 (ddd, J=2.8, 10.4, 47.6 Hz, 1H), 3.95 (t, J=9.2 Hz, 1H), 3.90 (s, 3H), 3.76 (dd, J=5.6, 9.6 Hz, 1H), 1.53 (d, J=6.8 Hz, 3H). LCMS (ES) (M+H)=573.

4-((S)-1-((S)-3-(fluoromethyl)-6-(trifluoromethyl)-1-(3-(trifluoromethyl)benzyl)-2,3-dihydro-1H-imidazo[1,2-b]pyrazole-7-carboxamido)ethyl)benzoic acid (Compound 81) and (S)-4-(1-(3-methyl-6-(trifluoromethyl)-1-(3-(trifluoromethyl)benzyl)-1H-imidazo[1,2-b]pyrazole-7-carboxamido)ethyl)benzoic acid (Compound 82)

The above mixture comprising compounds 442 and 443 was dissolved in a mixture of THF (1 mL), methanol (1 mL) and water (1 mL), treated with LiOH—H$_2$O (5.1 mg, 122 µmol), and stirred at rt for 17 h. Additional LiOH—H$_2$O (5.1 mg, 122 µmol) was added and stirring was continued at rt for another 22 h. The reaction mixture was acidified with 1 N HCl (245 µL, 245 µmol) and extracted three times with ethyl acetate (2.8 mL). The organic layers were combined, dried over MgSO$_4$ and concentrated in vacuo. The residue was purified by prep. HPLC to give compound 81 (4.1 mg, 30%) and a 2:1 mixture of (S)-4-(1-(3-methyl-6-(trifluoromethyl)-1-(3-(trifluoromethyl)benzyl)-1H-imidazo[1,2-b]pyrazole-7-carboxamido)ethyl)benzoic acid (Compound 82) and (S)-4-(1-(3-methylene-6-(trifluoromethyl)-1-(3-(trifluoromethyl)benzyl)-2,3-dihydro-1H-imidazo[1,2-b]pyrazole-7-carboxamido)ethyl)benzoic acid (444) (2.4 mg, 18%).

Compound 81: $^1$H NMR (400 MHz, CDCl$_3$): δ 8.01 (d, 2H), 7.4-7.6 (m, 4H), 7.39 (d, 2H), 6.27 (m, 1H), 5.22 (m, 1H), 4.95 (d, J=14.8 Hz, 1H), 4.85 (ddd, J=3.6, 10.4, 47.2 Hz, 1H), 4.85 (ddd, J=2.8, 10.4, 47.2 Hz, 1H), 4.72 (d, J=14.8 Hz, 1H), 4.60 (m, 1H), 3.95 (t, J=10.0 Hz, 1H), 3.75 (dd, J=7.2, 10.0 Hz, 1H), 1.53 (d, J=6.4 Hz, 3H). LCMS (ES) (M+H)=559.

A mixture of (S)-4-(1-(3-methyl-6-(trifluoromethyl)-1-(3-(trifluoromethyl)benzyl)-1H-imidazo[1,2-b]pyrazole-7-carboxamido)ethyl)benzoic acid (Compound 82) and (S)-4-(1-

177

(3-methylene-6-(trifluoromethyl)-1-(3-(trifluoromethyl)benzyl)-2,3-dihydro-1H-imidazo[12-b]pyrazole-7-carboxamido)ethyl)benzoic acid (444): ¹H NMR (400 MHz, CDCl₃): δ 8.04 (d, 2H), 7.41 (d, 2H), 7.3-7.6 (m, 4H), 6.59 (d, J=1.6 Hz, 0.7H), 6.39 (m, 0.7H), 6.29 (m, 0.3H), 5.66 (d, J=14.4 Hz, 0.7H), 5.58 (d, J=14.4 Hz, 0.7H), 5.23 (m, 1.3H), 4.94 (d, J=14.4 Hz, 0.3H), 4.88 (d, J=14.4 Hz, 0.3H), 4.59 (m, 0.3H), 4.39 (m, 0.6H), 1.54 (d, J=6.4 Hz, 2.1H). LCMS (ES) (M+H)=539.

Example LXXX 4-((S)-1-((S)-3-(hydroxymethyl)-6-(trifluoromethyl)-1-(3-(trifluoromethyl)benzyl)-2,3-dihydro-1H-imidazo[1,2-b]pyrazole-7-carboxamido)ethyl)benzoic acid (Compound 83)

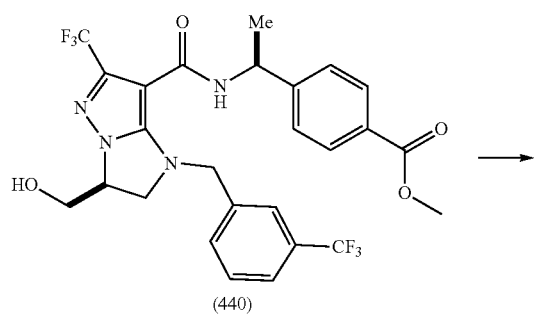

(440)

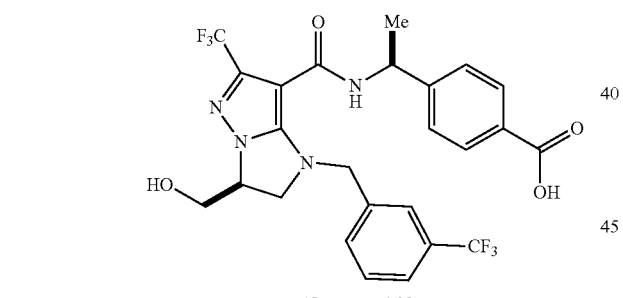

(Compound 83)

Following the same procedure for the preparation of (S)-4-(1-(1-(3-(hydroxymethyl)benzyl)-6-(trifluoromethyl)-2,3-dihydro-1H-imidazo[1,2-b]pyrazole-7-carboxamido)ethyl)benzoic acid (Compound 64), Compound 83 was prepared (13.3 mg, 87% yield) from methyl 4-((S)-1-((S)-3-(hydroxymethyl)-6-(trifluoromethyl)-1-(3-(trifluoromethyl)benzyl)-2,3-dihydro-1H-imidazo[1,2-b]pyrazole-7-carboxamido)ethyl)benzoate (440). ¹HNMR (400 MHz, CDCl₃): δ ppm 8.03 (d, J=8.0 Hz, 2H), 7.54-7.39 (m, 6H), 6.30 (d, J=4.4 Hz, 1H), 5.23 (t, J=7.2 Hz, 1H), 4.98 (d, J=15.2 Hz, 1H), 4.68 (d, J=14.8 Hz, 1H), 4.53-4.50 (m, 1H), 4.06 (dd, J=3.6, 12.4 Hz, 1H), 3.89 (t, J=10.0 Hz, 1H), 3.78 (dd, J=4.0, 12.0 Hz, 1H), 3.70 (dd, J=7.2, 9.6 Hz, 1H), 1.54 (d, J=7.2 Hz, 3H). LCMS (ES) (M+H)=557.

178

Example LXXXI (S)-4-(1-(1-(3-fluoro-5-(trifluoromethyl)benzyl)-6-(trifluoromethyl)-2,3-dihydro-1H-imidazo[1,2-b]pyrazole-7-carboxamido)ethyl)benzoic acid (Compound 84)

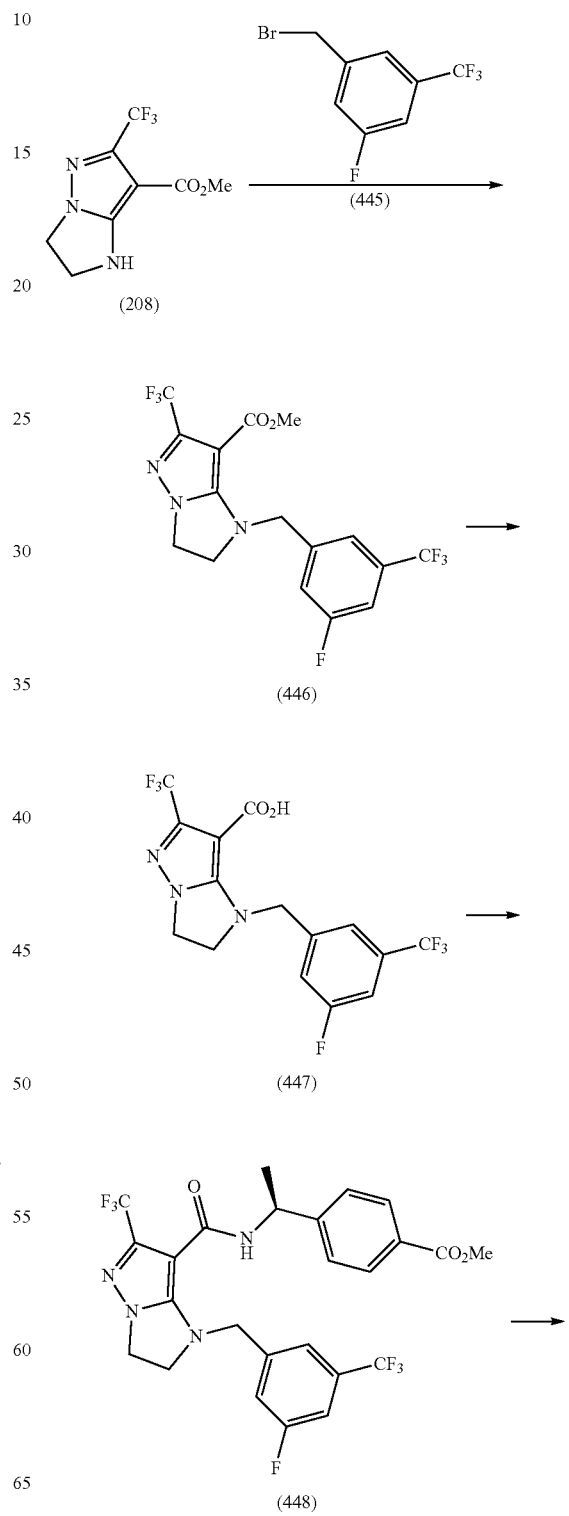

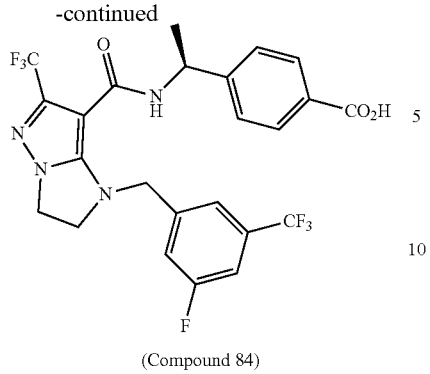

(Compound 84)

Following the similar procedure for the preparation of (S)-4-(1-(6-(trifluoromethyl)-1-(3-(trifluoromethyl)benzyl)-2,3-dihydro-1H-imidazo[1,2-b]pyrazole-7-carboxamido)ethyl)benzoic acid (Compound 1) from methyl 6-(trifluoromethyl)-2,3-dihydro-1H-imidazo[1,2-b]pyrazole-7-carboxylate (208) and 1-(chloromethyl)-3-(trifluoromethyl)benzene (214) described earlier, Compound 84 was similarly prepared from methyl 6-(trifluoromethyl)-2,3-dihydro-1H-imidazo[1,2-b]pyrazole-7-carboxylate (208) and 1-(bromomethyl)-3-fluoro-5-(trifluoromethyl)benzene (445).

Methyl 1-(3-fluoro-5-(trifluoromethyl)benzyl)-6-(trifluoromethyl)-2,3-dihydro-1H-imidazo[1,2-b]pyrazole-7-carboxylate (446)

$^1$HNMR (400 MHz): δ ppm 7.40 (s, 1H), 7.30 (s, 1H), 7.28 (s, 1H), 5.00 (s, 2H), 4.23 (t, J=8.8 Hz, 2H), 3.83 (t, J=8.8 Hz, 2H), 3.81 (s, 3H). LCMS (ES) (M+H)=412.

1-(3-fluoro-5-(trifluoromethyl)benzyl)-6-(trifluoromethyl)-2,3-dihydro-1H-imidazo[1,2-b]pyrazole-7-carboxylic acid (447)

LCMS (ES) (M+H)=398.

Methyl (S)-4-(1-(1-(3-fluoro-5-(trifluoromethyl)benzyl)-6-(trifluoromethyl)-2,3-dihydro-1H-imidazo[1,2-b]pyrazole-7-carboxamido)ethyl)benzoate (448)

$^1$HNMR (400 MHz): δ ppm 7.99 (d, J=8.4 Hz, 2H), 7.38 (d, J=8.4 Hz, 2H), 7.34 (s, 1H), 7.26 (s, 1H), 7.24 (s, 1H), 6.29 (bs, 1H), 5.21 (m, 1H), 4.86 (d, J=15.3 Hz, 1H), 4.81 (d, J=15.0 Hz, 1H), 4.20 (t, J=8.4 Hz, 2H), 3.90 (s, 3H), 3.79 (t, J=8.4 Hz, 2H), 1.53 (d, J=8.0 Hz, 3H). LCMS (ES) (M+H)=559.

(S)-4-(1-(1-(3-fluoro-5-(trifluoromethyl)benzyl)-6-(trifluoromethyl)-2,3-dihydro-1H-imidazo[1,2-b]pyrazole-7-carboxamido)ethyl)benzoic acid (Compound 84)

$^1$HNMR (400 MHz, CD$_3$OD): δ ppm 7.83 (d, J=8.2 Hz, 2H), 7.44 (s, 1H), 7.37 (d, J=8.2 Hz, 2H), 7.33 (s, 1H), 7.30 (s, 1H), 5.12 (m, 1H), 4.44 (d, J=15.4 Hz, 1H), 4.34 (d, J=15.4 Hz, 1H), 4.22 (m, 2H), 3.79 (m, 2H), 1.46 (d, J=7.0 Hz, 3H). LCMS (ES) (M+H)=545.

Example LXXXII (S)-4-(1-(1-(3-bromo-5-(trifluoromethyl)benzyl)-6-(trifluoromethyl)-2,3-dihydro-1H-imidazo[1,2-b]pyrazole-7-carboxamido)ethyl)benzoic acid (Compound 85)

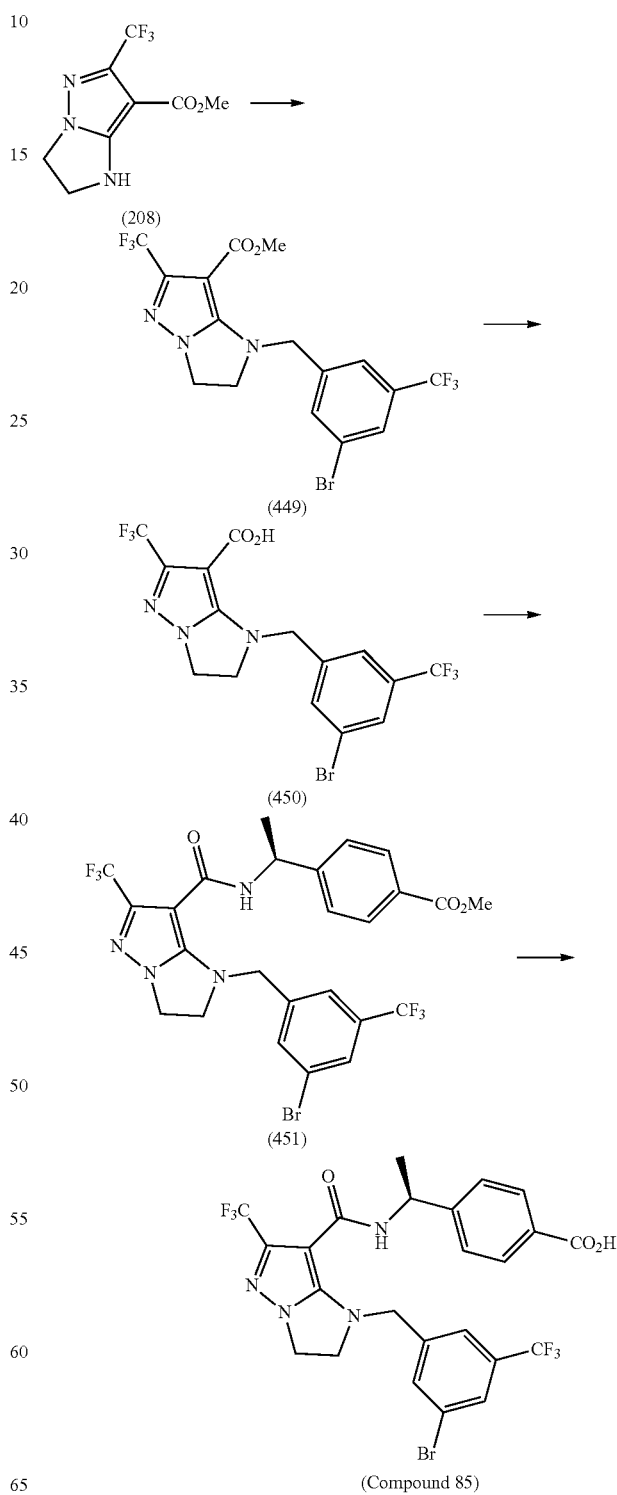

(Compound 85)

Following the similar procedure for the preparation of (S)-4-(1-(6-(trifluoromethyl)-1-(3-(trifluoromethyl)benzyl)-2,3-dihydro-1H-imidazo[1,2-b]pyrazole-7-carboxamido)ethyl)benzoic acid (Compound 1) from methyl 6-(trifluoromethyl)-2,3-dihydro-1H-imidazo[1,2-b]pyrazole-7-carboxylate (208) and 1-(chloromethyl)-3-(trifluoromethyl)benzene (214) described earlier, Compound 85 was similarly prepared from methyl 6-(trifluoromethyl)-2,3-dihydro-1H-imidazo[1,2-b]pyrazole-7-carboxylate (208) and 1-bromo-3-(bromomethyl)-5-(trifluoromethyl)benzene.

Methyl 1-(3-bromo-5-(trifluoromethyl)benzyl)-6-(trifluoromethyl)-2,3-dihydro-1H-imidazo[1,2-b]pyrazole-7-carboxylate (449)

$^1$HNMR (400 MHz): δ ppm 7.72 (s, 1H), 7.71 (s, 1H), 7.54 (s, 1H), 4.98 (s, 2H), 4.24 (dd, J=8.2 and 9.0 Hz, 2H), 3.82 (dd, J=8.2 and 9.0 Hz, 2H), 3.81 (s, 3H). LCMS (ES) (M+H)=472/474.

1-(3-bromo-5-(trifluoromethyl)benzyl)-6-(trifluoromethyl)-2,3-dihydro-1H-imidazo[1,2-b]pyrazole-7-carboxylic acid (450)

$^1$HNMR (400 MHz): δ ppm 7.71 (s, 1H), 7.68 (s, 1H), 7.52 (s, 1H), 4.95 (s, 2H), 4.24 (dd, J=8.2 and 9.0 Hz, 2H), 3.83 (dd, J=8.2 and 9.0 Hz, 2H). LCMS (ES) (M+H)=458/460.

Methyl (S)-4-(1-(1-(3-bromo-5-(trifluoromethyl)benzyl)-6-(trifluoromethyl)-2,3-dihydro-1H-imidazo[1,2-b]pyrazole-7-carboxamido)ethyl)benzoate (451)

$^1$HNMR (400 MHz): δ ppm 8.00 (d, J=8.4 Hz, 2H), 7.69 (s, 1), 7.67 (s, 1H), 7.49 (s, 1H), 7.38 (d, J=8.4 Hz, 2H), 6.29 (bs, 1H), 5.21 (m, 1H), 4.90 (d, J=15.0 Hz, 1H), 4.78 (d, J=15.0 Hz, 1H), 4.21 (dd, J=8.3 and 8.6 Hz, 2H), 3.90 (s, 3H), 3.78 (dd, J=8.3 and 8.6 Hz, 2H), 1.53 (d, J=8.0 Hz, 3H). LCMS (ES) (M+H)=619/621.

(S)-4-(1-(1-(3-bromo-5-(trifluoromethyl)benzyl)-6-(trifluoromethyl)-2,3-dihydro-1H-imidazo[1,2-b]pyrazole-7-carboxamido)ethyl)benzoic acid (Compound 85)

$^1$HNMR (400 MHz, CD$_3$OD): δ ppm 7.82 (d, J=8.4 Hz, 2H), 7.73 (s, 2H), 7.58 (s, 1H), 7.37 (d, J=8.4 Hz, 2H), 5.11 (m, 1H), 4.42 (d, J=15.6 Hz, 1H), 4.32 (d, J=15.6 Hz, 1H), 4.22 (m, 2H), 3.80 (m, 2H), 1.46 (d, J=7.0 Hz, 3H). LCMS (ES) (M+H)=605/607.

Example LXXXIII

Methyl (S)-4-(1-(1-(4-(benzyloxy)benzyl)-6-(trifluoromethyl)-2,3-dihydro-1H-imidazo[1,2-b]pyrazole-7-carboxamido)ethyl)benzoate (452)

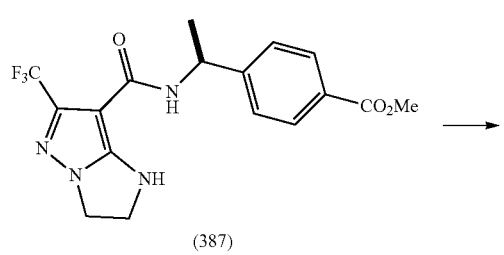

(387)

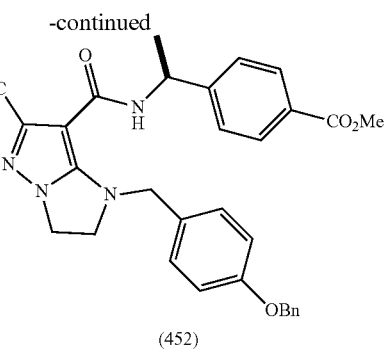

(452)

To a solution of methyl (S)-4-(1-(6-(trifluoromethyl)-2,3-dihydro-1H-imidazo[1,2-b]pyrazole-7-carboxamido)ethyl)benzoate (387) (82.0 mg, 0.214 mmol) and 1-(benzyloxy)-4-(bromomethyl)-benzene (71.3 mg, 0.257 mmol) in DMF (0.83 mL) was added cesium carbonate (210 mg, 0.643 mmol) and the suspension was stirred at rt for 3.0 h. LCMS showed only desired peak of [M+H]=579.3. The reaction was concentrated in vacuo to remove organic solvents. The white solid was purified by silica gel chromatography (10% to 70% E/H and then 70% isocratic E/H) to give compound 452 as a white solid (86.6 mg, 70% yield). $^1$HNMR (400 MHz): δ ppm 8.00 (d, J=8.2 Hz, 2H), 7.43-7.32 (m, 7H), 7.14 (d, J=8.6 Hz, 2H), 6.88 (d, J=8.6 Hz, 2H), 6.25 (bm, 1H), 5.26 (dq, J=7.0 Hz, 1H), 5.03 (s, 2H), 4.66 (dd, J=14.5, 14.5 Hz, 2H), 4.10 (dd, J=8.2, 8.2 Hz, 2H), 3.83 (s, 3H), 3.74 (dd, J=8.6, 8.6 Hz, 2H), 1.54 (d, J=7.0 Hz, 3H). LCMS (ES) (M+H)=579.3.

Methyl (S)-4-(1-(1-(4-hydroxybenzyl)-6-(trifluoromethyl)-2,3-dihydro-1H-imidazo[1,2-b]pyrazole-7-carboxamido)ethyl)benzoate (453)

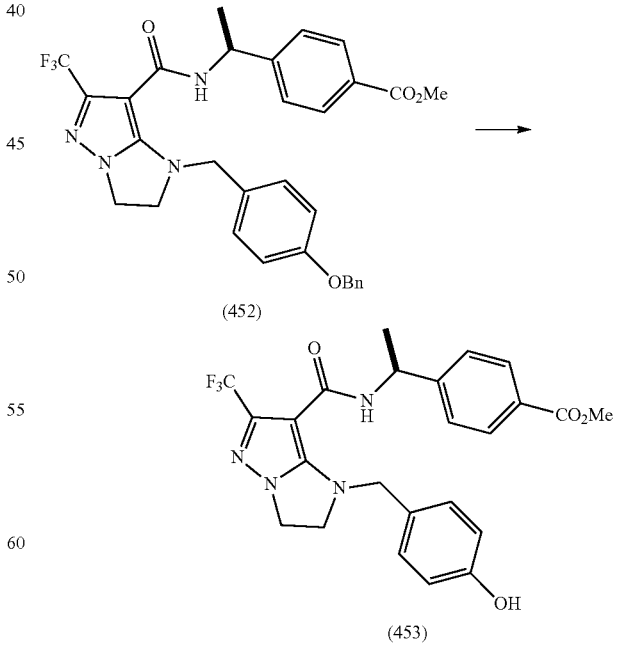

methyl (S)-4-(1-(1-(4-(benzyloxy)benzyl)-6-(trifluoromethyl)-2,3-dihydro-1H-imidazo[1,2-b]pyrazole-7-carboxamido)ethyl)benzoate (452) (800 mg, 1.38 mmol) was dissolved in EtOAc (18 mL) and methanol (15 mL), 10% Pd/Carbon was added under N$_2$. H$_2$ gas was then purged for 15 min and the mixture was stirred under H$_2$ atmosphere for 3.0 h. LCMS showed only desired peak of [M+H]=489.3. The reaction was filtered thru celite and eluted with EtOAc and concentrated to remove organic solvents. The white solid was purified by silica gel chromatography (20% to 80% E/H and then 80% isocratic E/H) to give desired product (453) as a white solid (500 mg, 74% yield). $^1$HNMR (400 MHz): δ ppm 7.98 (d, J=8.4 Hz, 2H), 7.39 (d, J=8.0 Hz, 2H), 7.00 (d, J=8.4 Hz, 2H), 6.67 (d, J=8.4 Hz, 2H), 6.30 (bm, 1H), 5.23 (dq, J=6.8, 6.8 Hz, 1H), 4.65 (d, J=14.8 Hz, 1H), 4.50 (d, J=14.8 Hz, 1H), 4.10 (dd, J=8.8, 8.8 Hz, 2H), 3.89 (s, 3H), 3.72 (dd, J=9.2, 7.6 Hz, 2H), 1.54 (d, J=7.2 Hz, 3H). LCMS (ES) (M+H)=489.36.

(S)-4-(1-(1-(4-hydroxybenzyl)-6-(trifluoromethyl)-2, 3-dihydro-1H-imidazo[1,2-b]pyrazole-7-carboxamido)ethyl)benzoic acid (Compound 86)

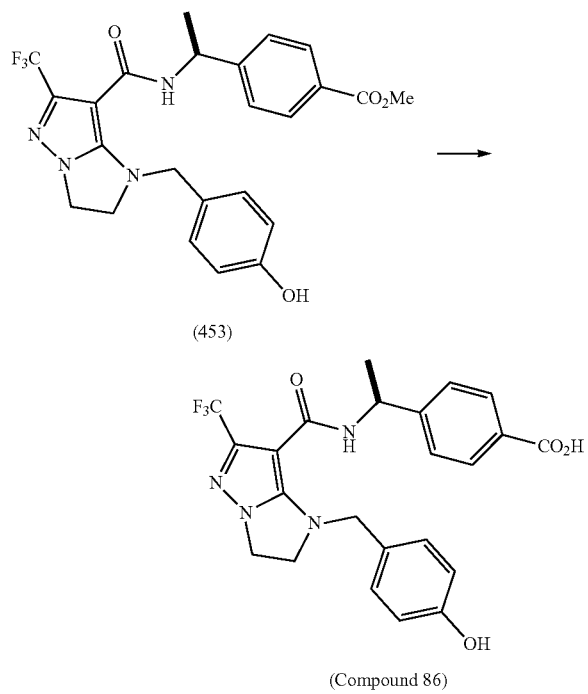

(453)

(Compound 86)

Following the same procedure for the preparation of (S)-4-(1-(1-(3-(hydroxymethyl)benzyl)-6-(trifluoromethyl)-2,3-dihydro-1H-imidazo[1,2-b]pyrazole-7-carboxamido) ethyl)benzoic acid (Compound 64) using the reactant shown in the scheme above, Compound 86 was prepared (22.0 mg, 60% yield) from Methyl (S)-4-(1-(1-(4-hydroxybenzyl)-6-(trifluoromethyl)-2,3-dihydro-1H-imidazo[1,2-b]pyrazole-7-carboxamido)ethyl)benzoate (453). $^1$HNMR (400 MHz): δ ppm 8.02 (d, J=8.0 Hz, 2H), 7.42 (d, J=8.4 Hz, 2H), 7.04 (d, J=8.8 Hz, 2H), 6.70 (d, J=8.4 Hz, 2H), 6.28 (bm, 1H), 5.25 (dq, J=8.8, 8.8 Hz, 1H), 4.71 (d, J=14.4 Hz, 1H), 4.52 (d, J=14.4 Hz, 1H), 4.12 (dd, J=8.8, 8.8 Hz, 2H), 3.75 (app dt, J=7.6, 1.6 Hz, 2H), 1.54 (d, J=7.2 Hz, 3H). LCMS (ES) (M+H)=475.3.

Example LXXXIV

Methyl (R)-4-(2-hydroxy-1-(6-(trifluoromethyl)-1-(3-(trifluoromethyl)benzyl)-2,3-dihydro-1H-imidazo [1,2-b]pyrazole-7-carboxamido)ethyl)benzoate (455)

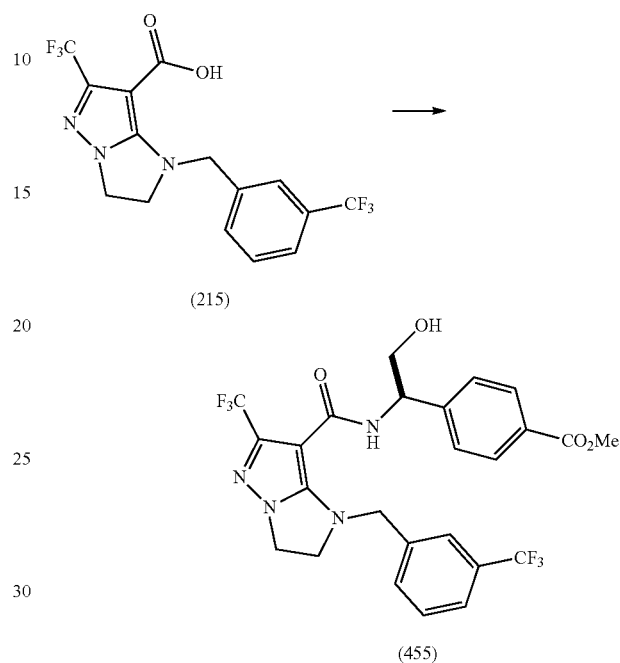

(215)

(455)

Following the same procedure for the preparation of Methyl (S)-4-(1-(6-(trifluoromethyl)-1-(3-(trifluoromethyl) benzyl)-2,3-dihydro-1H-imidazo[1,2-b]pyrazole-7-carboxamido)ethyl)benzoate (217) using the reactant shown above, compound 455 was prepared as a white solid (57.0 mg, 86% yield) from 6-(trifluoromethyl)-1-(3-(trifluoromethyl)benzyl)-2,3-dihydro-1H-imidazo[1,2-b]pyrazole-7-carboxylic acid (215). $^1$HNMR (400 MHz): δ ppm 8.01 (d, J=8.4 Hz, 2H), 7.56-7.39 (m, 6H), 6.86 (bm, 1H), 5.24-5.20 (bm, 1H), 4.84 (s, 2H), 4.19 (dd, J=8.4, 8.4 Hz, 2H), 3.99-3.90 (m, 2H), 3.90 (s, 3H), 3.77 (dd, J=8.4, 8.4 Hz, 2H). LCMS (ES) (M+H)=557.3.

(R)-4-(2-hydroxy-1-(6-(trifluoromethyl)-1-(3-(trifluoromethyl)benzyl)-2,3-dihydro-1H-imidazo[1,2-b] pyrazole-7-carboxamido)ethyl)benzoic acid (Compound 87)

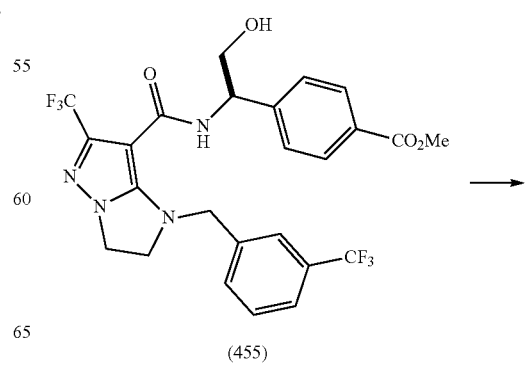

(455)

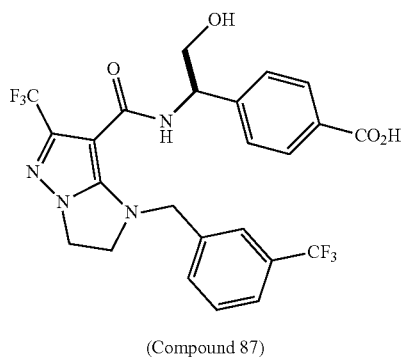

(Compound 87)

Following the same procedure for the preparation of (S)-4-(1-(1-(3-(hydroxymethyl)benzyl)-6-(trifluoromethyl)-2,3-dihydro-1H-imidazo[1,2-b]pyrazole-7-carboxamido)ethyl)benzoic acid (Compound 64) using the reactant shown above, Compound 87 was prepared as a white solid (11.5 mg, 37% yield) from methyl (R)-4-(2-hydroxy-1-(6-(trifluoromethyl)-1-(3-(trifluoromethyl)benzyl)-2,3-dihydro-1H-imidazo[1,2-b]pyrazole-7-carboxamido)ethyl)benzoate (455). $^1$HNMR (400 MHz): δ ppm 8.05 (d, J=8.4 Hz, 2H), 7.56-7.42 (m, 6H), 6.90 (bm, 1H), 5.26-5.22 (bm, 1H), 4.84 (s, 2H), 4.18 (dd, J=8.0, 8.0 Hz, 2H), 3.95 (ddd, J=26.8, 11.1, 4.0 Hz, 2H), 3.77 (dd, J=8.8, 8.8 Hz, 2H). LCMS (ES) (M+H)=543.3.

Example LXXXV

Methyl (S)-4-(1-(1-(4-(dimethylamino)benzyl)-6-(trifluoromethyl)-2,3-dihydro-1H-imidazo[1,2-b]pyrazole-7-carboxamido)ethyl)benzoate (456)

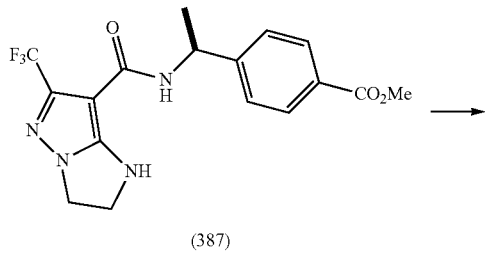

(387)

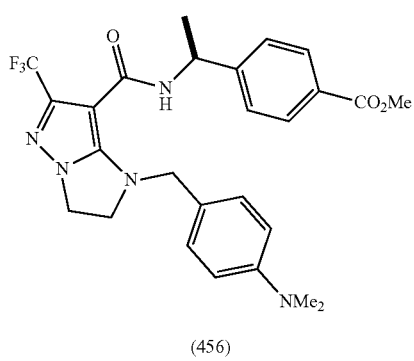

(456)

Following the same procedure for the preparation of methyl (S)-4-(1-(6-(trifluoromethyl)-1-(3-(trifluoromethyl)benzyl)-2,3-dihydro-1H-imidazo[1,2-b]pyrazole-7-carboxamido)ethyl)benzoate (217) using the reactant shown above, compound 456 was prepared as a white solid (103.0 mg, 76% yield) from methyl (S)-4-(1-(6-(trifluoromethyl)-2,3-dihydro-1H-imidazo[1,2-b]pyrazole-7-carboxamido)ethyl)benzoate (387). $^1$HNMR (400 MHz): δ ppm 8.00 (d, J=8.4 Hz, 2H), 7.42 (d, J=8.4 Hz, 2H), 7.0 (bm, 2H), 6.62 (bm, 2H), 6.26 (bm, 1H), 5.28 (dq, J=8.8 Hz, 1H), 4.66 (d, J=13.6 Hz, 1H), 5.55 (d, J=15.2 Hz, 1H), 4.09 (dd, J=8.0, 8.0 Hz, 2H), 3.89 (s, 3H), 3.75 (dd, J=8.8, 8.8 Hz, 2H), 2.93 (s, 6H), 1.55 (d, J=7.2 Hz, 3H). LCMS (ES) (M+H)=516.1.

(S)-4-(1-(1-(4-(dimethylamino)benzyl)-6-(trifluoromethyl)-2,3-dihydro-1H-imidazo[1,2-b]pyrazole-7-carboxamido)ethyl)benzoic acid (Compound 88)

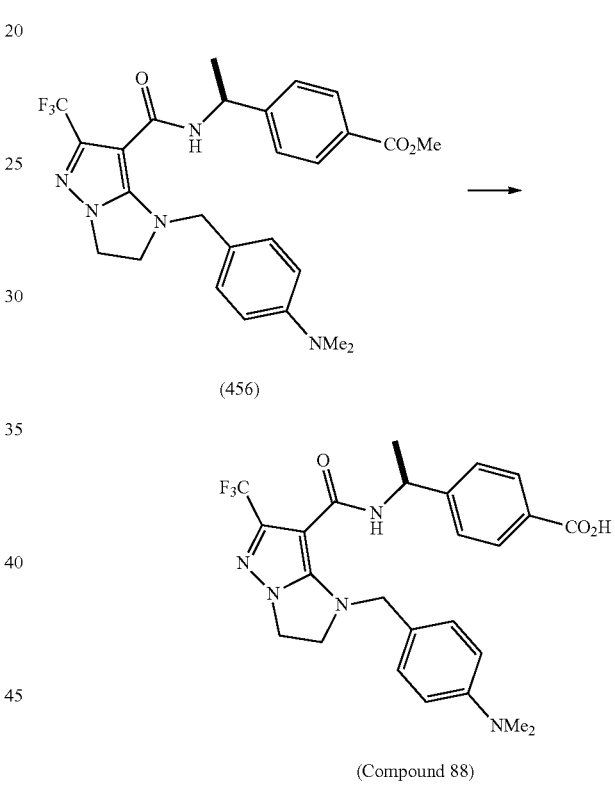

(456)

(Compound 88)

Following the same procedure for the preparation of (S)-4-(1-(1-(3-(hydroxymethyl)benzyl)-6-(trifluoromethyl)-2,3-dihydro-1H-imidazo[1,2-b]pyrazole-7-carboxamido)ethyl)benzoic acid (Compound 64) using the reactant shown above, (Compound 88) was prepared as a white solid (15.0 mg, 38% yield) from methyl (S)-4-(1-(1-(4-(dimethylamino)benzyl)-6-(trifluoromethyl)-2,3-dihydro-1H-imidazo[1,2-b]pyrazole-7-carboxamido)ethyl)benzoate (456). $^1$HNMR (400 MHz): δ ppm 8.06 (d, J=8.0 Hz, 2H), 7.45 (d, J=8.0 Hz, 2H), 7.06 (d, J=14.4 Hz, 1H), 6.65 (bd, J=7.2 Hz, 2H), 6.26 (bm, 1H), 5.29 (dq, J=6.8 Hz, 1H), 4.66 (d, J=14.4 Hz, 1H), 4.52 (d, J=14.4 Hz, 1H), 4.09 (dd, J=8.4, 8.4 Hz, 2H), 3.76 (app dt, J=7.6, 1.2 Hz, 2H), 2.93 (s, 6H), 1.55 (d, J=6.8 Hz, 3H). LCMS (ES) (M+H)=502.7.

Example LXXXVI

Methyl (S)-4-(1-(1-(3-(dimethylamino)benzyl)-6-(trifluoromethyl)-2,3-dihydro-1H-imidazo[1,2-b]pyrazole-7-carboxamido)ethyl)benzoate (457)

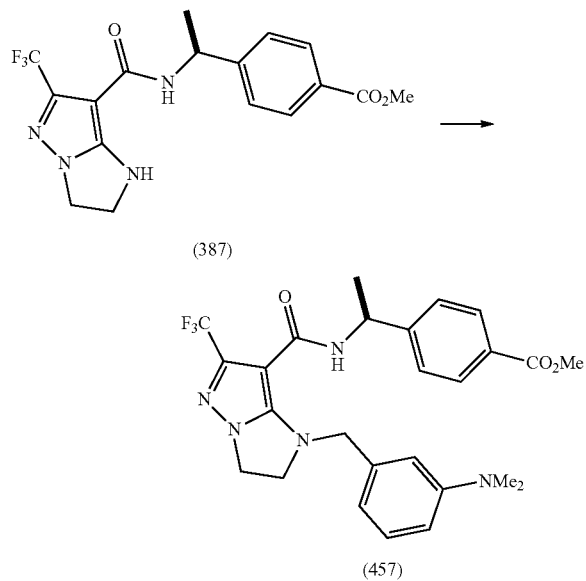

Following the same procedure for the preparation of (S)-methyl 4-(1-(1-(4-chloro-3-(trifluoromethyl)benzyl)-6-(trifluoromethyl)-2,3-dihydro-1H-imidazo[1,2-b]pyrazole-7-carboxamido)ethyl)benzoate (390) using the reactant shown above, compound 457 was prepared as a white solid (103.0 mg, 76% yield) from methyl (S)-4-(1-(6-(trifluoromethyl)-2,3-dihydro-1H-imidazo[1,2-b]pyrazole-7-carboxamido)ethyl)benzoate (387). ¹HNMR (400 MHz): δ ppm 7.97 (d, J=8.0 Hz, 2H), 7.38 (d, J=8.4 Hz, 2H), 7.15 (dd, J=8.4, 8.4 Hz, 1H), 6.65-6.55 (m, 3H), 6.23 (bm, 1H), 5.25 (dq, J=8.8 Hz, 1H), 4.68 (s, 2H), 4.11 (dd, J=8.8, 8.8 Hz, 2H), 3.90 (s, 6H), 3.79 (dd, J=8.8, 8.8 Hz, 2H), 2.89 (s, 3H), 1.52 (d, J=6.8 Hz, 3H). LCMS (ES) (M+2H)=517.6.

(S)-4-(1-(1-(3-(dimethylamino)benzyl)-6-(trifluoromethyl)-2,3-dihydro-1H-imidazo[1,2-b]pyrazole-7-carboxamido)ethyl)benzoic acid (Compound 89)

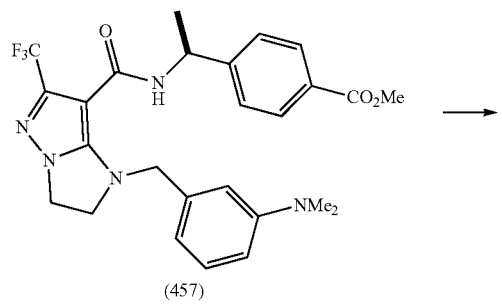

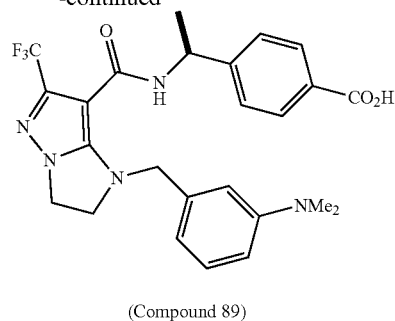

(Compound 89)

Following the same procedure for the preparation of (S)-4-(1-(1-(3-(hydroxymethyl)benzyl)-6-(trifluoromethyl)-2,3-dihydro-1H-imidazo[1,2-b]pyrazole-7-carboxamido)ethyl)benzoic acid (Compound 64) using the reactant shown above, Compound 89 was prepared as a white solid (20.0 mg, 56% yield) from methyl (S)-4-(1-(1-(3-(dimethylamino)benzyl)-6-(trifluoromethyl)-2,3-dihydro-1H-imidazo[1,2-b]pyrazole-7-carboxamido)ethyl)benzoate (457). ¹HNMR (400 MHz): δ ppm 8.02 (d, J=8.4 Hz, 2H), 7.40 (d, J=8.0 Hz, 2H), 7.17 (dd, J=7.6, 7.6 Hz, 1H), 6.65 (bm, 3H), 6.25 (bm, 1H), 5.26 (dq, J=7.2 Hz, 1H), 4.68 (dd, J=14.8, 14.8 Hz, 2H), 4.11 (dd, J=8.8, 8.8 Hz, 2H), 3.79 (dd, J=9.2, 9.2 Hz, 2H), 2.90 (s, 6H), 1.53 (d, J=7.2 Hz, 3H). LCMS (ES) (M+2H)=503.4.

Example LXXXVII

Methyl (S)-4-(1-(1-(3-(dimethylamino)-5-(trifluoromethyl)benzyl)-6-(trifluoromethyl)-2,3-dihydro-1H-imidazo[1,2-b]pyrazole-7-carboxamido)ethyl)benzoate (458)

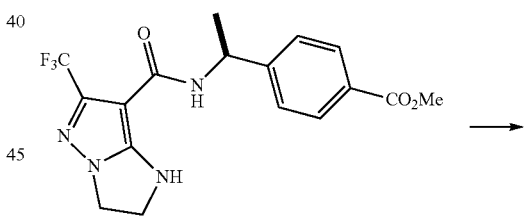

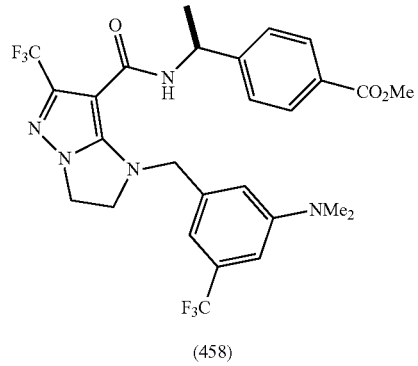

Following the same procedure for the preparation of (S)-methyl 4-(1-(1-(4-chloro-3-(trifluoromethyl)benzyl)-6-(trifluoromethyl)-2,3-dihydro-1H-imidazo[1,2-b]pyrazole- 7-carboxamido)ethyl)benzoate (390) using the reactant shown above, compound 458 was prepared as a white solid (20.5 mg, 84% yield) from methyl (S)-4-(1-(6-(trifluoromethyl)-2,3-dihydro-1H-imidazo[1,2-b]pyrazole-7-carboxamido)ethyl)benzoate (387). $^1$HNMR (400 MHz): δ ppm 7.97 (d, J=8.0 Hz, 2H), 7.38 (d, J=8.4 Hz, 2H), 6.81-6.76 (m, 3H), 6.25 (bm, 1H), 5.23 (dq, J=7.2 Hz, 1H), 4.73 (dd, J=14.8, 14.8 Hz, 2H), 4.15 (dd, J=8.4, 8.4 Hz, 2H), 3.90 (s, 3H), 3.77 (dd, J=8.8, 8.8 Hz, 2H), 2.93 (s, 6H), 1.52 (d, J=6.8 Hz, 3H). LCMS (ES) (M+2H)=585.6.

(S)-4-(1-(1-(3-(dimethylamino)-5-(trifluoromethyl)benzyl)-6-(trifluoromethyl)-2,3-dihydro-1H-imidazo[1,2-b]pyrazole-7-carboxamido)ethyl)benzoic acid (Compound 90)

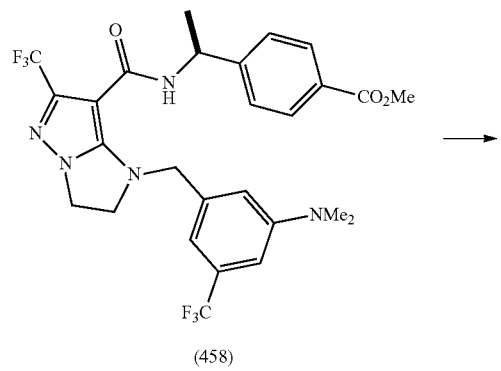

(458)

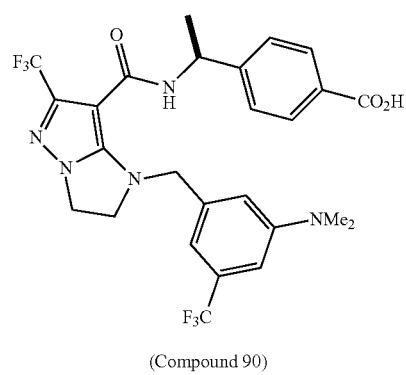

(Compound 90)

Following the same procedure for the preparation of (S)-4-(1-(1-(3-(hydroxymethyl)benzyl)-6-(trifluoromethyl)-2,3-dihydro-1H-imidazo[1,2-b]pyrazole-7-carboxamido)ethyl)benzoic acid (Compound 64) using the reactant shown above, (Compound 90) was prepared as a white solid (30.0 mg, 58% yield) from methyl (S)-4-(1-(1-(3-(dimethylamino)-5-(trifluoromethyl)benzyl)-6-(trifluoromethyl)-2,3-dihydro-1H-imidazo[1,2-b]pyrazole-7-carboxamido)ethyl)benzoate (458). $^1$HNMR (400 MHz): δ ppm 8.03 (d, J=8.0 Hz, 2H), 7.40 (d, J=8.0 Hz, 2H), 6.84-6.82 (m, 3H), 6.28 (bm, 1H), 5.24 (dq, J=6.8 Hz, 1H), 4.74 (s, 3H), 4.16 (dd, J=8.4, 8.4 Hz, 2H), 3.78 (dd, J=8.8, 8.8 Hz, 2H), 2.94 (s, 6H), 1.53 (d, J=6.8 Hz, 3H). LCMS (ES) (M+2H)=571.4.

Example LXXXVIII

Intermediates Used in Examples LXXXIX-XCII Below 1-tert-Butyl 7-ethyl 6-bromo-2,3-dihydro-1H-imidazo[1,2-b]pyrazole-1,7-dicarboxylate

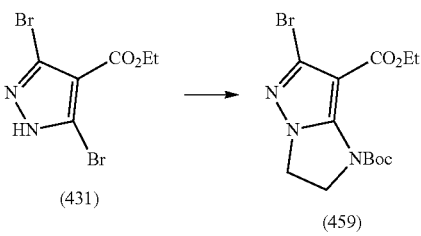 [SMILES: CCOC(=O)c1c(Br)n[nH]c1Br ; CCOC(=O)c1c(Br)nn2c1N(C(=O)OC(C)(C)C)CC2]

(431) (459)

To a solution of ethyl 3,5-dibromo-1H-pyrazole-4-carboxylate (431) (10.0 g, 33.6 mmol) and tert-butyl (2-bromoethyl)carbamate (9.78 g, 43.6 mmol) in DMF (150 mL) at rt were treated with Cs$_2$CO$_3$ (13.1 g, 40.3 mmol, powder) at 80° C. for 1.5 h; After cooling to rt, the inorganic salt was filtered over sand (pre-washed with acetonitrile) under. N$_2$ atmosphere. The cake was rinsed with dry DMF (5 mL). Then, the filtrate was treated with Cs$_2$CO$_3$ (13.1 g, 40.3 mmol), and aged for 2 h at 120° C. After cooling to rt, the resulting reaction mixtures were diluted with ethyl acetate (250 mL) and water (200 mL). After phase separation, aq layer was back-extracted with ethyl acetate (150 mL). The combined org layers were washed successively with water (150 mL), sat. aqueous ammonium chloride (200 mL) and brine (200 mL). After phases-cut, the organic phase was dried (MgSO$_4$), filtered and concentrated. The oily colorless residue was purified by Biotage chromatography (n-Heptane-EtOAc) to give the desired product as a solid (8.6 g, 71% yield). The purified product (459) was solidified as a solid (on standing). $^1$H NMR (400 MHz, CDCl$_3$): δ ppm 4.33 (dd, J=9.7, 7.8 Hz, 2H), 4.20 (q, J=7.1 Hz, 2H), 4.15 (dd, J=8.9, 7.8 Hz, 2H), 1.24 (t, J=7.1 Hz, 3H). LCMS (ES) (M+H)=359.99.

Ethyl 6-bromo-2,3-dihydro-1H-imidazo[1,2-b]pyrazole-7-carboxylate (460)

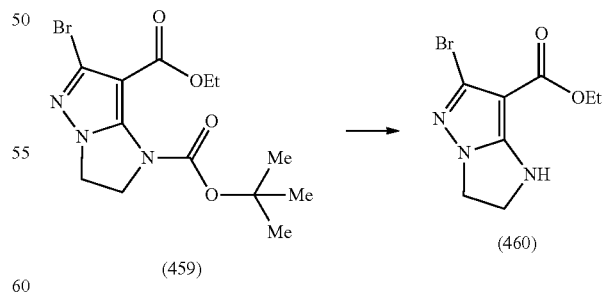

(459) (460)

To a solution of 1-(tert-butyl) 7-ethyl 6-bromo-2,3-dihydro-1H-imidazo[1,2-b]pyrazole-1,7-dicarboxylate (459) (1.60 g, 4.44 mmol) in DCM (32 mL) was added trifluoroacetic acid (6.40 mL) at ambient temperature. After stirring at ambient temperature for 3 h, LCMS showed completion of the reaction. The reaction solution was concentrated. The solid residue was mixed with EtOAc (100 mL) and sat. NaHCO₃ solution (80 mL). Layers were separated. The aqueous layer was extracted again with EtOAc (80 mL). The combined organic layers were dried over MgSO₄. The dried solution was filtered and concentrated to give the desired product (460) (1.12 g, 97%), which was used in the next step without further purification. LCMS (ES) (M+H)=260.2.

Ethyl 6-bromo-1-(3-(trifluoromethyl)benzyl)-2,3-dihydro-1H-imidazo[1,2-b]pyrazole-7-carboxylate (461)

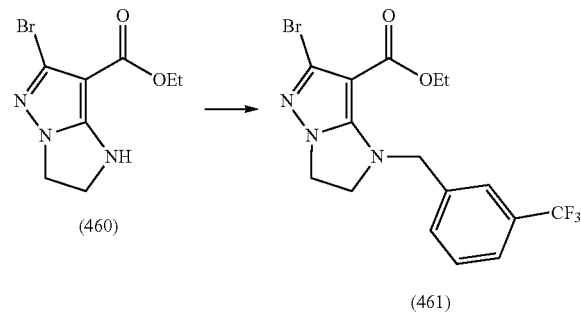 [SMILES: CCOC(=O)c1c(Br)nn2c1NCC2 ; CCOC(=O)c1c(Br)nn2c1N(Cc1cccc(C(F)(F)F)c1)CC2]

To a mixture of ethyl 6-bromo-2,3-dihydro-1H-imidazo[1,2-b]pyrazole-7-carboxylate (460) (1.11 g, 4.27 mmol) and 1-(bromomethyl)-3-(trifluoromethyl)benzene (0.78 mL, 5.12 mmol) in DMF (11 mL) was added cesium carbonate (4.17 g, 12.80 mmol) at ambient temperature. The reaction flask was heated in an oil bath at 100° C. After 1 h, additional 1-(bromomethyl)-3-(trifluoromethyl)benzene (0.10 mL, 0.66 mmol) was added. After 20 minutes, the heating bath was removed and the reaction mixture was allowed to cool to 23° C. The mixture was diluted with sat. NaHCO₃ (20 mL) and was partitioned between water (20 mL) and MTBE/EtOAc (25 mL/35 mL). The aqueous layer was extracted again with MTBE/EtOAc (25 mL/15 mL). The combined organic layers were washed with 18% NaCl aqueous solution (30 mL). The washed solution was concentrated. The residue was purified by silica gel chromatography (5% to 30% EtOAc in heptane and then 30% isocratic) to provide the desired product (461) as a white solid (1.46 g, 82% yield). LCMS (ES) (M+H)=418.2.

Ethyl 1-(3-(trifluoromethyl)benzyl)-6-vinyl-2,3-dihydro-1H-imidazo[1,2-b]pyrazole-7-carboxylate (462)

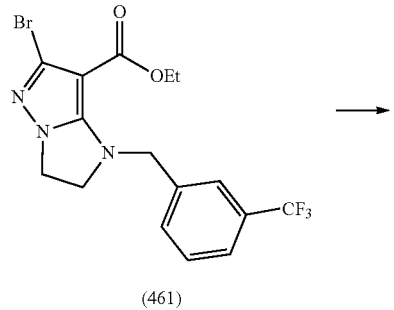

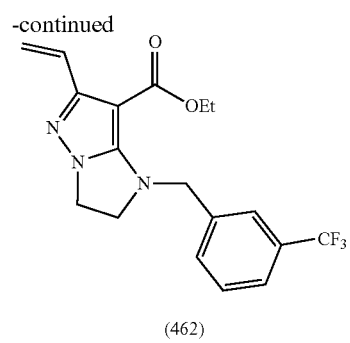

A reaction flask containing a solution of ethyl 6-bromo-1-(3-(trifluoromethyl)benzyl)-2,3-dihydro-1H-imidazo[1,2-b]pyrazole-7-carboxylate (461) (1.46 g, 3.49 mmol) in toluene (36.5 mL) was evacuated under vacuum and backfilled with nitrogen (two times). At ambient temperature, Pd(PPh₃)₄ (0.24 g, 0.21 mmol) and tributyl(vinyl)stannane (1.22 ml, 4.19 mmol) were added. The resulting mixture was stirred in a 100° C. oil bath. After stirring for 17 h, additional Pd(PPh₃)₄ (0.24 g, 0.21 mmol) and tributyl(vinyl)stannane (1.22 ml, 4.19 mmol) were added. After another 17 h, the heating bath was removed and the reaction mixture was allowed to cool to 23° C. The reaction volume was reduced to approximately 3 mL by concentration. The residue was purified by silica gel chromatography (5% to 30% EtOAc in heptane and then 30% isocratic) to provide the desired product (462) as a white solid (891 mg, 70% yield). ¹HNMR (400 MHz, CDCl₃): δ ppm 7.57 (s, 1H), 7.55-7.51 (m, 2H), 7.45 (dd, J=8.0, 8.0 Hz, 1H), 7.14 (dd, J=18, 11 Hz, 1H), 5.97 (dd, J=18, 2.4 Hz, 1H), 5.28 (dd, J=11, 2.0 Hz, 1H), 4.93 (s, 2H), 4.24 (q, J=7.6 Hz, 2H), 4.11 (t, J=7.6 Hz, 2H), 3.70 (t, J=8.0 Hz, 2H), 1.26 (t, J=7.6 Hz, 3H). LCMS (ES) (M+H)=366.3.

1-(3-(Trifluoromethyl)benzyl)-6-vinyl-2,3-dihydro-1H-imidazo[1,2-b]pyrazole-7-carboxylic acid

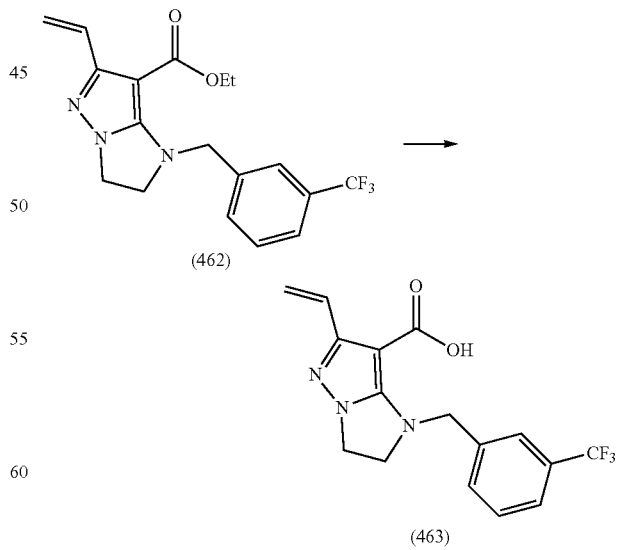

To a solution of ethyl 1-(3-(trifluoromethyl)benzyl)-6-vinyl-2,3-dihydro-1H-imidazo[1,2-b]pyrazole-7-carboxylate (462) (880 mg, 2.41 mmol) in methanol (5.3 mL) and THF (5.3 mL) at ambient temperature was added a solution of lithium hydroxide monohydrate (505 mg, 12.0 mmol) in water (5.3 mL). The reaction mixture was stirred in a 60° C. oil bath. After 3 h, additional solution of lithium hydroxide monohydrate (250 mg, 6.0 mmol) in water (2.5 mL) was added. After 17 h, the heating bath was removed and the reaction mixture was allowed to cool to 23° C. The mixture was diluted with water (30 mL) and acidified with 1N HCl (25 mL). The acidified solution was extracted with EtOAc (2×100 mL). The combined organic layers were washed with brine, dried (Na$_2$SO$_4$), filtered and concentrated to give the crude desired product (463) as a white solid (815 mg, 99% yield), which was used in the next step without further purification. $^1$H NMR (400 MHz, DMSO-d$_6$): δ ppm 12.2 (br s, 1H), 7.69 (s, 1H), 7.66-7.57 (m, 3H), 7.09 (dd, J=18, 11 Hz, 1H), 5.81 (dd, J=18, 2.4 Hz, 1H), 5.17 (dd, J=11, 2.4 Hz, 1H), 4.92 (s, 2H), 4.07 (t, J=8.0 Hz, 2H), 3.72 (t, J=8.0 Hz, 2H). LCMS (ES) (M+H)=339.2.

Methyl (S)-4-(1-(1-(3-(trifluoromethyl)benzyl)-6-vinyl-2,3-dihydro-1H-imidazo[1,2-b]pyrazole-7-carboxamido)ethyl)benzoate (465)

mmol). The resulting mixture was stirred at ambient temperature overnight. After 16 h, the reaction was quenched by addition of water (4 mL). The reaction mixture was partitioned between 10% NaCl aqueous solution (70 mL) and EtOAc (100 mL). The organic layer was concentrated. The residue was purified by silica gel chromatography (30% to 70% EtOAc/heptane and then 70% isocratic) to provide the desired product (465) as a white solid (495 mg, 81% yield). $^1$H NMR (400 MHz, CDCl$_3$): δ ppm 7.96 (d, J=8.4 Hz, 2H), 7.52-7.37 (m, 4H), 7.35 (d, J=8.0 Hz, 2H), 6.73 (dd, J=18, 12 Hz, 1H), 5.96 (br d, J=8.0 Hz, 1H), 5.88 (dd, J=18, 1.6 Hz, 1H), 5.43 (dd, J=11, 1.6 Hz, 1H), 5.25 (dq, J=7.2, 7.2 Hz, 1H), 4.85 (d, J=14.8 Hz, 1H), 4.81 (d, J=14.8 Hz, 1H), 4.09 (dd, J=8.8, 8.8 Hz, 2H), 3.88 (s, 3H), 3.66 (dd, J=8.8, 8.8 Hz, 2H), 1.51 (d, J=7.2 Hz, 3H). LCMS (ES) (M+H)=500.3.

Methyl (S)-4-(1-(6-formyl-1-(3-(trifluoromethyl)benzyl)-2,3-dihydro-1H-imidazo[1,2-b]pyrazole-7-carboxamido)ethyl)benzoate (466)

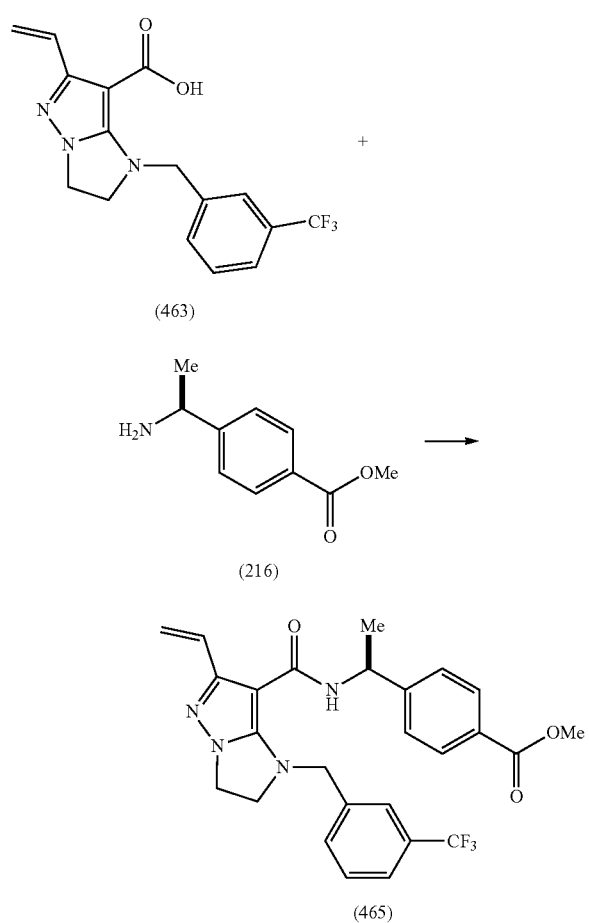

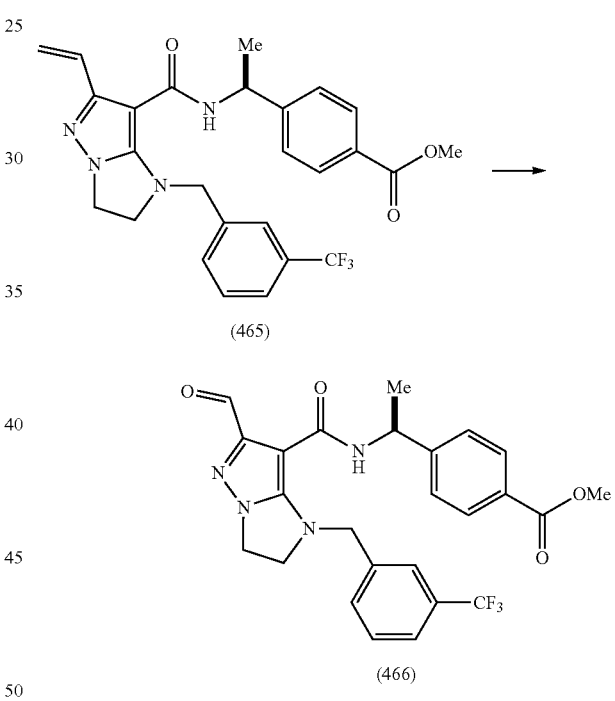

To a suspension of 1-(3-(trifluoromethyl)benzyl)-6-vinyl-2,3-dihydro-1H-imidazo[1,2-b]pyrazole-7-carboxylic acid (463) (412 mg, 1.22 mmol) and (S)-methyl 4-(1-aminoethyl)benzoate (216) (443 mg, 2.47 mmol) in DCM (12 mL) was added TEA (0.68 mL, 4.87 mmol) and HATU (604 mg, 1.59

To a solution of methyl (S)-4-(1-(1-(3-(trifluoromethyl)benzyl)-6-vinyl-2,3-dihydro-1H-imidazo[1,2-b]pyrazole-7-carboxamido)ethyl)benzoate (465) (250 mg, 0.50 mmol) in THF (3.8 mL) and water (3.8 mL) was added 4% wt. osmium tetroxide aqueous solution (48 μL, 7.52 μmol) at ambient temperature. After stirring for 15 minutes, sodium periodate (215 mg, 1.00 mmol) was added. The resulting mixture was stirred at ambient temperature overnight. After 16 h, the reaction mixture was partitioned between water (40 mL) and EtOAc (50 mL). The aqueous layer was extracted again with EtOAc (50 mL). The combined organic layers were dried (Na2SO4), filtered and concentrated to give the crude desired product (466) as a dark oil (251 mg, 99% yield), which was used in the next step without further purification. $^1$H NMR (400 MHz, CDCl$_3$): δ ppm 9.85 (br d, J=7.2 Hz, 1H), 9.69 (s, 1H), 7.98 (d, J=8.0 Hz, 2H), 7.54-7.39 (m, 4H), 7.44 (d, J=8.0 Hz, 2H), 5.24 (d, J=14.4 Hz, 1H), 5.22 (m, 1H), 5.09 (d, J=15 Hz, 1H), 4.24 (dd, J=8.4, 8.4 Hz, 2H), 3.88 (s, 3H), 3.80 (dd, J=8.4, 8.4 Hz, 2H), 1.56 (d, J=7.0 Hz, 3H). LCMS (ES) (M+H)=501.3.

Methyl (S)-4-(1-(6-(hydroxymethyl)-1-(3-(trifluoromethyl)benzyl)-2,3-dihydro-1H-imidazo[1,2-b]pyrazole-7-carboxamido)ethyl)benzoate (467)

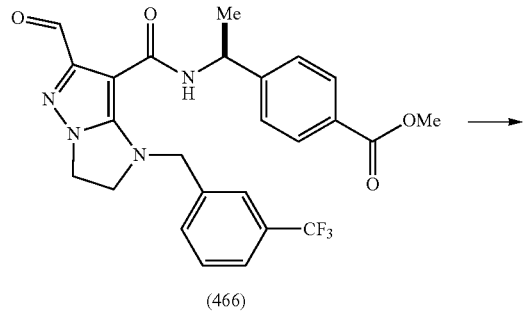

(466)

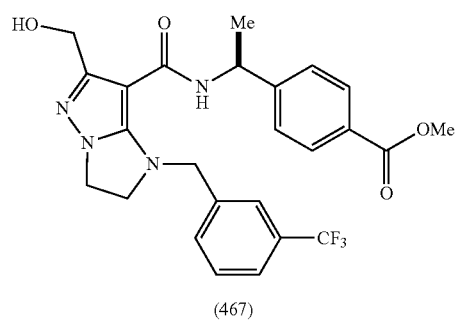

(467)

To a solution of methyl (S)-4-(1-(6-formyl-1-(3-(trifluoromethyl)benzyl)-2,3-dihydro-1H-imidazo[1,2-b]pyrazole-7-carboxamido)ethyl)benzoate (466) (83 mg, 0.17 mmol) in MeOH (2.5 mL) was added sodium borohydride (12.6 mg, 0.33 mmol) at −5° C. After stirring at that temperature for 2 h, reaction was completed (monitored by TLC) and the reaction was quenched by addition of 6% wt citric acid aqueous solution. The quenched mixture was partitioned between 18% wt NaCl aqueous solution (20 mL) and EtOAc (30 mL). The aqueous layer was extracted again with EtOAc (30 mL). The combined organic layers were concentrated. The residue was purified by silica gel chromatography (30% to 70% EtOAc/heptane and then 70% isocratic) to provide the desired product (467) as an oil (81 mg, 97% yield). $^1$H NMR (400 MHz, CDCl$_3$): δ ppm 8.22 (br d, J=8.0 Hz, 1H), 7.97 (d, J=8.4 Hz, 2H), 7.55-7.48 (m, 3H), 7.43-7.39 (m, 2H), 5.25 (dq, J=7.2, 7.2 Hz, 1H), 4.96 (dd, J=14.8, 14.8 Hz, 1H), 4.92 (dd, J=14.8, 14.8 Hz, 1H), 4.70 (d, J=16 Hz, 1H), 4.67 (d, J=16 Hz, 1H), 4.05 (dd, J=8.0, 8.0 Hz, 2H), 3.89 (s, 3H), 3.67 (dd, J=8.4, 8.4 Hz, 2H), 1.51 (d, J=7.2 Hz, 3H). LCMS (ES) (M+H)=503.2.

Example LXXXIX

Methyl (S)-4-(1-(6-(fluoromethyl)-1-(3-(trifluoromethyl)benzyl)-2,3-dihydro-1H-imidazo[1,2-b]pyrazole-7-carboxamido)ethyl)benzoate (468)

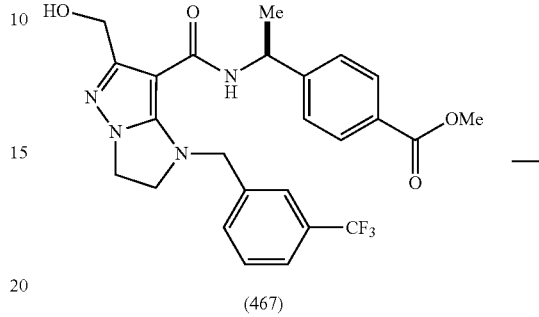

(467)

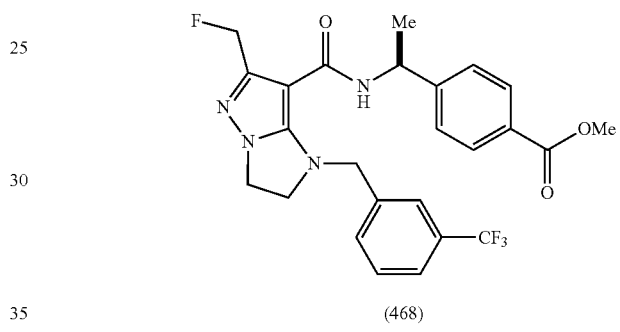

(468)

To a mixture of methyl (S)-4-(1-(6-(hydroxymethyl)-1-(3-(trifluoromethyl)benzyl)-2,3-dihydro-1H-imidazo[1,2-b]pyrazole-7-carboxamido)ethyl)benzoate (467) (17 mg, 0.034 mmol) in toluene (0.6 mL) was added 2-pyridinesulfonyl fluoride (PyFluor) (7.1 mg, 0.044 mmol) and 7-methyl-1,5,7-triazabicyclo[4.4.0]dec-5-ene (MTBD) (7.29 μL, 0.051 mmol) at ambient temperature. After stirring for 3 h, reaction was completed (monitored by LCMS) and the reaction was quenched by addition of MeOH (0.3 mL). The quenched mixture was partitioned between water (15 mL) and EtOAc (20 mL). The aqueous layer was extracted again with EtOAc (20 mL). The combined organic layers were washed with brine (15 mL), dried (Na$_2$SO$_4$), filtered, and concentrated. The residue was purified by silica gel chromatography (5% to 30% EtOAc/heptane, 30% isocratic, 30% to 70% EtOAc/heptane, and then 70% isocratic) to provide the desired product (468) (8.6 mg, 50% yield). $^1$H NMR (400 MHz, CDCl$_3$): δ ppm 8.01-7.97 (m, 2H), 7.55-7.48 (m, 3H), 7.43-7.38 (m, 3H), 6.83 (dd, J=12.8, 7.6 Hz, 1H), 5.48 (dd, J=16, 11 Hz, 1H), 5.36 (dd, J=16, 11 Hz, 1H), 5.25 (m, 1H), 4.94 (d, J=15 Hz, 1H), 4.88 (d, J=15 Hz, 1H), 4.14-4.08 (m, 2H), 3.89 (s, 3H), 3.70 (dd, J=8.8, 8.8 Hz, 2H), 1.53 (d, J=6.8 Hz, 3H). LCMS (ES) (M+H)=505.3.

197

(S)-4-(1-(6-(Fluoromethyl)-1-(3-(trifluoromethyl)benzyl)-2,3-dihydro-H-imidazo[1,2-b]pyrazole-7-carboxamido)ethyl)benzoic acid (Compound 91)

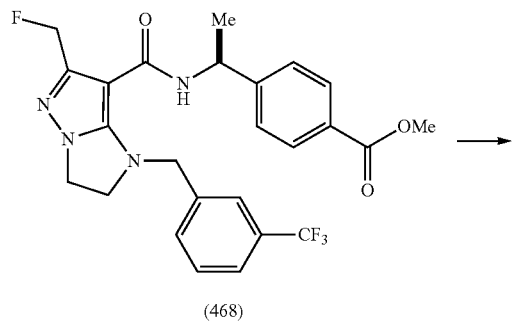

(468)

(Compound 91)

To a solution of methyl (S)-4-(1-(6-(fluoromethyl)-1-(3-(trifluoromethyl)benzyl)-2,3-dihydro-1H-imidazo[1,2-b]pyrazole-7-carboxamido)ethyl)benzoate (468) (8.6 mg, 0.017 mmol) in methanol (0.5 mL) and THF (0.5 mL) at ambient temperature was added a solution of lithium hydroxide monohydrate (7.2 mg, 0.17 mmol) in water (0.5 mL). The reaction mixture was stirred in a 60° C. oil bath. After 2 h, the heating bath was removed and the reaction mixture was allowed to cool to 23° C. The mixture was acidified with 1N HCl (0.26 mL). The acidified solution was partitioned between water (15 mL) and $CH_2Cl_2$ (20 mL). The aqueous layer was extracted again with $CH_2Cl_2$ (20 mL). The combined organic layers were washed with brine (15 mL), dried ($Na_2SO_4$), filtered, and concentrated. The residue was purified by silica gel chromatography (50% to 80% EtOAc/heptane, 80% isocratic, 2% MeOH/EtOAc isocratic) to provide the desired product (Compound 91) (3.5 mg, 41% yield). 1H NMR (400 MHz, $CDCl_3$): δ ppm 8.05 (d, J=8.4 Hz, 2H), 7.56-7.49 (m, 3H), 7.45-7.40 (m, 3H), 6.86 (dd, J=12.8, 7.6 Hz, 1H), 5.51 (dd, J=15, 11 Hz, 1H), 5.39 (dd, J=15, 11 Hz, 1H), 5.27 (m, 1H), 4.96 (d, J=15 Hz, 1H), 4.89 (d, J=15 Hz, 1H), 4.15-4.09 (m, 2H), 3.71 (dd, J=8.4, 8.4 Hz, 2H), 1.55 (d, J=7.2 Hz, 3H). LCMS (ES) (M+H)=491.3.

198

Example XC (S)-4-(1-(1-(3-(Trifluoromethyl)benzyl)-6-vinyl-2,3-dihydro-1H-imidazo[12-b]pyrazole-7-carboxamido)ethyl)benzoic acid (Compound 92)

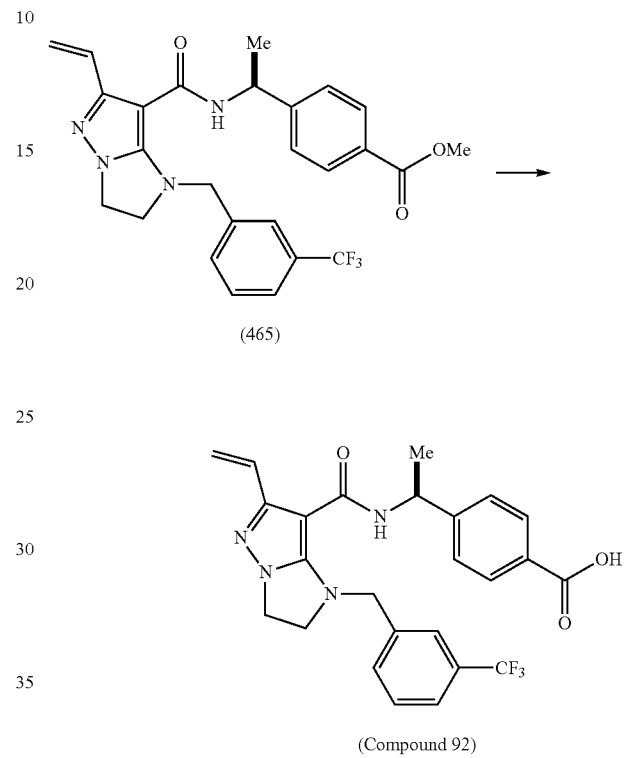

(465)

(Compound 92)

To a solution of methyl (S)-4-(1-(1-(3-(trifluoromethyl)benzyl)-6-vinyl-2,3-dihydro-1H-imidazo[1,2-b]pyrazole-7-carboxamido)ethyl)benzoate (465) (50 mg, 0.10 mmol) in methanol (1.5 mL) and THF (1.5 mL) at ambient temperature was added a solution of lithium hydroxide monohydrate (21.1 mg, 0.50 mmol) in water (1.5 mL). The reaction mixture was stirred at ambient temperature. After 16 h, the mixture was diluted with water (5 mL) and acidified with 1N HCl (0.7 mL). The acidified solution was partitioned between water (5 mL) and EtOAc (20 mL). The aqueous layer was extracted again with EtOAc (20 mL). The combined organic layers were concentrated. The residue was purified by silica gel chromatography (50% to 100% EtOAc/heptane, 100% isocratic) to provide the desired product (Compound 92) (32 mg, 66% yield) as a white solid. 1H NMR (400 MHz, $CD_3OD$): δ ppm 8.27 (d, J=7.6 Hz, 1H), 7.84 (d, J=8.0 Hz, 2H), 7.60 (s, 1H), 7.54 (m, 1H), 7.47-7.43 (m, 2H), 7.38 (d, J=8.0 Hz, 2H), 6.70 (dd, J=18, 11 Hz, 1H), 5.80 (dd, J=18, 1.6 Hz, 1H), 5.28 (dd, J=11, 1.6 Hz, 1H), 5.14 (m, 1H), 4.53 (d, J=15 Hz, 1H), 4.43 (d, J=15 Hz, 1H), 4.12-4.02 (m, 2H), 3.73-3.63 (m, 2H), 1.46 (d, J=7.2 Hz, 3H). LCMS (ES) (M+H)=485.3.

Example XCI (S)-4-(1-(6-(Hydroxymethyl)-1-(3-(trifluoromethyl)benzyl)-2,3-dihydro-1H-imidazo[1,2-b]pyrazole-7-carboxamido)ethyl)benzoic acid (Compound 93)

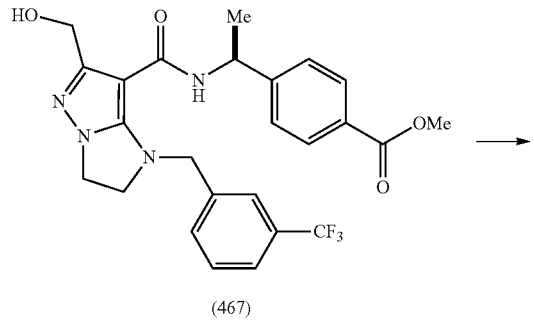

(467)

(Compound 93)

To a solution of methyl (S)-4-(1-(6-(hydroxymethyl)-1-(3-(trifluoromethyl)benzyl)-2,3-dihydro-1H-imidazo[1,2-b]pyrazole-7-carboxamido)ethyl)benzoate (467) (50 mg, 0.10 mmol) in methanol (1.5 mL) and THF (1.5 mL) at ambient temperature was added a solution of lithium hydroxide monohydrate (21.1 mg, 0.50 mmol) in water (1.5 mL). The reaction mixture was stirred at ambient temperature. After 16 h, the mixture was diluted with water (5 mL) and acidified with 1N HCl (0.7 mL). The acidified solution was partitioned between water (5 mL) and EtOAc (20 mL). The aqueous layer was extracted again with EtOAc (20 mL). The combined organic layers were concentrated. The residue was purified by silica gel chromatography (50% to 100% EtOAc/heptane, 100% isocratic) to provide the desired product (Compound 93) (35 mg, 72% yield) as a white semi-solid. $^1$H NMR (400 MHz, CD$_3$OD): δ ppm 9.22 (d, J=7.6 Hz, 1H), 7.99-7.95 (m, 2H), 7.64 (s, 1H), 7.58-7.54 (m, 2H), 7.50-7.44 (m, 3H), 5.15 (m, 1H), 4.94-4.80 (m, 2H), 4.63 (d, J=15 Hz, 1H), 4.60 (d, J=15 Hz, 1H), 4.07-4.02 (m, 2H), 3.74-3.69 (m, 2H), 1.51 (d, J=7.2 Hz, 3H). LCMS (ES) (M+H)=489.3.

Example XCII

Methyl (S)-4-(1-(6-(difluoromethyl)-1-(3-(trifluoromethyl)benzyl)-2,3-dihydro-1H-imidazo[1,2-b]pyrazole-7-carboxamido)ethyl)benzoate (469)

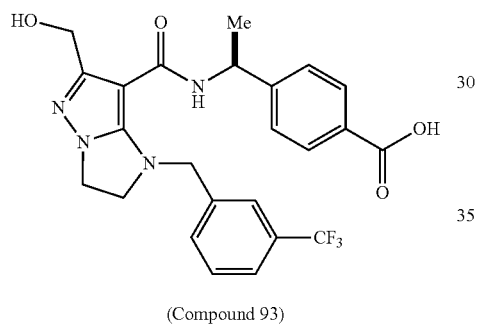

(466)

(469)

To a solution of methyl (S)-4-(1-(6-formyl-1-(3-(trifluoromethyl)benzyl)-2,3-dihydro-1H-imidazo[1,2-b]pyrazole-7-carboxamido)ethyl)benzoate (466) (83 mg, 0.17 mmol) in CH$_2$Cl$_2$ (1.7 mL) was added 1 M DAST solution in CH$_2$Cl$_2$ (0.37 mL, 0.37 mmol) at ambient temperature. After stirring for 2 h, additional DAST solution in CH$_2$Cl$_2$ (0.37 mL, 0.37 mmol) was added. After 16 h, LCMS showed approximately 60% conversion. Additional DAST solution in CH$_2$Cl$_2$ (0.37 mL, 0.37 mmol) was added. The reaction flask was placed in a 40° C. oil bath. After stirring at 40° C. for 7 h, additional DAST solution in CH$_2$Cl$_2$ (0.37 mL, 0.37 mmol) was added. After additional 16 h, the heating bath was removed and the reaction mixture was allowed to cool to 23° C. The reaction was quenched by addition of sat. NaHCO$_3$ carefully. The quenched mixture was partitioned between 5% wt NaHCO$_3$ aqueous solution (20 mL) and EtOAc (30 mL). The aqueous layer was extracted again with EtOAc (30 mL). The combined organic layers were concentrated. The residue was purified by silica gel chromatography (10% to 30% EtOAc/heptane, 30% isocratic, 30% to 50% EtOAc/heptane) to provide the desired product (469) (57 mg, 65% yield). $^1$H NMR (400 MHz, CDCl$_3$): δ ppm 8.00-7.97 (m, 2H), 7.54-7.48 (m, 3H), 7.43-7.39 (m, 3H), 6.73 (m, 1H), 6.60 (t, J=54 Hz, 1H), 5.22 (m, 1H), 4.98 (d, J=15 Hz, 1H), 4.89 (d, J=15 Hz, 1H), 4.14-4.09 (m, 2H), 3.88 (s, 3H), 3.75-3.70 (m, 2H), 1.52 (d, J=6.4 Hz, 3H). LCMS (ES) (M+H)=523.3.

(S)-4-(1-(6-(Difluoromethyl)-1-(3-(trifluoromethyl)benzyl)-2,3-dihydro-1H-imidazo[1,2-b]pyrazole-7-carboxamido)ethyl)benzoic acid (Compound 94)

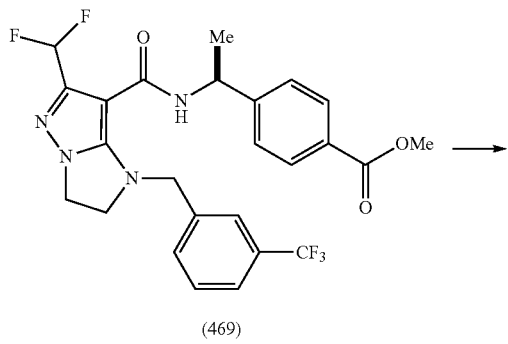

(469)

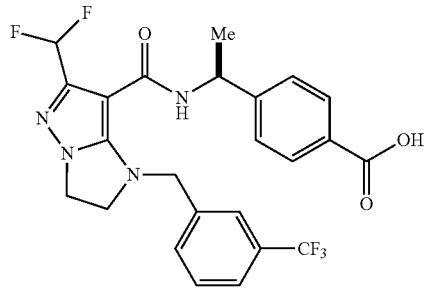

(Compound 94)

To a solution of methyl (S)-4-(1-(6-(difluoromethyl)-1-(3-(trifluoromethyl)benzyl)-2,3-dihydro-1H-imidazo[1,2-b]pyrazole-7-carboxamido)ethyl)benzoate (469) (56 mg, 0.11 mmol) in methanol (1.6 mL) and THF (1.6 mL) at ambient temperature was added a solution of lithium hydroxide monohydrate (22.5 mg, 0.54 mmol) in water (1.6 mL). The reaction mixture was stirred at ambient temperature. After 16 h, the mixture was diluted with water (5 mL) and acidified with 1N HCl (0.7 mL). The acidified solution was partitioned between water (5 mL) and EtOAc (20 mL). The aqueous layer was extracted again with EtOAc (20 mL). The combined organic layers were concentrated. The residue was purified by silica gel chromatography (30% to 66% EtOAc/heptane, 66% isocratic, 66% to 80%) to provide the desired product (Compound 94) (53 mg, 96% yield) as a white semi-solid. $^1$H NMR (400 MHz, CDCl$_3$): δ ppm 8.04 (d, J=8.4 Hz, 2H), 7.54-7.39 (m, 6H), 6.76 (m, 1H), 6.62 (t, J=54 Hz, 1H), 5.23 (m, 1H), 4.99 (d, J=15 Hz, 1H), 4.89 (d, J=15 Hz, 1H), 4.15-4.10 (m, 2H), 3.75-3.71 (m, 2H), 1:53 (d, J=6.8 Hz, 3H). LCMS (ES) (M+H)=509.3

Example XCIII

Methyl (S)-4-(1-(1-(3-(2-ethoxy-1,1-difluoro-2-oxoethyl)benzyl)-6-(trifluoromethyl)-2,3-dihydro-1H-imidazo[1,2-b]pyrazole-7-carboxamido)ethyl)benzoate (471)

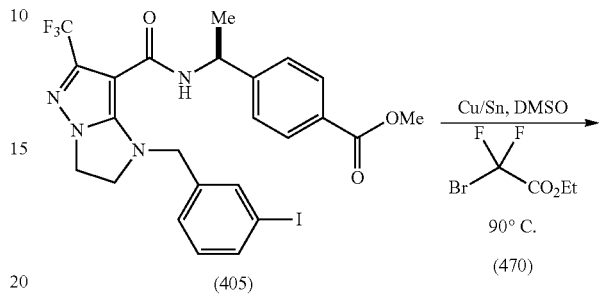

(405)   (470)

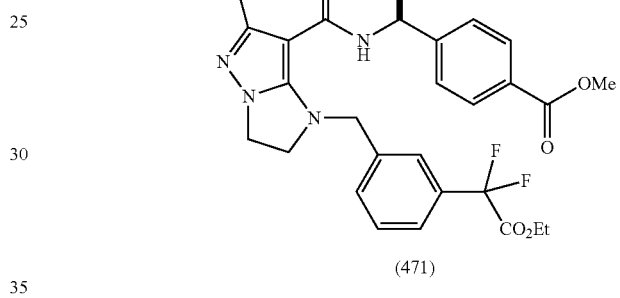

(471)

To a solution of methyl (S)-4-(1-(1-(3-iodobenzyl)-6-(trifluoromethyl)-2,3-dihydro-1H-imidazo[1,2-b]pyrazole-7-carboxamido)ethyl)benzoate (405) (200 mg, 0.33 mmol) and ethyl 2-bromo-2,2-difluoroacetate (470) (0.22 mL, 1.67 mmol) in DMSO (6.0 mL) was added Cu/Sn alloy (106 mg) at ambient temperature. The reaction flask was placed in a 90° C. oil bath. After stirring at 90° C. for 16 h, the heating bath was removed and the reaction mixture was allowed to cool to 23° C. The reaction was quenched by addition of half sat. NH4Cl aqueous solution (50 mL). The quenched mixture was extracted with EtOAc (50 mL). The aqueous layer was extracted again with EtOAc (50 mL). The combined organic layers were washed with brine (25 mL) and the washed organic layer was concentrated. The residue was purified by silica gel chromatography (10% to 30% EtOAc/heptane, 30% isocratic, 30% to 50% EtOAc/heptane) to provide the desired product (471) (144 mg, 72% yield) as a white solid. $^1$H NMR (400 MHz, CDCl$_3$): δ ppm 7.99 (d, J=8.4 Hz, 2H), 7.54-7.50 (m, 2H), 7.44-7.38 (m, 4H), 6.29 (m, 1H), 5.23 (m, 1H), 4.86 (d, J=15 Hz, 1H), 4.78 (d, J=15 Hz, 1H), 4.27 (q, J=7.2 Hz, 2H), 4.16 (dd, J=8.4, 8.4 Hz, 2H), 3.90 (s, 3H), 3.75 (dd, J=8.4, 8.4 Hz, 2H), 1.54 (d, J=7.2 Hz, 3H), 1.28 (t, J=7.2 Hz, 3H). LCMS (ES) (M+H)=595.3.

203

Methyl (S)-4-(1-(1-(3-(1,1-difluoro-2-hydroxyethyl)
benzyl)-6-(trifluoromethyl)-2,3-dihydro-1H-imidazo
[1,2-b]pyrazole-7-carboxamido)ethyl)benzoate (472)

204

(S)-4-(1-(1-(3-(1,1-Difluoro-2-hydroxyethyl)ben-
zyl)-6-(trifluoromethyl)-2,3-dihydro-1H-imidazo[1,
2-b]pyrazole-7-carboxamido)ethyl)benzoic acid
(Compound 95)

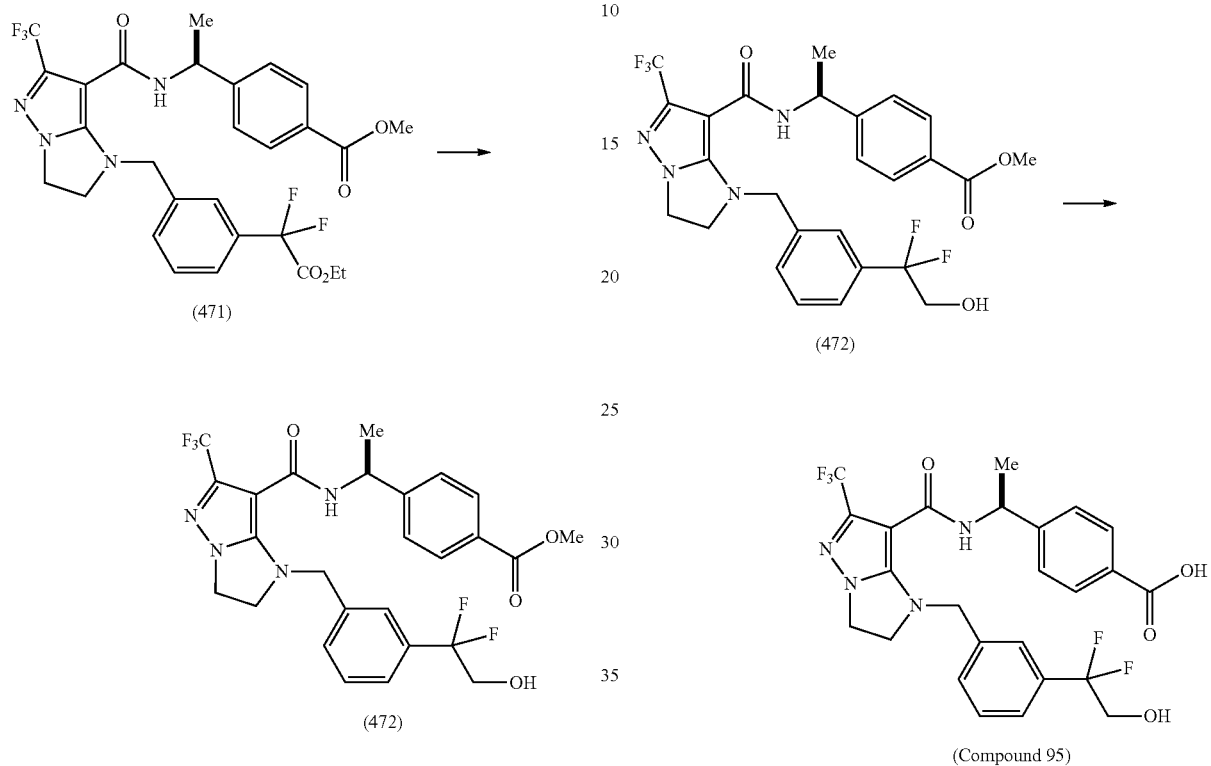

To a solution of methyl (S)-4-(1-(1-(3-(2-ethoxy-1,1-dif-luoro-2-oxoethyl)benzyl)-6-(trifluoromethyl)-2,3-dihydro-1H-imidazo[1,2-b]pyrazole-7-carboxamido)ethyl)benzoate (471) (110 mg, 0.19 mmol) in MeOH (6.6 mL) was added sodium borohydride (56 mg, 1.48 mmol) in three equal portions at −5° C. After stirring at that temperature for 2 h, additional sodium borohydride (30 mg, 0.79 mmol) was added. After 2 h, reaction was completed (monitored by LCMS) and the reaction was quenched by addition of 6% wt citric acid aqueous solution (6 mL). The quenched mixture was partitioned between water (20 mL) and EtOAc (25 mL). The aqueous layer was extracted again with EtOAc (25 mL). The combined organic layers were concentrated. The residue was purified by silica gel chromatography (30% to 50% EtOAc/heptane and then 50% isocratic) to provide the desired product (472) as an oil (95 mg, 93% yield). $^1$H NMR (400 MHz, CDCl$_3$): δ ppm 7.95 (d, J=8.4 Hz, 2H), 7.43-7.33 (m, 6H), 6.24 (m, 1H), 5.19 (m, 1H), 4.81 (d, J=15 Hz, 1H), 4.72 (d, J=15 Hz, 1H), 4.16-4.12 (m, 2H), 3.94-3.88 (m, 2H), 3.88 (s, 3H), 3.77-3.73 (m, 2H), 1.51 (d, J=7.2 Hz, 3H). LCMS (ES) (M+H)=553.3.

To a solution of methyl (S)-4-(1-(1-(3-(1,1-difluoro-2-hydroxyethyl)benzyl)-6-(trifluoromethyl)-2,3-dihydro-1H-imidazo[1,2-b]pyrazole-7-carboxamido)ethyl)benzoate (472) (23 mg, 0.042 mmol) in methanol (0.70 mL) and THF (0.70 mL) at ambient temperature was added a solution of lithium hydroxide monohydrate (8.7 mg, 0.21 mmol) in water (0.70 mL). The reaction mixture was stirred at ambient temperature. After 16 h, the mixture was diluted with water (5 mL) and acidified with 1N HCl (0.7 mL). The acidified solution was partitioned between water (5 mL) and EtOAc (20 mL). The aqueous layer was extracted again with EtOAc (20 mL). The combined organic layers were concentrated. The residue was purified by silica gel chromatography (50% to 100% EtOAc/heptane, 100% EtOAc isocratic) to provide the desired product (Compound 95) (9.8 mg, 44% yield) as an oil. $^1$H NMR (400 MHz, CDCl$_3$): δ ppm 8.00 (d, J=8.4 Hz, 2H), 7.42-7.32 (m, 6H), 6.28 (m, 1H), 5.20 (m, 1H), 4.80 (d, J=15 Hz, 1H), 4.72 (d, J=15 Hz, 1H), 4.17-4.12 (m, 2H), 3.89 (t, J=13.2 Hz, 2H), 3.77-3.73 (m, 2H), 1.52 (d, J=7.2 Hz, 3H). LCMS (ES) (M+H)=539.3.

Example XCIV

Methyl (S)-4-(1-(1-(3-(3-oxopropyl)benzyl)-6-(trifluoromethyl)-2,3-dihydro-1H-imidazo[1,2-b]pyrazole-7-carboxamido)ethyl)benzoate (475)

Methyl (S)-4-(1-(1-(3-(3-hydroxypropyl)benzyl)-6-(trifluoromethyl)-2,3-dihydro-1H-imidazo[1,2-b]pyrazole-7-carboxamido)ethyl)benzoate (476)

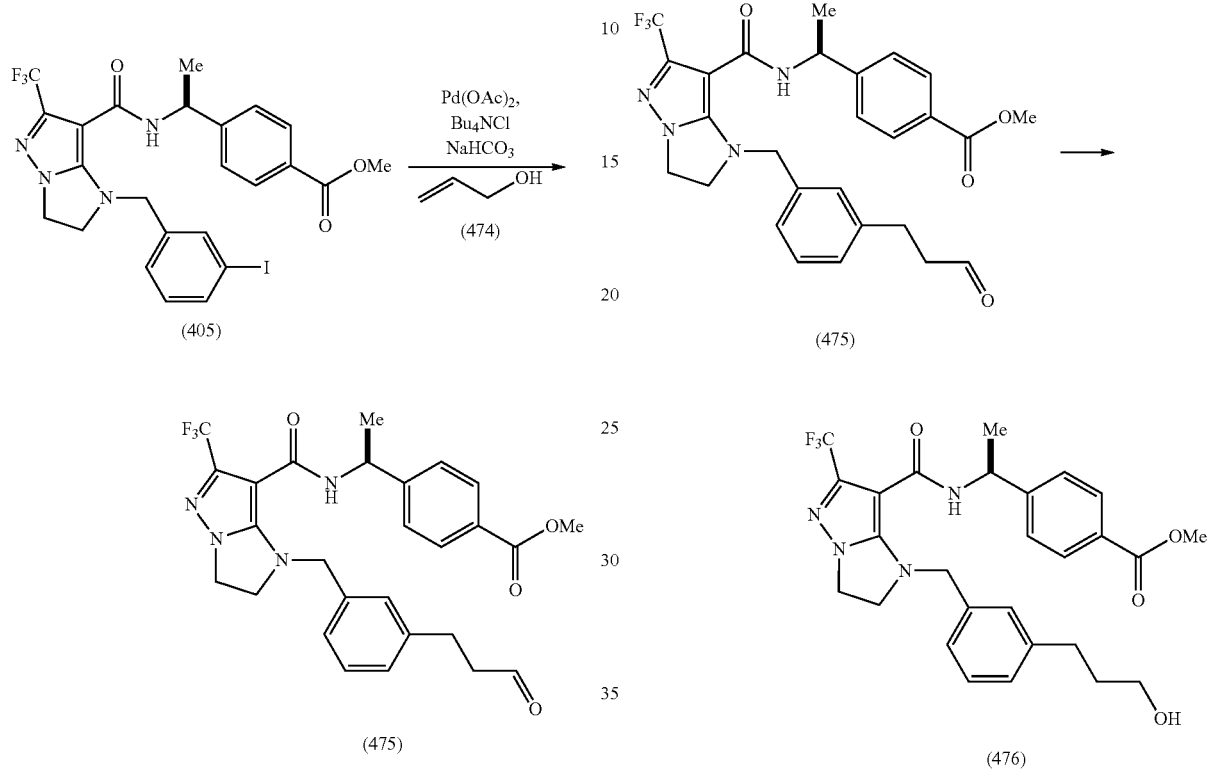

A reaction flask was charged with methyl (S)-4-(1-(1-(3-iodobenzyl)-6-(trifluoromethyl)-2,3-dihydro-1H-imidazo[1,2-b]pyrazole-7-carboxamido)ethyl)benzoate (405) (60 mg, 0.10 mmol), tetra-n-butylammonium chloride (474) (31 mg, 0.11 mmol), sodium bicarbonate (21 mg, 0.25 mmol), and toluene (2.4 mL). The reaction mixture was evacuated and backfilled with nitrogen (two times). Allyl alcohol (11 µL, 0.15 mmol) and palladium(II) acetate (2.3 mg, 10 µmol) were added. The reaction flask was placed in a 80° C. oil bath. After stirring at 80° C. for 16 h, the heating bath was removed and the reaction mixture was allowed to cool to 23° C. The reaction volume was reduced to approximately 1 mL by concentration. The residue was purified by silica gel chromatography (30% to 50% EtOAc/heptane, 50% isocratic EtOAc/heptane) to provide the desired product (475) (52 mg, 98% yield), which was contaminated with a byproduct (~10%). $^1$H NMR (400 MHz, CDCl$_3$): δ ppm 9.77 (d, J=1.2 Hz, 1H), 8.00-7.97 (m, 2H), 7.41-7.38 (m, 2H), 7.23 (m, 1H), 7.11-7.07 (m, 3H), 6.28 (m, 1H), 5.25 (m, 1H), 4.73 (d, J=15 Hz, 1H), 4.69 (d, J=15 Hz, 1H), 4.19-4.12 (m, 2H), 3.90 (s, 3H), 3.77-3.73 (m, 2H), 2.91 (t, J=7.6 Hz, 2H), 2.74 (t, J=7.6 Hz, 2H), 1.54 (d, J=7.2 Hz, 3H). LCMS (ES) (M+H)=529.2.

To a solution of methyl (S)-4-(1-(1-(3-(3-oxopropyl)benzyl)-6-(trifluoromethyl)-2,3-dihydro-1H-imidazo[1,2-b]pyrazole-7-carboxamido)ethyl)benzoate (475) (49 mg, 0.093 mmol) in MeOH (2.0 mL) was added sodium borohydride (5.3 mg, 0.14 mmol) at 0° C. After stirring at that temperature for 2 h, reaction was completed (monitored by TLC) and the reaction was quenched by addition of 10% wt citric acid aqueous solution (0.6 mL). The quenched mixture was partitioned between water (15 mL) and EtOAc (25 mL). The aqueous layer was extracted again with EtOAc (25 mL). The combined organic layers were washed with brine (20 mL) and concentrated. The residue was purified by silica gel chromatography (50% to 70% EtOAc/heptane and then 70% isocratic) to provide the desired product (476) as a white solid (31 mg, 63% yield from the iodo compound). $^1$H NMR (400 MHz, CDCl$_3$): δ ppm 7.98 (d, J=8.0 Hz, 2H), 7.39 (d, J=8.4 Hz, 2H), 7.22 (dd, J=8.0, 8.0 Hz, 1H), 7.12-7.05 (m, 3H), 6.29 (m, 1H), 5.25 (m, 1H), 4.72 (d, J=14.4 Hz, 1H), 4.66 (d, J=14.4 Hz, 1H), 4.12 (dd, J=8.8, 7.6 Hz, 2H), 3.89 (s, 3H), 3.75 (dd, J=8.8, 8.4 Hz, 2H), 3.63-3.60 (m, 2H), 2.66 (t, J=7.6 Hz, 2H), 1.86-1.80 (m, 2H), 1.53 (d, J=7.2 Hz, 3H). LCMS (ES) (M+H)=531.2.

207

Methyl (S)-4-(1-(1-(3-(3-((methylsulfonyl)oxy)propyl)benzyl)-6-(trifluoromethyl)-2,3-dihydro-1H-imidazo[1,2-b]pyrazole-7-carboxamido)ethyl)benzoate (477)

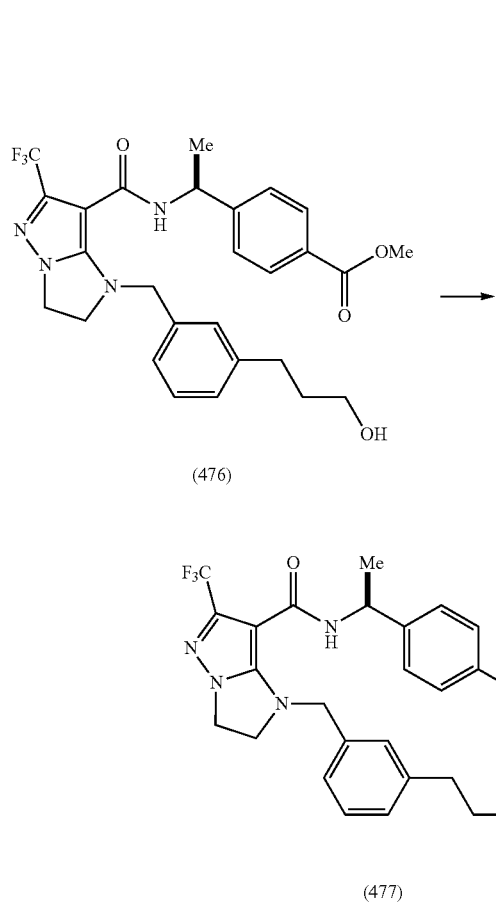

(476)

(477)

To a solution of methyl (S)-4-(1-(1-(3-(3-hydroxypropyl)benzyl)-6-(trifluoromethyl)-2,3-dihydro-1H-imidazo[1,2-b]pyrazole-7-carboxamido)ethyl)benzoate (476) (37 mg, 0.070 mmol) in CH$_2$Cl$_2$ (1.5 mL) was added Et$_3$N (0.03 mL, 0.21 mmol) followed by a solution of methanesulfonyl chloride (8.2 μL, 0.105 mmol) in CH$_2$Cl$_2$ (0.19 mL) at 0° C. After stirring at that temperature for 1 h, reaction was completed (monitored by LCMS) and the reaction was quenched by addition of sat. NaHCO$_3$ aqueous solution (1.0 mL). The quenched mixture was partitioned between 5% wt NaHCO$_3$ aqueous solution (15 mL) and CH$_2$Cl$_2$ (20 mL). The aqueous layer was extracted again with CH$_2$Cl$_2$ (20 mL). The combined organic layers were concentrated. The residue was purified by silica gel chromatography (50% to 70% EtOAc/heptane and then 70% isocratic) to provide the desired product (477) as a white solid (29 mg, 68% yield). $^1$H NMR (400 MHz, CDCl$_3$): δ ppm 7.98 (d, J=8.0 Hz, 2H), 7.39 (d, J=8.0 Hz, 2H), 7.23 (m, 1H), 7.11-7.08 (m, 3H), 6.27 (m, 1H), 5.25 (m, 1H), 4.74 (d, J=14.4 Hz, 1H), 4.69 (d, J=14.8 Hz, 1H), 4.19-4.12 (m, 4H), 3.89 (s, 3H), 3.75 (dd, J=8.4, 8.4 Hz, 2H), 2.97 (s, 3H), 2.71 (t, J=7.6 Hz, 2H), 2.07-2.00 (m, 2H), 1.53 (d, J=6.8 Hz, 3H). LCMS (ES) (M+H)=609.1.

208

(S)-4-(1-(1-(3-(3-Fluoropropyl)benzyl)-6-(trifluoromethyl)-2,3-dihydro-1H-imidazo[1,2-b]pyrazole-7-carboxamido)ethyl)benzoic acid (Compound 96)

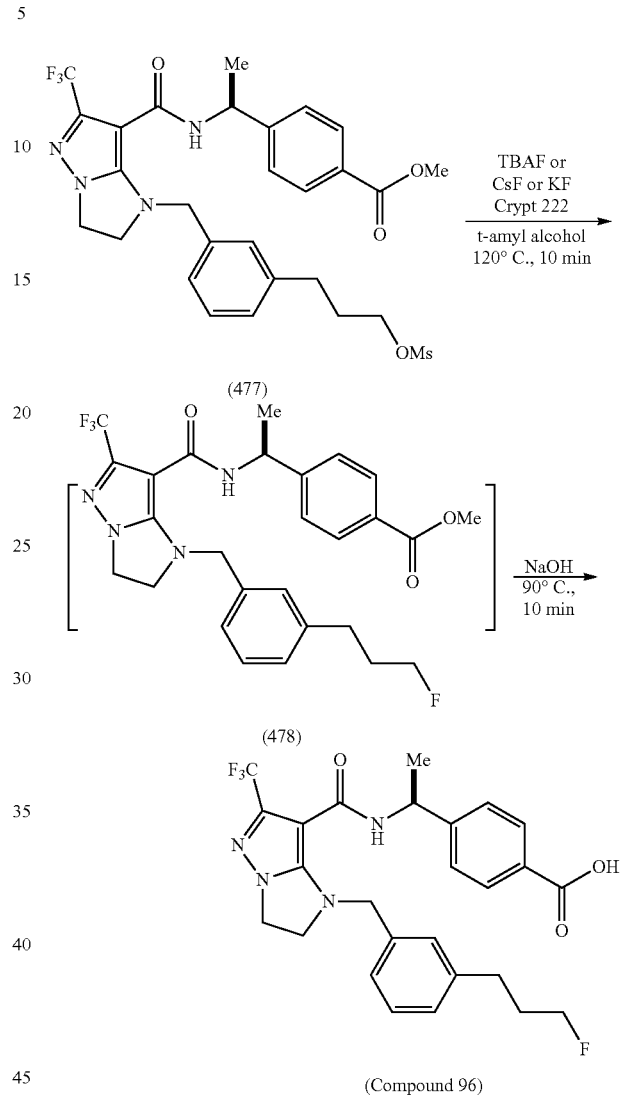

(477)

(478)

(Compound 96)

To a mixture of methyl (S)-4-(1-(1-(3-(3-((methylsulfonyl)oxy)propyl)benzyl)-6-(trifluoromethyl)-2,3-dihydro-1H-imidazo[1,2-b]pyrazole-7-carboxamido)ethyl)benzoate (477) (8 mg, 0.013 mmol) in t-amyl alcohol (0.8 mL) was added TBAF hydrate (18 mg, 0.066 mmol) at ambient temperature. The reaction vial was placed in a 110-120° C. oil bath. After stirring at that temperature for 10-15 minutes, the heating bath temperature was adjusted to 90° C. A 3 M NaOH aqueous solution (48 ML, 0.14 mmol) was added. After heating at 90° C. for 15 to 20 minutes, the heating bath was removed and the reaction mixture was allowed to cool to 23° C. The reaction was quenched by addition of 1 M HCl aqueous solution (0.2 mL, 0.20 mmol). The quenched mixture was partitioned between water (5 mL) and CH$_2$Cl$_2$ (5 mL). The aqueous layer was extracted again with CH$_2$Cl$_2$ (2×5 mL). The combined organic layers were concentrated. The residue was purified by silica gel chromatography (50% to 80% EtOAc/heptane, 80% isocratic, 0% to 5% MeOH/EtOAc, 5% isocratic) to provide the desired product (Compound 96) as a white solid (4.5 mg, 66% yield). $^1$H NMR (400 MHz, CDCl₃): δ ppm 8.04 (d, J=8.8 Hz, 2H), 7.43 (d, J=8.4 Hz, 2H), 7.23 (m, 1H), 7.13-7.07 (m, 3H), 6.28 (m, 1H), 5.27 (m, 1H), 4.72 (s, 2H), 4.41 (ddd, J=6.0, 6.0, 47 Hz, 2H), 4.16-4.11 (m, 2H), 3.76 (dd, J=8.4, 8.4 Hz, 2H), 2.70 (t, J=8.0 Hz, 2H), 2.03-1.89 (m, 2H), 1.55 (d, J=7.2 Hz, 3H). LCMS (ES) (M+H)=519.1.

Example XCV (S)-4-(1-(1-(4-(3-fluoropropyl)benzyl)-6-(trifluoromethyl)-2,3-dihydro-1H-imidazo[1,2-b]pyrazole-7-carboxamido)ethyl)benzoic acid (Compound 97)

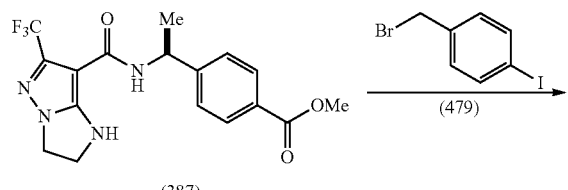
(387)

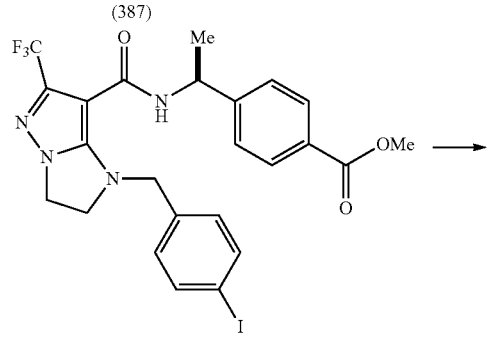
(480)

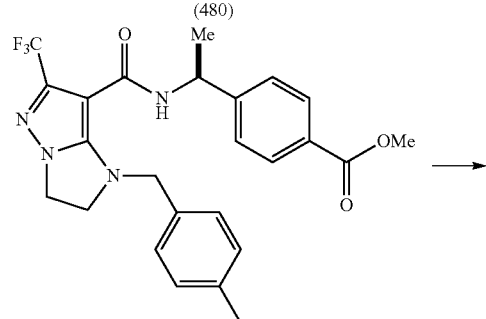
(481)

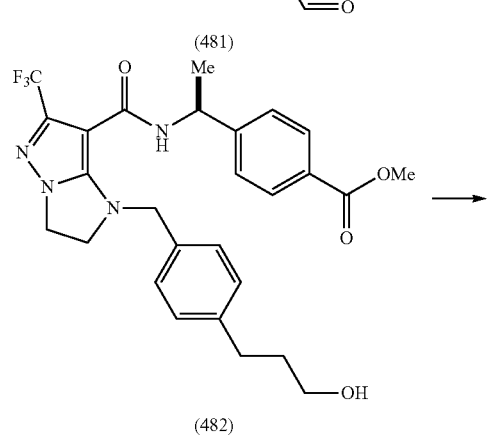
(482)

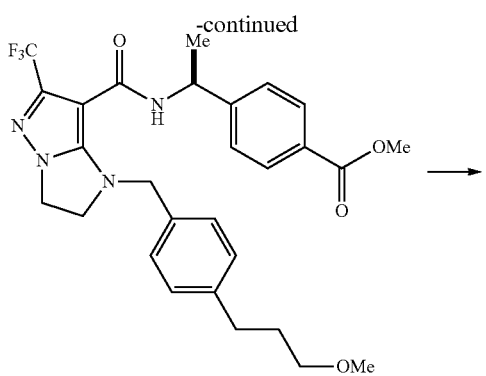
(483)

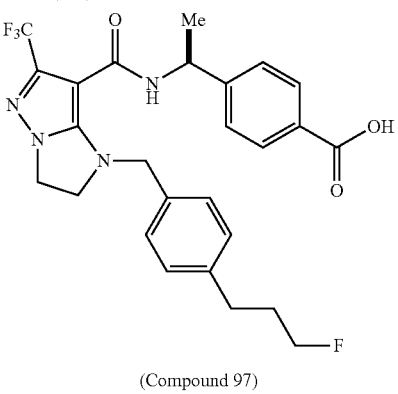 [SMILES: C[C@H](NC(=O)c1c(C(F)(F)F)nn2c1N(Cc1ccc(CCCF)cc1)CC2)c1ccc(C(=O)O)cc1]
(Compound 97)

Following the similar procedure for the preparation of (S)-4-(1-(1-(3-(3-fluoropropyl)benzyl)-6-(trifluoromethyl)-2,3-dihydro-H-imidazo[1,2-b]pyrazole-7-carboxamido)ethyl)benzoic acid (Compound 96) from methyl (S)-4-(1-(1-(3-iodobenzyl)-6-(trifluoromethyl)-2,3-dihydro-1H-imidazo[1,2-b]pyrazole-7-carboxamido)ethyl)benzoate (405) described in Example XCIV, Compound 97 was similarly prepared from methyl (S)-4-(1-(1-(4-iodobenzyl)-6-(trifluoromethyl)-2,3-dihydro-1H-imidazo[1,2-b]pyrazole-7-carboxamido)ethyl)benzoate (480), which was prepared from methyl (S)-4-(1-(6-(trifluoromethyl)-2,3-dihydro-1H-imidazo[1,2-b]pyrazole-7-carboxamido)ethyl)benzoate (387) and 1-(bromomethyl)-4-iodobenzene (479) following the similar procedure for the preparation of methyl (S)-4-(1-(1-(3-iodobenzyl)-6-(trifluoromethyl)-2,3-dihydro-1H-imidazo[1,2-b]pyrazole-7-carboxamido)ethyl)benzoate (405) described in Example LXIX.

Methyl (S)-4-(1-(1-(4-iodobenzyl)-6-(trifluoromethyl)-2,3-dihydro-1H-imidazo[1,2-b]pyrazole-7-carboxamido)ethyl)benzoate (480)

¹H NMR (400 MHz, CDCl3): δ ppm 8.00 (d, J=8.4 Hz, 2H), 7.62 (d, J=8.0 Hz, 2H), 7.39 (d, J=8.4 Hz, 2H), 7.00 (d, J=8.4 Hz, 2H), 6.25 (m, 1H), 5.23 (m, 1H), 4.72 (d, J=14.8 Hz, 1H), 4.67 (d, J=14.8 Hz, 1H), 4.14 (dd, J=8.8, 8.0 Hz, 2H), 3.91 (s, 3H), 3.74 (dd, J=8.8, 8.0 Hz, 2H), 1.53 (d, J=6.8 Hz, 3H). LCMS (ES) (M+H)=599.4.

Methyl (S)-4-(1-(1-(4-(3-oxopropyl)benzyl)-6-(trifluoromethyl)-2,3-dihydro-1H-imidazo[1,2-b]pyrazole-7-carboxamido)ethyl)benzoate (481)

¹H NMR (400 MHz, CDCl3): δ ppm 9.81 (s, 1H), 7.99 (d, J=8.0 Hz, 2H), 7.40 (d, J=8.0 Hz, 2H), 7.15 (d, J=7.6 Hz, 2H), 7.11 (d, J=7.6 Hz, 2H), 6.24 (m, 1H), 5.25 (m, 1H), 4.74 (d, J=14.4 Hz, 1H), 4.67 (d, J=14.4 Hz, 1H), 4.12 (dd, J=8.8, 8.4 Hz, 2H), 3.90 (s, 3H), 3.75 (dd, J=8.4, 8.4 Hz, 2H), 2.94 (t, J=7.6 Hz, 2H), 2.76 (t, J=7.6 Hz, 2H), 1.54 (d, J=6.8 Hz, 3H). LCMS (ES) (M+H)=529.2.

Methyl (S)-4-(1-(1-(4-(3-hydroxypropyl)benzyl)-6-(trifluoromethyl)-2,3-dihydro-1H-imidazo[1,2-b]pyrazole-7-carboxamido)ethyl)benzoate (482)

LCMS (ES) (M+H)=531.2.

Methyl (S)-4-(1-(1-(4-(3-((methylsulfonyl)oxy)propyl)benzyl)-6-(trifluoromethyl)-2,3-dihydro-1H-imidazo[1,2-b]pyrazole-7-carboxamido)ethyl)benzoate (483)

¹H NMR (400 MHz, CDCl3): δ ppm 7.99 (d, J=8.0 Hz, 2H), 7.40 (d, J=8.0 Hz, 2H), 7.17 (d, J=8.0 Hz, 2H), 7.11 (d, J=8.0 Hz, 2H), 6.25 (m, 1H), 5.25 (m, 1H), 4.74 (d, J=14.4 Hz, 1H), 4.68 (d, J=14.4 Hz, 1H), 4.21 (t, J=6.8 Hz, 2H), 4.13 (dd, J=8.8, 8.0 Hz, 2H), 3.89 (s, 3H), 3.76 (dd, J=8.4, 8.4 Hz, 2H), 3.00 (s, 3H), 2.73 (t, J=6.8 Hz, 2H), 2.09-2.02 (m, 2H), 1.54 (d, J=7.2 Hz, 3H). LCMS (ES) (M+H)=609.1.

(S)-4-(1-(1-(4-(3-Fluoropropyl)benzyl)-6-(trifluoromethyl)-2,3-dihydro-1H-imidazo[1,2-b]pyrazole-7-carboxamido)ethyl)benzoic acid (Compound 97)

¹H NMR (400 MHz, CDCl₃): δ ppm 8.05 (d, J=7.6 Hz, 2H), 7.43 (d, J=8.0 Hz, 2H), 7.15-7.12 (m, 4H), 6.26 (m, 1H), 5.27 (m, 1H), 4.75 (d, J=14.4 Hz, 1H), 4.67 (d, J=14.4 Hz, 1H), 4.44 (ddd, J=6.0, 6.0, 47 Hz, 2H), 4.15-4.11 (m, 2H), 3.79-3.74 (m, 2H), 2.72 (t, J=7.6 Hz, 2H), 2.04-1.93 (m, 2H), 1.55 (d, J=6.8 Hz, 3H). LCMS (ES) (M+H)=519.1.

Example XCVI (S)-4-(1-(1-(4-(3-Fluoropropyl)-3-(trifluoromethyl)benzyl)-6-(trifluoromethyl)-2,3-dihydro-1H-imidazo[1,2-b]pyrazole-7-carboxamido)ethyl)benzoic acid (Compound 98)

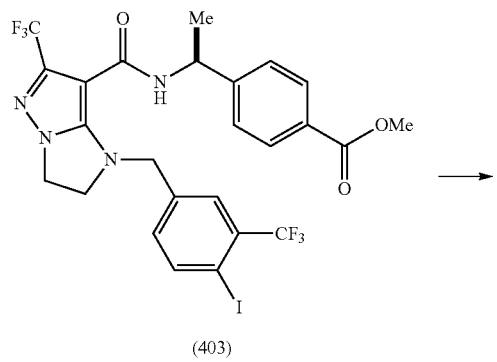

(403)

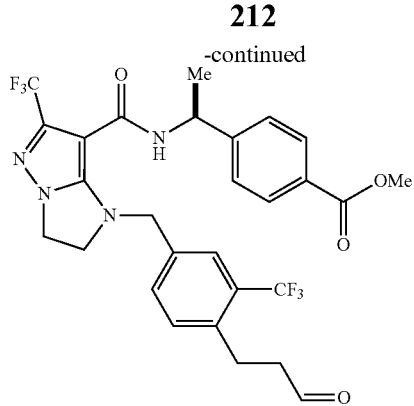

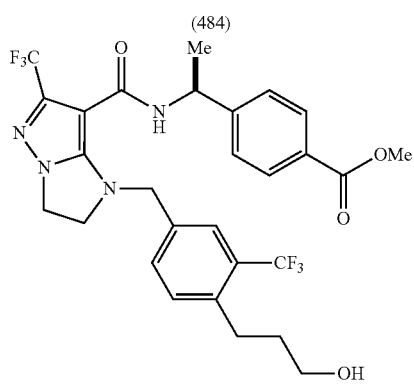

(484)

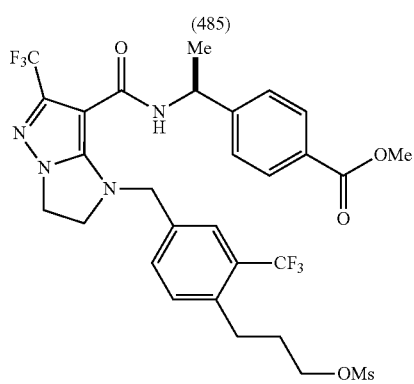

(485)

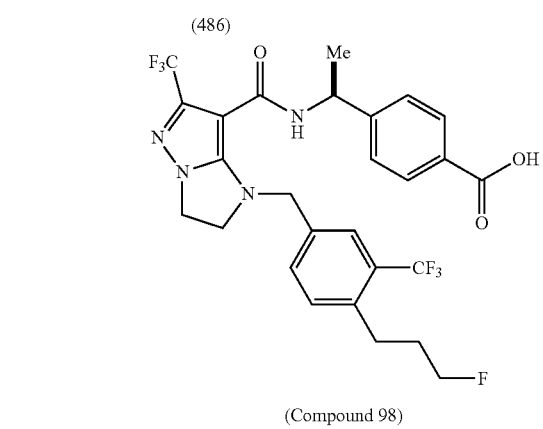

(486)

(Compound 98)

Following the similar procedure for the preparation of (S)-4-(1-(1-(3-(3-fluoropropyl)benzyl)-6-(trifluoromethyl)-2,3-dihydro-1H-imidazo[1,2-b]pyrazole-7-carboxamido) ethyl)benzoic acid (Compound 96) from methyl (S)-4-(1-(1-(3-iodobenzyl)-6-(trifluoromethyl)-2,3-dihydro-1H-imidazo[1,2-b]pyrazole-7-carboxamido)ethyl)benzoate (405) described in Example XCIV, Compound 98 was similarly prepared from methyl (S)-4-(1-(1-(4-iodo-3-(trifluoromethyl)benzyl)-6-(trifluoromethyl)-2,3-dihydro-1H-imidazo[1,2-b]pyrazole-7-carboxamido)ethyl)benzoate (403).

Methyl (S)-4-(1-(1-(4-(3-oxopropyl)-3-(trifluoromethyl)benzyl)-6-(trifluoromethyl)-2,3-dihydro-1H-imidazo[1,2-b]pyrazole-7-carboxamido)ethyl)benzoate (484)

$^1$H NMR (400 MHz, CDCl3): δ ppm 9.82 (s, 1H), 7.99 (d, J=8.4 Hz, 2H), 7.53 (s, 1H), 7.39 (d, J=8.4 Hz, 2H), 7.27-7.24 (m, 2H), 6.29 (m, 1H), 5.22 (m, 1H), 4.82 (d, J=14.8 Hz, 1H), 4.76 (d, J=14.8 Hz, 1H), 4.20-4.14 (m, 2H), 3.90 (s, 3H), 3.78-3.73 (m, 2H), 3.10 (t, J=7.2 Hz, 2H), 2.77 (t, J=7.6 Hz, 2H), 1.54 (d, J=6.8 Hz, 3H). LCMS (ES) (M+H)=597.2.

Methyl (S)-4-(1-(1-(4-(3-hydroxypropyl)-3-(trifluoromethyl)benzyl)-6-(trifluoromethyl)-2,3-dihydro-1H-imidazo[1,2-b]pyrazole-7-carboxamido)ethyl)benzoate (485)

LCMS (ES) (M+H)=599.2.

Methyl (S)-4-(1-(1-(4-(3-((methylsulfonyl)oxy)propyl)-3-(trifluoromethyl)benzyl)-6-(trifluoromethyl)-2,3-dihydro-1H-imidazo[1,2-b]pyrazole-7-carboxamido)ethyl)benzoate (486)

$^1$H NMR (400 MHz, CDCl3): δ ppm 7.99 (d, J=8.4 Hz, 2H), 7.53 (s, 1H), 7.42-7.38 (m, 3H), 7.27 (m, 1H), 6.28 (m, 1H), 5.23 (m, 1H), 4.82 (d, J=14.8 Hz, 1H), 4.76 (d, J=14.8 Hz, 1H), 4.27 (t, J=6.4 Hz, 2H), 4.19-4.14 (m, 2H), 3.90 (s, 3H), 3.78-3.74 (m, 2H), 2.89 (t, J=8.0 Hz, 2H), 2.08-2.02 (m, 2H), 1.54 (d, J=7.2 Hz, 3H). LCMS (ES) (M+H)=677.2.

(S)-4-(1-(1-(4-(3-Fluoropropyl)-3-(trifluoromethyl)benzyl)-6-(trifluoromethyl)-2,3-dihydro-1H-imidazo[1,2-b]pyrazole-7-carboxamido)ethyl)benzoic acid (Compound 98)

$^1$H NMR (400 MHz, CDCl$_3$): δ ppm 8.05 (d, J=8.4 Hz, 2H), 7.52 (s, 1H), 7.44-7.38 (m, 3H), 7.27 (m, 1H), 6.30 (m, 1H), 5.24 (m, 1H), 4.82 (d, J=14.8 Hz, 1H), 4.76 (d, J=14.8 Hz, 1H), 4.48 (ddd, J=6.0, 6.0, 48 Hz, 2H), 4.19-4.15 (m, 2H), 3.78-3.74 (m, 2H), 2.89 (t, J=8.4 Hz, 2H), 2.05-1.92 (m, 2H), 1.55 (d, J=6.8 Hz, 3H). LCMS (ES) (M+H)=587.3.

Example XCVI (S)-4-(1-(1-(3-(3-Fluoropropyl)-5-(trifluoromethyl)benzyl)-6-(trifluoromethyl)-2,3-dihydro-1H-imidazo[1,2-b]pyrazole-7-carboxamido)ethyl)benzoic acid (Compound 99)

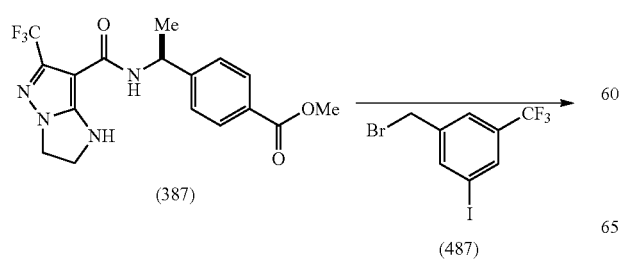

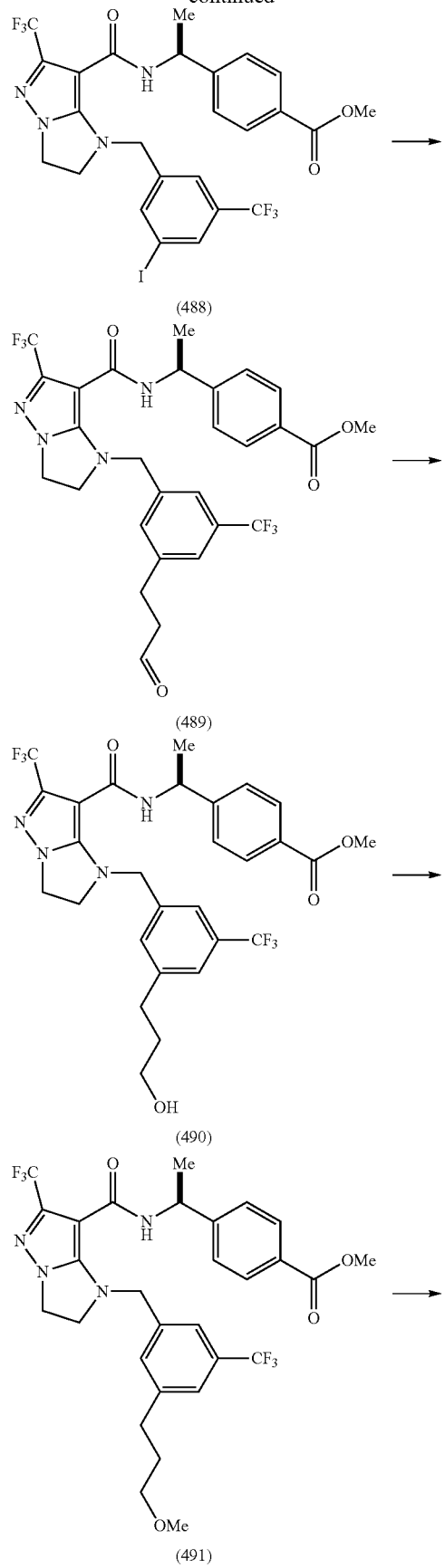

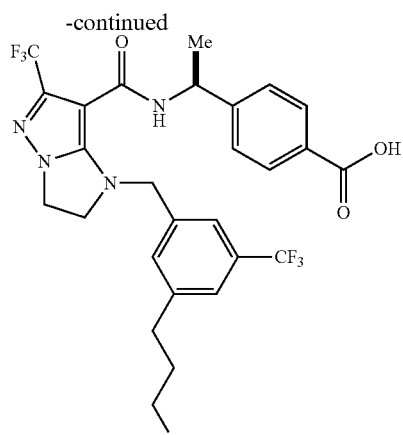

(Compound 99)

Following the similar procedure for the preparation of (S)-4-(1-(1-(3-(3-fluoropropyl)benzyl)-6-(trifluoromethyl)-2,3-dihydro-1H-imidazo[1,2-b]pyrazole-7-carboxamido)ethyl)benzoic acid (Compound 96) from methyl (S)-4-(1-(1-(3-iodobenzyl)-6-(trifluoromethyl)-2,3-dihydro-1H-imidazo[1,2-b]pyrazole-7-carboxamido)ethyl)benzoate (405) described in Example XCIV, Compound 99 was similarly prepared from methyl (S)-4-(1-(1-(3-iodo-5-(trifluoromethyl)benzyl)-6-(trifluoromethyl)-2,3-dihydro-H-imidazo[1,2-b]pyrazole-7-carboxamido)ethyl)benzoate (488), which was prepared from methyl (S)-4-(1-(6-(trifluoromethyl)-2,3-dihydro-1H-imidazo[1,2-b]pyrazole-7-carboxamido)ethyl)benzoate (387) and 1-(bromomethyl)-3-iodo-5-(trifluoromethyl)benzene (487) following the similar procedure for the preparation of methyl (S)-4-(1-(1-(3-iodobenzyl)-6-(trifluoromethyl)-2,3-dihydro-1H-imidazo[1,2-b]pyrazole-7-carboxamido)ethyl)benzoate (405) described in Example LXIX.

Methyl (S)-4-(1-(1-(3-iodo-5-(trifluoromethyl)benzyl)-6-(trifluoromethyl)-2,3-dihydro-1H-imidazo[1,2-b]pyrazole-7-carboxamido)ethyl)benzoate (488)

$^1$H NMR (400 MHz, CDCl3): δ ppm 8.00 (d, J=8.4 Hz, 2H), 7.87-7.86 (m, 2H), 7.52 (s, 1H), 7.38 (d, J=8.4 Hz, 2H), 6.29 (m, 1H), 5.21 (m, 1H), 4.88 (d, J=14.8 Hz, 1H), 4.75 (d, J=14.8 Hz, 1H), 4.23-4.18 (m, 2H), 3.90 (s, 3H), 3.79-3.75 (m, 2H), 1.54 (d, J=7.2 Hz, 3H). LCMS (ES) (M+H)=677.3.

Methyl (S)-4-(1-(1-(3-(3-oxopropyl)-5-(trifluoromethyl)benzyl)-6-(trifluoromethyl)-2,3-dihydro-1H-imidazo[1,2-b]pyrazole-7-carboxamido)ethyl)benzoate (489)

$^1$H NMR (400 MHz, CDCl3): δ ppm 9.78 (s, 1H), 7.98 (d, J=8.0 Hz, 2H), 7.40-7.34 (m, 5H), 6.31 (m, 1H), 5.23 (m, 1H), 4.84 (d, J=14.8 Hz, 1H), 4.76 (d, J=14.8 Hz, 1H), 4.20-4.16 (m, 2H), 3.90 (s, 3H), 3.77-3.73 (m, 2H), 2.97 (t, J=7.6 Hz, 2H), 2.79 (t, J=7.2 Hz, 2H), 1.54 (d, J=6.8 Hz, 3H). LCMS (ES) (M+H)=597.2.

Methyl (S)-4-(1-(1-(3-(3-hydroxypropyl)-5-(trifluoromethyl)benzyl)-6-(trifluoromethyl)-2,3-dihydro-1H-imidazo[1,2-b]pyrazole-7-carboxamido)ethyl)benzoate (490)

LCMS (ES) (M+H)=599.3.

Methyl (S)-4-(1-(1-(3-(3-((methylsulfonyl)oxy)propyl)-5-(trifluoromethyl)benzyl)-6-(trifluoromethyl)-2,3-dihydro-1H-imidazo[1,2-b]pyrazole-7-carboxamido)ethyl)benzoate (491)

$^1$H NMR (400 MHz, CDCl3): δ ppm 8.00-7.96 (m, 2H), 7.39-7.34 (m, 5H), 6.29 (m, 1H), 5.21 (m, 1H), 4.83 (d, J=14.8 Hz, 1H), 4.76 (d, J=14.8 Hz, 1H), 4.20-4.14 (m, 4H), 3.89 (s, 3H), 3.77-3.73 (m, 2H), 2.80 (s, 3H), 2.78 (t, J=7.6 Hz, 2H), 2.08-2.01 (m, 2H), 1.53 (d, J=6.8 Hz, 3H). LCMS (ES) (M+H)=677.3.

(S)-4-(1-(1-(3-(3-Fluoropropyl)-5-(trifluoromethyl)benzyl)-6-(trifluoromethyl)-2,3-dihydro-1H-imidazo[1,2-b]pyrazole-7-carboxamido)ethyl)benzoic acid (Compound 99)

$^1$H NMR (400 MHz, CDCl$_3$): δ ppm 8.05 (d, J=8.4 Hz, 2H), 7.42 (d, J=8.8 Hz, 2H), 7.38-7.32 (m, 3H), 6.32 (m, 1H), 5.24 (m, 1H), 4.86 (d, J=14.8 Hz, 1H), 4.76 (d, J=14.8 Hz, 1H), 4.42 (ddd, J=6.0, 6.0, 48 Hz, 2H), 4.20-4.16 (m, 2H), 3.78-3.74 (m, 2H), 2.77 (t, J=7.6 Hz, 2H), 2.04-1.91 (m, 2H), 1.55 (d, J=7.2 Hz, 3H). LCMS (ES) (M+H)=587.2.

Example XCVII 1-tert-Butyl 7-ethyl 6-(2-ethoxy-1,1-difluoro-2-oxoethyl)-2,3-dihydro-1H-imidazo[1,2-b]pyrazole-1,7-dicarboxylate (493)

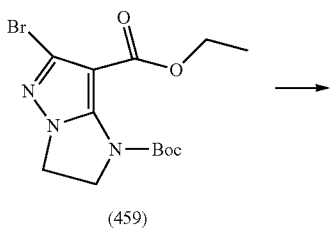

(459)

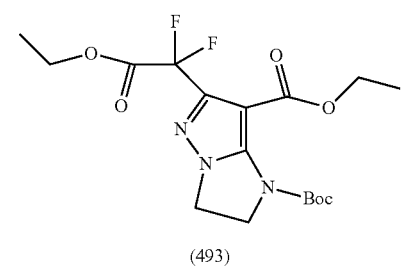

(493)

A heterogeneous solution of Cu powder (0.88 g, 13.88 mmol) in DMSO (20 mL) was degassed at rt (vacuum-N$_2$ purging, 3 times), and aged for 30 min at 80° C. Then 1-tert-butyl 7-ethyl 6-bromo-2,3-dihydro-1H-imidazo[1,2-b]pyrazole-1,7-dicarboxylate (459) (1.0 g, 2.78 mmol) and ethyl 2-bromo-2,2-difluoroacetate (470) (1.5 mL, 11.7 mmol) were added. After degassing, the resulting reaction was aged for 6 h at this temp. After cooling to room temp, the reaction was quenched by addition of sat. aqueous ammonium chloride (10 mL). After dilution with ethyl acetate (50 mL) and 4:1 (vol/vol) mixtures of sat aqueous ammonium chloride—28% ammonium hydroxide (25 mL), phases were separated. After back-extraction of the aqueous layer, the combined organic phase was dried (MgSO$_4$), filtered and concentrated. The resulting crude product was purified by Biotage chromatography (n-Heptane-EtOAc) to give the desired product (493) as an oil (1.2 g, 86% yield). ¹H NMR (400 MHz, CDCl₃): δ ppm 4.5~4.4 (m, 2H), 4.4~4.1 (m, 6H), 1.5 (br s, 9H), 1.4~1.2 (m, 6H). LCMS (ES) (M+H)=404.15.

1-tert-Butyl 7-ethyl 6-(1,1-difluoro-2-hydroxy-ethyl)-2,3-dihydro-1H-imidazo[1,2-b]pyrazole-1,7-dicarboxylate (494)

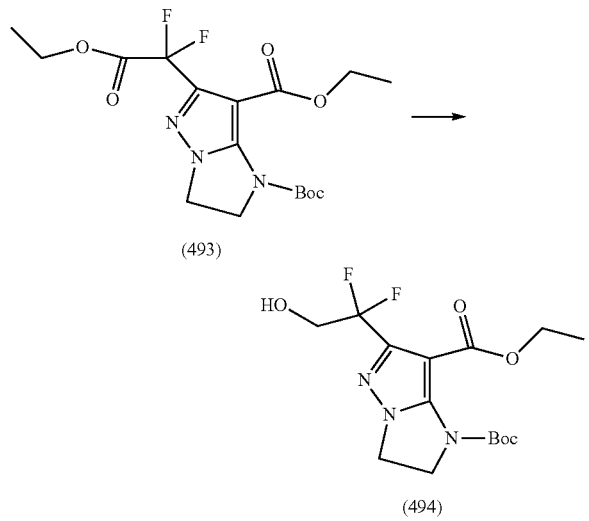

To a stirred solution of 1-tert-butyl 7-ethyl 6-(2-ethoxy-1,1-difluoro-2-oxoethyl)-2,3-dihydro-1H-imidazo[1,2-b]pyrazole-1,7-dicarboxylate (493) (0.2 g, 0.59 mmol) in a solution of 10:1 THF-MeOH (5 mL-0.5 mL) was added NaBH₄ (75 mg, 1.98 mmol, granules) at rt. The resulting solution was aged for 4 h. At this time the reaction was quenched with sat. aqueous ammonium chloride solution (2 mL), and extracted with ethyl acetate (3×10 mL). The combined org layers were washed with brine (15 mL), and dried over MgSO₄. After filtration, the filtrate was concentrated and the residue was directly purified by Biotage (load column with DCM solution and eluted with 10% to 50% E/H) to give the desired product (494) as an oil (160 mg, 89% yield). ¹H NMR (400 MHz, CDCl₃): δ ppm 4.50~4.40 (m, 2H), 4.35~4.25 (d, 4H), 4.2~4.10 (m, 3H), 1.50 (br s. 9H), 1.4~1.3 (m, 3H). LCMS (ES) (M+H)=362.12.

1-(tert-Butoxycarbonyl)-6-(1,1-difluoro-2-hydroxy-ethyl)-2,3-dihydro-1H-imidazo[1,2-b]pyrazole-7-carboxylic acid (495)

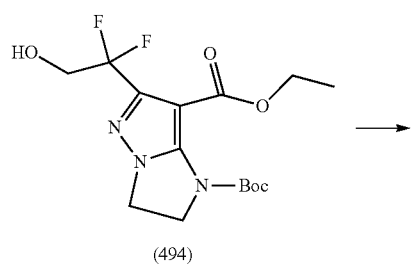

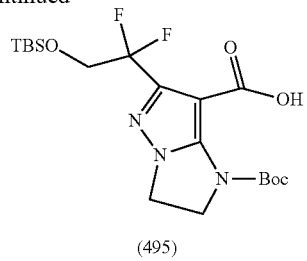

To a stirred solution of 1-tert-butyl 7-ethyl 6-(1,1-difluoro-2-hydroxyethyl)-2,3-dihydro-1H-imidazo[1,2-b]pyrazole-1,7-dicarboxylate (494) (0.2 g, 1.24 mmol) in MeOH—THF—H₂O (1:1:1, 2 mL each) was added LiOH (53 mg, 2.21 mmol). After aging for 13 h at rt, the reaction was warmed to 40° C. and aged for additional 6 h. The reaction was diluted with ethyl acetate (20 mL), and adjusted pH to 4 with 1N HCl. After phase separation, the aqueous layer was back-extracted with ethyl acetate (2×15 mL). The combined org layer was dried over MgSO₄, concentration and azeotropically dried with acetonitrile (2×). The crude product was used for the next reaction without further purification (175 mg as crude, 95% yield without purity adjustment).

The azeotropically dried 1-(tert-butoxycarbonyl)-6-(1,1-difluoro-2-hydroxyethyl)-2,3-dihydro-1H-imidazo[1,2-b]pyrazole-7-carboxylic acid (495) (170 mg, 0.51 mmol) was dissolved in DMF (6 mL) and treated with TBSCl (200 mg, 1.31 mmol) and imidazole (107 mg, 1.57 mmol) at 5° C. The reaction was warmed to rt, and aged for 15 h at this temp. At the end of reaction, the reaction was quenched by addition of aq sodium bicarbonate (5 mL). After dilution with aq. sodium bicarbonate, the reaction product (495) was extracted with ethyl acetate (3×20 mL). After drying with MgSO₄, the combined org layers were evaporated to give the crude product (200 mg). The resulting crude bis-TBS ester ether was redissolved in THF (6 mL), and treated with NaOH (0.63 mL, 0.63 mmol). After aging for 8 h at rt, the reaction was diluted with Ethyl acetate (15 mL), and pH was adjusted to 4 by addition of 1N HCl. Extractive workup with ethyl acetate (2×20 mL) followed by drying (MgSO₄), filtration, and concentration of the org layer gave the crude product. Filtration over silica gel plug and eluted with ethyl acetate gave the product (495) (200 mg, 80% overall yield). 1H NMR (400 MHz, CDCl₃): δ ppm 4.55~4.45 (m, 2H), 4.354.20 (m, 4H), 1.55 (br s, 9H), 0.85 (br s, 9H), 0.0 (s, 6H). LCMS (ES) (M+H)=448.22.

Methyl (S)-4-(1-(6-(2-((tert-butyldimethylsilyl)oxy)-1,1-difluoroethyl)-2,3-dihydro-1H-imidazo[1,2-b]pyrazole-7-carboxamido)ethyl)benzoate (496)

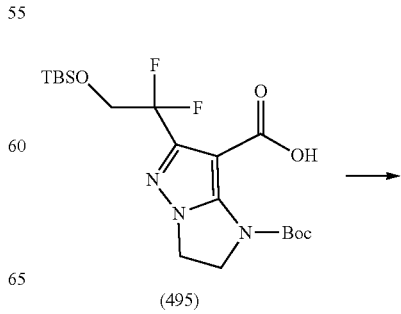

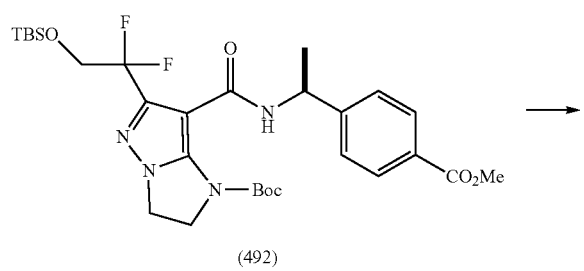

(492)

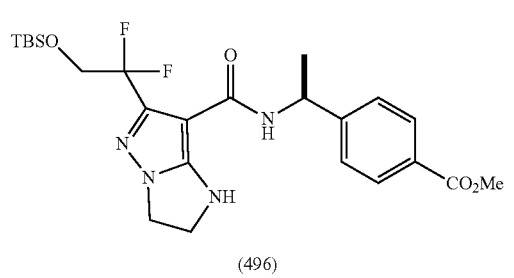

(496)

To a stirred 1-(tert-butoxycarbonyl)-6-(1,1-difluoro-2-((2-(trimethylsilyl)propan-2-yl)oxy)ethyl)-2,3-dihydro-1H-imidazo[1,2-b]pyrazole-7-carboxylic acid (495) (350 mg, 0.78 mmol) in DMF (5 mL) were treated with (S)-methyl 4-(1-aminoethyl)benzoate (216) (250 mg, 1.39 mmol), 1-(3-Dimethylaminopropyl)-3-ethylcarbodiimide hydrochloride (300 mg, 1.56 mmol), TEA (0.27 mL, 1.95 mmol), and catalytic amount of DMAP (19 mg, 0.16 mmol).

After aging 14 h at rt, the reaction was diluted with aq ammonium chloride (10 mL) and ethyl acetate (20 mL). After phase separation, the org layer was back-extracted with ethyl acetate (15 mL). The combined org layer was washed with brine (15 mL), and dried over MgSO₄. After filtration, the filtrate was concentrated to give the crude product as an oil. This crude material was used for the next step without further purification.

To a stirred solution of (S)-tert-butyl 6-(2-((tert-butyldimethylsilyl)oxy)-1,1-difluoroethyl)-7-((1-(4-(methoxycarbonyl)phenyl)ethyl)carbamoyl)-2,3-dihydro-1H-imidazo[1,2-b]pyrazole-1-carboxylate (492) (400 mg) in dichloromethane (3 mL), and treated with TFA (1.5 mL) at 0° C., then warmed to rt. After aging 16 h at room temperature, organic solvents were removed under reduced pressure, and the residue was diluted with methylene chloride (20 mL). After extraction with sat aq. NaHCO₃ (15 mL), the aqueous layer was back extracted with methylene chloride. The combined org layers were washed with brine, dried over MgSO₄. Removal of the solvent and filtration over a small plug of silica gel pad followed by washing with ethyl acetate afforded the amino alcohol. The resulting TBS deprotected alcohol was subjected to the previously described condition using TBSCl (300 mg, 0.91 mmol), Imidazole (150 mg, 2.2 mmol) in DMF (6 mL). At the end of reaction, sat. aqueous ammonium chloride (15 mL) was added. Then, the reaction was diluted with ethyl acetate (15 mL). After extractive workup, the org layer was dried over MgSO₄, and concentrated. The crude product was purified over Biotage to give the desired product (496) as an oil (260 mg, 65% overall yield).

¹H NMR (400 MHz, CDCl₃): δ ppm 8.10-7.90 (m, 2H), 7.40-7.0 (m, 3H), 5.25-5.10 (m, 1H), 4.20-4.00 (m, 3H), 3.90 (s, 3H), 3.84-3.74 (m, 2H), 2.94-2.76 (m, 1H), 1.50-1.40 (m, 3H), 0.90 (br s, 9H). 0.10 (br s, 6H). LCMS (ES) (M+H)=509.33.

(S)-4-(1-(6-(1,1-Difluoro-2-hydroxyethyl)-1-(3-(trifluoromethyl)benzyl)-2,3-dihydro-1H-imidazo[1,2-b]pyrazole-7-carboxamido)ethyl)benzoic acid (Compound 100)

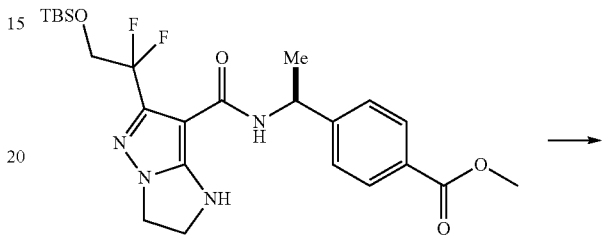

(496)

(Compound 100)

To a stirred solution of (S)-methyl 4-(1-(6-(2-((tert-butyldimethylsilyl)oxy)-1,1-difluoroethyl)-2,3-dihydro-1H-imidazo[1,2-b]pyrazole-7-carboxamido)ethyl)benzoate (496) (110 mg, 0.222 mmol) in DMF (3 mL) was added 1-(chloromethyl)-3-(trifluoromethyl)benzene (214) (43 mg, 0.238 mmol) and cesium carbonate (106 mg, 0.324 mmol) at rt. After aging for 15 h at rt, the resulting reaction was quenched by addition of sat. aqueous ammonium chloride (3 mL) and ethyl acetate (20 mL). After extraction with ethyl acetate (2×20 mL), the combined org layer was washed with brine (15 mL), and dried over MgSO₄. After filtration, the filtrate was concentrated to dryness (crude, 150 mg). A portion of the crude ester (20 mg, 0.039 mmol) was treated with aq 1N NaOH (0.4 mL, 0.4 mmol) in THF (2 mL). After aging for 16 h at rt. The reaction was pH adjustment with 1N HCl to pH 4, the reaction mixtures were directly purified by Reverse phase HPLC to give the desired product (Compound 100) (0.4 mg, 3% yield, 100% purity). ¹H NMR (500 MHz, CDCl₃): δ ppm 7.89 (br s, 2H), 7.52-7.06 (m, 6H), 5.37-5.35 (m, 1H), 5.12 (br s, 1H), 4.91 (m, 1H), 4.70-4.68 (br s, 1H), 4.15-4.04 (m, 3H), 3.65 (br s, 2H), 3.54-3.52 (m, 1H). 2.95-2.93 (m, 1H), 1.32-1.25 (m, 3H). LCMS (ES) (M+H)=529.2.

Example XCVIII (S)—N-(1-(4-((1-Cyanocyclopropyl)carbamoyl)phenyl)ethyl)-6-(trifluoromethyl)-1-(3-(trifluoromethyl)benzyl)-2,3-dihydro-1H-imidazo[1,2-b]pyrazole-7-carboxamide (Compound 101)

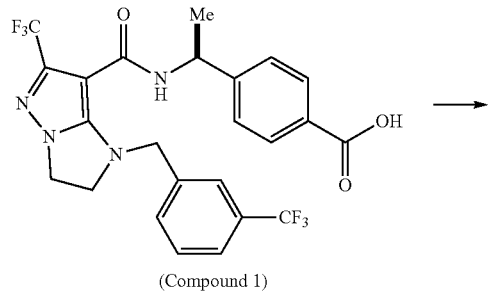

(Compound 1)

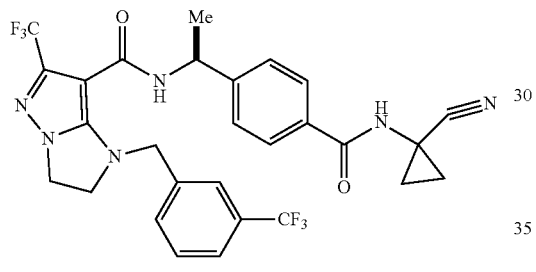

(Compound 101)

To a stirred solution of 6-(trifluoromethyl)-1-(3-(trifluoromethyl)benzyl)-2,3-dihydro-1H-imidazo[1,2-b]pyrazole-7-carboxylic acid (Compound 1) (25 mg, 0.047 mmol), 1-aminocyclopropanecarbonitrile hydrochloride (12.9 mg, 0.11 mmol) and 4-ethylmorpholine (20 uL, 0.166 mmol) in acetonitrile (3 mL) were added 1-Propanephosphonic acid cyclic anhydride (85 uL, 0.142 mmol, 50% solution in ethyl acetate) at rt. The resulting solution was aged for 14 h at rt. At this time, the reaction was quenched by addition of sat. aqueous NaHCO₃ (2 mL). The crude product was extracted with ethyl acetate (2×10 mL), and the organic layers were dried over MgSO₄. After filtration, the filtrate was concentrated and directly purified by Reverse phase HPLC to give the desired product (Compound 101) (10 mg, 35% yield). $^1$H NMR (400 MHz, CDCl₃): δ ppm 7.59 (d, J=8.1 Hz, 2H), 7.46 (m, 2H), 7.39-7.27 (m, 4H), 5.55 (br s, 1H), 6.18 (d, J=3.9 Hz, 1H), 5.10 (dd, J=13.1, 7.1 Hz, 1H), 4.73 (m, 2H), 4.10 (dd, J=8.5, 7.3 Hz, 2H), 3.76 (dd, J=8.5, 8.2 Hz, 2H), 1.54-1.41 (m, 5H), 1.23 (m, J=7.2 Hz, 2H). LCMS (ES) (M+H)=591.21.

Example XCIX

Methyl (S)-4-(1-(1-(2-fluorobenzoyl)-6-(trifluoromethyl)-2,3-dihydro-1H-imidazo[1,2-b]pyrazole-7-carboxamido)ethyl)benzoate (Compound 105)

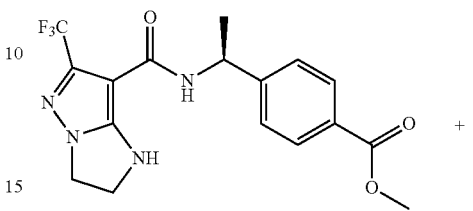

(387)

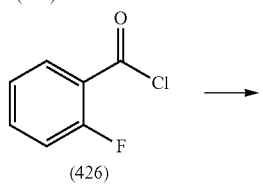

(426)

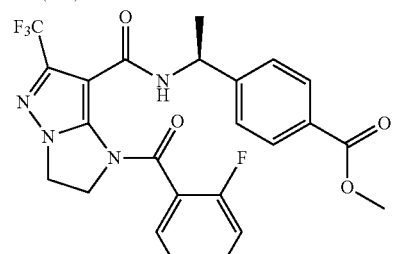

(Compound 105)

(S)-methyl 4-(1-(6-(trifluoromethyl)-2,3-dihydro-1H-imidazo[1,2-b]pyrazole-7-carboxamido)ethyl)benzoate (387) (30 mg, 0.078 mmol) was dissolved in THF (0.6 ml) and cooled to 0° C. Et₃N (32.8 μl, 0.235 mmol) was added followed by the addition of 2-Fluorobenzoyl chloride (14.05 μl, 0.118 mmol). The mixture was stirred at r.t. overnight. Upon completion of the reaction, it was quenched with NaHCO₃ solution (5 ml), extracted with DCM (30 ml), washed with brine (5 ml). The organic layer was concentrated and purified by flash chromatography to give Compound 105 as colorless oil (35.2 mg, 89% yield). $^1$HNMR (400 MHz, CDCl₃): δ ppm 7.97 (d, J=8.8 Hz, 2H), 7.60 (d, J=8.8 Hz, 1H), 7.59-7.52 (m, 1H), 7.43 (d, J=8.0 Hz, 2H), 7.31 (t, J=6.4 Hz, 1H), 7.18 (t, J=9.2 Hz, 1H), 7.06 (br s, 1H), 5.25 (t, J=7.2 Hz, 1H), 4.56-4.50 m, 2H), 4.37 (t, J=8.0 Hz, 2H), 3.90 (s, 3H), 1.54 (d, J=6.8 Hz, 3H). LCMS (ES) (M+Na)=527.

Example C

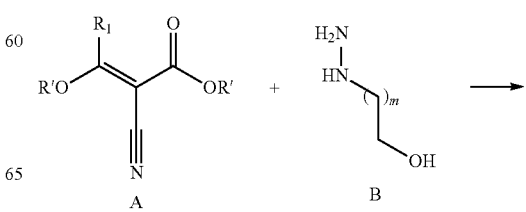

223
-continued

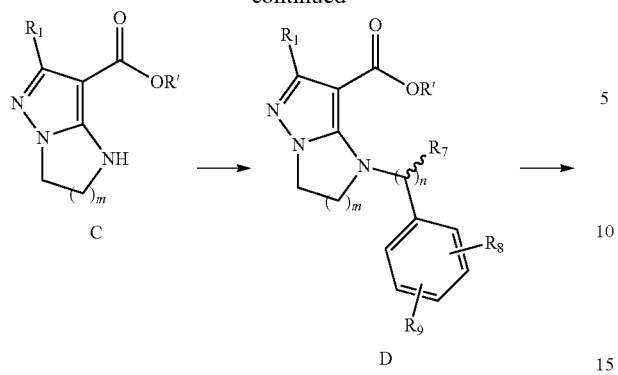

C

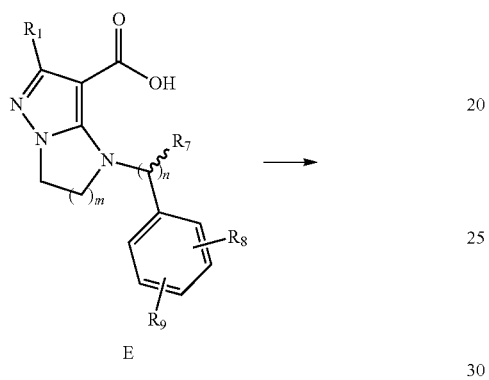

E

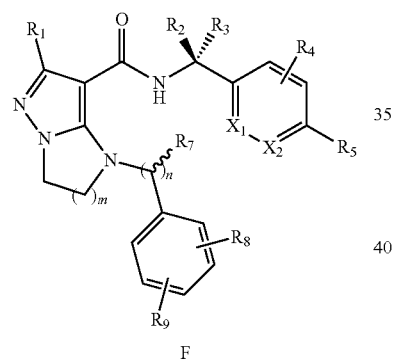

F

Following similar procedures for the preparation of (S)-4-(1-(6-(trifluoromethyl)-1-(3-(trifluoromethyl)benzyl)-2,3-dihydro-1H-imidazo[1,2-b]pyrazole-7-carboxamido)ethyl) benzoic acid (Compound 1) or (S)-4-(1-(6-ethyl-1-(3-(trifluoromethyl)benzyl)-2,3-dihydro-1H-imidazo[1,2-b] pyrazole-7-carboxamido)ethyl)benzoic acid (Compound 59), the general compound structure F could be prepared from suitable compounds A and B using suitably substituted ($R_8$ and $R_9$) aromatic or benzylic halides and suitably substituted ($R_4$ and $R_5$) (hetero)aromatic acid derivatives or (hetero)aromatic acid precursors or (hetero)aromatic tetrazole (here n=0-1). It will be noted that "(hetero)aromatic" indicates an aromatic group that optionally has one or more heteroatom substitutions in the aromatic ring.

In some embodiments, substituents may be selected wherein $R_1$ is —$CH_3$, —$CF_3$, —$CH_2CH_3$, or phenyl; $R_2$ is —H, or —$CH_3$; $R_3$ is —H; or $R_2$ and $R_3$ taken together form a cyclopropyl with the carbon to which they are attached; $R_4$ is —H, —F, or —$CH_3$; $R_5$ is —C(O)OH, —C(O)$OCH_3$, —$CH_2$C(O)OH, cyclopropyl, —C(O)NHCN,

224

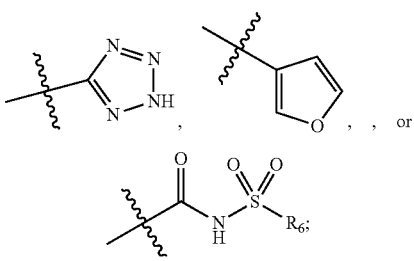

wherein $R_6$ is phenyl, —$CH_3$, cyclopropyl, or

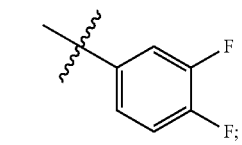 [SMILES: *c1ccc(F)c(F)c1]

m is 1-2; n is 0-1; $R_7$ is —H, —$CH_3$, or absent when n is 0; $R_8$ is —$CF_3$, —H, —Cl, —F, —$CH_2CH_3$, —$OCH_3$, —$CH_3$, or —$OCF_3$; $R_9$ is —H, —Cl, or —$CF_3$; and $X_1$ and $X_2$ are either both C, or one is C and the other is N.

Example CI

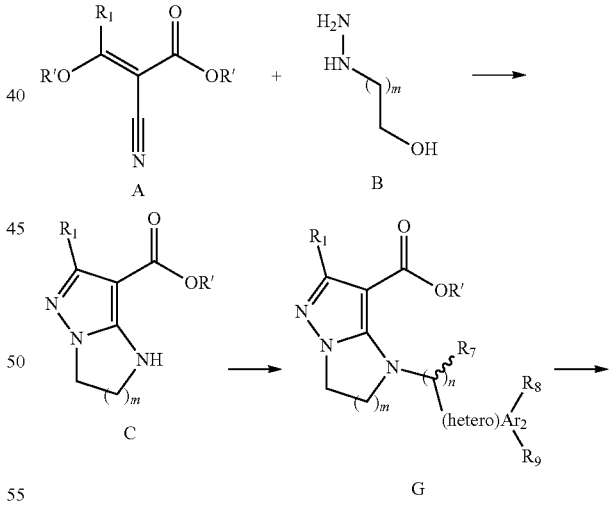

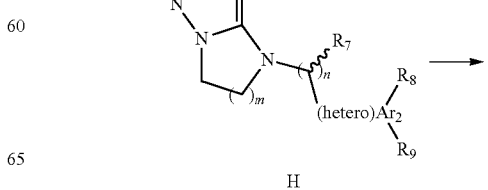

H

-continued

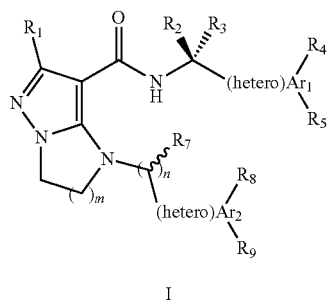

I

Following similar procedures for the preparation of compound F, the general compound structure I could be prepared from suitable compounds A and B using suitably substituted ($R_8$ and $R_9$) heteroaromatic, aromatic, benzylic or heterobenzylic halides and suitably substituted ($R_4$ and $R_5$) heteroaromatic acid derivatives, aromatic acid derivatives, heteroaromatic acid precursors, aromatic acid precursors, aromatic tetrazole, or heteroaromatic tetrazole. (here n=0-2). It will be noted that in the reaction scheme of Example CIII, "(hetero)Ar" indicates an aryl group, or, optionally, a heteroaryl group.

In typical embodiments $R_1$ is —$CF_3$, $C_1$-$C_6$ alkyl, $C_1$-$C_6$ alkoxy, cyano, aryl, aryloxy, amino, $C_1$-$C_6$ alkylamino, carbonyl, or phenyl; $R_2$ and $R_3$ are independently selected from —H, —$CH_3$, or —$CH_{3-z}F_z$, where z is 1 to 3; or $R_2$ and $R_3$ taken together form a cyclopropyl or cyclobutyl with the carbon to which they are attached; $R_4$ is —H, halogen, —$CF_3C_1$-$C_3$ alkyl optionally substituted with one or more —F, or $C_1$-$C_3$ alkoxy; $R_5$ is —C(O)OH, —C(O)OCH$_3$, —CH$_2$C(O)OH, cyclopropyl, —C(O)NHCN,

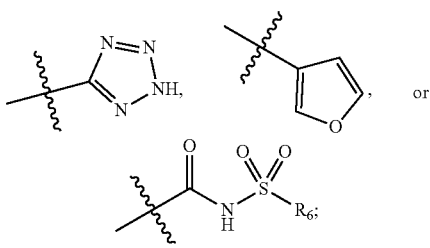

wherein $R_6$ is phenyl, —$CH_3$, cyclopropyl, or

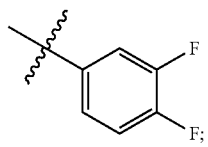 [SMILES: *c1ccc(F)c(F)c1]

m is 1-3; n is 0-5; $R_7$ is —H, —$CH_3$, or absent when n is 0; $R_8$ and $R_9$ are independently selected from —H, —$CF_3$, halogen, amino, OCH$_3$, $C_1$-$C_6$ alkoxy optionally substituted with one or more fluorine, or $C_1$-$C_6$ alkyl, optionally substituted with at least one fluorine and with at least one carbon of the $C_1$-$C_6$ alkyl optionally replaced by O or N; and (hetero)Ar1 and (hetero)Ar2 are aryl or, optionally, heteroaryl; wherein $R_{10}$ is $C_1$-$C_3$ alkyl optionally substituted with one or more fluorine, and wherein p is 0-3.

Example CII

Unless otherwise stated, reagents, cells and animals used in experiments described herein are as follows.

PGE$_2$ and [$^3$H]-labelled PGE$_2$ were purchased from Cayman Chemical (Ann Arbor, Mich.) and Perkin Elmer (Waltham, Mass.), respectively. Mouse breast 4T1 cells (CRL-2539) were obtained from American Tissue Culture Collection. SE302 cell line is a clone of the HEK293 cells containing cAMP response element (CRE) promoter that when activated drives secretion of placental-like alkaline phosphatase (PLAP). HEK293 cells express endogenous EP$_4$ and show induction of PLAP in response to PGE$_2$ and EP$_4$ agonists, but not EP1, 2 or 3 agonists (Chen Q, Muramoto K, Masaaki N, Ding Y, Yang H, Mackey M, Li W, Inoue Y, Ackermann K, Shrota H, Matsumoto I, Spyvee M, Schiller S, Sumida T, Gusovsky F, and Lamphier M. A novel antagonist of the prostaglandin E2 EP4 receptor inhibits Th1 differentiation and Th17 expansion and is orally active in arthritis models. *British J Pharmacol,* 2010, 160: 292-310). BalB/C female mice at 7-8 week age were purchased from Jackson Laboratory (Bar Harbor, Me.). Mice were maintained under specific pathogen-free conditions.

E$_4$ Antagonism by CRE-PLAP Reporter Assay:

SE302 cells were maintained in DMEM/F12 (50:50) (MediaTech) supplemented with 10% FBS (Tissue Culture Biologicals) plus penicillin/streptomycin. When used for assays, cells were plated in a 96-well plate at 2×10$^4$ cells/100 µL/well in serum-free assay medium (DMEM/F12 supplemented with 0.1% BSA plus penicillin/streptomycin) and incubated for 4-6 h. Cells were then stimulated with 3 ng/mL of PGE$_2$ in the presence or absence of various concentrations of test compound overnight, and PLAP activity was measured by mixing 15 µL of culture supernatants with 75 µL of Lumi-phos (Lumigen, Inc.) and 60 µL of assay buffer containing 8 mmol/L MgSO4 in 0.1 mol/L carbonate-bicarbonate buffer pH11 in a new 96-well black plate and incubated for 2 h at room temperature. The intensity of luminescence, which reflected the PLAP activity in the supernatant, was quantified with an Envision 2101 Multilabel Reader. Values obtained from DMSO treated samples in the presence of PGE$_2$ were defined as 100% of control, whereas values obtained from DMSO treated samples in the absence of PGE$_2$ were defined as 0% of control. % of control for compound treated samples was calculated as follows: (actual reading−0% of control)/(100% of control−0% of control)×100. IC$_{50}$ value for each individual experiment was calculated using GraphPad Prism 6.02 (Lake Forest, Calif.) with % of control values.

Compounds of the present invention were assayed according to the methods as described above, and IC$_{50}$ values, which may be single assay values or multiple assay average values, are summarized in Table 1. Compounds marked "ABS" show absolute stereochemistry.

TABLE 1
| Compound | Formula | Compound # | CRE-PLAP (nM) |
|---|---|---|---|
| 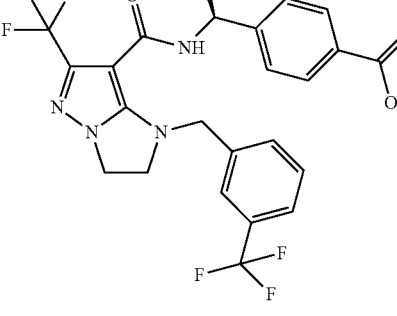 | C$_{24}$H$_{20}$F$_6$N$_4$O$_3$ | 1 | 0.34 (n = 2) |
| 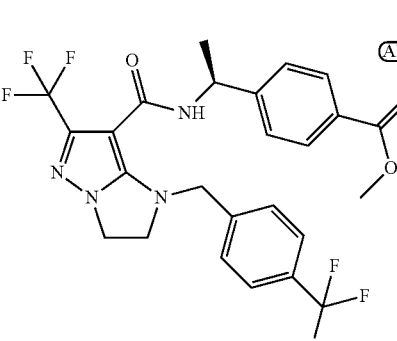 | C$_{25}$H$_{22}$F$_6$N$_4$O$_3$ | 2 | 3.90 |
| 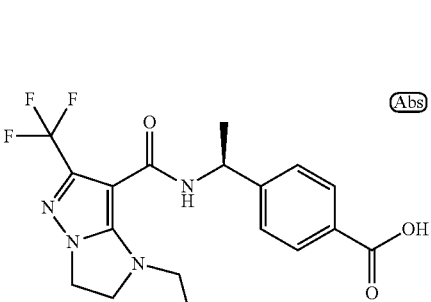 | C$_{24}$H$_{20}$F$_6$N$_4$O$_3$ | 3 | 3.19 |

TABLE 1-continued

| Compound | Formula | Compound # | CRE-PLAP (nM) |
|---|---|---|---|
| (Abs) structure | $C_{24}H_{20}F_6N_4O_3$ | 4 | 22.45 |
| (Abs) structure | $C_{25}H_{19}F_9N_4O_3$ | 5 | 45.94 |
| (Abs) structure | $C_{24}H_{19}ClF_6N_4O_3$ | 6 | 0.14 |

TABLE 1-continued
| Compound | Formula | Compound # | CRE-PLAP (nM) |
|---|---|---|---|
| 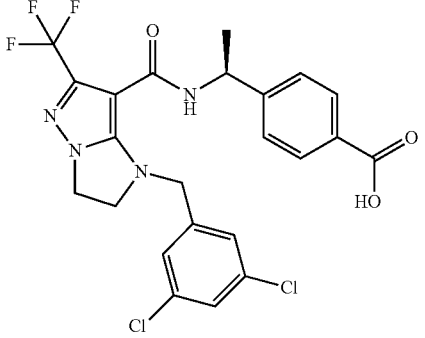 | $C_{23}H_{19}Cl_2F_3N_4O_3$ | 7 | 0.32 |
| 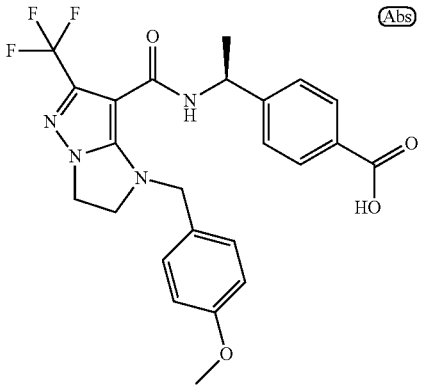 [SMILES: COc1ccc(CN2CCn3nc(C(F)(F)F)c(C(=O)N[C@@H](C)c4ccc(C(=O)O)cc4)c32)cc1] | $C_{24}H_{23}F_3N_4O_4$ | 8 | 8.03 |
| 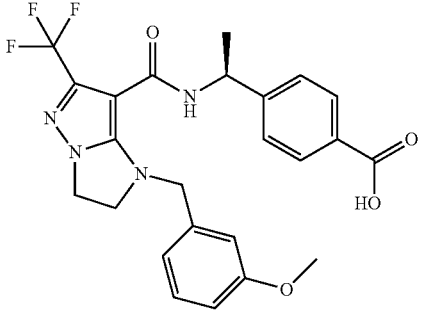 | $C_{24}H_{23}F_3N_4O_4$ | 9 | 1.41 |
| 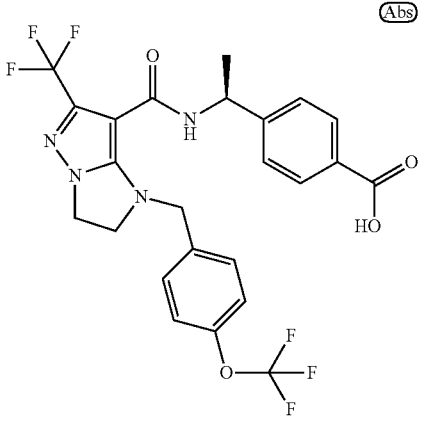 [SMILES: C[C@H](NC(=O)c1c(C(F)(F)F)nn2c1N(Cc1ccc(OC(F)(F)F)cc1)CC2)c1ccc(C(=O)O)cc1] | $C_{24}H_{20}F_6N_4O_4$ | 10 | 12.50 |

TABLE 1-continued
| Compound | Formula | Compound # | CRE-PLAP (nM) |
|---|---|---|---|
| 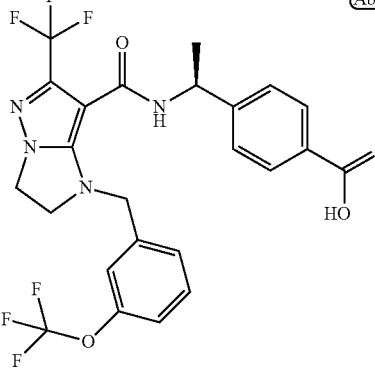 | C$_{24}$H$_{20}$F$_{6}$N$_{4}$O$_{4}$ | 11 | 0.41 |
| 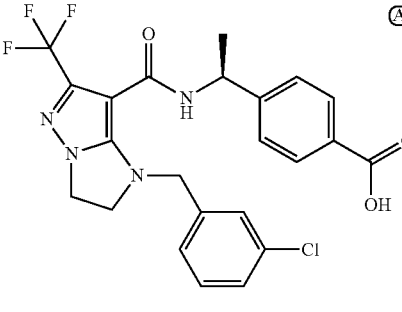 | C$_{23}$H$_{20}$ClF$_{3}$N$_{4}$O$_{3}$ | 12 | 2.23 |
| 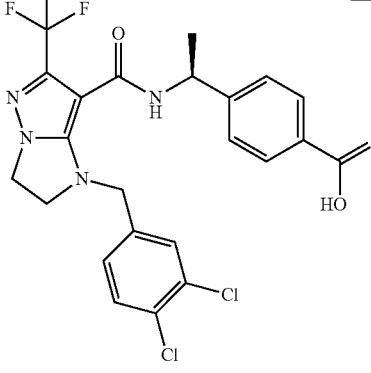 | C$_{23}$H$_{19}$Cl$_{2}$F$_{3}$N$_{4}$O$_{3}$ | 13 | 0.44 |
| 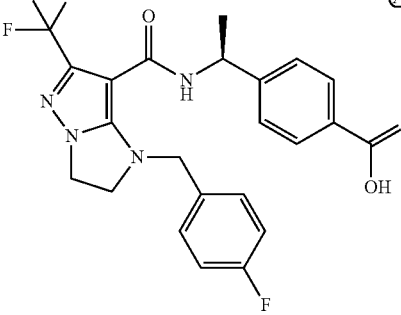 | C$_{23}$H$_{20}$F$_{4}$N$_{4}$O$_{3}$ | 14 | 0.58 |

TABLE 1-continued
| Compound | Formula | Compound # | CRE-PLAP (nM) |
|---|---|---|---|
| 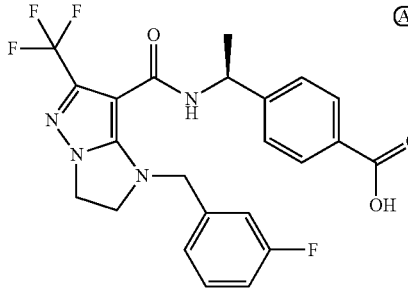 | C$_{23}$H$_{20}$F$_4$N$_4$O$_3$ | 15 | 1.65 |
| 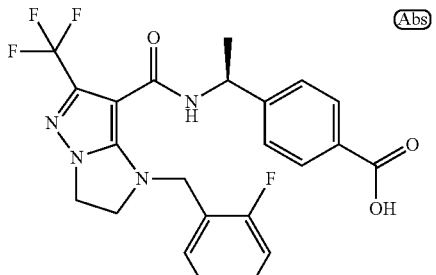 | C$_{23}$H$_{20}$F$_4$N$_4$O$_3$ | 16 | 1.40 |
| 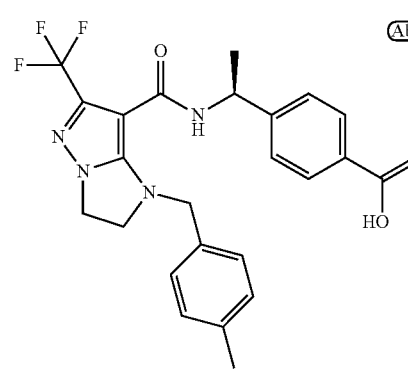 | C$_{24}$H$_{23}$F$_3$N$_4$O$_3$ | 17 | 1.65 |
| 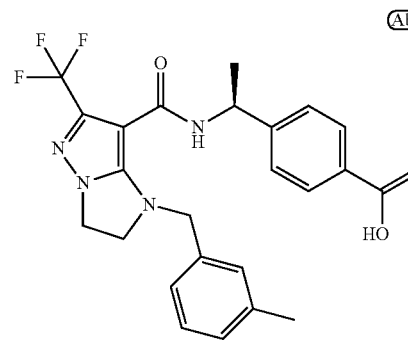 | C$_{24}$H$_{23}$F$_3$N$_4$O$_3$ | 18 | 0.64 |

TABLE 1-continued

| Compound | Formula | Compound # | CRE-PLAP (nM) |
|---|---|---|---|
| | $C_{24}H_{23}F_3N_4O_3$ | 19 | 3.60 |
| | $C_{25}H_{25}F_3N_4O_3$ | 20 | 2.23 |
| | $C_{24}H_{19}F_7N_4O_3$ | 21 | 2.85 |
| | $C_{24}H_{19}F_7N_4O_3$ | 22 | 1.91 |

TABLE 1-continued
| Compound | | Formula | Compound # | CRE-PLAP (nM) |
|---|---|---|---|---|
| 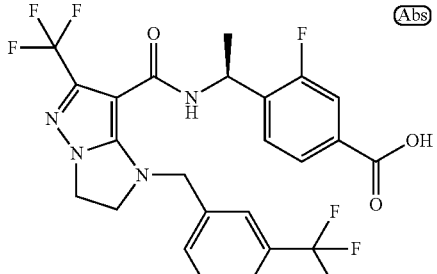 | (Abs) | C₂₄H₁₉F₇N₄O₃ | 23 | 0.41 |
| 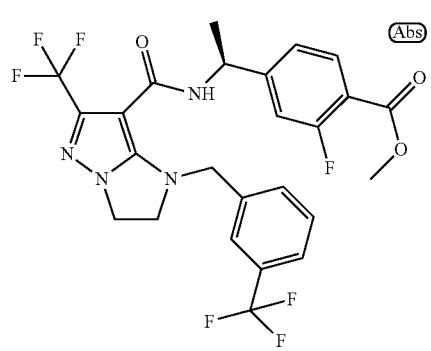 [SMILES: COC(=O)c1ccc([C@H](C)NC(=O)c2c(C(F)(F)F)nn3c2N(Cc2cccc(C(F)(F)F)c2)CC3)cc1F] | (Abs) | C₂₅H₂₁F₇N₄O₃ | 24 | 8.20 |
| 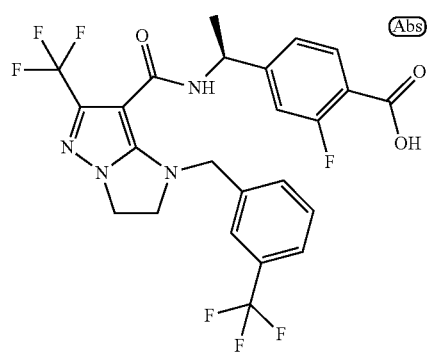 [SMILES: C[C@H](NC(=O)c1c(C(F)(F)F)nn2c1N(Cc1cccc(C(F)(F)F)c1)CC2)c1ccc(C(=O)O)c(F)c1] | (Abs) | C₂₄H₁₉F₇N₄O₃ | 25 | 1.1 |
| 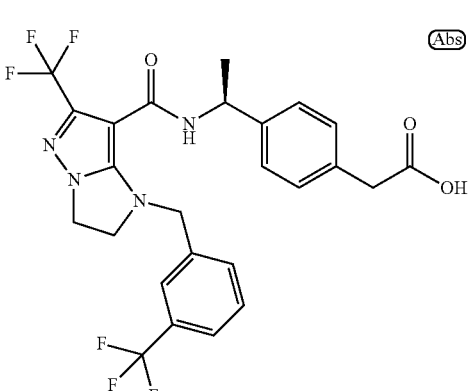 | (Abs) | C₂₅H₂₂F₆N₄O₃ | 26 | 3.54 |

TABLE 1-continued

| Compound | Formula | Compound # | CRE-PLAP (nM) |
|---|---|---|---|
| | $C_{25}H_{22}F_6N_4O_3$ | 27 | 7.08 |
| | $C_{25}H_{23}F_3N_4O_3$ | 28 | 8.68 |
| | $C_{25}H_{20}F_6N_4O_3$ | 29 | 2.19 |
| | $C_{24}H_{20}ClF_3N_4O_3$ | 30 | 1.35 |

TABLE 1-continued

| Compound | Formula | Compound # | CRE-PLAP (nM) |
|---|---|---|---|
| (Abs) | C₂₃H₂₀ClF₃N₄O₃ | 31 | 0.99 |
| (Abs) | C₂₃H₂₃ClN₄O₃ | 32 | 4.23 |
| | C₂₂H₂₁ClN₄O₃ | 33 | 27.58 |
| (Abs) | C₂₆H₂₅F₃N₄O₃ | 34 | 9.19 |

TABLE 1-continued
| Compound | Formula | Compound # | CRE-PLAP (nM) |
|---|---|---|---|
|  | C$_{25}$H$_{25}$F$_3$N$_4$O$_3$ | 35 | 11.13 |
|  | C$_{24}$H$_{20}$F$_6$N$_8$O | 36 | 0.31 |
|  | C$_{24}$H$_{20}$F$_6$N$_8$O | 37 | 0.45 |
|  | C$_{23}$H$_{19}$F$_6$N$_5$O$_3$ | 38 | 17.1 |

TABLE 1-continued

| Compound | Formula | Compound # | CRE-PLAP (nM) |
|---|---|---|---|
| (structure) | $C_{23}H_{19}F_6N_5O_3$ | 39 | 4.73 |
| (structure) | $C_{27}H_{22}F_6N_4O_2$ | 40 | 150.00 |
| (structure) | $C_{24}H_{22}ClF_3N_4O_3$ | 41 | 1.53 |
| (structure) | $C_{24}H_{22}ClF_3N_4O_3$ | 42 | 13.58 |

TABLE 1-continued

| Compound | Formula | Compound # | CRE-PLAP (nM) |
|---|---|---|---|
| (structure) | $C_{23}H_{20}ClF_3N_4O_3$ | 43 | 4.17 |
| (structure) | $C_{25}H_{22}F_6N_4O_3$ | 44 | 6.83 |
| (structure) | $C_{25}H_{22}F_6N_4O_3$ | 45 | 1.15 |
| (structure) | $C_{25}H_{22}F_6N_4O_3$ | 46 | 100.00 |

TABLE 1-continued
| Compound | Formula | Compound # | CRE-PLAP (nM) |
|---|---|---|---|
| 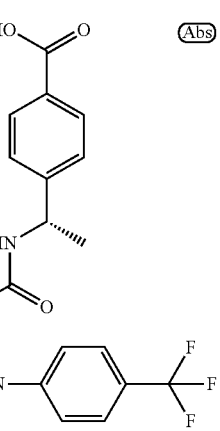 | C₂₃H₁₈F₆N₄O₃ | 47 | 48.93 |
| 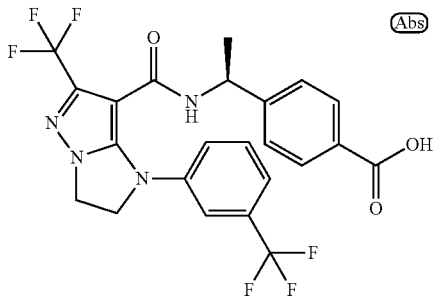 [SMILES: C[C@H](NC(=O)c1c(C(F)(F)F)nn2c1N(c1cccc(C(F)(F)F)c1)CC2)c1ccc(C(=O)O)cc1] | C₂₃H₁₈F₆N₄O₃ | 48 | 100.00 |
| 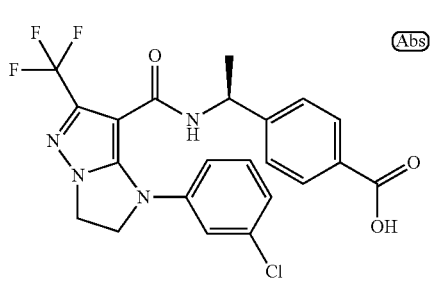 [SMILES: C[C@H](NC(=O)c1c(C(F)(F)F)nn2c1N(c1cccc(Cl)c1)CC2)c1ccc(C(=O)O)cc1] | C₂₂H₁₈ClF₃N₄O₃ | 49 | 100.00 |
| 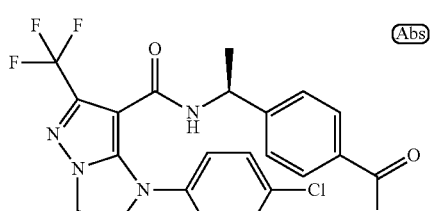 | C₂₂H₁₈ClF₃N₄O₃ | 50 | 91.26 |

TABLE 1-continued
| Compound | | Formula | Compound # | CRE-PLAP (nM) |
|---|---|---|---|---|
| 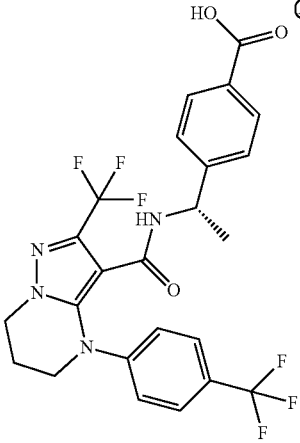 | (Abs) | C₂₄H₂₀F₆N₄O₃ | 51 | 100.00 |
| 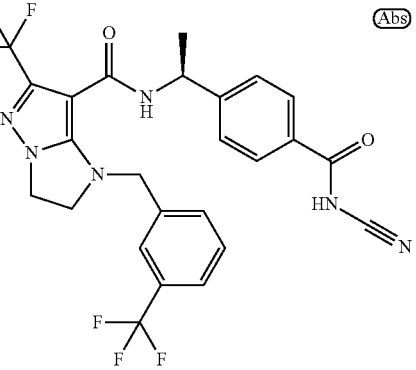 | (Abs) | C₂₅H₂₀F₆N₆O₂ | 52 | 0.07 |
| 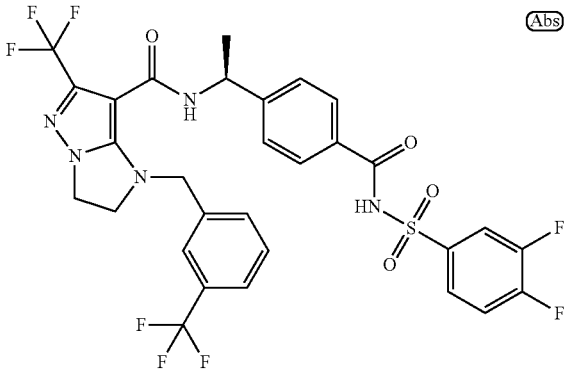 [SMILES: C[C@H](NC(=O)c1c(C(F)(F)F)nn2c1N(Cc1cccc(C(F)(F)F)c1)CC2)c1ccc(C(=O)NS(=O)(=O)c2ccc(F)c(F)c2)cc1] | (Abs) | C₃₀H₂₃F₈N₅O₄S | 53 | 3.91 |
| 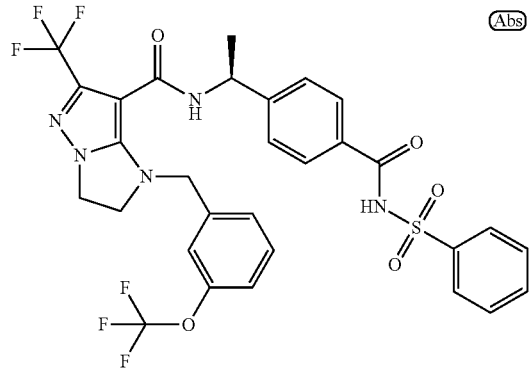 [SMILES: C[C@H](NC(=O)c1c(C(F)(F)F)nn2c1N(Cc1cccc(OC(F)(F)F)c1)CC2)c1ccc(C(=O)NS(=O)(=O)c2ccccc2)cc1] | (Abs) | C₃₀H₂₅F₆N₅O₅S | 54 | 21.64 |

TABLE 1-continued

| Compound | Formula | Compound # | CRE-PLAP (nM) |
|---|---|---|---|
| (Abs) | C₂₅H₂₃F₆N₅O₄S | 55 | 39.30 |
| (Abs) | C₂₇H₂₅F₆N₅O₄S | 56 | 72.95 |
| (Abs) | C₂₆H₂₄F₆N₄O | 57 | 310.00 |
| (Abs) | C₂₅H₂₂F₆N₈O | 58 | 4.71 |

TABLE 1-continued
| Compound | Formula | Compound # | CRE-PLAP (nM) |
|---|---|---|---|
| 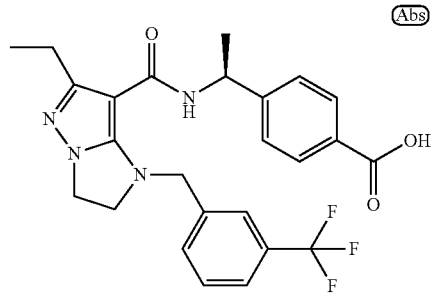 [SMILES: CCc1nn2c(c1C(=O)N[C@@H](C)c1ccc(C(=O)O)cc1)N(Cc1cccc(C(F)(F)F)c1)CC2] | C$_{25}$H$_{25}$F$_3$N$_4$O$_3$ | 59 | 0.68 |
| 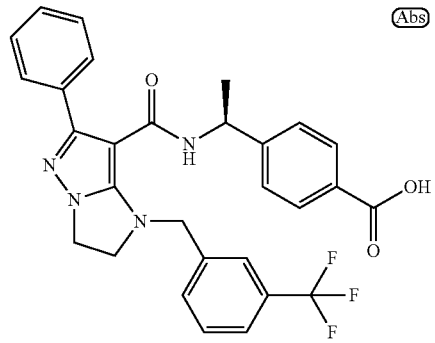 [SMILES: C[C@H](NC(=O)c1c(-c2ccccc2)nn2c1N(Cc1cccc(C(F)(F)F)c1)CC2)c1ccc(C(=O)O)cc1] | C$_{29}$H$_{25}$F$_3$N$_4$O$_3$ | 60 | 7.65 |
| 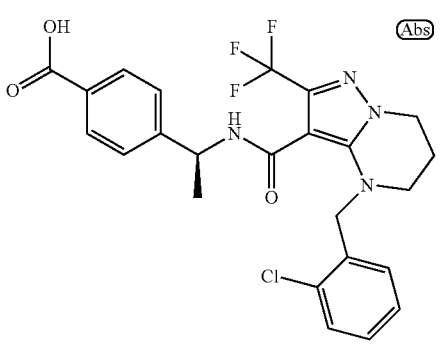 [SMILES: C[C@H](NC(=O)c1c(C(F)(F)F)nn2c1N(Cc1ccccc1Cl)CCC2)c1ccc(C(=O)O)cc1] | C$_{24}$H$_{22}$ClF$_3$N$_4$O$_3$ | 61 | 100.00 |
| 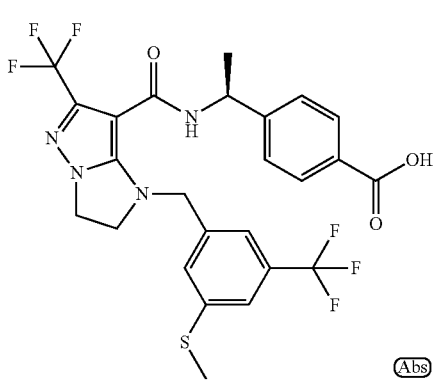 [SMILES: CSc1cc(CN2CCn3nc(C(F)(F)F)c(C(=O)N[C@@H](C)c4ccc(C(=O)O)cc4)c32)cc(C(F)(F)F)c1] | C$_{25}$H$_{22}$F$_6$N$_4$O$_3$S | 62 | 0.57 |

TABLE 1-continued
| Compound | Formula | Compound # | CRE-PLAP (nM) |
|---|---|---|---|
| 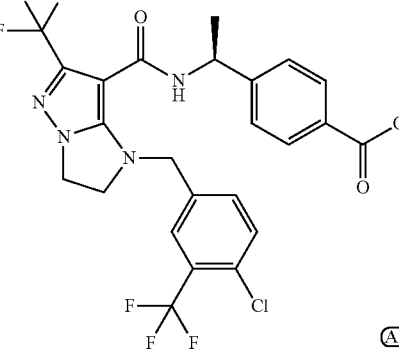 | C_{24}H_{19}ClF_6N_4O_3 | 63 | 1.3 |
| 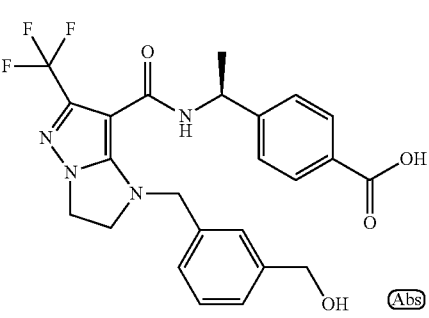 [SMILES: C[C@H](NC(=O)c1c(C(F)(F)F)nn2c1N(Cc1cccc(CO)c1)CC2)c1ccc(C(=O)O)cc1] | C_{24}H_{23}F_3N_4O_4 | 64 | 0.82 |
| 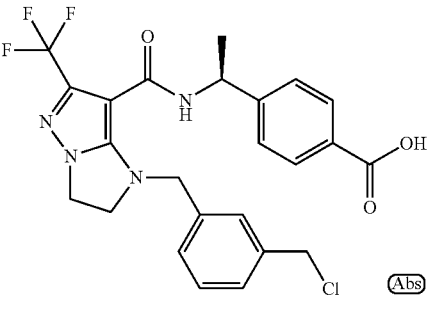 [SMILES: C[C@H](NC(=O)c1c(C(F)(F)F)nn2c1N(Cc1cccc(CCl)c1)CC2)c1ccc(C(=O)O)cc1] | C_{24}H_{22}ClF_3N_4O_3 | 65 | 0.93 |
| 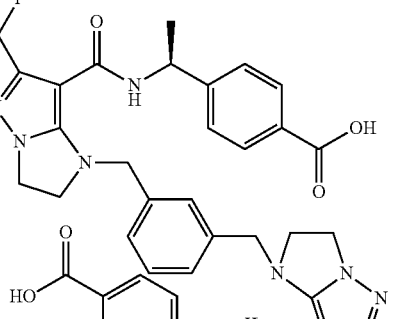 | C_{40}H_{36}F_6N_8O_6 | 66 | 35.8 |

TABLE 1-continued
| Compound | Formula | Compound # | CRE-PLAP (nM) |
|---|---|---|---|
| 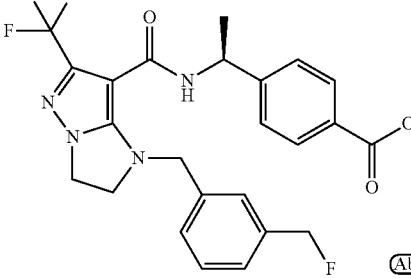 | C₂₄H₂₂F₄N₄O₃ | 67 | 1.2 |
| 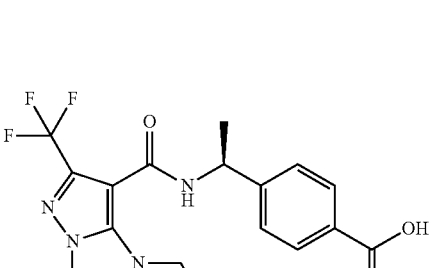 | C₂₄H₁₉F₆IN₄O₃ | 68 | 10.9 |
| 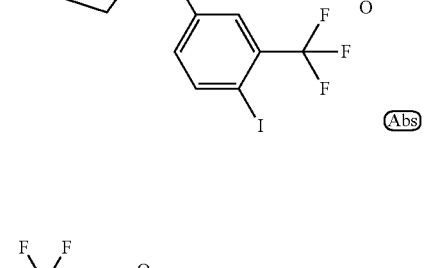 | C₂₃H₂₀F₃IN₄O₃ | 69 | 0.7 |
| 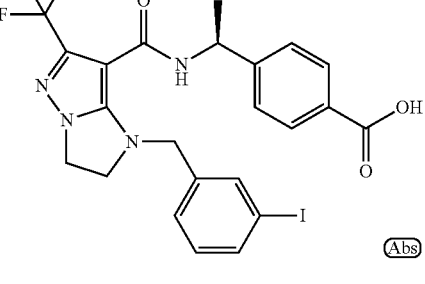 | C₂₃H₂₁F₃N₄O₃ | 70 | 0.84 |

TABLE 1-continued
| Compound | Formula | Compound # | CRE-PLAP (nM) |
|---|---|---|---|
| 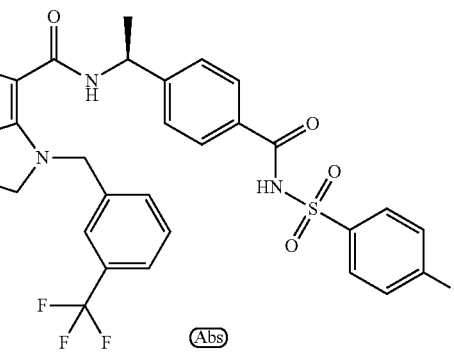 | C<sub>30</sub>H<sub>24</sub>F<sub>6</sub>N<sub>6</sub>O<sub>6</sub>S | 71 | 5.87 |
| 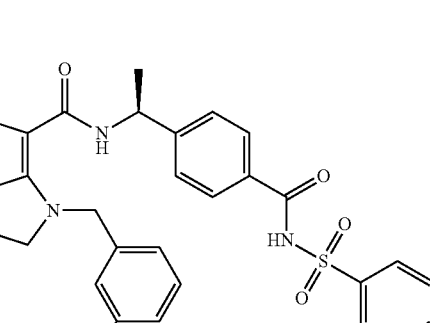 | C<sub>30</sub>H<sub>26</sub>F<sub>6</sub>N<sub>6</sub>O<sub>4</sub>S | 72 | 51.2 |
| 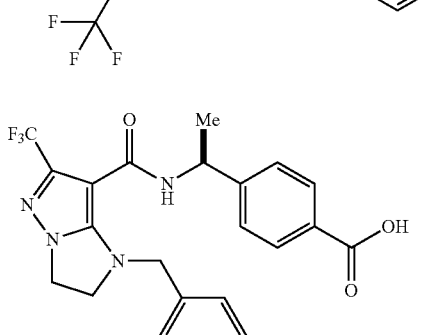 | C<sub>23</sub>H<sub>22</sub>F<sub>3</sub>N<sub>5</sub>O<sub>3</sub> | 73 | 1.49 |
| 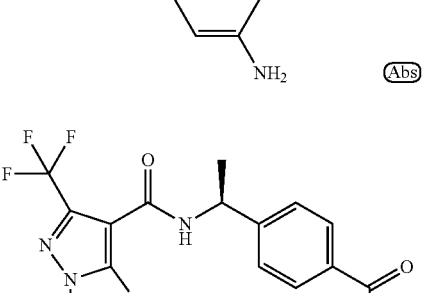 | C<sub>26</sub>H<sub>26</sub>F<sub>4</sub>N<sub>4</sub>O<sub>4</sub> | 74 | 28 |

TABLE 1-continued
| Compound | Formula | Compound # | CRE-PLAP (nM) |
|---|---|---|---|
| 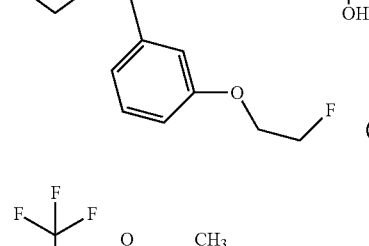 | C₂₅H₂₄F₄N₄O₄ | 75 | 4.66 |
| 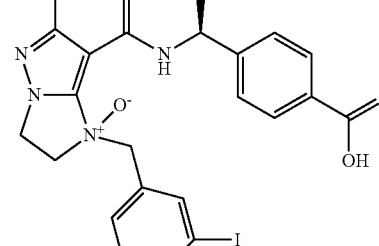 | C₂₃H₂₀F₃IN₄O₄ | 76 | 4.12 |
| 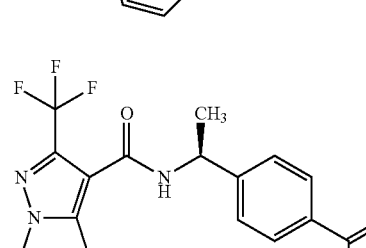 | C₂₄H₂₀F₆N₄O₄ | 77 | 0.182 |
| 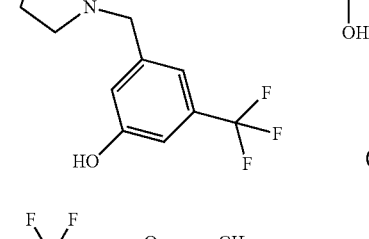 | C₂₄H₂₈F₄N₄O₃ | 78 | 63 |

TABLE 1-continued

| Compound | Formula | Compound # | CRE-PLAP (nM) |
|---|---|---|---|
| (structure) | C₂₄H₂₇F₃N₄O₃ | 79 | 18.9 |
| (structure) | C₃₂H₂₈F₆N₄O₄ | 80 | 58.15 |
| (structure) | C₂₅H₂₁F₇N₄O₃ | 81 | 0.26 |
| (structure) | C₂₅H₂₀F₆N₄O₃ | 82 | 1.1 |

TABLE 1-continued
| Compound | Formula | Compound # | CRE-PLAP (nM) |
|---|---|---|---|
| 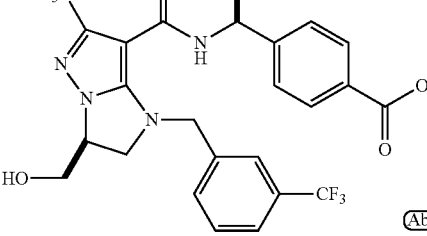 | C<sub>25</sub>H<sub>22</sub>F<sub>6</sub>N<sub>4</sub>O<sub>4</sub> | 83 | 0.64 |
| 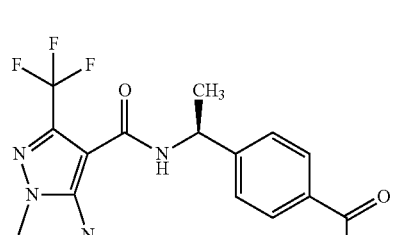 | C<sub>24</sub>H<sub>19</sub>F<sub>7</sub>N<sub>4</sub>O<sub>3</sub> | 84 | 0.358 |
| 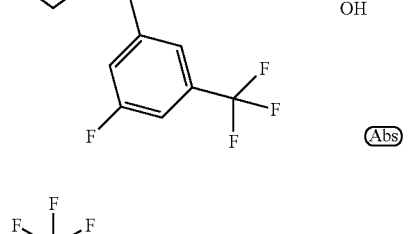 | C<sub>24</sub>H<sub>19</sub>BrF<sub>6</sub>N<sub>4</sub>O<sub>3</sub> | 85 | 0.12 |
| 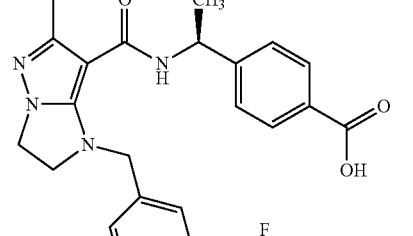 | C<sub>23</sub>H<sub>21</sub>F<sub>3</sub>N<sub>4</sub>O<sub>4</sub> | 86 | 1.48 |

TABLE 1-continued
| Compound | Formula | Compound # | CRE-PLAP (nM) |
|---|---|---|---|
| 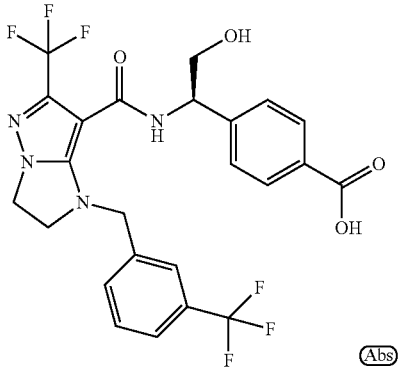 [SMILES: O=C(O)c1ccc([C@H](CO)NC(=O)c2c(C(F)(F)F)nn3c2N(Cc2cccc(C(F)(F)F)c2)CC3)cc1] | C₂₄H₂₀F₆N₄O₄ | 87 | 34.74 |
| 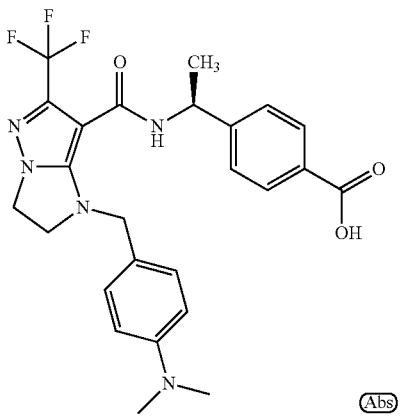 [SMILES: C[C@H](NC(=O)c1c(C(F)(F)F)nn2c1N(Cc1ccc(N(C)C)cc1)CC2)c1ccc(C(=O)O)cc1] | C₂₅H₂₆F₃N₅O₃ | 88 | 18.52 |
| 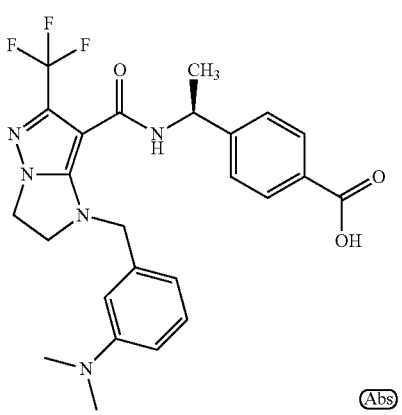 [SMILES: C[C@H](NC(=O)c1c(C(F)(F)F)nn2c1N(Cc1cccc(N(C)C)c1)CC2)c1ccc(C(=O)O)cc1] | C₂₅H₂₆F₃N₅O₃ | 89 | 1.57 |

TABLE 1-continued
| Compound | Formula | Compound # | CRE-PLAP (nM) |
|---|---|---|---|
| 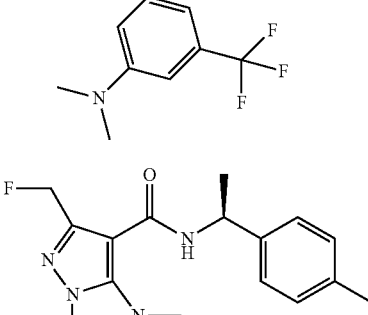 | C<sub>26</sub>H<sub>25</sub>F<sub>6</sub>N<sub>5</sub>O<sub>3</sub> | 90 | 6.37 |
| 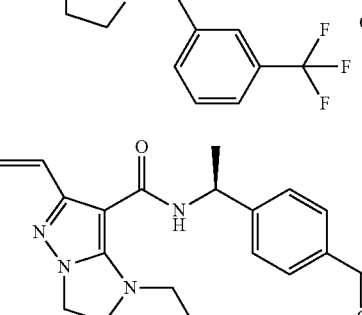 | C<sub>24</sub>H<sub>22</sub>F<sub>4</sub>N<sub>4</sub>O<sub>3</sub> | 91 | 0.636 |
| 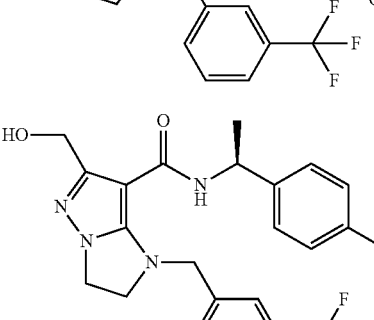 | C<sub>25</sub>H<sub>23</sub>F<sub>3</sub>N<sub>4</sub>O<sub>3</sub> | 92 | 5.43 |
| 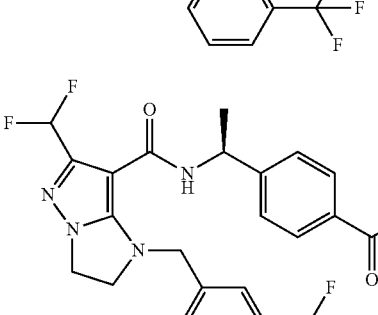 | C<sub>24</sub>H<sub>23</sub>F<sub>3</sub>N<sub>4</sub>O<sub>4</sub> | 93 | 6.59 |
|  | C<sub>24</sub>H<sub>21</sub>F<sub>5</sub>N<sub>4</sub>O<sub>3</sub> | 94 | 0.343 |

TABLE 1-continued
| Compound | Formula | Compound # | CRE-PLAP (nM) |
|---|---|---|---|
| 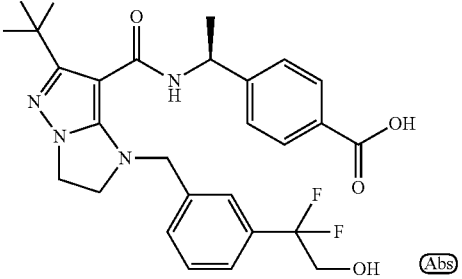 | C25H23F5N4O4 | 95 | 4.26 |
| 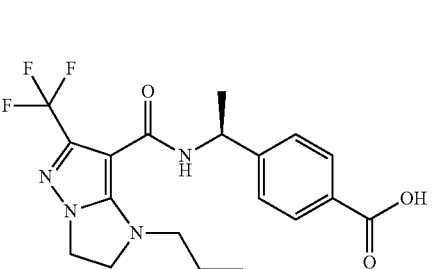 | C26H26F4N4O3 | 96 | 0.866 |
| 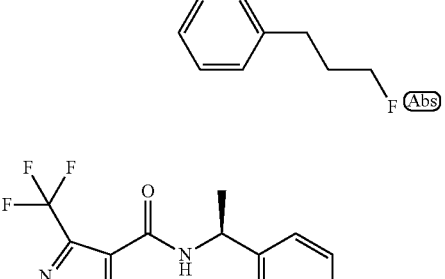 | C26H26F4N4O3 | 97 | 21.8 |
| 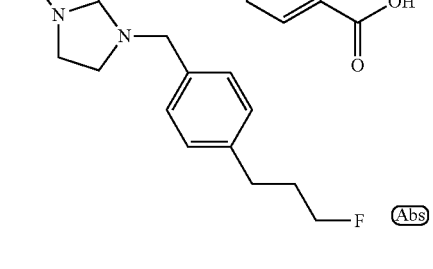 | C27H25F7N4O3 | 98 | 17.7 |

TABLE 1-continued

| Compound | Formula | Compound # | CRE-PLAP (nM) |
|---|---|---|---|
| 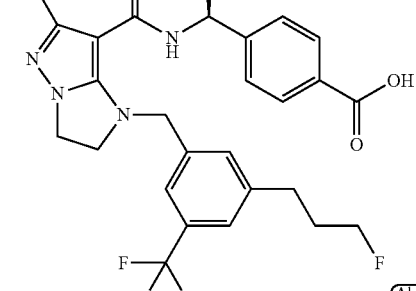 | $C_{27}H_{25}F_7N_4O_3$ | 99 | 11.6 |
| 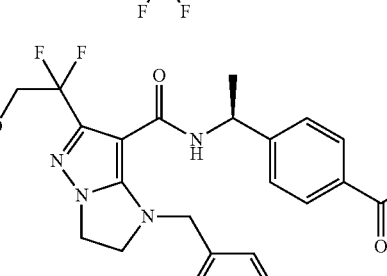 | $C_{25}H_{23}F_5N_4O_4$ | 100 | 8.96 |
| 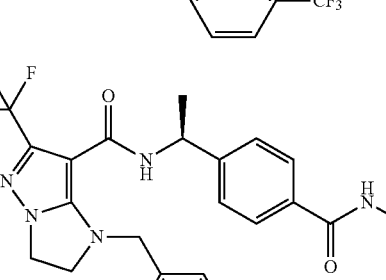 | $C_{28}H_{24}F_6N_6O_2$ | 101 | 32.95 |
| 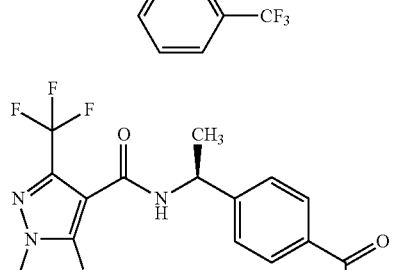 | $C_{24}H_{20}F_4N_4O_4$ | 102 | 39 |

Example CV

Competitive Radioligand $EP_4$ Receptor Binding Assay:

The assay was performed using ChemiScreen recombinant human $EP_4$ receptor membrane preparations from Millipore using Chem-1 cells and mouse $EP_4$ receptor membrane preparations from Genscript using U2OS clone, according to manufacturer's instructions. For human $EP_4$ binding, 10 µg Chem-1 cell membranes overexpressing human $EP_4$ cDNA were mixed with 12 nM [$^3$H]-$PGE_2$ and 5 µmol/L unlabelled $PGE_2$ or 0.1% DMSO in the presence or absence of various concentrations of testing compounds in binding buffer (50 mM HEPES, pH 7.4, 5 mM $MgCl_2$, 1 mM $CaCl_2$, 0.2% BSA) in a nonbinding 96-well plate, and incubated for 2 h at room temperature. For mouse $EP_4$ binding, 60 µg of U2OS membranes were used in the same condition. Prior to filtration, a GF/C 96-well filter plate was coated with 0.33% polyethyleneimine for 30 min, then washed with 50 mM HEPES, pH 7.4, 0.5% BSA. Binding reactions were transferred to the filter plate, and washed 3 times with assay Wash Buffer (50 mM HEPES, pH7.4, 500 mM NaCl, 0.1% BSA). The plate was dried and radioactivity counted. The data were processed using PRISM software, and $IC_{50}$ and Ki values were calculated using the same software.

Competitive Binding of Compound 1 to $EP_4$ Receptor:

Compound 1 was further evaluated for its inhibitory activity in the binding of radiolabeled $PGE_2$ to either human or mouse $EP_4$-overexpressing cell membrane fractions in vitro. As shown in FIG. 1A and FIG. 1B, the test compound inhibited the binding of radio-labelled $PGE_2$ to both human or mouse $EP_4$ in a dose-dependent manner. The Ki values of the inhibition for human and mouse $EP_4$ were 4.2 nM and 26.3 nM, respectively.

Example CVI

In Vivo Anti-Tumor Pharmacology

4T1 cells were maintained in RPMI 1640 medium supplemented with 10% FBS at 37° C. and 5% $CO_2$ atmosphere. Cell detachment was obtained using standard trypsinization methods, quantification of cell numbers and viability information using the NC-200 automated cell counter. Compound 1 was thoroughly suspended in 0.5% methyl cellulose (MC) by sonication at 4° C. for 15 min before oral administration (p.o.) to animals. BALB/c mice were injected subcutaneously (s.c.) with live $1\times10^5$ 4T1 cells. Mice developed tumors of approximately 36 $mm^3$ in 5 days. 4T1 tumor-bearing mice were randomized and mapped into 5 groups of 10 mice each: group A received vehicle (0.5% MC); group B received 0.1 mg/kg of compound 1; group C received 1 mg/kg of compound 1, group D received 25 mg/kg of compound 1; and group E received 150 mg/kg of compound 1. All treatments were give p.o. daily for 21 consecutive days. Tumor volumes and body weights were measured twice weekly. Study was terminated 27 days after tumor cell injection. Tumor volumes were expressed as mean±SEM. Tumor volume differences among treated mouse groups on day 27 were analyzed by the one-way ANOVA followed by Tukey's test. P≤0.05 values were considered significant.

In Vivo Anti-Tumor Activity:

As described above, compound 1 was examined for its activity in tumor growth using a mouse breast 4T1 syngeneic tumor model. Daily oral administration of the compound inhibited the tumor growth in a dose-dependent manner in general in the range of 0.1 mg/kg-150 mg/kg (FIG. 2A). At both lower doses (0.1 and 1.0 mg/kg) tested, some inhibition was observed, but without statistical significance. On the other hand, significant and comparable anti-tumor activity was detected for doses at 25 and 150 mg/kg, indicating that an optimal efficacious dose was reached by 25 mg/kg in the experimental setting. None of the doses tested showed gross toxicity judged from the animal body weight and overall animal behavior (FIG. 2B), indicating an excellent tolerability in the tested animal species.

All publications and patent documents cited herein are incorporated herein by reference as if each such publication or document was specifically and individually indicated to be incorporated herein by reference. Where the text of this disclosure and the text of one or more documents incorporated by reference conflicts, this disclosure controls. Citation of publications and patent documents is not intended as an admission that any is pertinent prior art, nor does it constitute any admission as to the contents or date of the same. The embodiments described herein having now been described by way of written description, those of skill in the art will recognize that the embodiments described herein may be practiced in a variety of embodiments and that the description and examples provided herein are for purposes of illustration and not limitation of the claims.

We claim:

1. A compound represented by formula (I):

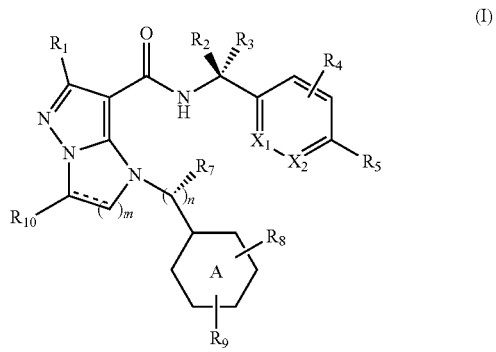

or a pharmaceutically acceptable salt thereof,
wherein
$R_1$ is —$CH_3$, —$CF_3$, —$CH_2CH_3$, —$CH_2F$, $CF_2CH_2OH$, —$CHF_2$, —CH=$CH_2$, —$CH_2OH$, or phenyl;
$R_2$ is —H, —$CH_2OH$, or —$CH_3$;
$R_3$ is —H;
or $R_2$ and $R_3$ taken together form a cyclopropyl with the carbon to which they are attached;
$R_4$ is —H, —F, or —$CH_3$;
$R_5$ is —C(O)OH, —C(O)$OCH_3$, —$CH_2$C(O)OH, cyclopropyl, —C(O)NHCN,

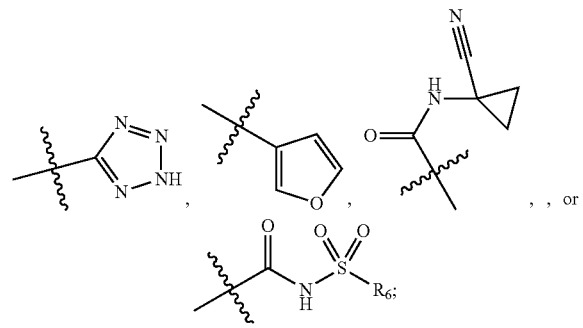

wherein $R_6$ is phenyl, —$CH_3$, cyclopropyl,

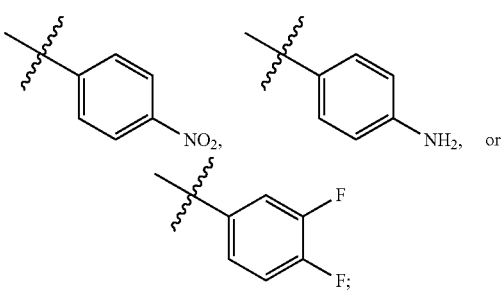

n is 0-1;

m is 1-2;

R₇ is —H, —CH₃, or absent when n is 0;

R₈ is —CF₃, —H, —Cl, —F, —CH₂CH₃, —OCH₃, —CH₃, —SCH₃, —CH₂OH, —CH₂F, —CH₂Cl, —I, —Br, —NH₂, —CH₂OCH₂CH₂F, —OCH₂CH₂F, —CH₂CH₂CH₂F, —OCF₃, —OH, —N(CH₃)₂, —CF₂CH₂OH, or

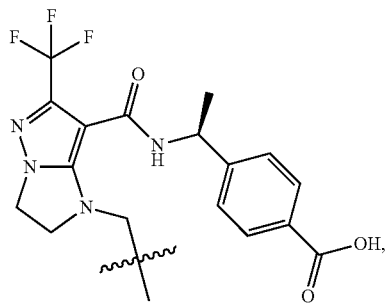 [SMILES: *CN1CCn2nc(C(F)(F)F)c(C(=O)N[C@@H](C)c3ccc(C(=O)O)cc3)c21]

or the bond connecting R₈ and ring A is a double bond and R₈ is CH₂;

R₉ is —H, —Cl, or —CF₃;

R₁₀ is —H, —CH₃, —CH₂F, —CH₂OH, or —CH₂OCH₂-phenyl;

X₁ and X₂ are either both C, or one is C and the other is N;

- - - - - represents a single bond or a double bond; and ring A is phenyl or cyclohexyl.

2. A compound of claim 1, wherein the compound is represented by formula (II):

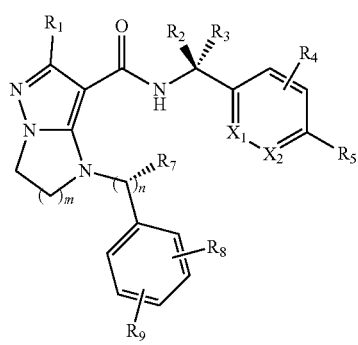

(II)

or a pharmaceutically acceptable salt thereof,
wherein

R₁ is —CH₃, —CF₃, —CH₂CH₃, or phenyl;

R₂ is —H, or —CH₃;

R₃ is —H;

or R₂ and R₃ taken together form a cyclopropyl with the carbon to which they are attached;

R₄ is —H, —F, or —CH₃;

R₅ is —C(O)OH, —C(O)OCH₃, —CH₂C(O)OH, cyclopropyl, —C(O)NHCN,

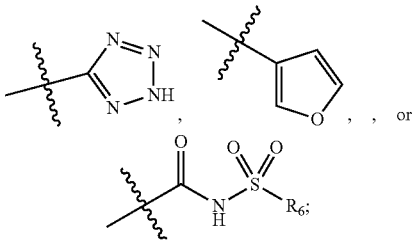

wherein R₆ is phenyl, —CH₃, cyclopropyl, or

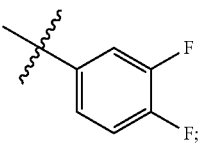

m is 1-2;

n is 0-1;

R₇ is —H, —CH₃, or absent when n is 0;

R₈ is —CF₃, —H, —Cl, —F, —CH₂CH₃, —OCH₃, —CH₃, or —OCF₃;

R₉ is —H, —Cl, or —CF₃; and

X₁ and X₂ are either both C, or one is C and the other is N.

3. The compound of claim 1, wherein R₁₀ is —H.

4. The compound of claim 1, wherein - - - - - represents a single bond.

5. The compound of claim 1, wherein R₁ is —CF₃.

6. The compound of claim 1, wherein m is 1.

7. The compound of claim 1, wherein R₂ is methyl and R₃ is —H.

8. The compound of claim 1, wherein X₁ and X₂ are both —CH—.

9. The compound of claim 1, wherein R₄ is —H.

10. The compound of claim 1, wherein n is 1.

11. The compound of claim 1, wherein R₇ is —H.

12. The compound of claim 1, wherein R₉ is —H.

13. The compound of claim 1, wherein R₈ is —CF₃.

14. The compound of claim 1, wherein R₅ is —C(O)OH.

15. The compound of claim 1, wherein R₈ is —Cl.

16. The compound of claim 1, wherein R₅ is —C(O)OH, —C(O)OCH₃, —CH₂C(O)OH, —C(O)NHCN,

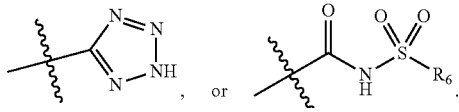

17. The compound of claim 1, wherein m is 2, and wherein R₈ and R₉, if present, are in a meta position or a para position.

18. A compound of claim 1 or pharmaceutically acceptable salt thereof, said compound selected from the group consisting of:

(S)-4-(1-(1-(3-(methylthio)-5-(trifluoromethyl)benzyl)-6-(trifluoromethyl)-2,3-dihydro-1H-imidazo[1,2-b]pyrazole-7-carboxamido)ethyl)benzoic acid;

(S)-4-(1-(1-(3-(hydroxymethyl)benzyl)-6-(trifluoromethyl)-2,3-dihydro-1H-imidazo[1,2-b]pyrazole-7-carboxamido)ethyl)benzoic acid;

(S)-4-(1-(1-(3-(fluoromethyl)benzyl)-6-(trifluoromethyl)-2,3-dihydro-1H-imidazo[1,2-b]pyrazole-7-carboxamido)ethyl)benzoic acid;

(S)-4-(1-(1-(3-(chloromethyl)benzyl)-6-(trifluoromethyl)-2,3-dihydro-1H-imidazo[1,2-b]pyrazole-7-carboxamido)ethyl)benzoic acid;

4,4'-((1S,1'S)-((1,1'-(1,3-phenylenebis(methylene))bis(6-(trifluoromethyl)-2,3-dihydro-1H-imidazo[1,2-b]pyrazole-1,7-diyl-7-carbonyl))bis(azanediyl))bis(ethane-1,1-diyl))dibenzoic acid;

(S)-4-(1-(1-(4-iodo-3-(trifluoromethyl)benzyl)-6-(trifluoromethyl)-2,3-dihydro-1H-imidazo[1,2-b]pyrazole-7-carboxamido)ethyl)benzoic acid;

(S)-4-(1-(1-(3-iodobenzyl)-6-(trifluoromethyl)-2,3-dihydro-1H-imidazo[1,2-b]pyrazole-7-carboxamido)ethyl)benzoic acid;

(S)-4-(1-(1-benzyl-6-(trifluoromethyl)-2,3-dihydro-1H-imidazo[1,2-b]pyrazole-7-carboxamido)ethyl)benzoic acid;

(S)—N-(1-(4-(((4-nitrophenyl)sulfonyl)carbamoyl)phenyl)ethyl)-6-(trifluoromethyl)-1-(3-(trifluoromethyl)benzyl)-2,3-dihydro-1H-imidazo[1,2-b]pyrazole-7-carboxamide;

(S)-4-(1-(1-(4-aminobenzyl)-6-(trifluoromethyl)-2,3-dihydro-1H-imidazo[1,2-b]pyrazole-7-carboxamido)ethyl)benzoic acid;

(S)—N-(1-(4-(((4-aminophenyl)sulfonyl)carbamoyl)phenyl)ethyl)-6-(trifluoromethyl)-1-(3-(trifluoromethyl)benzyl)-2,3-dihydro-1H-imidazo[1,2-b]pyrazole-7-carboxamide;

(S)-4-(1-(1-(3-((2-fluoroethoxy)methyl)benzyl)-6-(trifluoromethyl)-2,3-dihydro-1H-imidazo[1,2-b]pyrazole-7-carboxamido)ethyl)benzoic acid;

(S)-4-(1-(1-(3-(2-fluoroethoxy)benzyl)-6-(trifluoromethyl)-2,3-dihydro-1H-imidazo[1,2-b]pyrazole-7-carboxamido)ethyl)benzoic acid;

(S)-4-(1-(1-(3-hydroxy-5-(trifluoromethyl)benzyl)-6-(trifluoromethyl)-2,3-dihydro-1H-imidazo[1,2-b]pyrazole-7-carboxamido)ethyl)benzoic acid;

(S)-4-(1-(1-(3-fluoro-5-(trifluoromethyl)benzyl)-6-(trifluoromethyl)-2,3-dihydro-1H-imidazo[1,2-b]pyrazole-7-carboxamido)ethyl)benzoic acid;

(S)-4-(1-(1-((4-(fluoromethyl)cyclohexyl)methyl)-6-(trifluoromethyl)-2,3-dihydro-1H-imidazo[1,2-b]pyrazole-7-carboxamido)ethyl)benzoic acid;

(S)-4-(1-(1-((4-methylenecyclohexyl)methyl)-6-(trifluoromethyl)-2,3-dihydro-1H-imidazo[1,2-b]pyrazole-7-carboxamido)ethyl)benzoic acid;

(S)-4-(1-(1-(3-(3-fluoropropyl)benzyl)-6-(trifluoromethyl)-2,3-dihydro-1H-imidazo[1,2-b]pyrazole-7-carboxamido)ethyl)benzoic acid;

(S)-4-(1-(1-(4-(3-fluoropropyl)benzyl)-6-(trifluoromethyl)-2,3-dihydro-1H-imidazo[1,2-b]pyrazole-7-carboxamido)ethyl)benzoic acid;

(S)-4-(1-(1-(3-(3-fluor propyl)-5-(trifluoromethyl)benzyl)-6-(trifluoromethyl)-2,3-dihydro-1H-imidazo[1,2-b]pyrazole-7-carboxamido)ethyl)benzoic acid;

(S)-4-(1-(1-(4-(3-fluor propyl)-3-(trifluoromethyl)benzyl)-6-(trifluoromethyl)-2,3-dihydro-1H-imidazo[1,2-b]pyrazole-7-carboxamido)ethyl)benzoic acid;

(S)-4-(1-(6-(fluoromethyl)-1-(3-(trifluoromethyl)benzyl)-2,3-dihydro-1H-imidazo[1,2-b]pyrazole-7-carboxamido)ethyl)benzoic acid;

(S)-4-(1-(1-(4-chloro-3-(trifluoromethyl)benzyl)-6-(trifluoromethyl)-2,3-dihydro-1H-imidazo[1,2-b]pyrazole-7-carboxamido)ethyl)benzoic acid;

(S)-4-(1-(3-methyl-6-(trifluoromethyl)-1-(3-(trifluoromethyl)benzyl)-1H-imidazo[1,2-b]pyrazole-7-carboxamido)ethyl)benzoic acid;

4-((S)-1-((S)-3-(fluoromethyl)-6-(trifluoromethyl)-1-(3-(trifluoromethyl)benzyl)-2,3-dihydro-1H-imidazo[1,2-b]pyrazole-7-carboxamido)ethyl)benzoic acid;

(S)-4-(1-(1-(4-hydroxybenzyl)-6-(trifluoromethyl)-2,3-dihydro-1H-imidazo[1,2-b]pyrazole-7-carboxamido)ethyl)benzoic acid;

(R)-4-(2-hydroxy-1-(6-(trifluoromethyl)-1-(3-(trifluoromethyl)benzyl)-2,3-dihydro-1H-imidazo[1,2-b]pyrazole-7-carboxamido)ethyl)benzoic acid;

(S)-4-(1-(1-(4-(dimethylamino)benzyl)-6-(trifluoromethyl)-2,3-dihydro-1H-imidazo[1,2-b]pyrazole-7-carboxamido)ethyl)benzoic acid;

(S)-4-(1-(1-(3-(dimethylamino)benzyl)-6-(trifluoromethyl)-2,3-dihydro-1H-imidazo[1,2-b]pyrazole-7-carboxamido)ethyl)benzoic acid;

(S)-4-(1-(1-(3-(dimethylamino)-5-(trifluoromethyl)benzyl)-6-(trifluoromethyl)-2,3-dihydro-1H-imidazo[1,2-b]pyrazole-7-carboxamido)ethyl)benzoic acid;

(S)-4-(1-(6-(1,1-difluoro-2-hydroxyethyl)-1-(3-(trifluoromethyl)benzyl)-2,3-dihydro-1H-imidazo[1,2-b]pyrazole-7-carboxamido)ethyl)benzoic acid;

(S)—N-(1-(4-(((1-cyanocyclopropyl)carbamoyl)phenyl)ethyl)-6-(trifluoromethyl)-1-(3-(trifluoromethyl)benzyl)-2,3-dihydro-1H-imidazo[1,2-b]pyrazole-7-carboxamide;

4-((S)-1-((S)-3-(hydroxymethyl)-6-(trifluoromethyl)-1-(3-(trifluoromethyl)benzyl)-2,3-dihydro-1H-imidazo[1,2-b]pyrazole-7-carboxamido)ethyl)benzoic acid;

4-((S)-1-((S)-3-((benzyloxy)methyl)-6-(trifluoromethyl)-1-(3-(trifluoromethyl)benzyl)-2,3-dihydro-1H-imidazo[1,2-b]pyrazole-7-carboxamido)ethyl)benzoic acid;

(S)-4-(1-(1-(3-bromo-5-(trifluoromethyl)benzyl)-6-(trifluoromethyl)-2,3-dihydro-1H-imidazo[1,2-b]pyrazole-7-carboxamido)ethyl)benzoic acid;

(S)-4-(1-(6-(difluoromethyl)-1-(3-(trifluoromethyl)benzyl)-2,3-dihydro-1H-imidazo[1,2-b]pyrazole-7-carboxamido)ethyl)benzoic acid;

(S)-4-(1-(1-(3-(trifluoromethyl)benzyl)-6-vinyl-2,3-dihydro-1H-imidazo[1,2-b]pyrazole-7-carboxamido)ethyl)benzoic acid;

(S)-4-(1-(6-(hydroxymethyl)-1-(3-(trifluoromethyl)benzyl)-2,3-dihydro-1H-imidazo[1,2-b]pyrazole-7-carboxamido)ethyl)benzoic acid;

(S)-4-(1-(1-(3-(1,1-difluoro-2-hydroxyethyl)benzyl)-6-(trifluoromethyl)-2,3-dihydro-1H-imidazo[1,2-b]pyrazole-7-carboxamido)ethyl)benzoic acid;

(S)-4-(1-(6-(trifluoromethyl)-1-(3-(trifluoromethyl)benzyl)-2,3-dihydro-1H-imidazo[1,2-b]pyrazole-7-carboxamido)ethyl)benzoic acid;

(S)-4-(1-(6-(trifluoromethyl)-1-(4-(trifluoromethyl)benzyl)-2,3-dihydro-1H-imidazo[1,2-b]pyrazole-7-carboxamido)ethyl)benzoic acid;

Methyl (S)-4-(1-(6-(trifluoromethyl)-1-(4-(trifluoromethyl)benzyl)-2,3-dihydro-1H-imidazo[1,2-b]pyrazole-7-carboxamido)ethyl)benzoate;

(S)-4-(1-(6-(trifluoromethyl)-1-(2-(trifluoromethyl)benzyl)-2,3-dihydro-1H-imidazo[1,2-b]pyrazole-7-carboxamido)ethyl)benzoic acid;

(S)-4-(1-(1-(3,5-bis(trifluoromethyl)benzyl)-6-(trifluoromethyl)-2,3-dihydro-1H-imidazo[1,2-b]pyrazole-7-carboxamido)ethyl)benzoic acid;

(S)-4-(1-(1-(3-chloro-5-(trifluoromethyl)benzyl)-6-(trifluoromethyl)-2,3-dihydro-1H-imidazo[1,2-b]pyrazole-7-carboxamido)ethyl)benzoic acid;

(S)-4-(1-(1-(3,5-dichlorobenzyl)-6-(trifluoromethyl)-2,3-dihydro-1H-imidazo[1,2-b]pyrazole-7-carboxamido)ethyl)benzoic acid;
(S)-4-(1-(1-(4-methoxybenzyl)-6-(trifluoromethyl)-2,3-dihydro-1H-imidazo[1,2-b]pyrazole-7-carboxamido)ethyl)benzoic acid;
(S)-4-(1-(1-(3-methoxybenzyl)-6-(trifluoromethyl)-2,3-dihydro-1H-imidazo[1,2-b]pyrazole-7-carboxamido)ethyl)benzoic acid;
(S)-4-(1-(1-(4-(trifluoromethoxy)benzyl)-6-(trifluoromethyl)-2,3-dihydro-1H-imidazo[1,2-b]pyrazole-7-carboxamido)ethyl)benzoic acid;
(S)-4-(1-(1-(3-(trifluoromethoxy)benzyl)-6-(trifluoromethyl)-2,3-dihydro-1H-imidazo[1,2-b]pyrazole-7-carboxamido)ethyl)benzoic acid;
(S)-4-(1-(1-(3-chlorobenzyl)-6-(trifluoromethyl)-2,3-dihydro-1H-imidazo[1,2-b]pyrazole-7-carboxamido)ethyl)benzoic acid;
(S)-4-(1-(1-(3,4-dichlorobenzyl)-6-(trifluoromethyl)-2,3-dihydro-1H-imidazo[1,2-b]pyrazole-7-carboxamido)ethyl)benzoic acid;
(S)-4-(1-(1-(4-fluorobenzyl)-6-(trifluoromethyl)-2,3-dihydro-1H-imidazo[1,2-b]pyrazole-7-carboxamido)ethyl)benzoic acid;
(S)-4-(1-(1-(3-fluorobenzyl)-6-(trifluoromethyl)-2,3-dihydro-1H-imidazo[1,2-b]pyrazole-7-carboxamido)ethyl)benzoic acid;
(S)-4-(1-(1-(2-fluorobenzyl)-6-(trifluoromethyl)-2,3-dihydro-1H-imidazo[1,2-b]pyrazole-7-carboxamido)ethyl)benzoic acid;
(S)-4-(1-(1-(4-methylbenzyl)-6-(trifluoromethyl)-2,3-dihydro-1H-imidazo[1,2-b]pyrazole-7-carboxamido)ethyl)benzoic acid;
(S)-4-(1-(1-(3-methylbenzyl)-6-(trifluoromethyl)-2,3-dihydro-1H-imidazo[1,2-b]pyrazole-7-carboxamido)ethylbenzoic acid;
(S)-4-(1-(1-(2-methylbenzyl)-6-(trifluoromethyl)-2,3-dihydro-1H-imidazo[1,2-b]pyrazole-7-carboxamido)ethyl)benzoic acid;
(S)-4-(1-(1-(4-ethylbenzyl)-6-(trifluoromethyl)-2,3-dihydro-1H-imidazo[1,2-b]pyrazole-7-carboxamido)ethyl)benzoic acid;
(S)-2-fluoro-4-(1-(6-(trifluoromethyl)-1-(4-(trifluoromethyl)benzyl)-2,3-dihydro-1H-imidazo[1,2-b]pyrazole-7-carboxamido)ethyl)benzoic acid;
(S)-3-fluoro-4-(1-(6-(trifluoromethyl)-1-(4-(trifluoromethyl)benzyl)-2,3-dihydro-1H-imidazo[1,2-b]pyrazole-7-carboxamido)ethyl)benzoic acid;
(S)-3-fluoro-4-(1-(6-(trifluoromethyl)-1-(3-(trifluoromethyl)benzyl)-2,3-dihydro-1H-imidazo[1,2-b]pyrazole-7-carboxamido)ethyl)benzoic acid;
(S)-2-fluoro-4-(1-(6-(trifluoromethyl)-1-(3-(trifluoromethyl)benzyl)-2,3-dihydro-1H-imidazo[1,2-b]pyrazole-7-carboxamido)ethyl)benzoic acid;
methyl (S)-2-fluoro-4-(1-(6-(trifluoromethyl)-1-(3-(trifluoromethyl)benzyl)-2,3-dihydro-1H-imidazo[1,2-b]pyrazole-7-carboxamido)ethyl)benzoate;
(S)-2-(4-(1-(6-(trifluoromethyl)-1-(3-(trifluoromethyl)benzyl)-2,3-dihydro-1H-imidazo[1,2-b]pyrazole-7-carboxamido)ethyl)phenyl)acetic acid;
(S)-2-(4-(1-(6-(trifluoromethyl)-1-(4-(trifluoromethyl)benzyl)-2,3-dihydro-1H-imidazo[1,2-b]pyrazole-7-carboxamido)ethyl)phenyl)acetic acid;
4-(1-(6-methyl-1-(4-(trifluoromethyl)benzyl)-2,3-dihydro-1H-imidazo[1,2-b]pyrazole-7-carboxamido)cyclopropyl)benzoic acid;
4-(1-(6-(trifluoromethyl)-1-(4-(trifluoromethyl)benzyl)-2,3-dihydro-1H-imidazo[1,2-b]pyrazole-7-carboxamido)cyclopropyl)benzoic acid;
4-(1-(1-(4-chlorobenzyl)-6-(trifluoromethyl)-2,3-dihydro-1H-imidazo[1,2-b]pyrazole-7-carboxamido)cyclopropyl)benzoic acid;
(S)-4-(1-(1-(4-chlorobenzyl)-6-(trifluoromethyl)-2,3-dihydro-1H-imidazo[1,2-b]pyrazole-7-carboxamido)ethyl)benzoic acid;
(S)-4-(1-(1-(4-chlorobenzyl)-6-methyl-2,3-dihydro-1H-imidazo[1,2-b]pyrazole-7-carboxamido)ethyl)benzoic acid;
4-((1-(4-chlorobenzyl)-6-methyl-2,3-dihydro-1H-imidazo[1,2-b]pyrazole-7-carboxamido)methyl)benzoic acid;
(R)-4-(1-(6-methyl-1-(4-(trifluoromethyl)phenyl)ethyl)-2,3-dihydro-1H-imidazo[1,2-b]pyrazole-7-carboxamido)cyclopropyl)benzoic acid;
4-((S)-1-(6-methyl-1-((R)-1-(4-(trifluoromethyl)phenyl)ethyl)-2,3-dihydro-1H-imidazo[1,2-b]pyrazole-7-carboxamido)ethyl)benzoic acid;
(S)—N-(1-(4-(2H-tetrazol-5-yl)phenyl)ethyl)-6-(trifluoromethyl)-1-(3-(trifluoromethyl)benzyl)-2,3-dihydro-1H-imidazo[1,2-b]pyrazole-7-carboxamide;
(S)—N-(1-(4-(2H-tetrazol-5-yl)phenyl)ethyl)-6-(trifluoromethyl)-1-(4-(trifluoromethyl)benzyl)-2,3-dihydro-1H-imidazo[1,2-b]pyrazole-7-carboxamide;
(S)-5-(1-(6-(trifluoromethyl)-1-(3-(trifluoromethyl)benzyl)-2,3-dihydro-1H-imidazo[1,2-b]pyrazole-7-carboxamido)ethyl)picolinic acid;
(S)-6-(1-(6-(trifluoromethyl)-1-(3-(trifluoromethyl)benzyl)-2, 3-dihydro-1H-imidazo[1,2-b]pyrazole-7-carboxamido)ethyl)nicotinic acid;
(S)-4-(1-(4-(4-chlorobenzyl)-2-(trifluoromethyl-4,5,6,7-tetrahydropyrazolo[1,5-a]pyrimidine-3-carboxamido)ethyl)benzoic acid;
(S)-4-(1-(4-(3-chlorobenzyl)-2-(trifluoromethyl)-4,5,6,7-tetrahydropyrazolo[1,5-a]pyrimidine-3-carboxamido)ethyl)benzoic acid;
(S)-4-(1-(4-(2-chlorobenzyl)-2-(trifluoromethyl)-4,5,6,7-tetrahydropyrazolo[1,5-a]pyrimidine-3-carboxamido)ethyl)benzoic acid;
(S)-4-(1-(2-(trifluoromethyl)-4-(3-(trifluoromethyl)benzyl)-4,5,6,7-tetrahydropyrazolo[1,5-a]pyrimidine-3-carboxamido)ethyl)benzoic acid;
(S)-4-(1-(2-(trifluoromethyl)-4-(4-(trifluoromethyl)benzyl)-4,5,6,7-tetrahydropyrazolo[1,5-a]pyrimidine-3-carboxamido)ethyl)benzoic acid;
(S)-4-(1-(2-(trifluoromethyl)-4-(2-(trifluoromethyl)benzyl)-4,5,6,7-tetrahydropyrazolo[1,5-a]pyrimidine-3-carboxamido)ethyl)benzoic acid;
(S)-4-(1-(6-(trifluoromethyl)-1-(4-(trifluoromethyl)phenyl)-2,3-dihydro-1H-imidazo[1,2-b]pyrazole-7-carboxamido)ethyl)benzoic acid;
(S)-4-(1-(6-(trifluoromethyl)-1-(3-(trifluoromethyl)phenyl)-2,3-dihydro-1H-imidazo[1,2-b]pyrazole-7-carboxamido)ethyl)benzoic acid;
(S)-4-(1-(1-(3-chlorophenyl)-6-(trifluoromethyl)-2,3-dihydro-1H-imidazo[1,2-b]pyrazole-7-carboxamido)ethyl)benzoic acid;
(S)-4-(1-(1-(4-chlorophenyl)-6-(trifluoromethyl)-2,3-dihydro-1H-imidazo[1,2-b]pyrazole-7-carboxamido)ethyl)benzoic acid;

(S)-4-(1-(2-(trifluoromethyl)-4-(4-(trifluoromethyl)phenyl)-4,5,6,7-tetrahydropyrazolo[1,5-a]pyrimidine-3-carboxamido)ethyl)benzoic acid;

(S)—N-(1-(4-(cyanocarbamoyl)phenyl)ethyl)-6-(trifluoromethyl)-1-(3-(trifluoromethyl)benzyl)-2,3-dihydro-1H-imidazo[1,2-b]pyrazole-7-carboxamide;

(S)—N-(1-(4-(((3,4-difluorophenyl)sulfonyl)carbamoyl)phenyl)ethyl)-6-(trifluoromethyl)-1-(3-(trifluoromethyl)benzyl)-2,3-dihydro-1H-imidazo[1,2-b]pyrazole-7-carboxamide;

(S)—N-(1-(4-((phenylsulfonyl)carbamoyl)phenyl)ethyl)-1-(3-(trifluoromethoxy)benzyl)-6-(trifluoromethyl)-2,3-dihydro-1H-imidazo[1,2-b]pyrazole-7-carboxamide;

(S)—N-(1-(4-((methylsulfonyl)carbamoyl)phenyl)ethyl)-6-(trifluoromethyl)-1-(3-(trifluoromethyl)benzyl)-2,3-dihydro-1H-imidazo[1,2-b]pyrazole-7-carboxamide;

(S)—N-(1-(4-((cyclopropylsulfonyl)carbamoyl)phenyl)ethyl)-6-(trifluoromethyl)-1-(3-(trifluoromethyl)benzyl)-2,3-dihydro-1H-imidazo[1,2-b]pyrazole-7-carboxamide;

(S)—N-(1-(4-(furan-3-yl)phenyl)ethyl)-6-(trifluoromethyl)-1-(4-(trifluoromethyl)benzyl)-2,3-dihydro-1H-imidazo[1,2-b]pyrazole-7-carboxamide;

(S)—N-(1-(4-cyclopropyl)phenyl)ethyl)-6-(trifluoromethyl)-1-(4-(trifluoromethyl)benzyl)-2,3-dihydro-1H-imidazo[1,2-b]pyrazole-7-carboxamide;

(S)—N-(1-(3-methyl-4-(2H-tetrazol-5-yl)phenyl)ethyl)-6-(trifluoromethyl)-1-(4-(trifluoromethyl)benzyl)-2,3-dihydro-1H-imidazo[1,2-b]pyrazole-7-carboxamide;

(S)-4-(1-(6-ethyl-1-(3-(trifluoromethyl)benzyl)-2,3-dihydro-1H-imidazo[1,2-b]pyrazole-7-carboxamido)ethyl)benzoic acid;

(S)-4-(1-(1-(2-chlorobenzyl)-6-(trifluoromethyl)-2,3-dihydro-1H-imidazo[1,2-b]pyrazole-7-carboxamido)ethyl)benzoic acid; and (S)-4-(1-(6-phenyl-1-(3-(trifluoromethyl)benzyl)-2,3-dihydro-1H-imidazo[1,2-b]pyrazole-7-carboxamido)ethyl)benzoic acid.

19. A compound selected from the group consisting of:

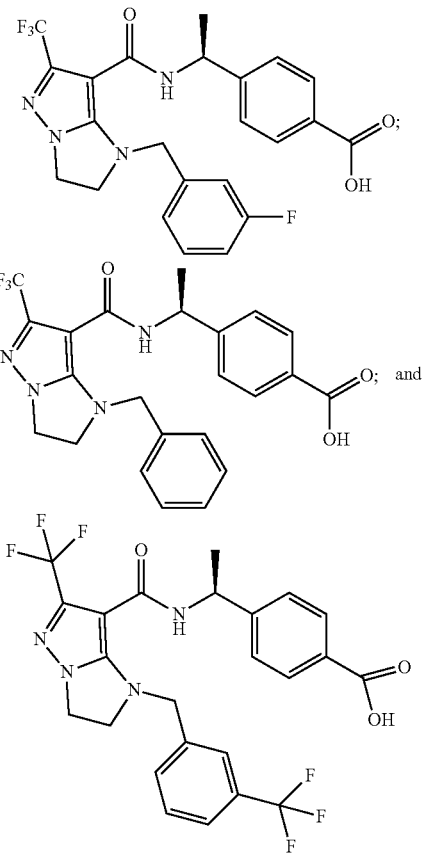

or a pharmaceutically acceptable salt thereof.

20. A pharmaceutical composition comprising a compound or pharmaceutically acceptable salt according to claim 19 and a pharmaceutically acceptable excipient.

* * * * *